United States Patent
Aebi et al.

(10) Patent No.: US 8,445,674 B2
(45) Date of Patent: May 21, 2013

(54) HETEROCYCLYL COMPOUNDS

(75) Inventors: Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH)

(73) Assignee: Hoffmann-La Roche Inc, Nutley, NJ (US)

( * ) Notice: Subject to any disclaimer, the term of this patent is extended or adjusted under 35 U.S.C. 154(b) by 156 days.

(21) Appl. No.: 12/901,592

(22) Filed: Oct. 11, 2010

(65) Prior Publication Data
US 2011/0092698 A1 Apr. 21, 2011

(30) Foreign Application Priority Data
Oct. 21, 2009 (EP) .................. 09173682

(51) Int. Cl.
C07D 401/06 (2006.01)
(52) U.S. Cl.
USPC .................. 540/492; 544/230; 544/360
(58) Field of Classification Search
None
See application file for complete search history.

(56) References Cited

FOREIGN PATENT DOCUMENTS

| WO | 2005/123697 | 12/2005 |
|----|-------------|---------|
| WO | 2008/081910 | 7/2008 |
| WO | 2009/010429 | 1/2009 |
| WO | 2010/012619 | 2/2010 |

OTHER PUBLICATIONS

"Burger's Medicinal Chemistry", edited by Manfred E. Wolff, 5th Ed. Part 1, pp. 975-977 (1995).*
Banker et al. "Modern Pharmaceutics", 3rd Ed. p. 596 (1996).*
McCarron et al., Database—Chemical Abstracts Service XP-002611213, (2007). Abstract and European Journal of Nuclear Medicine and Molecular Imaging vol. 34(10) pp. 1670-1682.
Sun, Chung-Ming, Department of Chemistry, National Dong-Hwa University, Hualien, Taiwan. Letters in Drug Discovery (2005) vol. 2(1) pp. 48-50.
Mukaiyama et al., Chemistry Letters (1975) pp. 1045-1048.
Evans et al., Tetrahedron Letters (1997) vol. 38 pp. 4535-4538.
Radosevich et al., Journal of American Chemistry Society (2005) vol. 127(4), pp. 1090-1091.
Vice et al., Journal of Organic Chemistry (2001) vol. 66, pp. 2487-2492.
Brown Ripin et al., Tetrahedron Letters (2000) vol. 41, pp. 5817-5819.
Mori et al., Tetrahedron (1983) vol. 39 pp. 3107-3109.
Solares et al., Tetrahedron (2006) vol. 62, pp. 3284-3291.

* cited by examiner

*Primary Examiner* — Emily Bernhardt

(57) ABSTRACT

The invention is concerned with novel bicyclic compounds of formula (I),

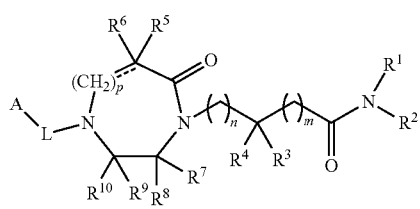

wherein n, m, p, A, L, $R^1$, $R^2$, $R^3$, $R^4$, $R^5$, $R^6$, $R^7$, $R^7$, $R^8$, $R^9$, and $R^{10}$ are as defined in the description and in the claims, as well as physiologically acceptable salts thereof. These compounds are antagonists of CCR2 receptor, CCR5 receptor and/or CCR3 receptor may be used, for example, in the prevention and/or treatment of inflammatory diseases, particularly peripheral arterial occlusive diseases or atherothrombosis.

14 Claims, No Drawings

HETEROCYCLYL COMPOUNDS

PRIORITY TO RELATED APPLICATION(S)

This application claims the benefit of European Patent Application No. 09173682.7 filed Oct. 21, 2009, which is hereby incorporated by reference in its entirety.

FIELD OF THE INVENTION

The compounds of formula (I) are CCR2 receptor (Chemokine Receptor 2/Monocyte chemotactic protein 1 receptor) antagonists and/or also CCR5 receptor (Chemokine Receptor 5) and/or CCR3 receptor (Chemokine Receptor 3) antagonists. The compounds may be used, for example, in the prevention and/or treatment of inflammatory diseases, particularly peripheral arterial occlusive diseases or atherothrombosis.

BACKGROUND OF THE INVENTION

Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

SUMMARY OF THE INVENTION

The present invention relates to a compound of formula (I):

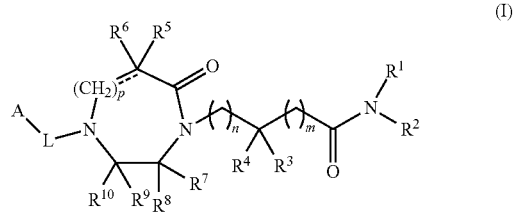

wherein $\overset{\cdots}{\diagup}$ is either a single or a double bond with the proviso that when $\overset{\cdots}{\diagup}$ is a double bond one of $R^5$ or $R^6$ is absent;

A is aryl or arylmethyl wherein said aryl or the aryl of arylmethyl is optionally substituted by one to three substituents independently selected from the group consisting of halogen, aryl, heteroaryl, $C_{1-6}$ alkyl, halo $C_{1-6}$ alkyl, $C_{1-6}$ alkoxy and halo $C_{1-6}$ alkoxy;

L is selected from the group consisting of: a bond, N(R')—C(=O), NH—C(=S), and CH=CH—C(=O), wherein R' is hydrogen or $C_{1-4}$ alkyl;

$R^1$ and $R^2$ are each, independently-of each other, selected from the group consisting of:
  $C_{1-6}$ alkyl,
  $C_{3-6}$ alkenyl,
  $C_{3-6}$ alkynyl,
  hydroxy $C_{2-6}$ alkyl,
  $C_{1-6}$ alkoxy $C_{2-6}$ alkyl,
  $C_{3-7}$ cycloalkyl which is optionally substituted by one to three $R^d$ groups,
  $C_{3-7}$ cycloalkyl $C_{1-6}$ alkyl wherein the $C_{3-7}$ cycloalkyl is optionally substituted by one to three $R^d$ groups,
  $C_{7-10}$ bicycloalkyl,
  phenyl $C_{1-3}$ alkyl, wherein the phenyl ring is optionally substituted by one to three $R^d$ groups,
  heteroaryl $C_{1-3}$ alkyl, wherein the heteroaryl is optionally substituted by one to three $R^d$ groups,
  heterocyclyl which is optionally substituted by one to three $R^d$ groups, and
  heterocyclyl $C_{1-6}$ alkyl, wherein the heterocyclyl is optionally substituted by one to three $R^d$ groups, or $R^1$ and $R^2$, together with the nitrogen atom to which they are attached, form a heterocyclyl optionally substituted by one to three $R^d$ groups, wherein one of the ring carbon atoms of said heterocyclyl is optionally replaced with C=O or $SO_2$; and/or
  one of the ring carbon atoms of the heterocyclyl formed by $R^1$ and $R^2$ is also a ring carbon atom of another ring which is $C_{3-7}$ cycloalkyl or heterocyclyl, which is optionally substituted by $C_{1-6}$ alkyl and wherein one or two ring carbon atoms of the second ring is optionally replaced by a carbonyl group;

$R^3$ and $R^4$ are, independently of each other, selected from the group consisting of:
  hydrogen,
  hydroxy,
  $C_{1-6}$ alkyl,
  $C_{1-6}$ alkoxy,
  $C_{3-7}$ cycloalkyl,
  $C_{3-7}$ cycloalkyl $C_{1-6}$ alkyl, $C_{1-6}$ alkoxycarbonyl,
carboxyl,
carbamoyl,
mono or di-$C_{1-6}$ alkyl substituted carbamoyl,
$C_{1-6}$ alkoxycarbonyloxy,
mono or di-$C_{1-6}$ alkyl substituted aminocarbonyloxy,
$C_{1-20}$ alkylcarbonyloxy-$C_{1-6}$ alkyl,
$C_{1-20}$ alkoxycarbonyloxy-$C_{1-6}$ alkyl,
arylcarbonyloxy-$C_{1-6}$ alkyl, in which said aryl is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;
mono or di-$C_{1-6}$ alkyl substituted aminocarbonyloxy-$C_{1-6}$ alkyl,
aryl substituted aminocarbonyloxy-$C_{1-6}$ alkyl, in which said aryl is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy
hydroxy-$C_{1-6}$ alkyl,
$C_{1-6}$ alkoxy-$C_{1-6}$ alkyl,
halogen and
halo $C_{1-6}$ alkyl;
P is 0 or 1;
$R^5$ and $R^6$ are each independently selected from the group consisting of: hydrogen, $C_{1-6}$ alkyl and $C_{3-7}$ cycloalkyl, wherein said $C_{1-6}$ alkyl and said $C_{3-7}$ cycloalkyl are optionally substituted by one to three substituents independently selected from the group consisting of amino, hydroxy, carboxyl, carbamoyl, mono or di-$C_{1-6}$ alkyl substituted carbamoyl and $C_{1-6}$ alkoxycarbonyl; or
$R^5$ and $R^6$, together with the carbon atom to which they are attached, form $C_{3-7}$ cycloalkyl or heterocyclyl;
$R^7$, $R^8$, $R^9$ and $R^{10}$ are each, independently of each other, selected from the group consisting of:
hydrogen,
carboxyl,
carbamoyl,
mono or di-$C_{1-6}$ alkyl substituted carbamoyl,
$C_{1-6}$ alkyl optionally substituted by one to three substituents independently selected from the group consisting of hydroxy, $C_{1-6}$ alkoxy, carboxyl, carbamoyl, mono or di-$C_{1-6}$ alkyl substituted carbamoyl and $C_{1-6}$ alkoxycarbonyl, aryl and heteroaryl, in which said aryl and said heteroaryl are optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;
$C_{3-7}$ cycloalkyl, and
aryl;
each $R^d$ is independently selected from the group consisting of: hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, $C_{1-6}$ alkyl-carbonyloxy, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and wherein said phenyl, the phenyl of said phenyl $C_{1-3}$ alkyl, said heteroaryl, the heteroaryl of said heteroaryl $C_{1-3}$ alkyl, and said heterocyclyl are optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, one or two ring carbon atoms of said heterocyclyl being optionally replaced with a carboxyl group;
$R^a$, $R^b$ and $R^c$ are each independently hydrogen or $C_{1-6}$ alkyl;
n is 0, 1, or 2;
m is 0, 1, or 2; and
m+n is 0, 1, 2, or 3;
or a prodrug or pharmaceutically acceptable salt thereof.

DETAILED DESCRIPTION OF THE INVENTION

Unless otherwise indicated, the following definitions are set forth to illustrate and define the meaning and scope of the various terms used to describe the invention herein.

The term "halogen", "halogen atom" or "halo" refers to fluoro, chloro, bromo or iodo. Preferred "halogen" groups are fluoro or chloro.

The term "$C_{1-6}$ alkyl" or "lower alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl or $C_{1-3}$ alkyl is more preferred. The term "$C_{2-6}$ alkyl" means the same as a "$C_{1-6}$ alkyl", except that the $C_{2-6}$ alkyl has two to six carbon atoms; and the term "$C_{3-6}$ alkyl" means the same as a "$C_{1-6}$ alkyl", except that the $C_{3-6}$ alkyl has three to six carbon atoms; etc. The term "$C_{1-20}$ alkyl" means the same as a "$C_{1-6}$ alkyl", except that that the $C_{1-20}$ alkyl has one to 20 carbon atoms.

The term "$C_{1-20}$ alkylcarbonyloxy-$C_{1-6}$ alkyl" refers to the group $R^{b1}$—C(O)—O—$R^{b2}$—, wherein $R^{b2}$ is a $C_{1-6}$ alkylene and $R^{b1}$ is a $C_{1-20}$ alkyl, as defined above.

The term "$C_{1-20}$ alkoxycarbonyloxy-$C_{1-6}$ alkyl" refers to the group $R^{a3}$—C(O)—O—$R^{b3}$—, wherein $R^{b3}$ is a $C_{1-6}$ alkylene and $R^{a3}$ is a $C_{1-20}$ alkoxy, as defined above.

The term "$C_{1-6}$ alkoxy," alone or in combination with other groups, means the group R'—O—, wherein R' is a $C_{1-6}$ alkyl.

The term "$C_{1-6}$ alkoxy-carbonyl" refers to the group $R^{a1}$—C(O)—, wherein $R^{a1}$ is a $C_{1-6}$ alkoxy as defined above.

The term "$C_{1-6}$ alkoxy-$C_{1-6}$ alkyl" means a $C_{1-6}$ alkyl substituted by a $C_{1-6}$ alkoxy group, as defined herein.

The term "$C_{1-6}$ alkoxy-carbonyloxy" refers to the group $R^{a2}$—C(O)—O—, wherein $R^{a2}$ is a $C_{1-6}$ alkoxy as defined above."

The term "$C_{1-6}$ alkyl-carbonyloxy" refers to the group $R^{a2}$—C(O)—O—, wherein $R^{a2}$ is a $C_{1-6}$ alkyl as defined above.

The term "aryl", alone or combination with other groups, means cyclic aromatic hydrocarbon radical consisting of one or more fused rings containing 6-14 carbon atoms, for example phenyl or naphthyl. The term "arylmethyl" preferably means a phenyl-$CH_2$— or a naphthyl-$CH_2$ radical.

The term "phenyl-$C_{1-3}$ alkyl" means a $C_{1-3}$ alkyl, as defined herein, substituted by phenyl.

The term "arylcarbonyloxy-$C_{1-6}$ alkyl" refers to the group $R^{c1}$—C(O)—O—$R^{c2}$—, wherein $R^{c2}$ is a $C_{1-6}$ alkylene and $R^{c1}$ is an aryl, as defined above The term "$C_{3-6}$ alkenyl", alone or in combination with other groups, means a straight-chain or branched hydrocarbon residue comprising a carbon-carbon double bond, having three to six carbon atoms, provided that the carbon atom of the attachment point of the $C_{3-6}$ alkenyl to the rest of the molecule is not bonded to another carbon atom of the $C_{3-6}$ alkenyl by a carbon-carbon double bond. An example of a $C_{3-6}$ alkenyl is 2-propenyl.

The term "$C_{1-6}$ alkylene", alone or in combination with other groups, means a branched or straight-chain saturated divalent hydrocarbon radical of one to six carbon atoms, such as methylene, ethylene, tetramethylethylene.

The term "$C_{3-6}$-alkynyl", alone or in combination with other groups, means a straight-chain or branched hydrocarbon residue comprising a carbon-carbon triple bond, having three to six carbon atoms, provided that the carbon atom of the attachment point of the $C_{3-6}$ alkynyl to the rest of the molecule is not bonded to another carbon atom of the $C_{3-6}$ alkynyl by a carbon-carbon triple bond. An example of a $C_{3-6}$ alkynyl is 2-propynyl.

The term "carboxyl" refers to a group —C(O)OH.

The term "carbamoyl" refers to a group —C(O)NH$_2$.

The term "$C_{3-7}$ cycloalkyl," alone or in combination with other groups, means a saturated monovalent mono-cyclic hydrocarbon radical of three to seven ring carbons (e.g., cyclopropyl, cyclobutyl, or cyclohexyl).

The term "$C_{3-7}$ cycloalkyl $C_{1-6}$ alkyl" means a $C_{1-6}$ alkyl substituted by one or more, preferably one or two, $C_{3-7}$ cycloalkyl groups, as defined herein.

The term "$C_{7-10}$ bicycloalkyl," alone or in combination with other groups, means a saturated monovalent cyclic hydrocarbon radical of seven to ten ring carbons, having two rings, in which two or more ring carbon atoms of one ring are ring carbon atoms of the other ring (e.g., bicyclo[2.2.1]heptyl).

The term "halo $C_{1-6}$ alkoxy," alone or in combination with other groups, means a $C_{1-6}$ alkoxy substituted by one or more halogens. In particular embodiments the $C_{1-6}$ alkoxy is substituted by one to three halogens.

The term "halo $C_{1-6}$ alkyl" means a $C_{1-6}$ alkyl substituted by one or more of the same or different halogen atoms. Examples are 1-fluoromethyl, difluoromethyl, trifluoromethyl, 1-fluoroethyl, 2-fluoroethyl and 2,2,2-trifluoroethyl. The most preferred "halo $C_{1-6}$ alkyl" is trifluoromethyl.

The term "heteroaryl," alone or combination with other groups, means an aromatic monocyclic- or bicyclic-aromatic radical of 5 to 10 ring atoms having one to three ring heteroatoms independently selected from N, O, and S, with the remaining ring atoms being C. More specifically the term "heteroaryl" includes, but is not limited to, pyridyl, furanyl, thienyl, thiazolyl, isothiazolyl, triazolyl, imidazolyl, isoxazolyl, pyrrolyl, pyrimidinyl, pyrazolyl, pyrazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. The most preferred heteroaryl are isoquinolyl, pyridyl, and quinolyl. The term "heteroarylmethyl" means a heteroaryl-CH$_2$-radical.

The term "heteroaryl-$C_{1-3}$ alkyl" means a $C_{1-3}$ alkyl substituted by a heteroaryl, as defined herein.

The term "heterocyclyl", alone or combination with other groups, means a non-aromatic mono- or bi-cyclic radical of four to nine ring atoms in which one to three ring atoms are heteroatoms independently selected from N, O and S(O)$_n$ (where n is an integer from 0 to 2), with the remaining ring atoms being C. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl, imidazolinyl or 6-aza-spiro[2.5]oct-6yl. The more preferred heterocyclyl is piperidyl or 6-aza-spiro[2.5]oct-6yl.

The term "heterocyclyl-$C_{1-3}$ alkyl" means a $C_{1-3}$ alkyl, substituted by one heterocyclyl, as defined herein.

The term "hydroxy $C_{1-6}$ alkyl" means $C_{1-6}$ alkyl substituted by one or more, preferably one hydroxy group(s).

The term "mono or di-$C_{1-6}$ alkyl substituted aminocarbonyl" refers to a group —OC(O)NR$^{b1}$R$^{c1}$ wherein at least one of R$^{b1}$ and R$^{c1}$ is $C_{1-6}$ alkyl and the other is hydrogen or $C_{1-6}$ alkyl.

The term "mono or di-$C_{1-6}$ alkyl substituted aminocarbonyloxy" refers to a group —OC(O)NR$^{v1}$R$^{v2}$ wherein at least one of R$^{v1}$ and R$^{v2}$ is $C_{1-6}$ alkyl and the other is hydrogen or $C_{1-6}$ alkyl.

The term "acyl" means R—C(O)—, in which R is a $C_{1-6}$ alkyl, halo $C_{1-6}$ alkyl, $C_{3-7}$ cycloalkyl or $C_{3-7}$ cycloalkyl $C_{1-6}$ alkyl.

The term "mono or di-$C_{1-6}$ alkyl substituted aminocarbonyloxy-$C_{1-6}$ alkyl" means $C_{1-6}$ alkyl substituted by a mono or di-$C_{1-6}$ alkyl substituted aminocarbonyloxy, as defined above.

The term, "$C_{1-6}$ alkylsulfonyl", "$C_{1-6}$ alkylsulfinyl" and "$C_{1-6}$ alkylthio" means a $C_{1-6}$ alkyl-SO$_2$—, $C_{1-6}$ alkyl-SO— and $C_{1-6}$ alkyl-S—, respectively.

Preferred radicals for the chemical groups whose definitions are given above are those specifically exemplified in the Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R$^1$, R$^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in chemically stable compounds.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The present invention relates to a compound of formula (I):

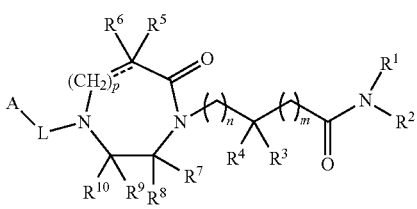

wherein

⁓ is either a single or a double bond with the proviso that when ⁓ is a double bond one of $R^5$ or $R^6$ is absent;

A is aryl or arylmethyl wherein said aryl or the aryl of arylmethyl is optionally substituted by one to three substituents independently selected from the group consisting of halogen, aryl, heteroaryl, $C_{1-6}$ alkyl, halo $C_{1-6}$ alkyl, $C_{1-6}$ alkoxy and halo $C_{1-6}$ alkoxy;

L is selected from the group consisting of: a bond, N(R')—C(=O), NH—C(=S), and CH=CH—C(=O), wherein R' is hydrogen or $C_{1-4}$ alkyl;

$R^1$ and $R^2$ are each, independently-of each other, selected from the group consisting of:
$C_{1-6}$ alkyl,
$C_{3-6}$ alkenyl,
$C_{3-6}$ alkynyl,
hydroxy $C_{2-6}$ alkyl,
$C_{1-6}$ alkoxy $C_{2-6}$ alkyl,
$C_{3-7}$ cycloalkyl which is optionally substituted by one to three $R^d$ groups,
$C_{3-7}$ cycloalkyl $C_{1-6}$ alkyl wherein the $C_{3-7}$ cycloalkyl is optionally substituted by one to three $R^d$ groups,
$C_{7-10}$ bicycloalkyl,
phenyl $C_{1-3}$ alkyl, wherein the phenyl ring is optionally substituted by one to three $R^d$ groups,
heteroaryl $C_{1-3}$ alkyl, wherein the heteroaryl is optionally substituted by one to three $R^d$ groups, and
heterocyclyl which is optionally substituted by one to three $R^d$ groups,
heterocyclyl $C_{1-6}$ alkyl, wherein the heterocyclyl is optionally substituted by one to three $R^d$ groups, or
$R^1$ and $R^2$, together with the nitrogen atom to which they are attached, form a heterocyclyl optionally substituted by one to three $R^d$ groups, wherein one of the ring carbon atoms of said heterocyclyl is optionally replaced with C=O or $SO_2$; and/or
one of the ring carbon atoms of the heterocyclyl formed by $R^1$ and $R^2$ is also a ring carbon atom of another ring which is $C_{3-7}$ cycloalkyl or heterocyclyl, which is optionally substituted by $C_{1-6}$ alkyl and wherein one or two ring carbon atoms of the second ring is optionally replaced by a carbonyl group;

$R^3$ and $R^4$ are, independently of each other, selected from the group consisting of:
hydrogen,
hydroxy,
$C_{1-6}$ alkyl,
$C_{1-6}$ alkoxy,
$C_{3-7}$ cycloalkyl,
$C_{3-7}$ cycloalkyl $C_{1-6}$ alkyl,
$C_{1-6}$ alkoxycarbonyl,
carboxyl,
carbamoyl,
mono or di-$C_{1-6}$ alkyl substituted carbamoyl,
$C_{1-6}$ alkoxycarbonyloxy,
mono or di-$C_{1-6}$ alkyl substituted aminocarbonyloxy,
$C_{1-20}$ alkylcarbonyloxy-$C_{1-6}$ alkyl,
$C_{1-20}$ alkoxycarbonyloxy-$C_{1-6}$ alkyl,
arylcarbonyloxy-$C_{1-6}$ alkyl, in which said aryl is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;
mono or di-$C_{1-6}$ alkyl substituted aminocarbonyloxy-$C_{1-6}$ alkyl,
aryl substituted aminocarbonyloxy-$C_{1-6}$ alkyl, in which said aryl is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy
hydroxy-$C_{1-6}$ alkyl,
$C_{1-6}$ alkoxy-$C_{1-6}$ alkyl,
halogen and
halo $C_{1-6}$ alkyl;

p is 0 or 1;

$R^5$ and $R^6$ are each independently selected from the group consisting of: hydrogen, $C_{1-6}$ alkyl and $C_{3-7}$ cycloalkyl, wherein said $C_{1-6}$ alkyl and said $C_{3-7}$ cycloalkyl are optionally substituted by one to three substituents independently selected from the group consisting of amino, hydroxy, carboxyl, carbamoyl, mono or di-$C_{1-6}$ alkyl substituted carbamoyl and $C_{1-6}$ alkoxycarbonyl; or
$R^5$ and $R^6$, together with the carbon atom to which they are attached, form $C_{3-7}$ cycloalkyl or heterocyclyl;

$R^7$, $R^8$, $R^9$ and $R^{10}$ are each, independently of each other, selected from the group consisting of:
hydrogen,
carboxyl,
carbamoyl,
mono or di-$C_{1-6}$ alkyl substituted carbamoyl,
$C_{1-6}$ alkyl optionally substituted by one to three substituents independently selected from the group consisting of hydroxy, $C_{1-6}$ alkoxy, carboxyl, carbamoyl, mono or di-$C_{1-6}$ alkyl substituted carbamoyl and $C_{1-6}$ alkoxycarbonyl, aryl and heteroaryl, in which said aryl and said heteroaryl are optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;
$C_{3-7}$ cycloalkyl, and
aryl;

each $R^d$ is independently selected from the group consisting of: hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, $C_{1-6}$ alkyl-carbonyloxy, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and wherein said phenyl, the phenyl of said phenyl $C_{1-3}$ alkyl, said heteroaryl, the heteroaryl of said heteroaryl $C_{1-3}$ alkyl, and said heterocyclyl are optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, one or two ring carbon atoms of said heterocyclyl being optionally replaced with a carboxyl group;

$R^a$, $R^b$ and $R^c$ are each independently hydrogen or $C_{1-6}$ alkyl;

n is 0, 1, or 2;

m is 0, 1, or 2; and m+n is 0, 1, 2, or 3;

or a prodrug or pharmaceutically acceptable salt thereof.

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) In the compounds of formula (I), A is phenyl or naphthyl, wherein said phenyl and said naphthyl are optionally substituted by one to three substituents selected from the group consisting of halogen, halo $C_{1-6}$ alkyl and halo $C_{1-6}$ alkoxy. Preferably, A is phenyl substituted by one or two substituents selected from the group consisting of halogen atoms, trifluoromethyl and trifluoromethoxy, more preferably the substituents are independently selected from the group consisting of chloro, fluoro, trifluoromethyl and trifluoromethoxy. A is especially 3-chloro-4-trifluoromethyl-phenyl, 4 trifluoromethyl-phenyl, 3,4 bis trifluoromethyl-phenyl or 3,4-dichlorophenyl, more especially 3-chloro-4-trifluoromethyl-phenyl, 4 trifluoromethyl-phenyl or 3,4-dichlorophenyl.

ii) In the compounds of formula (I), $R^1$ and $R^2$, together with the nitrogen atom to which they are attached, form heterocyclyl optionally substituted by one to three substituents independently selected from the group consisting of hydroxy, halogen, $C_{1-6}$ alkyl $C_{1-6}$ alkoxy $C_{1-6}$ alkyl, —NH—C(O)—O ($C_{1-4}$ alkyl), $C_{1-6}$ alkyl-carbonyloxy, imidazolyl, phenyl, pyridyl, pyrazolyl and hydroxy $C_{1-6}$ alkyl; and/or one of the ring carbon atoms of the heterocyclyl formed by $R^1$ and $R^2$ is also a ring carbon atom of another ring which is $C_{3-7}$ cycloalkyl or heterocyclyl.

The heterocyclyl formed by $R^1$ and $R^2$, together with the nitrogen atom to which they are attached, is preferably piperidyl or pyrrolidinyl, said piperidyl and pyrrolidinyl being is optionally substituted by one or two substituents independently selected from the group consisting of hydroxy $C_{1-6}$ alkyl and hydroxy $C_{1-6}$ alkyl, and/or one of the ring carbon atoms of said piperidyl and pyrrolidinyl formed by $R^1$ and $R^2$ is also shared by a $C_{3-7}$ cycloalkyl or a heterocyclyl.

More preferably, in the compounds of formula (I), $R^1$ and $R^2$ together with the nitrogen atom to which they are attached form a spiro-heterocyclyl such as 6-aza-spiro[2.5]oct-6-yl, 5-azaspiro[2.5]oct-5-yl, 7-aza-spiro[3.5]non-7-yl, 8-aza-spiro[4.5]dec-8-yl, 1,8-diaza-spiro[4.5]dec-8-yl, 1,3,8-triaza-spiro[4.5]dec-8-yl, 2,8-diaza-spiro[4.5]dec-8-yl, 1-oxa-3,8-diaza-spiro[4.5]dec-8-yl, 1-oxa-8-aza-spiro[4.5]dec-8-yl, 2-oxa-8-aza-spiro[4.5]dec-8-yl, 2-oxa-7-aza-spiro[3.5]non-7-yl, 1-oxa-7-aza-spiro[3.5]non-7-yl, 9-aza-spiro[5.5]undec-9-yl, 1-oxa-4,9-diaza-spiro[5.5]undec-9-yl, triaza-spiro[4.5]decane-2,4-dione, 2-oxo-1-oxa-3,8-diaza-spiro[4.5]dec-8-yl, 2,8-diaza-spiro[4.5]decane, aza-spiro[4.5]dec-8-yl, wherein the spiro-heterocyclyl ring is optionally substituted by one to three substituents independently selected from the group consisting of hydroxy, oxo, alkoxy, fluorine and $C_{1-6}$ alkyl. Most preferably the spiro heterocyclyl is 6-aza-spiro[2.5]oct-6-yl wherein the spiro-heterocyclyl ring is optionally substituted by one to two substituents independently selected from the group consisting of hydroxy and $C_{1-6}$ alkyl.

In the compounds of formula (I), $R^1$ and $R^2$ together with the nitrogen atom to which they are attached form (S)-4-hydroxy-6-aza-spiro[2.5]oct-6-yl.

iii) In the compounds of formula (I), wherein $R^1$ and $R^2$ are methyl.

iv) In the compound of formula (I), ⟋⟋ is preferably a single bond.

v) In the compounds of formula (I), p is preferably 0.

vi) In the compounds of formula (I), n+m is especially 1 or 2, preferably n is 0 or 1, m is 1 or 2 and n+m is 1 or 2.

vii) In the compounds of formula (I), wherein one of $R^3$ and $R^4$ is hydrogen and the other is selected from the group consisting of: hydrogen, halogen, hydroxy, $C_{1-4}$ alkyl, hydroxy-$C_{1-4}$ alkyl, $C_{1-4}$alkoxy-$C_{1-4}$alkyl, carboxyl, carbamoyl, mono-$C_{1-4}$ alkyl substituted carbamoyl, and $C_{1-4}$ alkoxy-carbonyl. Especially one of $R^3$ and $R^4$ is hydrogen and the other is selected from the group consisting of: hydrogen, hydroxy, $C_{1-4}$ alkyl, hydroxy-$C_{1-4}$ alkyl, $C_{1-4}$alkoxy-$C_{1-4}$alkyl, carboxyl and $C_{1-4}$ alkoxy-carbonyl. Preferably $R^3$ and $R^4$ is hydrogen, fluoro or hydroxy-$C_{1-4}$ alkyl and the other is hydrogen. More preferably, one of $R^3$ and $R^4$ is hydrogen or hydroxy-$C_{1-4}$ alkyl and the other is hydrogen.

viii) In the compounds of formula (I), one of $R^5$ and $R^6$ is preferably hydrogen or $C_{1-4}$alkyl and the other is hydrogen. More preferably one of $R^5$ and $R^6$ is hydrogen or methyl and the other is hydrogen ix) In the compounds of formula (I), $R^7$, $R^8$, $R^9$ and $R^{10}$ are each independently selected from the group consisting of: hydrogen, $C_{1-6}$ alkyl and carbamoyl, preferably $R^7$, $R^8$, $R^9$ and $R^{10}$ are independently hydrogen or $C_{1-6}$ alkyl. Preferably, one of $R^9$ and $R^{10}$ is hydrogen or $C_{1-4}$ alkyl and the other is hydrogen, and one of $R^7$ and $R^8$ is hydrogen and the other is selected from the group consisting of: carbamoyl, carboxyl and hydrogen. More preferably, one of $R^9$ or $R^{10}$ is methyl and the other is hydrogen, and $R^7$ and $R^8$ are both hydrogen. Most preferably $R^7$, $R^8$, $R^9$ and $R^{10}$ are hydrogen.

x) In the compounds of formula (I), L is preferably selected from the group consisting of: a bond, NH—C(=O) and CH=CH—C(=O). More preferably L is NH—C(=O) or a bond. Most preferably L is NH—C(=O).

xi) the compounds of formula (I), one of $R^5$ and $R^6$ is preferably hydrogen or methyl and the other is hydrogen, $R^7$, $R^8$, $R^9$ and $R^{10}$ are each hydrogen, L is NHC(=O), and $R^1$ and $R^2$ together with the nitrogen atom to which they are attached form (S)-4-hydroxy-6-aza-spiro[2.5]oct-6-yl.

xii) Preferred compounds of the invention is a compound of formula (I), are:

(S)-4-[4-((S)-4-Hydroxy-6-aza-spiro[2.5]oct-6-yl)-4-oxo-butyl]-2-methyl-3-oxo-piperazine-1-carboxylic acid (4-trifluoromethyl-phenyl)-amide;

(S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethyl-phenyl)-amide;

(S)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one;

1-[(E)-3-(3,4-Dichloro-phenyl)-acryloyl]-4-[3-(4-hydroxy-4-methyl-piperidin-1-yl)-3-oxo-propyl]-[1,4]diazepan-5-one;

4-[4-((S)-4-Hydroxy-6-aza-spiro[2.5]oct-6-yl)-4-oxo-butyl]-5-oxo-[1,4]diazepane-1-carboxylic acid (3-chloro-4-trifluoromethyl-phenyl)-amide;

1-(3-Chloro-4-trifluoromethyl-phenyl)-4-[(S)-4-(S)-4-hydroxy-6-aza-spiro[2.5]oct-6-yl)-1-hydroxymethyl-4-oxo-butyl]-[1,4]diazepan-5-one;

(R)-1-(3,4-Bis-trifluoromethyl-phenyl)-4-[(S)-4-(S)-4-hydroxy-6-aza-spiro[2.5]oct-6-yl)-1-hydroxymethyl-4-oxo-butyl]-2-methyl-[1,4]diazepan-5-one;

(S)-4-[(S or R)-3-Fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide;

(S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3,4-bis-trifluoromethyl-phenyl)-amide;

(3S,6S)—N1-(3-chloro-4-(trifluoromethyl)phenyl)-4-(4-((S)-4-hydroxy-6-azaspiro[2.5]octan-6-yl)-4-oxobutyl)-6-methyl-5-oxopiperazine-1,3-dicarboxamide; and (3S,6S)-4-[4-((S)-4-Hydroxy-6-aza-spiro[2.5]oct-6-yl)-4-oxo-butyl]-6-methyl-5-oxo-piperazine-1,3-dicarboxylic acid 3-amide 1-[(3,4-bis-trifluoromethyl-phenyl)-amide].

In another embodiment the invention provides a compound of formula (I'):

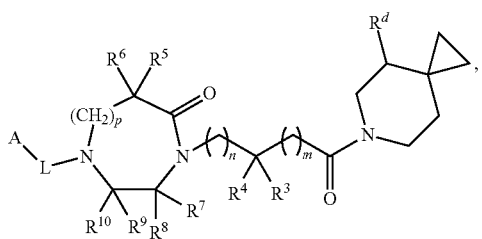

(I')

wherein A, L, n, m, p, $R^3$, $R^4$, $R^5$, $R^6$, $R^7$, $R^8$, $R^9$, $R^{10}$, $R^d$ are as defined above.

In a further embodiment the invention provides a compound of formula (I''):

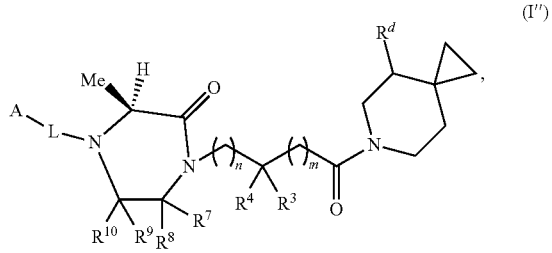

(I'')

wherein A, L, n, m, $R^3$, $R^4$, $R^7$, $R^8$, $R^9$, $R^{10}$, $R^d$ are as defined above.

General Synthetic Procedures

In scheme 1, A, L, $R^1$, $R^2$, $R^3$, $R^4$, $R^5$, $R^6$, $R^7$, $R^8$, $R^9$, $R^{10}$ and n, m, p are as defined before.

Compounds of formula (I) in which ⚍ is a single bond. are represented by formula ($I_a$) in schemes 1 and 4, wherein A, L, $R^1$, $R^2$, $R^3$, $R^4$, $R^5$, $R^6$, $R^7$, $R^8$, $R^9$, $R^{10}$ and n, m, p are as defined before.

The free heterocycle 1 of scheme 1 is commercially available or can be synthesized with methods well known in the art or as described later. $R^5$, $R^6$-groups can be introduced on a suitable protected hetereocycle 1 through deprotonation at low temperature and alkylation followed by a second deprotonation and alkylation. The 7-membered heterocycle 1 can also be synthesized from the corresponding piperazinone (see e.g. Design and synthesis of combinatorial scaffolds-diazepinone and homopiperazine. Sun, Chung-Ming. Department of Chemistry, National Dong-Hwa University, Hualien, Taiwan. Letters in Drug Design & Discovery (2005), 2(1), 48-50).

Compounds of formula 2 (L=CH=CH—CO) can be synthesized from secondary amine 1 by reaction with a cinnamic acid derivative, A-CH=CH—COOH (step a). For instance, the reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine, and in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate.

Alternatively, this reaction can be performed in two steps involving first formation of the cinnamyl chloride A-CH=CH—COCl, and subsequent coupling reaction with amine 1 in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained cinnamylchloride can be isolated or reacted as such with amine 1 in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine, aqueous saturated $NaHCO_3$ or mixtures thereof.

Compounds of formula 2 (L=a bond) can be synthesized from secondary amine 1 by reaction with halide A-Hal (Hal is F, Cl, Br, or I) or boronic acid A-B(OH)$_2$, using methods and reagents known in the art (step a).

For instance, the reaction can be performed with halide A-Hal at temperatures between 20° C. and 200° C., in the presence of a base, e.g., potassium carbonate, cesium carbonate or triethylamine, in a solvent such as acetonitrile, N,N-dimethylformamide or N-methylpyrrolidinone, optionally under microwave irradiation.

Alternatively, the reaction can be performed with halide A-Hal in the presence of a copper(I) salt, e.g., copper(I) iodide, or copper(I) oxide in the presence of a base, e.g., potassium phosphate, sodium tert-butylate or cesium carbonate, and optionally a diol ligand, e.g., 1,2-ethanediol, in a solvent such as 2-propanol or N-methylpyrrolidinone, at temperatures between 60° C. and 120° C.

Alternatively, the reaction may be performed with halide A-Hal in the presence of a palladium source, e.g., bis(tri-tert-butylphosphine)palladium(0), palladium(II) chloride or palladium(II) acetate, and a phosphine ligand, e.g., 2,2'-bis(diphenylphosphino)-1,1'-binaphthyl or 2',4',6'-triisopropyl-1,1'-biphenyl-2-yldicyclohexylphosphine, a base, e.g., tripotassium phosphate, potassium phosphate, sodium methylate, or cesium carbonate, in a solvent such as toluene, 1,2-dimethoxyethane or 1,4-dioxane, at temperatures between 20° C. and 120° C. Microwave heating could be used.

Alternatively, the reaction may be performed with boronic acid A-B(OH)$_2$ in the presence of anhydrous copper(II) acetate, in the presence of a base, e.g., triethylamine or pyridine, in a solvent such as dichloromethane, at temperatures between 0° C. and 40° C., optionally in the presence of molecular sieves.

Deprotonation of amide 2 (L=CH=CH—CO or a bond) in the presence of 3 in solvents like THF or N,N-dimethylformamide with e.g. NaH as base at 0° C. optionally at RT gave intermediate 4 (step b). Building block 3 is commercially available or can be synthesized with methods well known in the art or as described in the experimental part.

Ester 4 can further be manipulated e.g. $R^4$ or $R^3$ can be introduced or modified. Alternatively, amide 2 (L=CH=CH—CO or a bond) can be deprotonated at −78° C. to −10° C. with a base such as lithium/potassium or sodium hexamethyldisilylazide in a solvent like THF and can first be alkylated with methyl bromoacetate to give ester 4 (m, m=0 and $R^3$=H, $R^4$=H). This ester can further be transformed to 4 (n=0, m=1 and $R^3$=H, $R^4$=COOMe, $R^e$=tert-butyl) by e.g. deprotonation of ester 4 (m, m=0 and $R^3$=H, $R^4$=H) with hexamethyldisilylazide in a solvent like THF and alkylation with t-butyl bromoacetate preferably at −78° C. Ester 4 (n=0, m=1 and $R^3$=H, $R^4$=COOMe, $R^e$=tert-butyl) can also further be selectively reduced e.g. with LiBH$_4$ in ethanol to 4 (n=0, m=1 and $R^3$=H, $R^4$=CH$_2$OH, $R^e$=tert-butyl), alkylation with methyliodide in N,N-dimethylformamide and NaH as base gives 4 (n=0, m=1 and $R^3$=H, $R^4$=CH$_2$OMe, $R^e$=tert-butyl).

In step c, scheme 1, ester 4 is deprotected to give acid 5. In the case where $R^e$ is tert-butyl, the deprotection is performed, e.g., with hydrogen chloride, in solvents such as 1,4-dioxane, water, or mixtures thereof, at temperatures between 0° C. and 20° C. In the case where $R^e$ is benzyl, the deprotection is performed, e.g., by hydrogenation at pressures between 1 bar and 10 bar, in solvents such as methanol, ethanol, tetrahydrofuran, ethyl acetate, or mixtures thereof, in the presence of a suitable catalyst, e.g., palladium on activated charcoal. In the case where $R^e$ is lower alkyl, the deprotection is performed, e.g., by base-mediated hydrolysis in solvents such as water, methanol, tetrahydrofuran and mixtures thereof at temperatures between −20° C. and 120° C. Typical reagents are aqueous or lithium hydroxide, sodium hydroxide, potassium hydroxide, sodium hydrogen carbonate, sodium carbonate, potassium hydrogencarbonate and potassium carbonate.

In scheme 1, step d, carboxylic acid 5 is converted to amide I$_a$ by reaction with amine HN($R^1$)($R^2$), using reagents and methods known in the art. For instance, the reaction is carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, or 4-methylmorpholine, and in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate and optionally in the presence of catalysts like 1-hydroxybenzo-triazole or dimethyl-pyridin-4-yl-amine.

It is also possible to convert directly the methyl ester 4 ($R^e$=Me) to final compound I$_a$ (step e). Ester 4 is dissolved in solvents such as methanol, ethanol, tetrahydrofuran or mixtures thereof and treated with an excess of the amine HNR$^1$R$^2$ and stirred at RT to 60° C. for 1 night up to 3 days.

In case of ester 4 (n=0, m=1 and $R^3$=H, $R^4$=CH$_2$OMe, $R^e$=tert-butyl; described above), $R^e$ deprotection and coupling with an amine HNR$^1$R$^2$ as described above gives the final compound I$_a$ (n=0, m=1 and $R^3$=H, $R^4$=CH$_2$OMe).

Alternatively protected heterocycle 6 which is commercially available or available by protection of 1 (step f, PG$^1$ is a suitable protective group, e.g., t-butyloxycarbonyl or benzyloxycarbonyl, which can be deprotected orthogonally to the COOR$^e$ ester), can be transformed to acid 7 following steps b and c described before. Carboxylic acid 7 is converted to amide 8 by reaction with amine HN($R^1$)($R^2$), using reagents and methods described above (see step d) followed by deprotection of PG$^1$ (step g). In the case where PG$^1$ is tert-butyloxycarbonyl, the deprotection is performed, e.g., with hydrogen chloride, in solvents such as 1,4-dioxane, dichloromethane, alcohol, or mixtures thereof, at temperatures between 0° C. and 20° C. In the case where PG$^1$ is benzyloxycarbonyl, the deprotection is performed, e.g., by hydrogenation at pressures between 1 bar and 10 bar, in solvents such as methanol, ethanol, tetrahydrofuran, ethyl acetate, or mixtures thereof, optionally in the presence of an acid like HCl or acetic acid and in the presence of a suitable catalyst, e.g., palladium on activated charcoal. In the case where PG' is benzyloxycarbonyl and N($R^1$)($R^2$) is a cyclopropyl containing amine, hydrogenation in acetic acid with hydrogen on Pt$_2$O (step g) yields the dimethyl analogue amide 8.

Compounds of formula I$_a$ (L=CH=CH—CO) can be synthesized from secondary amine 8 by reaction with a cinnamic acid derivative, A-CH=CH—COOH or A-CH=CH—COCl as described above for step a.

Compounds of formula I$_a$ (L=a bond) can be synthesized from the secondary amine 8 by reaction with halide A-Hal (Hal is F, Cl, Br, or I) or boronic acid A-B(OH)$_2$, using methods and reagents described above for step a.

Compounds of formula I$_a$ in which L is NH—C(=O) be synthesized from secondary amine 8 by reaction with an isocyanate of the general formula A-N=C=O or a phenyl carbamate of the general formula A-NH—C(=O)—O-Ph.

The reaction is typically carried out in aprotic solvents such as dichloromethane, tetrahydrofuran, N,N-dimethylformamide, N-methylpyrrolidinone, dimethyl sulfoxide, acetonitrile and mixtures thereof at temperatures between 0° C. and 120° C. in the presence or absence of a base such as triethylamine, diisopropylethylamine, 4-methylmorpholine, and/or 4-(dimethylamino)pyridine. Isocyanates of the general formula A-N=C=O or phenyl carbamates A-NH—C(=O)—O-Ph are commercially available or can be synthesized by methods known in the art. For instance, isocyanates A-N=C=O can be synthesized from the corresponding arylamines A-NH$_2$ by reaction with phosgene, diphosgene, or triphosgene, in the presence of a base such as pyridine, in a solvent like tetrahydrofuran at temperatures between 0° C. and 70° C. or dichloroethane at 0° C. to 90° C. Phenyl carbamates A-NH—C(=O)—O-Ph can be prepared from the corresponding arylamines A-NH$_2$ by reaction with phenyl chloroformate, in a solvent such as tetrahydrofuran, at temperatures between −20° C. and 20° C.

Compounds of formula I$_a$ in which L is NH—C(=S) can be synthesized from secondary amine 8 by reaction with a isothiocyanate of the general formula A-N=C=S. The reaction is typically carried out in aprotic solvents such as dichloromethane, tetrahydrofuran, N,N-dimethyl-formamide, N-methylpyrrolidinone, dimethyl sulfoxide, acetonitrile and mixtures thereof at temperatures between 0° C. and 120° C. in the presence or absence of a base such as triethylamine, diisopropylethylamine, 4-methylmorpholine, and/or 4-(dimethylamino)pyridine. Isothiocyanates of the general formula A-N=C=S can be synthesized from the corresponding arylamines A-NH$_2$ by reaction with thiophosgene in the presence of a base such as pyridine, in a solvent like tetrahydrofuran at temperatures between 0° C. and 70° C.

Substituents R$^3$ and/or R$^4$ in I$_a$ or in any synthetic intermediate can be interconverted using reagents and methods known in the art and discussed in scheme 4.

Scheme 1

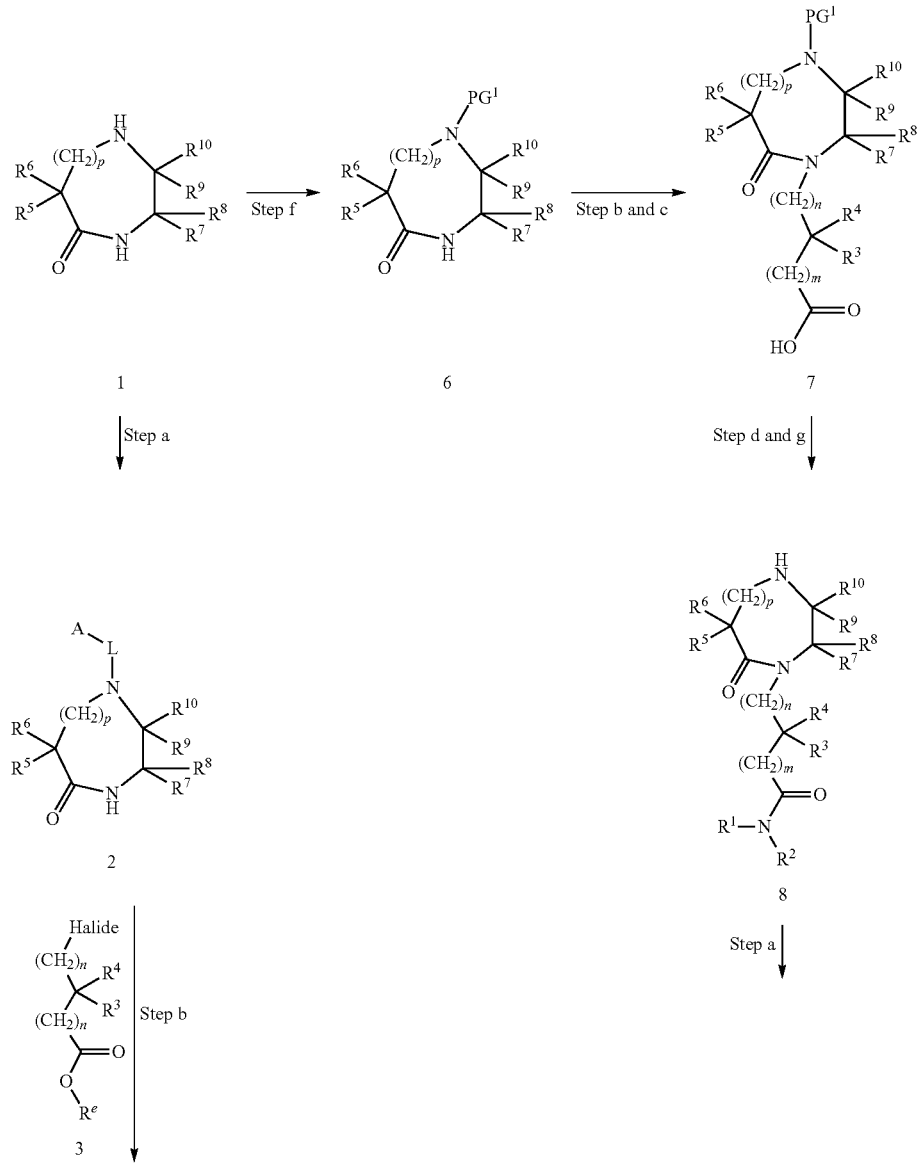

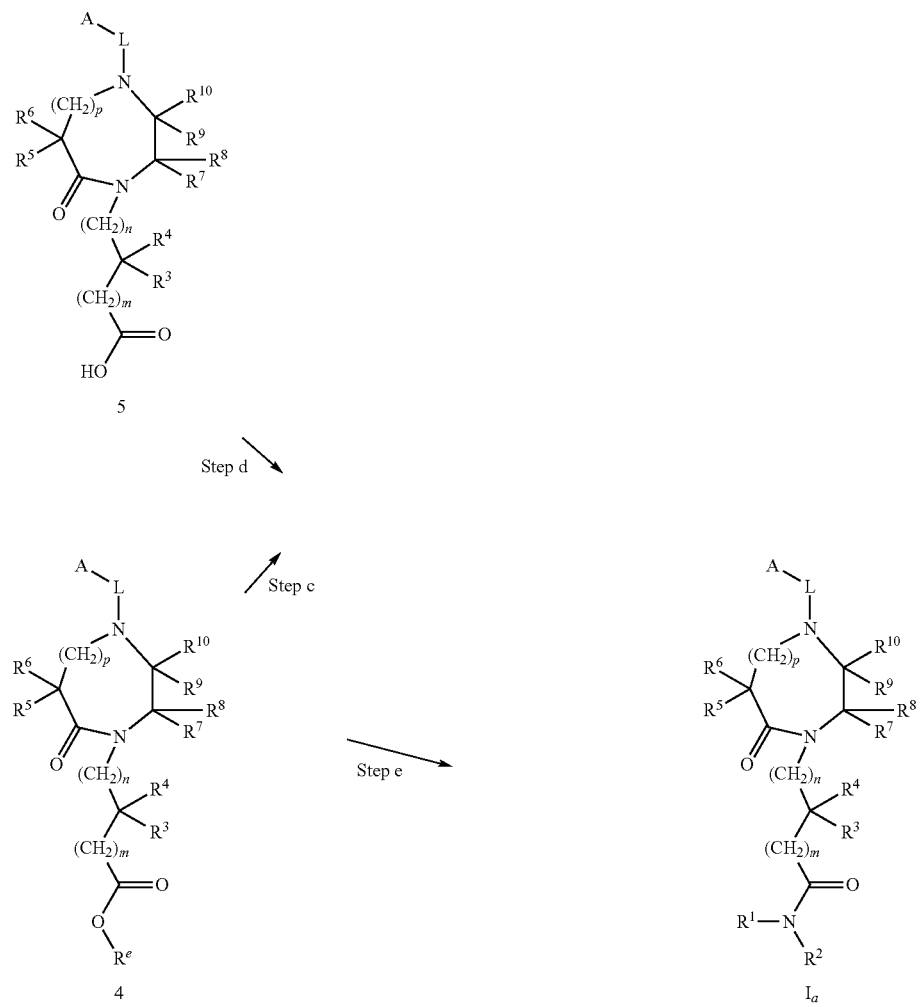

In Scheme 1, n, m, p, A, L, $R^1$, $R^2$, $R^3$, $R^4$, $R^5$, $R^6$, $R^7$, $R^8$, $R^9$, $R^{10}$ $PG^1$ and $R^e$ are as defined above.

Intermediate 15 can be synthesized as outlined in scheme 2

In scheme 2, $R^e$ is tert-butyl, benzyl, or lower alkyl, e.g., methyl or ethyl, $R^f$ is lower alkyl, e.g., methyl or ethyl, $R^h$ is $C_{1-3}$ alkyl or benzyl and $R^3$, $R^4$, $R^5$, $R^6$, $R^7$, $R^8$, $R^9$, $R^{10}$ and n, m, p are as defined before.

In step a, scheme 2, aldehyde or ketone 9 undergoes a reductive amination reaction with amine 10, leading to 11a. Suitable reagents for this conversion are borohydride reagents, e.g., sodium borohydride, sodium triacetoxyborohydride, or sodium cyanoborohydride. The reaction is performed solvents such as methanol, dichloromethane, 1,2-dichloroethane, acetic acid, water, or mixtures thereof, at temperatures between −20° C. and 50° C., optionally in the presence of dehydrating agents such as magnesium sulfate or molecular sieves. An organo-$R^{10}$ complex can be used for the introduction of the $R^{10}$ moiety. Aldehydes or ketones of formula 9 are either commercially available or can be synthesized following procedures well known in the art.

In step b, scheme 2, secondary amine 11a is converted to protected derivative 11b using methods and reagents known in the art. For instance, in the case where $PG^1$ is benzyloxycarbonyl, the reaction is performed using benzyl chloroformate in the presence of a base, e.g., sodium hydrogencarbonate, in solvents such as acetone, tetrahydrofuran, water, or mixtures thereof, at temperatures between 0° C. and 30° C.

In step c, scheme 2, the acetal group of 11b is cleaved, leading to carbonyl compound 12. The reaction is performed in the presence of an acidic catalyst, e.g., hydrochloric acid, formic acid, toluene 4-sulfonic acid, or pyridinium toluene 4-sulfonate, in a solvent such as water, methanol, acetone, 2-butanone or mixtures thereof, at temperatures between 0° C. and 100° C.

In step d, scheme 2, aldehyde or ketone 12 is transformed into 15 by reaction with amine 13, using methods well known in the art, e.g., reductive amination. The reaction to intermediate 14 is carried out using a suitable reducing agent, e.g., sodium borohydride, sodium triacetoxyborohydride, sodium cyanoborohydride, or borane pyridine complex, in solvents such as methanol, ethanol, acetic acid, 1,2-dichloroethane, or mixtures thereof, at temperatures between 0° C. and 80° C. In general, intermediate 14 cyclizes spontaneously to the heterocycle 15. In case of incompletion, catalytic amount of 1,5,7-triazabicyclo[5.4.0]dec-5-ene finishes the cyclisation.

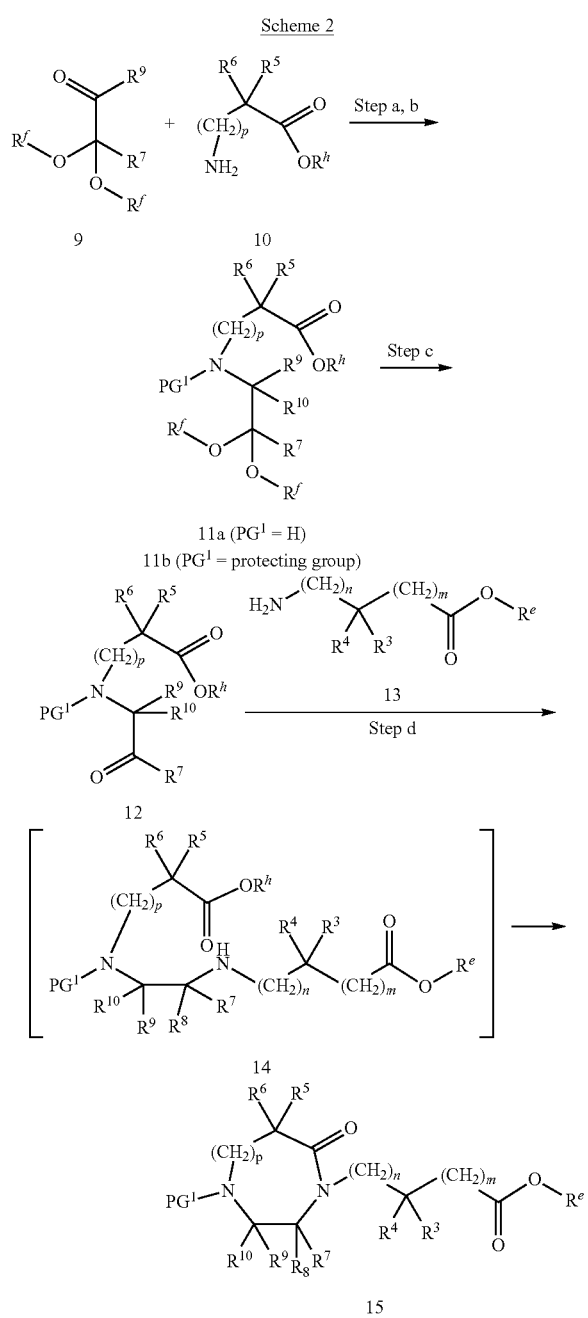

In Scheme 2, n, m, p, $R^3$, $R^4$, $R^5$, $R^6$, $R^7$, $R^8$, $R^9$, $R^{10}$, $PG^1$, $R^f$ and $R^e$ are as defined above. Amines of formula 13 are either commercially available or can be synthesized as described in the experimental section.

In scheme 3, A, L, $R^1$, $R^2$, $R^3$, $R^4$, $R^5$, $R^6$, $R^7$, $R^8$, $R^9$, $R^{10}$ and n, m, p are as defined before.

Intermediate 12 can be also synthesized as described in scheme 3. $R^h$ is $C_{1-3}$ alkyl or benzyl, $PG^1$ is a suitable protective group such as tert-butoxycarbonyl or benzyloxycarbonyl In step a, scheme 3, amino alcohol 16 is reacted with acrylate 17, either neat or in a solvent such as methanol, at temperatures between 0° C. and 60° C. The secondary amine intermediate is then protected with a suitable protective group, using reagents and methods known in the art, thus leading to 18. In the case where $PG^1$ is tert-butoxycarbonyl, the reaction is carried out, e.g., with di-tert-butyl dicarbonate, in a solvent such as dichloromethane or N,N-dimethylformamide, optionally in the presence of a base, e.g., triethylamine. In the case where $PG^1$ is benzyloxycarbonyl, the reaction is performed, e.g., with N-(benzyloxycarbonyloxy)succinimide or with benzyl chloroformate, in solvents such as water, acetone, tetrahydrofuran, or mixtures thereof, in the presence of a base, e.g., triethylamine or sodium hydrogencarbonate.

Amino alcohols of formula 16 are either commercially available or can be synthesized as described in the experimental section.

In step b, scheme 3, alcohol 18 is oxidized to aldehyde or ketone 12 using reagents and method known in the art. For instance, the oxidation is carried out with sodium hypochlorite, in a two-phase mixture of water and dichloromethane, in the presence of sodium hydrogen-carbonate and catalytic amounts of sodium bromide or potassium bromide and 2,2,6,6-tetramethylpiperidin-1-oxyl radical, at temperatures between 0° C. and 25° C. Alternatively, the oxidation can be performed with trichloroisocyanuric acid in the presence of catalytic amounts of 2,2,6,6-tetramethylpiperidin-1-oxyl radical, in a solvent such as dichloromethane, at temperatures between 0° C. and 40° C. Alternatively, the oxidation may be performed with catalytic amounts of tetrapropylammonium perruthenate in the presence of stoichoimetric amounts of a co-oxidant such as 4-methylmorpholine-4-oxide and molecular sieves, at temperatures between 0° C. and 40° C., in solvents such as dichloromethane, acetonitrile or mixtures thereof. Alternatively, dimethyl sulfoxide-based reagents can be employed, such as dimethyl sulfoxide-oxalyl chloride, or dimethyl sulfoxide-trifluoroacetic anhydride, in the presence of an organic base such as triethylamine in a solvent such as dichloromethane, at temperatures below 0° C., typically between −78° C. and −60° C. Alternatively, pyridine-sulfur trioxide can be employed in dimethyl sulfoxide or dimethylsulfoxide-dichloromethane solvent mixture in the presence of an organic base such as triethylamine, at temperatures between 0° C. and 25° C.

Scheme 3

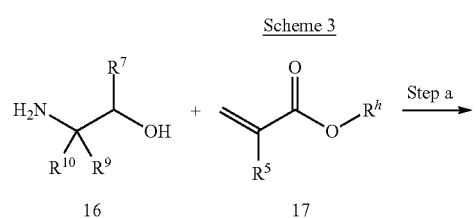

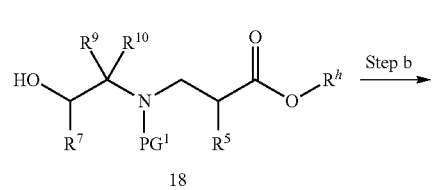

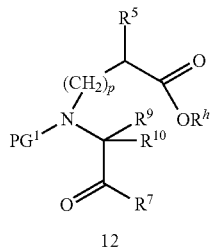

In Scheme 3, p, $R^5$, $R^7$, $R^8$, $R^9$, $R^{10}$, $PG^1$ and $R^h$ are as defined above.

In scheme 4, A, L, $R^1$, $R^2$, $R^3$, $R^4$, $R^5$, $R^6$, $R^7$, $R^8$, $R^9$, $R^{10}$, $R^e$ and n, m, p are as defined before.

Double-protected intermediate 15 can be transformed to final compound $I_a$ in two ways (scheme 4). For variations in the A-L part with fixed amide, ester 15 is hydrolyzed (step a), coupled with amine $HN(R^1)(R^2)$ (step b) to amide 19 and deprotected to the free amine 20 (step c) with conditions described in step c, step d and step g, scheme 1.

Compounds of formula $I_a$ (L=CH=CH—CO) can be synthesized from secondary amine 20 by reaction with a cinnamic acid derivative (step d), A-CH=CH—COOH or A-CH=CH—COCl as described in scheme 1.

Compounds of formula $I_a$ (L=a bond) can be synthesized from the secondary amine 20 by reaction with halide A-Hal (Hal is F, Cl, Br, or I) or boronic acid $A-B(OH)_2$ (step d), using methods and reagents described in scheme 1.

Compounds of formula $I_a$ in which L is NH—C(=O) can be synthesized from secondary amine 20 by reaction with an isocyanate of the general formula A-N=C=O or a phenyl carbamate of the general formula A-NH—C(=O)—O-Ph (step d) as described in scheme 1.

Compounds of formula $I_a$ in which L is NH—C(=S) can be synthesized from secondary amine 20 by reaction with a isothiocyanate of the general formula A-N=C=S (step d) as described in scheme 1.

For the second route with variations in the amide part and fixed A-L group, 15 is deprotected (step c) to amine 21, and A-L group is introduced to give 22 (step d), all with conditions described in scheme 1. Intermediate 22 (L=a bond, p=0, $R^8$ and $R^{10}$=H) can also be synthesized following the procedures described in scheme 5. Hydrolysis to the acid and coupling with amine $HN(R^1)(R^2)$ with conditions described in scheme 1 gives $I_a$ (step a and b).

Substituents $R^3$ and/or $R^4$ in $I_a$ or in any synthetic intermediate can be interconverted using reagents and methods known in the art. For instance, esters ($R^3$ and/or $R^4$=C1-6 alkoxycarbonyl) can be selectively reduced to the corresponding alcohols ($R^3$ and/or $R^4$=hydroxymethyl), e.g., with lithium borohydride in THF or EtOH or with in situ generated $LiBH_2(OMe)_2$ in THF. These alcohols can further be transformed to ethers ($R^3$ and/or $R^4$=$CH_2$OC1-6 alkyl), e.g., with an alkyl halide in solvents such as tetrahydrofuran, N,N-dimethylformamide or N,N-dimethylacetamide with sodium hydride as base, or with an alkyl halide in the presence of silver(I) oxide. For $I_a$ ($R^3$ and/or $R^4$=$CH_2$OH and L=NH—(CO or CS)) alkylation in acetonitrile with alkyl halide in the presence of silver(I) oxide gives urea alykylated $I_a$ ($R^3$ and/or $R^4$=$CH_2$OH and L=NC1-6alkyl-(CO or CS)). Similarly, esters ($R^3$ and/or $R^4$=C1-6 alkoxycarbonyl) can be hydrolyzed to the corresponding carboxylic acids, ($R^3$ and/or $R^4$=COOH), e.g., through base-mediated hydrolysis using bases such as lithium hydroxide or sodium hydroxide in solvents such as water, methanol, tetrahydrofuran, or mixtures thereof.

These acids can then be transformed to the corresponding amides ($R^3$ and/or $R^4$=aminocarbonyloxy, mono- or di-C1-6 alkyl substituted aminocarbonyloxy), as described in scheme 1, step d. For $I_a$ or in any synthetic intermediate ($R^3$ and/or $R^4$=C1-6 alkylO-$PG^2$), protecting group $PG^2$ can be cleaved, e.g. HCl in dioxane for tert-butyl-dimethylsilyl protecting group or by hydrogenation at pressures between 1 bar and 10 bar, in solvents such as methanol, ethanol, tetrahydrofuran, ethyl acetate, or mixtures thereof, with or without an acid like aqueous HCl in the presence of a suitable catalyst, e.g., palladium on activated charcoal, to give alcohol $I_a$ or intermediate ($R^3$ and/or $R^4$=C1-6 alkylOH).

Scheme 4

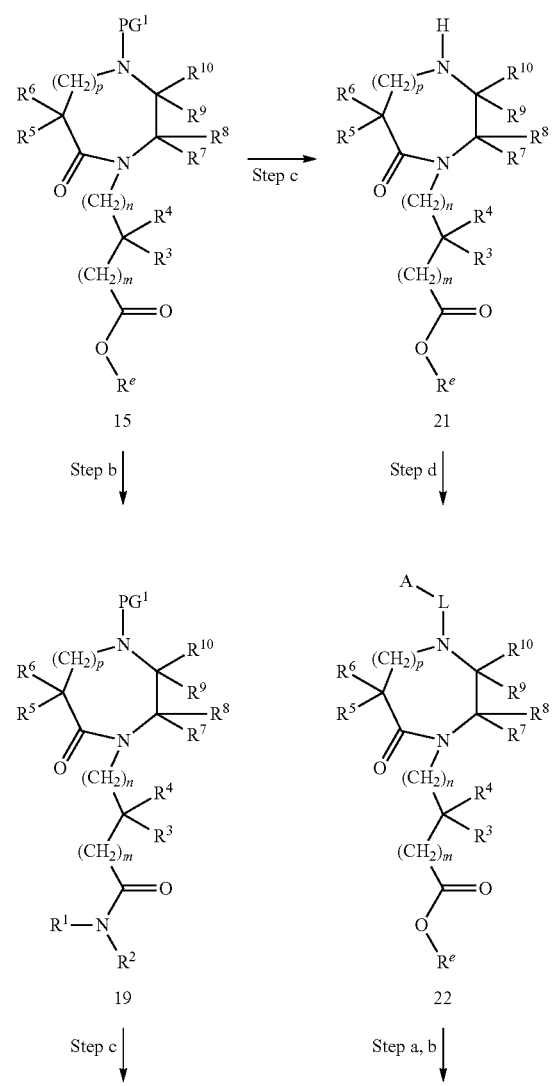

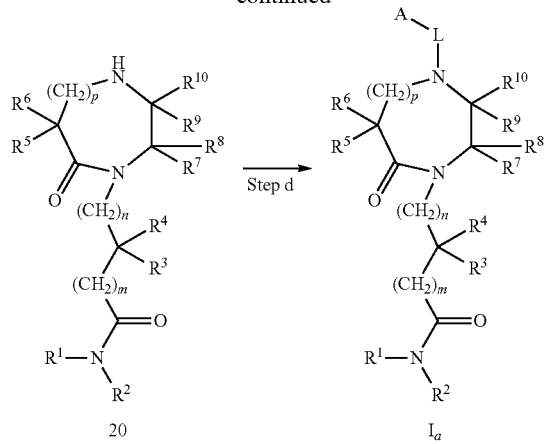

Compounds 22 can be also synthesized as described in scheme 5.

In scheme 5, A, $R^1$, $R^2$, $R^3$, $R^4$, $R^5$, $R^6$, $R^7$, $R^9$ and n, m are as defined before. $R^e$ is lower alkyl, benzyl or tert-butyl and $R^f$ is lower alkyl, e.g., methyl or ethyl, LG is a leaving group, e.g., chlorine or bromine. L=a bond, p=0, $R^8$ and $R^{10}$=H.

In step a, scheme 5, primary amine 13 is converted to secondary amine 24 by reductive amination reaction with carbonyl derivative 23A or by nucleophilic substitution reaction with halide 23B. The reductive amination reaction with 23A is performed in analogy with scheme 2, step d. The nucleophilic substitution reaction with 23B is performed, e.g., in a solvent such as methanol, ethanol, N,N-dimethylformamide or acetonitrile, at temperatures between 0° C. and the boiling point of the solvent, in the presence of a base, e.g., potassium hydrogencarbonate, potassium carbonate, optionally in the presence of sodium iodide.

In step b, scheme 5, secondary amine 24 is converted to amide of general formula 26 through reaction with N-aryl amino acid 25 using methods well known to someone skilled in the art. For instance, the reaction is carried out in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine, and/or 4-(dimethylamino)pyridine.

Alternatively, this reaction can be performed in two steps involving first formation of the acyl halide derivative of 25 and subsequent coupling reaction with amine 24 in the presence of a base. Typically employed reagents for the formation of the acyl chloride are thionyl chloride, phosphorus pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained acyl chloride can be isolated or reacted as such with amine 24 in an aprotic solvent, like dichloromethane, tetrahydrofuran or acetone, in the presence of a base. Typical bases are triethylamine, 4-methylmorpholine, pyridine, diisopropylethylamine or 4-(dimethylamino) pyridine or mixtures thereof.

Alternatively, such reactions can be performed in two steps involving first formation of a mixed anhydride derivative of 25 obtained by reaction with a reagent such as ethyl chloroformate, isobutyl chloroformate, or acetic anhydride, in a solvent such as dichloromethane or tetrahydrofuran, at temperatures between −30° C. and 20° C., and subsequent reaction with amine 24 as described above.

In the case where the presence of a hydroxy group in $R^3$ or $R^4$ (e.g., $R^3$ or $R^4$=hydroxy or hydroxymethyl) may interfere with the amide coupling reaction of step b, the hydroxyl of 24 may be temporarily protected as the trimethylsilyl ether by reaction with chlorotrimethylsilane, in the presence of a base, e.g., triethylamine of N-methylmorpholine.

N-Aryl amino acids 25 are commercially available or can be synthesized as described in the experimental section.

In step c, scheme 5, cleavage of the acetal and reductive cyclization of 26 leads to piperazinone 22 (L=a bond, p=0, $R^8$ and $R^{10}$=H), described as intermediate in scheme 4. This conversion is performed either in one step using an acid, e.g., trifluoroacetic acid or methanesulfonic acid, and a reducing agent such as sodium borohydride or triethylsilane, in solvents such as dichloromethane, 1,4-dioxane, tetrahydrofuran, water, or mixtures thereof. Alternatively, the reaction may be performed in two steps, by first forming a 3,4-dihydro-1H-pyrazin-2-one intermediate in the presence of an acid, e.g., trifluoroacetic acid or methanesulfonic acid, in a solvent such as water or dichloromethane, and subsequent catalytic hydrogenation at pressures between 1 bar and 10 bar, using a suitable catalyst, e.g., palladium on activated charcoal, in solvents such as methanol, ethanol, ethyl acetate, or mixtures thereof, at temperatures between 0° C. and 50° C.

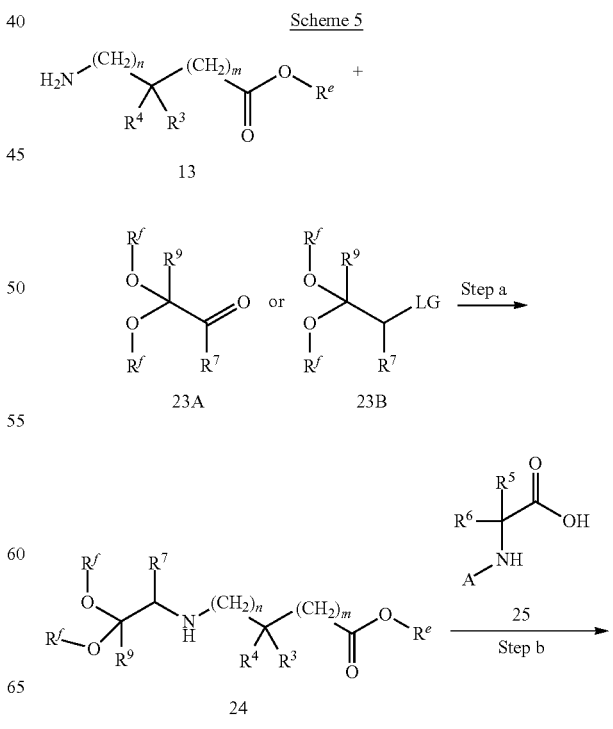

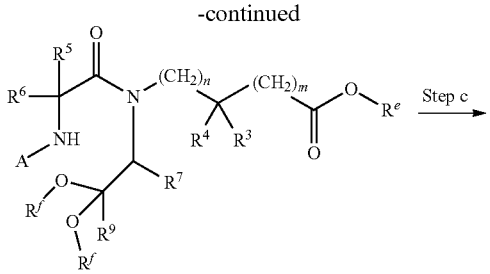

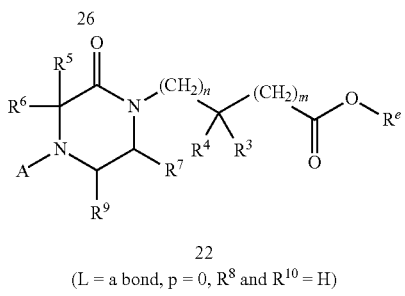

22
(L = a bond, p = 0, $R^8$ and $R^{10}$ = H)

In Scheme 5, n, m, p, A, $R^3$, $R^4$, $R^5$, $R^6$, $R^7$, $R^8$, $R^9$, $R^{10}$, LG, $R^f$ and $R^e$ are as defined above.

Compounds of formula $I_b$ can also be produced as outlined in scheme 6.

In scheme 6, A, $R^1$, $R^2$, $R^3$, $R^4$, $R^5$, $R^6$, $R^7$, $R^8$, $R^9$, $R^{10}$ and n, m are as defined before. $R^e$ is lower alkyl, benzyl or tert-butyl. Compounds of formula (I) in which is a single bond. are represented by formula ($I_b$) and compounds of formula (I) in which is a double bond. are represented by formula ($I_b$ (double bond) and wherein p is 1, in schemes 6 and 7, wherein A, $R^1$, $R^2$, $R^3$, $R^4$, $R^5$, $R^6$, $R^7$, $R^8$, $R^9$, $R^{10}$, n and m are as defined before.

N-Aryl amino acids 27, are commercially available or can be synthesized as described in the experimental section. Borane-reduction of gives alcohol 28 (step a). Optionally $R^7$ can be introduced from acid 27 via Weinreb-amide, followed by reaction with an organo-$R^7$ complex to give ketone 29. Alcohol 28 can be oxidized to aldehyde 29 (step b) as described in step b, scheme 3. Reductive amination with amine 13 following conditions described in step d, scheme 2 gives amine 30 (step c). Coupling with acid 31, which is commercially available or can be synthesized from the corresponding esters, using conditions described by Mukaiyama et al. (Chemistry Letters, pp. 1045-1048, 1975) gives intermediate 32 (step d), which can be cyclised with TFA and triethylsilane (following conditions shown in step c, scheme 5) to 33 ($R^5$, $R^6$=H) or 34 ($R^5$, $R^6$ not H) (step e). Intermediate 33, in scheme 6, can be hydrolyzed and coupled with an amine $HNR^1R^2$ (step f) to give the final unsaturated compound $I_b$ as described in step a and step b, scheme 4. The olefin can be hydrogenated selectively with $Pt_2O$ in methanol in the presence of acetic acid to give the corresponding saturated $I_b$ (step g). Alternatively 34 is received by hydrogenation of olefin 33 (conditions as described in step g) can also be hydrolyzed and coupled with an amine $HNR^1R^2$ to give the final unsaturated compound $I_b$ (step f) as described in step a and step b, scheme 4.

Scheme 6

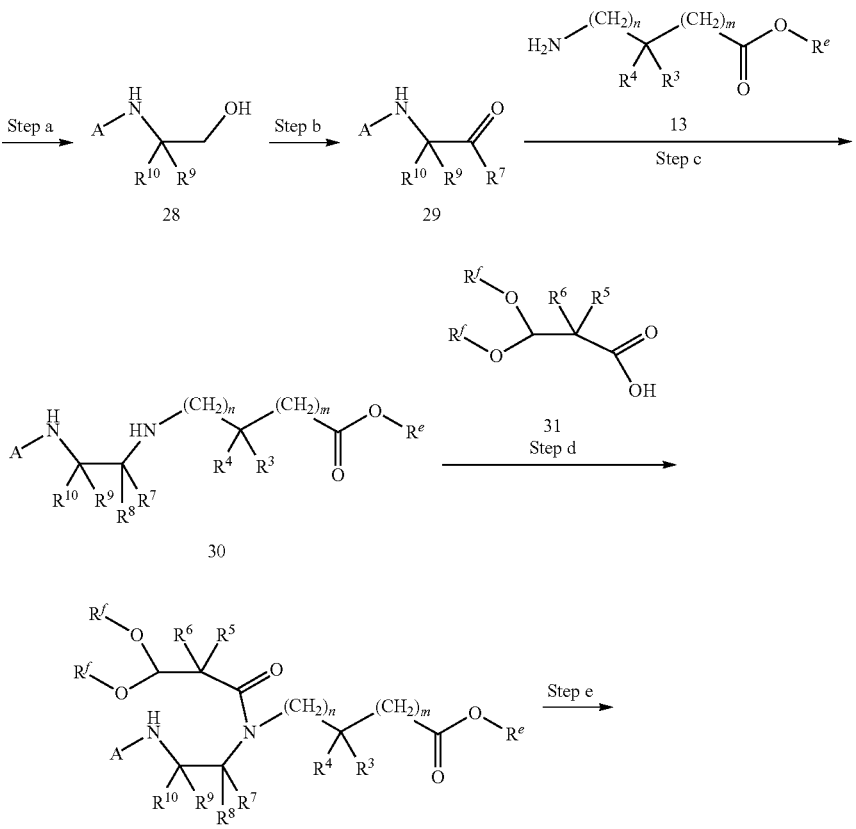

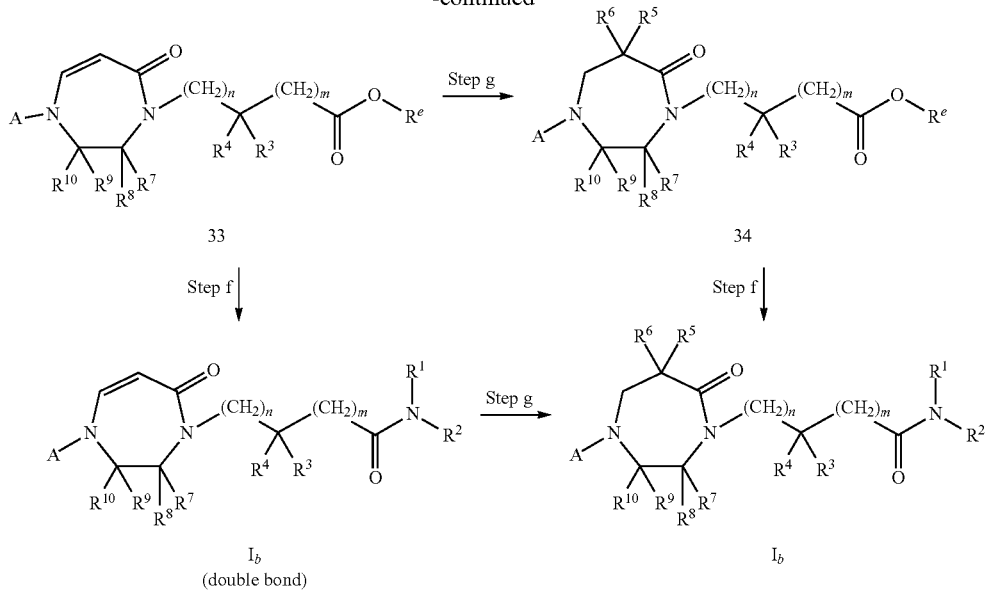

I$_b$
(double bond)

I$_b$ (For R$^5$, R$^6$ = H)

In Scheme 6, n, m, A, R$^1$, R$^2$, R$^3$, R$^4$, R$^5$, R$^6$, R$^7$, R$^8$, R$^9$, R$^{10}$, R$^f$ and R$^e$ are as defined above.

In scheme 7, A, R$^1$, R$^2$, R$^3$, R$^4$, R$^5$, R$^6$, R$^7$, R$^8$ and n, m are as defined before. R$^e$ is lower alkyl or benzyl, R$^9$, R$^{10}$=H, p=1.

Final compound I$_b$ (L=a bond, p=1) can also be synthesized as outlined in scheme 7. LG is a leaving group, e.g., chlorine, bromine, or iodine.

In step a, scheme 7, aniline 35 is mono alkylated with e.g. tert-butyl beta-haloalkanate 36, with 2,6-lutidine as base, initially without solvent, then in acetonitrile, at temperatures between 50° C. to 60° C. (step a). This intermediate is then alkylated a second time with methyl bromoacetate with same conditions to give intermediate 37 (step b).

In step c, scheme 7, the methyl ester of 37, is selectively reduced, leading to alcohol 38. This conversion is accomplished with a suitable reducing agent, e.g., lithium borohydride, in a solvent such as methanol or ethanol, at temperatures between 0° C. and 40° C. or with in situ generated LiBH$_2$(OMe)$_2$ in THF.

Optionally R$^7$ can be introduced via selective hydrolysis of methyl ester 37, Weinreb-amide formation, followed by reaction with an organo-R$^7$ complex to give ketone 39. Alcohol 38 can be oxidized to aldehyde 39 (step d) as described in step b, scheme 3. Reductive amination with amine 13 following conditions described in step d, scheme 2 gives amine 40 (step e). An organo-R$^8$ complex can be used for the introduction of the R$^8$ moiety in the imino-intermediate. t-Butyl ester 40 is cleaved and cyclised to [1,4]diazepan-5-one 41 (step f) with conditions described in step c and step d, scheme 1. Hydrolysis and coupling with an amine HNR$^1$R$^2$ gives the final compound I$_b$ (step g) as described in step c and step d, scheme 1.

Scheme 7

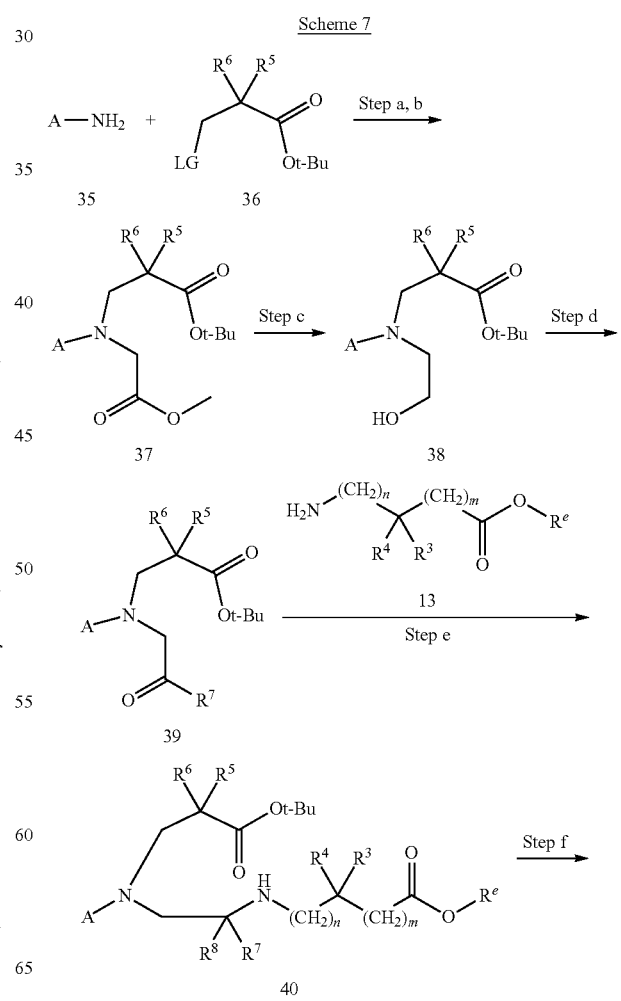

-continued

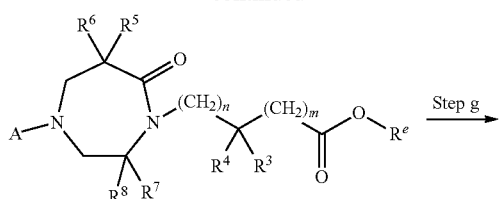

41

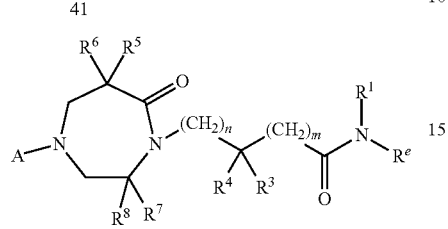

$I_b$

In

Scheme 7, n, m, A, $R^1$, $R^2$, $R^3$, $R^4$, $R^5$, $R^6$, $R^7$, $R^8$, $R^9$, $R^{10}$, LG, and $R^e$ are as defined above.

Intermediates of formula 5 can also be synthesized as outlined in scheme 8. A, L, $R^1$, $R^2$, $R^3$, $R^4$, $R^5$, $R^6$, $R^7$, $R^8$, $R^9$, $R^{10}$, m, n and p are as defined before.

In step a, scheme 8, secondary amine 42 is converted to compound 43, in analogy with scheme 1, step a.

In step b, scheme 8, alcohol 43 is oxidized to carboxylic acid 5, using reagents and conditions known in the art. For instance, the oxidation is carried out with sodium hypochlorite, in a two-phase mixture of water and dichloromethane, in the presence of sodium hydrogencarbonate and catalytic amounts of potassium bromide and 2,2,6,6-tetramethylpiperidin-1-oxyl radical, optionally in the presence of a phase transfer catalyst such as tetrabutyl ammonium hydrogensulfate, at temperatures between 0° C. and 25° C. Alternatively, the reaction is performed using sodium chlorite in the presence of catalytic amounts of sodium hypochlorite and 2,2,6,6-tetramethylpiperidine-1-oxyl radical, in a buffered (preferably phosphate buffer at pH around 7) solvent mixture of water and acetonitrile, at temperatures between 30° C. and 70° C.

The synthesis of amino alcohols of formula 42 is described hereunder in accordance with the procedure disclosed in WO2009/010429.

Scheme 8

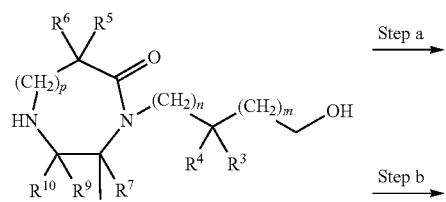

42

-continued

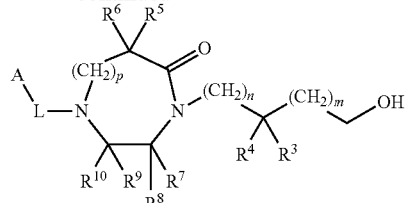

43

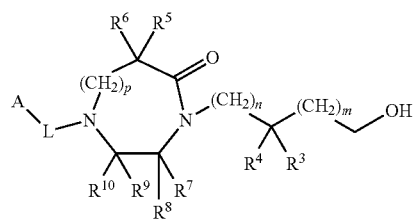

5

In Scheme 8, n, m, p, A, L, $R^3$, $R^4$, $R^5$, $R^6$, $R^7$, $R^8$, $R^9$ and $R^{10}$ are as defined above.

Intermediates of formula 15 and 19 can also be synthesized as outlined in scheme 9. A, L, $R^1$, $R^2$, $R^3$, $R^4$, $R^5$, $R^6$, $R^7$, $R^8$, $R^9$, $R^{10}$, m, n and p are as defined before. $R^e$ is tert-butyl. $R^h$ is $C_{1-3}$ alkyl or benzyl.

In step a and c, scheme 9, aldehyde/ketone 12 (from scheme 2) is converted to amino-nitriles 44 and 45 by reaction with amine 13 (or 46 respectively) using reagents and conditions known in the art. For instance, the aldehyde/ketone 12 is reacted with trimethylsilylcyanide and the hydrochloride salt of amine 13 (or 46) in dichloromethane, in the presence of a Lewis acid, e.g. zinc iodide, at temperatures between 0° C. and 25° C. Alternatively, the aldehyde/ketone 12 is first converted to the cyanohydrin, for instance, by reaction with trimethylsilylcyanide in the absence of any solvent, and then reacted with amine 13 in dichloromethane in the presence of an amine base, e.g. triethylamine, N-methylmorpholine, at temperatures between 0° C. and 25° C. In step b, compounds 44 and 45 are cyclised to 15 and 19 ($R^8$=CN), respectively. This can be achieved using a two step process of selective hydrolyis of ester $R^e$, e.g. through base-mediated hydrolysis using bases such as lithium hydroxide or sodium hydroxide in non-nucloephilic solvents such as water, tetrahydrofuran, 1,4-dioxane or mixtures thereof, and subsequent cyclisation via amide bond formation in analogy to step b, Scheme 5. In certain cases for compounds 45 the aforementioned hydrolysis conditions can lead directly to cyclised products (without the need for a second amide coupling step) with concomitant hydroysis of the nitrile to the carboxamide 19 ($R^8$=CONH$_2$). Alternatively, the nitrile in compounds 15 and 19 ($R^8$=CN) can be subsequently selectively hydrolysed to the carboxamide using reagents and conditions known in the art, for instance treatment with hydrogen peroxide, in the presence of catalytic or stoichiometric inorganic bases such as potassium carbonate, in polar solvents such as methanol, dimethylsulfoxide at temperatures from 0° C. to 100° C. or alternatively via the alkoxyamidine, using reagents and conditions known in the art e.g. treatment with catalytic base such as sodium methoxide, potassium tert-butylate or stoichometric acid such as dry hydrogen chloride, in nucleophilic solvents such as methanol, ethanol, 2-propanol at temperatures from 0° C. to 25° C. and subsequent hydrolytic work-up. Further selective hydrolysis of the carboxamide to the carboxylic acid can be achieved using conditions described by Evans et al. (Tetrahedron Lett. 1997, 38, 4535.)

Scheme 9

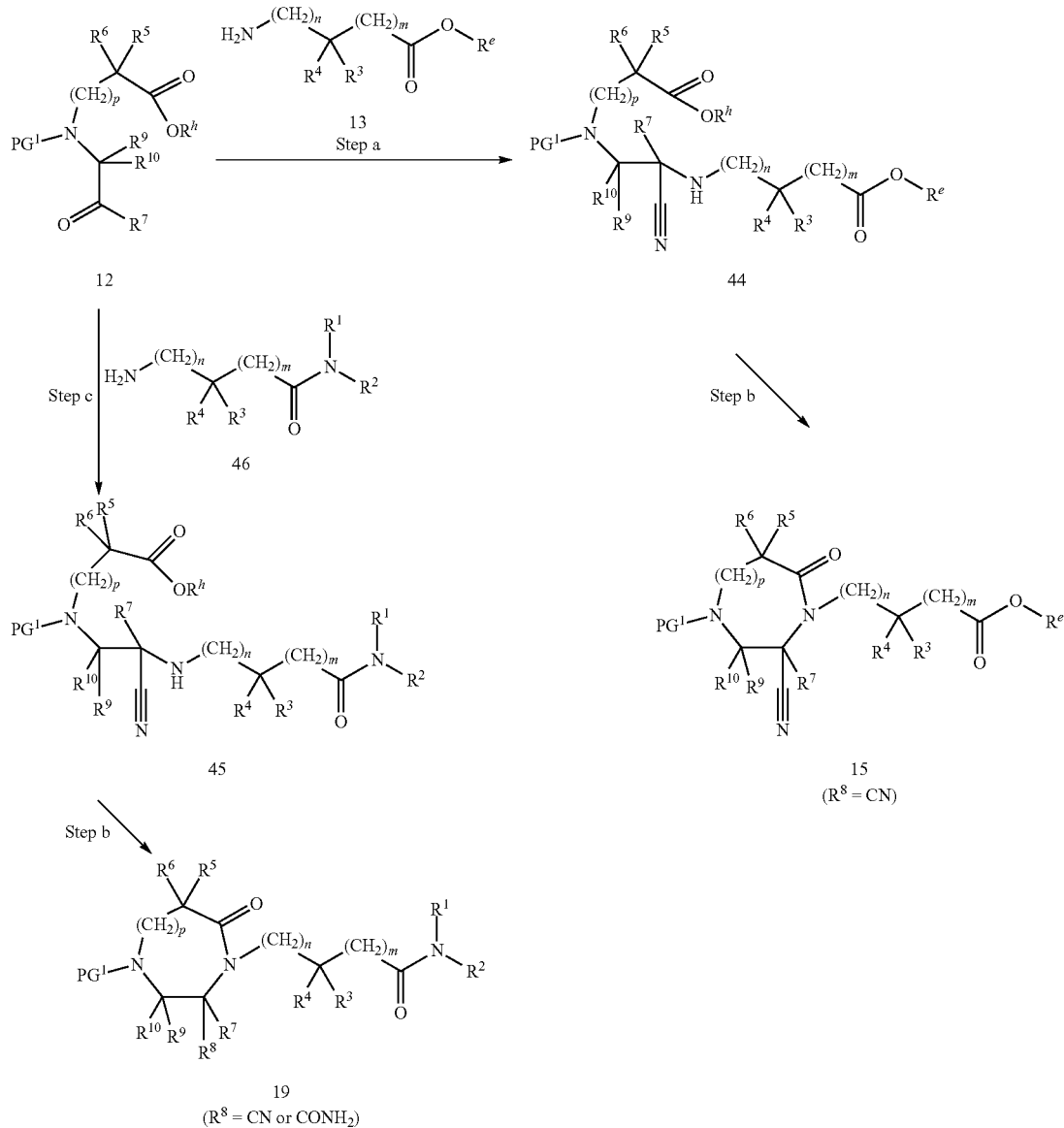

In Scheme 9, n, m, p, A, $R^1$, $R^2$, $R^3$, $R^4$, $R^5$, $R^6$, $R^7$, $R^9$, $R^{10}$, $PG^1$, $R^e$, $R^h$ and $R^e$ are as defined above.

Intermediate 42 can be synthesized as described in scheme 10, in analogy to the methods described in PCT Int Appl. WO2009/010429. $PG^1$ and $PG^2$ are suitable protective groups. For instance, $PG^1$ is tert-butoxycarbonyl and $PG^2$ is benzyl, LG is a leaving group, e.g., chlorine or bromine, $R^3$, $R^4$, $R^5$, $R^6$, $R^7$, $R^8$, $R^9$, $R^{10}$, m, n and p are as described before.

In step a, scheme 10, amino alcohol 46b is reacted with halide 47 by nucleophilic substitution, leading to secondary amine 48, using reagents and conditions known in the art. For instance, the reaction is carried out in a solvent such as methanol, ethanol, or acetonitrile, at temperatures between 20° C. and the boiling point of the solvent, optionally in the presence of a base, e.g., potassium hydrogencarbonate or potassium carbonate, optionally in the presence of sodium iodide.

Amino alcohols of formula 46b are either commercially available or can be synthesized as described in the literature.

In step b, scheme 10, secondary amine 48 is converted to amide of general formula 50 through reaction with N-protected amino acid of formula 49, using methods well known to someone skilled in the art. For instance, the reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)-pyridine, and in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate.

N-protected amino acids of formula 49 are either commercially available or can be synthesized using methods described in the literature.

In step c, scheme 10, compound 50 is converted to secondary amine 51 using methods and reagents known in the art. For instance, the protective group, $PG^1$, is cleaved, e.g., using hydrogen chloride in 1,4-dioxane or trifluoroacetic acid in dichloromethane in the case where $PG^1$ is tert-butoxycarbonyl. The resulting amino alcohol is cyclised to 51 using methods well known in the art, e.g., Mitsunobu reaction. This reaction requires a phosphine, preferably triphenylphosphine, and a dialkyl-azodicarboxylate, e.g., diethyl azodicarboxylate or diisopropyl azodicarboxylate and is performed in an inert solvent, e.g., tetrahydrofuran or toluene, at temperatures between 0° C. and 100° C. A base may be added in order to neutralise any residual acid from the deprotection step, e.g., triethylamine or 4-methylmorpholine.

Alternatively, in the case where $R^{10}$ is H, oxidation of the hydroxyl of 50 in analogy with scheme 3 step b leads to a hemiaminal intermediate, which undergoes both cleavage of $PG^1$ and reductive cyclisation to 51. The latter is performed, e.g., in the case where $PG^1$ is tert-butoxycarbonyl, using trifluoroacetic acid in the presence of triethylsilane, in a solvent such as dichloromethane, at temperatures between −78° C. and +20° C.

In step d, scheme 10, the hydroxyl protective group of 51, $PG^2$, is removed to produce 42. This deprotection is performed under suitable conditions, e.g., by hydrogenation at pressures between 1 bar and 100 bar, in a solvent such as methanol, ethanol, or acetic acid, in the presence of a suitable hydrogenation catalyst, e.g., palladium on activated charcoal.

Scheme 10

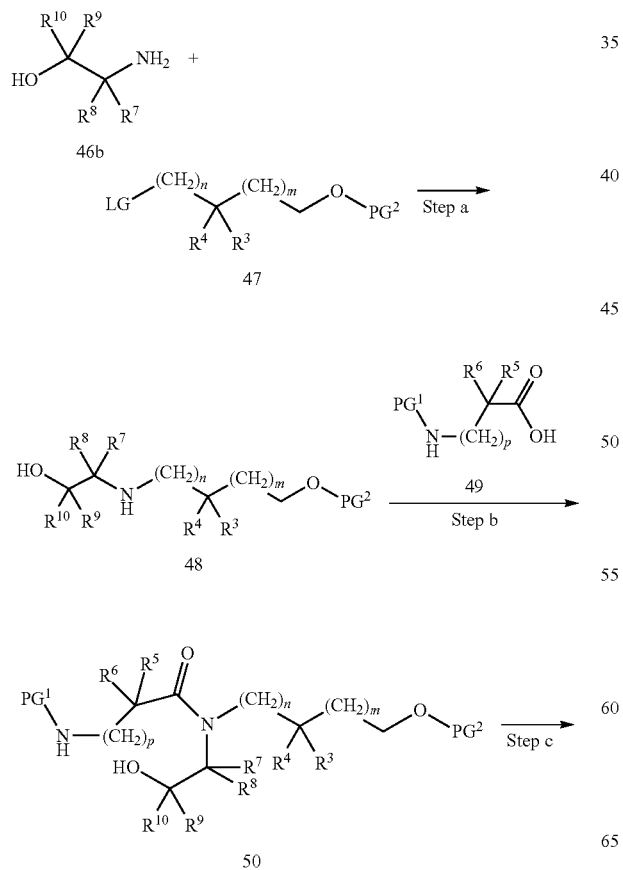

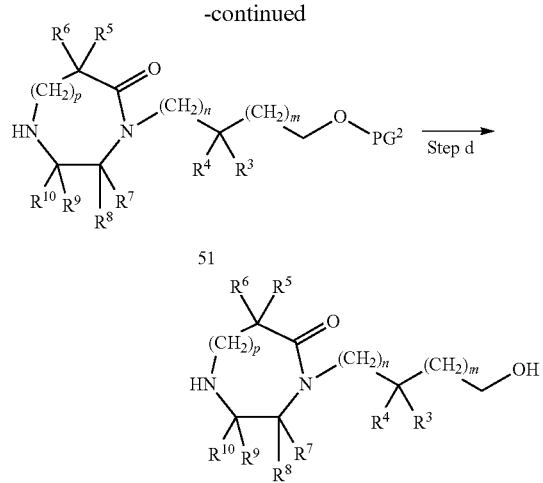

In Scheme 10, $PG^1$, $PG^2$, LG, $R^3$, $R^4$, $R^5$, $R^6$, $R^7$, $R^8$, $R^9$, $R^{10}$ m, n and p are as defined before.

In scheme 11, A, $R^1$, $R^2$, $R^3$, $R^4$, $R^5$, $R^6$, $R^7$, $R^8$ and n, m are as defined before. $Pg^1$ is benzyloxycarbonyl or tert-butoxycarbonyl, $R^9$, $R^{10}$=H, p=1.

Final compound $I_b$ (L=a bond, p=1) can also be synthesized as outlined in scheme 11.

In step a, scheme 11, protected amino acid 52 is coupled with amine $HNR^1R^2$ and deprotected as described in scheme 1 to give amine 46.

In step b, scheme 11, aldehyde or ketone 39 is converted with a reductive amination with amine 46 to the amine 53. An organo-$R^8$ complex can be used for the introduction of the $R^8$ moiety in the imino-intermediate. t-Butyl ester 53 is cleaved and cyclised to final [1,4]diazepan-5-one $I_b$ (step c) with conditions described in step c and step d, scheme 1.

Scheme 11

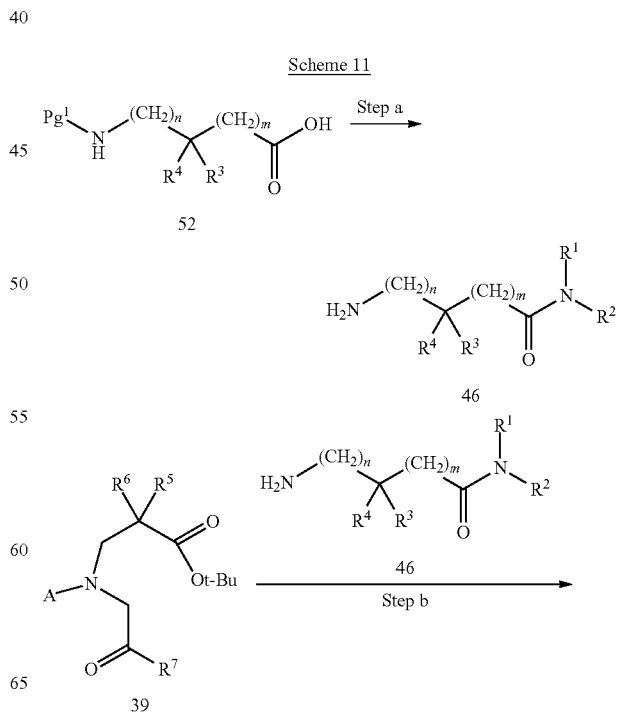

-continued

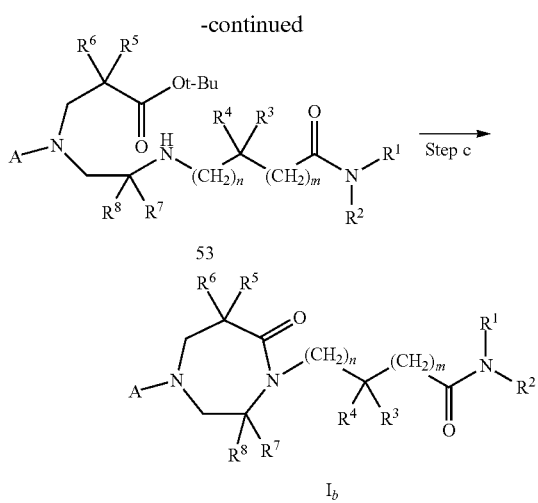

In Scheme 11, n, m, A, $R^1$, $R^2$, $R^3$, $R^4$, $R^5$, $R^6$, $R^7$, $R^8$, and $Pg^1$ are as defined above.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluent). The invention embraces all of these forms.

As described above, the compounds of formula (I) are CCR2 receptor antagonists, with some antagonist activity also at CCR3 and CCR5. These compounds consequently prevent migration of various leukocyte populations through the blockade of CCR2 stimulation. They therefore can be used for the treatment and/or prevention of inflammatory and/or allergic diseases, such as peripheral arterial occlusive disease, critical limb ischemia (CLI), vulnerable atherosclerotic plaque patients, unstable angina, congestive heart failure, left ventricular hypertrophy, ischemia reperfusion injury, stroke, cardiomyopathy, restenosis, rheumatoid arthritis, diabetes and diabetic complications, diabetic nephropathy, irritable bowel syndrome, Crohn's disease, multiple sclerosis, neuropathic pain, atherothrombosis and/or burns/ulcers in diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and asthma. Such medicaments comprise a compound as described above.

The invention also relates to the process and the intermediates for manufacturing the compounds of formula (I) as well as the process for manufacturing the intermediates.

CCR2 receptor antagonistic activity by the compounds of the present invention can be demonstrated by a receptor binding assay or by a calcium mobilization assay. examples of such assays are described in greater detail in the Examples.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

EXAMPLES

The following Examples serve to illustrate the present invention in more detail. They are, however, not intended to limit its scope in any manner.

Abbreviations aq.=aqueous, EDCI=N-(3-Dimethylaminopropyl)-N'-ethylcarbodiimide hydrochloride, eq.=equivalents, FTIR=Fourier transform infrared spectroscopy, GC=gas chromatography, HATU=O-(7-azabenzotriazol-1-yl)-1,1,3,3-tetramethyluronium hexafluorophosphate, HOBT=1-Hydroxybenzo-triazole, HPLC=high-pressure liquid chromatography, IPC=In-process control, ISP=ion spray, MS=mass spectrometry, NMR=nuclear magnetic resonance spectroscopy, sat=saturated, TEMPO=2,2,6,6-tetramethylpiperidin-1-oxyl, TLC=thin layer chromatography.

Intermediate 1

(rac)-4-(tert-Butyl-dimethyl-silanyloxy)-2-iodo-butyric acid methyl ester

A) (S)-4-(tert-Butyl-dimethyl-silanyloxy)-2-methanesulfonyloxy-butyric acid methyl ester A solution of 2.48 g (10.00 mmol) of methyl (S)-4-(tert-butyldimethylsilyloxy)-2-hydroxybutanoate (*J. Am. Chem. Soc.* 2005, 127, 1090) in 50 ml of dichloromethane was treated with 2.09 ml (15.00 mmol, 1.5 eq) of triethylamine and at 0° C. during 5 min with 0.82 ml (10.50 mmol, 1.051 eq) of methanesulfonyl chloride. After 1 h at 0° C. the reaction was partitioned between 10% aq. potassium dihydrogenphosphate solution/diethyl ether (×3), the organic phases were washed with sat. aq. sodium hydrogencarbonate solution (freshly prepared) and 10% aq. sodium chloride solution, dried over $Na_2SO_4$ and evaporated to give 2.91 g (89%) of the titled compound as yellow oil. MS: 327.1 ($MH^+$).

B) (rac)-4-(tert-Butyl-dimethyl-silanyloxy)-2-iodo-butyric acid methyl ester

A solution of 2.89 g (8.85 mmol) of (S)-4-(tert-butyl-dimethyl-silanyloxy)-2-methanesulfonyloxy-butyric acid methyl ester in 90 ml of 2-butanone was treated with 2.65 g (17.70 mmol) of sodium iodide and stirred at 90° C. for 1¼ h. The reaction was cooled, filtered and evaporated. The residue was suspended in dichloromethane treated with $Na_2SO_4$ and filtered to give after evaporation 2.94 g (93%) of the titled compound as dark brown oil. MS: 343.0 ($M-CH_3$)$^+$.

Intermediate 2

(S)-6-Aza-spiro[2.5]octan-4-ol; hydrochloride a) 4-Hydroxy-6-aza-spiro[2.5]octane-6-carboxylic acid tert-butyl ester Method A To a solution of diethylzinc (1.1 M solution in toluene, 37.5 ml, 0.04 mmol) in 1,2-dichloroethane (80 ml) at 0° C. was added chloroiodomethane (5.99 ml, 0.08 mmol) under Ar. This mixture was stirred for 15 minutes before a solution of 3-hydroxy-4-methylene-piperidine-1-carboxylic acid tert-butyl ester (*J. Org. Chem.* 2001, 66, 2487) (4.19 g, 19.6 mmol) in 1,2-dichloroethane (10 ml) was added, after which time the reaction was stirred for 0.5 h at 0° C. and then allowed to reach room temperature, stirring for a further 1 h. The reaction was then quenched by addition of sat. aq. ammonium chloride solution, separated, and the organic dried ($Na_2SO_4$) and concentrated. Purfication by flash column chromatography ($SiO_2$; ethyl acetate/heptane 2:8-1:1) afforded the titled product (2.4 g, 54%) as a crystalline solid. MS: 228.2 ($MH^+$).

Method B 2.00 g (9.4 mmol, 1 eq.) 3-hydroxy-4-methylene-piperidine-1-carboxylic acid tert-butyl ester were dissolved in toluene at 25° C. 17.05 ml (2 eq.) 1.1 M diethyl zinc solution in toluene were added at such a rate as to maintain the reaction temperature below 30° C. After 15-30 min at 25° C., 2.29 ml (3 eq.) diiodomethane were added over 2-3 h maintaining the reaction temperature at 25° C. (the reaction is best followed by Tr-Tj measurements and/or in-line FTIR reaction monitoring). After 30-60 min after the end of addition, 4.57 ml 2-ethyl-hexanoic acid were added to the resulting white suspension at such a rate as to maintain the reaction temperature between 25-30° C. The heavy white suspension was stirred for 30 min. 10 ml heptane were added followed by a mixture consisting of 20 ml 25% aq. ammonia solution and 30 ml water. The organic phase was separated and washed with a mixture consisting of 10 ml 25% aq. ammonia solution and 30 ml water. The organic phases were washed with 20 ml half saturated aq. sodium chloride solution, combined, dried over sodium sulfate, filtered and concentrated under reduced pressure to an oil (may crystallize upon standing). The crude spiro-piperidinol was purified by crystallization in heptane or alternatively in tert-butyl methyl ether/heptane providing the titled product in ca 80% yield as a white powder.

b) (S)-4-Hydroxy-6-aza-spiro[2.5]octane-6-carboxylic acid tert-butyl ester

Method A

The titled compound was prepared by chiral separation of (rac)-4-hydroxy-6-aza-spiro[2.5]octane-6-carboxylic acid tert-butyl ester on a Chiralpak® AD column (heptane/2-propanol 95:5).

Method B

4-Hydroxy-6-aza-spiro[2.5]octane-6-carboxylic acid tert-butyl ester (3.00 g; 13.07 mmol) was dissolved in tert-butyl methyl ether (20.5 ml) and vinyl butyrate (6.5 ml). The solution was heated to 50° C. and the reaction started by the addition of Lipase TL (3.0 g; Meito Sangyo, Tokyo). The solution was stirred at 50° C. for 46 h until the enantiomeric excess of the retained alcohol was >99%. The enzyme was filtered off, the filter cake washed with tert-butyl methyl ether and the filtrate concentrated in vacuo. The residual oil was chromatographed on silicagel (80 g; 0.040-0.063 mm; dichloromethane→dichloromethane/acetone 9:1) to separate the formed optically enriched (R)-butyrate from the retained (S)-alcohol (1.18 g white crystals; 40%). Analytics: >99 GC; >99% ee (GC on BGB-176; 30 m×0.25 mm; $H_2$; 1.2 bar; 80° C. to 210° C. with 3° C./min; inj. 200° C.; Det. 215° C.; Retention times: (R)-alcohol 28.58 min, (S)-alcohol 29.00 min). $[\alpha]_D = -43.35°$ (c=1.00, $CHCl_3$).

Method C

Step 1: 4-Oxo-6-aza-spiro[2.5]octane-6-carboxylic acid tert-butyl ester

The titled compound was produced from 4-hydroxy-6-aza-spiro[2.5]octane-6-carboxylic acid tert-butyl ester, either by TEMPO/bleach oxidation or by Swern oxidation a) TEMPO/Bleach Oxidation To a solution of 4-hydroxy-6-aza-spiro[2.5]octane-6-carboxylic acid tert-butyl ester (20.0 g, 88.0 mmol) in dichloromethane (170 ml) was added sodium bromide (1.092 g, 10.6 mmol), sodium bicarbonate (2.439 g, 29.0 mmol) and 2,2,6,6-tetramethylpiperidine 1-oxyl (237.1 mg, 1.49 mmol). The mixture was cooled to −5° C. and sodium hypochlorite solution (9.5% in water, 55.16 ml) was added within 10 min resulting in a red coloration and a temperature rise to 9° C. The mixture was stirred for 35 min at 0-5° C. and, as conversion was incomplete (2.5% starting material remaining), additional sodium hypochlorite solution (9.5% in water, 7.0 ml) was added within 30 min and the mixture stirred for another 30 min at 0° C. GC analysis indicated complete conversion (<0.1% starting material remaining) Sodium thiosulfate solution (10% in water, 100 ml) was added within 10 min resulting in decoloration. The organic phase was separated, washed with water (100 ml), dried over sodium sulfate (50 g), filtered and evaporated (15 mbar, 40° C.) to afford 4-oxo-6-aza-spiro[2.5]octane-6-carboxylic acid tert-butyl ester as yellowish powder (19.84 g, GC purity 99a %. The powder was dissolved in warm tert-butyl methyl ether (20 ml), heptane (60 ml) was added to induce crystallization and the white suspension stirred at 0-5° C. for 1.5 h. Filtration, washing with heptane (20 ml) and drying (10 mbar, 45° C.) afforded 4-oxo-6-aza-spiro[2.5]octane-6-carboxylic acid tert-butyl ester (17.25 g, 87%) as white crystalline material, GC purity 100a %. $^1$H-NMR ($CDCl_3$, 300 MHz): 4.08 (s, $CH_2$(5)), 3.66 (m, $CH_2$(7)), 1.88 (m, $CH_2$(8)), 1.48 (s, tent-Bu), 1.40 (m, 2H), 0.81 (m, 2H).

b) Swern Oxidation

To a solution of oxalyl chloride (42.35 ml, 0.480 mol) in dichloromethane (910 ml) was added a solution of dimethylsulfoxide (68.24 ml, 0.961 mol) in dichloromethane (910 ml) at −70° C. within 45 min. The solution was stirred for 15 min and a solution of 4-hydroxy-6-aza-spiro[2.5]octane-6-carboxylic acid tert-butyl ester (91.00 g, 0.400 mol) in dichloromethane (910 ml) was added within 40 min keeping the internal temperature at below −60°. The mixture was stirred for 35 min and triethylamine (280.4 ml, 2.00 mol) was added at below −60° C. within 10 min. The cooling bath was removed and the yellow suspension was stirred for 1 h then quenched with water (1.4 l). The organic phase was separated, washed with water (3×1 l) and sat. aq. sodium chloride solution (3 l) and evaporated. The residual orange powder was dissolved in tert-butyl methyl ether (1.40 l), the turbid solution filtered (Hyflo Speedex) to remove some insoluble material and the clear filtrate evaporated to provide crude 4-oxo-6-aza-spiro[2.5]octane-6-carboxylic acid tert-butyl ester as yellow powder (91.9 g). The material was re-dissolved in tert-butyl methyl ether (300 ml) and purified by filtration over silica gel (700 g) using a 3:1 heptane/tert-butyl methyl ether mixture (6.5 l). Evaporation and drying (10 mbar, 40° C.) afforded 4-oxo-6-aza-spiro[2.5]octane-6-carboxylic acid tert-butyl ester as whitish powder (80.58 g, 89%), GC purity 100a %.

Step 2: (S)-4-Hydroxy-6-aza-spiro[2.5]octane-6-carboxylic acid tert-butyl ester

D(+)-glucose monoydrate (300 g) and magnesium chloride hexahydrate (1.0 g) were dissolved in 10 mM MES buffer pH 6.5 (2.4 L; Sigma M3671). After addition of 4-oxo-6-aza-spiro[2.5]octane-6-carboxylic acid tert-butyl ester (300 g; 1.33 mmol) and 8-NAD (3.0 g; free acid; Roche Diagnostics Cat. No. 10 004 626) the pH was re-adjusted and the suspension heated to 35° C. The reaction was started by adding ketoreductase KRED-NADH-117 (3.0 g; former Biocatalytics, now Codexis) and glucose dehydrogenase GDH-102 (300 mg; Biocatalytics). The suspension was vigorously stirred at 35° C. keeping the pH constant at 6.5 by the controlled addition (pH-stat) of 1.0 M aq. sodium hydroxide solution. After a consumption of 1.307 L (corresponding to 98% conversion; after 17 h) the reaction mixture was extracted with ethyl acetate (10 L). The organic phase was dried over sodium sulfate and concentrated in vacuo (200 mbar/45° C.) until evaporation fell off. Upon cooling the oily residue (411 g) started to crystallize and was stirred with heptane (1 L) for 2 h. The crystals were filtered off and the filtrate evaporated to dryness, redissolved in ethyl acetate (150 ml) and concentrated in vacuo as described above. The crystal suspension formed again upon cooling was stirred with heptane (200 ml; 2 h) and the crystals filtered off. Both crops of crystals were washed with heptane and dried under high vacuum to yield the titled compound in 93% yield (250.77 g and 34.60 g white crystals), each having a purity of >98.5% GC and 99.8% ee. $[\alpha]_D = -44.97°$ (c=1.00, $CHCl_3$).

Method D

Step 1: (S)-3-hydroxy-4-methylene-piperidine-1-carboxylic acid tert-butyl ester

3-Hydroxy-4-methylene-piperidine-1-carboxylic acid tert-butyl ester (4.50 g; 21.10 mmol) was dissolved in tert-butyl methyl ether (63 ml) and vinyl butyrate (22.5 ml). The solution was heated to 50° C. and the reaction started by the addition of Lipase TL IM (1.08 g (carrier-fixed); Novozymes, Denmark). The solution was stirred at 50° C. for 20 h until the enantiomeric excess of the retained alcohol was >99%. The enzyme was filtered off, the filter cake washed with tert-butyl methyl ether and the filtrate concentrated in vacuo. The residual oil was chromatographed on silicagel (100 g; 0.040-0.063 mm; dichloromethane→dichloromethane/acetone 9:1) to separate the formed optically enriched (R)-butyrate from the retained (S)-alcohol (1.83 g white crystals; 41%). Analytics: >99 GC; >99% ee (GC on BGB-176; 30 m×0.25 mm; $H_2$; 1.2 bar; 80° C. to 210° C. with 3° C./min; inj. 200° C.; Det.

210° C.; retention times: (R)-alcohol 29.60 min, (S)-alcohol 29.81 min). [α]$_D$=−17.70° (c=1.00, CHCl$_3$).

Step 2:
(S)-4-Hydroxy-6-aza-spiro[2.5]octane-6-carboxylic acid tert-butyl ester

The titled compound is produced analogously to intermediate 2a, Method B from (S)-3-hydroxy-4-methylene-piperidine-1-carboxylic acid tert-butyl ester.

c) (S)-6-Aza-spiro[2.5]octan-4-ol; hydrochloride

A solution of (S)-4-hydroxy-6-aza-spiro[2.5]octane-6-carboxylic acid tert-butyl ester (3.26 g, 14.3 mmol) in ethanol (10 ml) was treated at room temperature with hydrogen chloride solution (4 M in 1,4-dioxane, 30 ml), then after 1 h tert-butyl methyl ether (40 ml) was added. The suspension was stirred for 1 h, then the precipitate was collected by filtration to afford the titled compound (2.11 g, 90%). White solid, MS: 128.1 (M+H)$^+$.

Alternative preparation of
(S)-6-Aza-spiro[2.5]octan-4-ol; hydrochloride i) Cyclopropanecarboxylic acid tert-butyl ester 219.1 g (1.91 mol, 1 eq.) potassium tert-butylate were suspended in 2.5 L tert-butyl methyl ether and cooled to 0-5° C. 200 g (1 eq.) cyclopropanecarbonyl chloride were added over 60 min, maintaining the temperature between 0-5° C. (ice-ethanol bath cooling). In-line FTIR reaction monitoring indicates a feed controlled reaction. The reaction mixture was stirred 30 min at 0-5° C. and 1 L of 5% aq. sodium hydrogencarbonate solution was added. The aqueous phase was separated and extracted with 500 ml tert-butyl methyl ether. The organic phases were washed with 500 ml half saturated aq. sodium chloride solution, combined and concentrated under reduced pressure (30° C./150 mbar) to provide 271 g of the titled compound (91% yield corrected for 8% residual tert-butyl methyl ether).

ii) 1-Allyl-cyclopropanecarboxylic acid tert-butyl ester 15.9 ml (1.15 eq.) diisopropylamine were dissolved in 65 ml tetrahydrofuran and cooled to ca −10° C. 65 ml (1.08 eq.) 1.6 M butyllithium solution in hexane were added over 25 min, maintaining the temperature between −10° C. and 0° C. After 50 min at ca. −5° C., the reaction mixture was cooled to −75° C. A solution of 15 g (96.7 mmol, 1 eq., 92% w/w purity) cyclopropanecarboxylic acid tert-butyl ester in 20 ml tetrahydrofuran was added over 15 min keeping the temperature between −75° C. and −70° C. The reaction mixture was stirred 5 h at −75° C. (milky reaction mixture obtained after 2.5 h). A solution of 12.87 g (1.10 eq.) allyl bromide was added over 20 min keeping the temperature between −75° C. and −60° C. The reaction mixture was stirred at −78° C. for 1 h, warmed to room temperature and stirred overnight. The reaction mixture was cooled to 0° C. 100 ml sat. aq. ammonium chloride solution were added followed by 30 ml water providing a clear biphasic mixture. The mixture was extracted 3 times with 50 ml tert-butyl methyl ether. The organic phases were combined, dried over sodium sulfate, filtered and concentrated under reduced pressure (40° C./20 mbar) to afford 16.44 g of crude product. The crude product was distilled (2 mbar; ca 40° C. distillation head temperature) to provide the titled compound in ca 65% yield.

iii) 1-(2-Oxo-ethyl)-cyclopropanecarboxylic acid tert-butyl ester 6.9 g (36.34 mmol, 1 eq., 96% a % by GC) 1-allyl-cyclopropanecarboxylic acid tert-butyl ester were dissolved in 40 ml dichloromethane and 40 ml methanol. The solution was cooled to −72° C. and the ozone was bubbled through the reaction mixture until a blue color was obtained. Then nitrogen was bubbled to remove excess ozone until a colorless solution was obtained. 10 ml (3.68 eq.) dimethyl sulfide and 14 ml (2.76 eq.) triethylamine were added. The reaction mixture was warmed to room temperature and stirred overnight at that temperature (peroxide test negative, pH 7-8). The yellowish reaction mixture was added to 100 ml sat. aq. ammonium chloride solution (exothermic) and extracted 3 times with 70 ml dichloromethane. The organic phases were combined, dried over sodium sulfate, filtered and concentrated under reduced pressure to provide the crude aldehyde, which was purified by filtration over SiO$_2$ (dichloromethane; TLC: ethyl acetate/heptane 1:2) to provide 3.90 g (96% GC, 56% yield) of the titled compound as an oil.

iv) 1-[2-(Benzyl-tert-butoxycarbonylmethyl-amino)-ethyl]-cyclopropanecarboxylic acid tert-butyl ester 10.5 g (54.7 mmol, 1 eq.) 1-(2-oxo-ethyl)-cyclopropanecarboxylic acid tert-butyl ester and 13.21 g (1.08 eq.) N-benzylglycine tert-butyl ester were dissolved in 140 ml toluene. 21 g (1.63 eq.) sodium triacetoxyborohydride were added (exotherm from 25° C. to 28° C.) and the reaction mixture was stirred 5 h at room temperature (IPC by GC). A solution of 2 ml (0.64 eq.) acetic acid in 15 ml toluene was added. After 30 min at room temperature, the reaction mixture was cooled to 0° C. and 100 ml sat. aq. sodium hydrogencarbonate solution was added over 40 min (foaming). 50 ml ethyl acetate were added. The mixture was stirred for 30 min at room temperature. The mixture was extracted with 200 ml and a second time with 50 ml ethyl acetate. The organic phases were washed with 50 ml sat. aq. sodium hydrogencarbonate solution followed by 50 ml sat. aq. sodium chloride solution. The organic phases were combined, dried over sodium sulfate, filtered and concentrated under reduced pressure to give 21.5 g of the titled compound as an oil (ca. 95% yield, corrected for ca 3% residual toluene and 3% amine starting material).

v) 6-Benzyl-6-aza-spiro[2.5]octan-4-one hydrochloride 10.8 g (24.4 mmol, 1 eq.) 1-[2-(benzyl-tert-butoxycarbonylmethyl-amino)-ethyl]-cyclopropanecarboxylic acid tert-butyl ester were dissolved in 35 ml tetrahydrofuran. 50 ml (2.05 eq.) 1 M lithium hexamethyldisilazanide solution in tetrahydrofuran were added dropwise over 2.5 h maintaining the temperature between 20° C. and 25° C. After 2 h at room temperature (IPC by HPLC), the reaction mixture (containing the lithium salt of 6-benzyl-4-hydroxy-6-aza-spiro[2.5]oct-4-ene-5-carboxylic acid tert-butyl ester) was cooled to −10° C. (ice ethanol cooling bath) and 75 ml 1 M aq. sulfuric acid solution were added (temperature increased to 2° C.). The reaction mixture was warmed to room temperature and the tetrahydrofuran removed under reduced pressure at 40° C. The resulting reaction mixture was heated to 40° C. for 1 h, was stirred 15 h at room temperature and an additional 3 h at 40° C. to complete the reaction (IPC by GC; intermediate 6-benzyl-4-hydroxy-6-aza-spiro[2.5]oct-4-ene-5-carboxylic acid tert-butyl ester is hydrolyzed and decarboxylation follows). The reaction mixture was cooled to 0° C. and was neutralized to pH 7.4 by addition of 10 ml 2 M aq. sodium hydroxide solution and 50 ml 1 M aq. sodium hydrogencarbonate solution were added, setting the pH to 9.4. The crude solution was extracted with tert-butyl methyl ether and ethyl acetate. The organic phases were combined, dried over sodium sulfate and filtered over a plug of $SiO_2$. The solution was concentrated under reduced pressure (45° C./20 mbar) to give 4.56 g of the crude product as free base. The crude oil was dissolved in 8 ml ethyl acetate, cooled to 0° C. and 5.1 ml hydrogen chloride solution (4.3 M in ethyl acetate) were added dropwise (exotherm 2° C. to 18° C.). The reaction mixture was stirred overnight at room temperature (gummy crystals) and filtered. The filter cake was washed with 10 ml ethyl acetate and dried under reduced pressure until constant weight to give 4.54 g of the titled compound as off-white crystals (74% yield).

vi) (S)-6-Benzyl-6-aza-spiro[2.5]octan-4-ol

A mixture of 300 mg of 6-benzyl-6-aza-spiro[2.5]octan-4-one hydrochloride (1.19 mmol, 1 eq.), 1.5 ml of 2-propanol and 28 ml of 30 mM aq. TRIS-HCl buffer (pH 8.1) was heated to 35° C. The pH was re-adjusted to 8.0. The reaction was started by adding 8-NAD (1 mg; free acid; Roche Diagnostics Cat. No. 10 004 626) and ketoreductase KRED-NADH-117 (29.3 mg; Codexis [ex. Biocatalytics]). The suspension was stirred at 35° C. keeping the pH constant at 8.0 by the controlled addition (pH-stat) of 1.0 M aq. sodium hydroxide solution. After roughly 80 area % conversion and 1d, further 2-propanol (0.3 ml), 8-NAD (3 mg; free acid; Roche Diagnostics Cat. No. 10 004 626), ketoreductase KRED-NADH-117 (30 mg; Codexis [ex. Biocatalytics]) and magnesium chloride (12.7 mg) were added. After 4 d, 98.5 area % conversion and 5.9 ml consumption of 1.0 M aq. sodium hydroxide solution the reaction mixture was stopped by the addition of sodium chloride (9 g), ethyl acetate (30 ml) and filter aid (1 g Dicalite Speedex). The mixture was stirred 30 min. and filtered. The filtrate was extracted 3 times with 30 ml ethyl acetate. The combined organic phases were dried over sodium sulfate, filtered and concentrated under reduced pressure to provide the crude product in over 99.9% e.e. Purification by flash chromatography provided the titled compound as a colorless oil.

vii) (S)-6-Aza-spiro[2.5]octan-4-ol 100 mg (S)-6-benzyl-6-aza-spiro[2.5]octan-4-ol were dissolved in 1 ml methanol and hydrogenated over palladium on barium sulfate. After de-benzylation (IPC by GC), the catalyst was filtered and the filtrate was concentrated under reduced pressure to provide the titled compound. The amino alcohol was treated with di-tert-butyl-dicarbonate in methanol in the presence of triethylamine. The crude tert-butoxycarbonyl-protected amine product was analyzed by chiral GC (BGB-176; 30 m×0.25 mm; 80° C. to 210° C. in 43 min) and proved to be identical with intermediate 2b.

The hydrochloride salt of the titled compound can be obtained by treating the aminoalcohol with HCl in ethyl acetate.

Preparation of N-Benzylglycine Tert-Butyl Ester 40 g (205 mmol, 1 eq.) tert-butyl bromoacetate were dissolved in 200 ml acetonitrile. The solution was cooled to 0-5° C. and 47 g benzylamine (2.14 eq.) in solution in 90 ml acetonitrile were added over 15 min. After 5 min, the reaction mixture was warmed to room temperature and stirred for 3 h (IPC by GC). The resulting suspension was filtered and evaporated to constant weight to give 49 g of a yellow oil. The oil was dissolved in 200 ml heptane and washed 3 times with 50 ml aq. sodium hydrogencarbonate solution. The organic phase was dried over sodium sulfate, filtered and evaporated to give 35.8 g of the crude product. Distillation under high vacuum afforded 27.2 g of the titled product (95% pure by GC).

Intermediate 3

(3S,4S)-4-Methyl-piperidin-3-ol; hydrochloride

A) (rac, trans)-3-Hydroxy-4-methyl-piperidine-1-carboxylic acid tert-butyl ester (rac, trans)-1-Benzyl-4-methyl-piperidin-3-ol (*Tetrahedron. Lett.* 2000, 41, 5817) (13.0 g, 63 mmol) was dissolved in methanol with palladium hydroxide (20% on activated charcoal, 4 g) and stirred under a hydrogen atmosphere (balloon) for 16 h after which time di-tert-butyl dicarbonate (13.8 g, 63 mmol) was added, the reaction stirred for 1 h, filtered through Hyflo and concentrated to afford the titled product (13.3 g, 98%) as a crystalline solid. MS: 216.2 ($MH^+$).

B) (rac, cis)-4-Methyl-3-(4-nitro-benzoyloxy)-piperidine-1-carboxylic acid tert-butyl ester (rac, trans)-3-Hydroxy-4-methyl-piperidine-1-carboxylic acid tert-butyl ester (6.0 g, 28 mmol) was dissolved in tetrahydrofuran (40 ml) with triphenylphosphine (8.9 g, 34 mmol), 4-nitrobenzoic acid (5.7 g, 34 mmol) and cooled to 0° C. before dropwise addition of diisopropyl azodicarboxylate (6.9 g, 34 mmol). The ice bath was removed and the reaction allowed to come to room temperature, stirring for 16 h. The reaction was then directly absorbed onto silica gel and purified by flash column chromatography (ethyl acetate/heptane 2:8) to afford the titled product (4.0 g, 40%) as a white solid. MS: 365.2 ($MH^+$).

C) (rac, cis)-3-Hydroxy-4-methyl-piperidine-1-carboxylic acid tert-butyl ester (rac, cis)-4-Methyl-3-(4-nitro-benzoyloxy)-piperidine-1-carboxylic acid tert-butyl ester (5.0 g, 14 mmol) was dissolved in methanol (70 ml) and 6 M aq. sodium hydroxide solution (4.5 ml, 27 mmol) was added. The reaction was stirred for 1 h after which time the solvent removed under vacuum, the residue portioned between water and dichloromethane and the organic collected, dried ($Na_2SO_4$) and concentrated to afford the titled product (2.6 g, 87%) as a crystalline solid. MS: 216.1 ($MH^+$).

D) (3S,4S)-4-Methyl-piperidin-3-ol; hydrochloride (rac, cis)-3-Hydroxy-4-methyl-piperidine-1-carboxylic acid tert-butyl ester was separated on a Chiralpak AD column (Isopropanol/Heptane 5:95) and subsequently, the (−)-enantiomer was deprotected with hydrogen chloride solution in dioxane to afford the titled compound as a white powder. MS: 116.2 ($MH^+$).

Intermediate 4

(3S,5S)-5-Methyl-piperidin-3-ol; hydrochloride

A)
(S)-3-(Benzyl-ethoxycarbonylmethyl-amino)-butyric acid ethyl ester

To ethanol (55 ml) cooled to 0° C. was added acetyl bromide (41 ml, 0.6 mol) dropwise, followed by a solution of (S)-4-methyl-dihydro-furan-2-one (*Tetrahedron* 1983, 39, 3107; 18.6 g, 0.2 mol) in ethanol (20 ml). The ice bath was removed and the reaction allowed to reach room temperature. After 2 h of stirring the reaction was concentrated, the residue redissolved in dichloromethane, washed with sat. aq. sodium hydrogencarbonate solution, dried ($Na_2SO_4$) and concentrated affording (S)-4-bromo-3-methyl-butyric acid ethyl ester (33.6 g, quantitative). This was redissolved in ethanol (100 ml), cooled to 0° C. and N-benzylglycine ethyl ester (28.2 g, 0.14 mol) and triethylamine (22.4 ml, 0.16 mmol) were added. The reaction was then warmed to 75° C. for 4 d after which time the reaction was concentrated, the residue redissolved in dichloromethane, washed with sat. aq. sodium hydrogencarbonate solution, dried ($Na_2SO_4$) and concentrated. Purification by flash column chromatography (ethyl acetate/heptane 5:95) afforded the titled product as a light gold oil (20.3 g, 43%). MS (ISP)=322.2 $(M+H)^+$.

B) (S)-1-Benzyl-5-methyl-piperidin-3-one

To a suspension of sodium hydride (55% dispersion in mineral oil, 6.4 g, 14 mmol) in toluene (90 ml) was added (S)-3-(benzyl-ethoxycarbonylmethyl-amino)-butyric acid ethyl ester (20.3 g, 0.06 mol) in toluene (10 ml), followed by ethanol (1 ml). A vigorous reaction ensued, after 15 minutes the reaction was diluted with ethyl acetate, washed with 10% aq. citric acid solution, dried ($Na_2SO_4$) and concentrated. The residue was purified by flash column chromatography (ethyl acetate/heptane 1:9) affording a complex mixture of diastereomers (7.2 g, 42%). A portion of this material (3.5 g, 13 mmol) was dissolved in 25% aq. hydrochloric acid solution (20 ml) and heated in a loosely closed tube at 120° C. for 36 h. The solvent was evaporated, the residue redissolved in dichloromethane, washed with sat. aq. sodium hydrogencarbonate solution, dried ($Na_2SO_4$) and concentrated. Purification by flash column chromatography (ethyl acetate/heptane 1:4) afforded the titled product as a crystalline solid (1.1 g, 43%). MS (ISP)=204.3 $(M+H)^+$.

C) (3S,5S)-1-Benzyl-5-methyl-piperidin-3-ol

To a solution of (S)-1-benzyl-5-methyl-piperidin-3-one (1.1 g, 5 mmol) in dry tetrahydrofuran (15 ml) at −78° C. was added K-selectride (10.8 ml, 11 mmol, 1 M solution in tetrahydrofuran). After 2 h at −78° C. a few drops of water were cautiously added, the reaction allowed to reach room temperature, the tetrahydrofuran removed by evaporation and the residue the residue redissolved in dichloromethane, washed with sat. aq. sodium hydrogencarbonate solution, dried ($Na_2SO_4$) and concentrated. Purification by flash column chromatography (ethyl acetate/heptane 1:4) afforded the titled product as a crystalline solid (0.9 g, 43%). MS (ISP)=204.3 $(M+H)^+$.

D) (3S,5S)-5-Methyl-piperidin-3-ol; hydrochloride

To a solution of (S)-1-benzyl-5-methyl-piperidin-3-one (0.9 g, 4 mmol) was dissolved in methanol, 25% aq. hydrochloric acid solution added until the pH was acidic, followed by palladium (10% on activated charcoal, 0.2 g). The mixture was stirred under 1 atmosphere of hydrogen (balloon) for 6 h. The reaction was then filtered through Hyflo and concentrated to afford the titled product as a white powder (0.66 g, quantitative). MS (ISP)=116.1 $(M+H)^+$.

Intermediate 5

3-{4-[(E)-3-(3,4-Dichloro-phenyl)-acryloyl]-7-oxo-[1,4]diazepan-1-yl}-propionic acid A) 1-[(E)-3-(3,4-Dichloro-phenyl)-acryloyl]-[1,4]diazepan-5-one A solution of 9.77 g (43.65 mmol) of (E)-3,4-dichlorocinnamic acid in 250 ml of Dichloromethane was treated at RT with 3 drops of DMF. 4.15 ml (48.02 mmol, 1.1 eq) of oxalyl chloride in 30 ml dichloromethane were added dropwise and stirring was continued for 3 h. The solution was evaporated, redissolved in 170 ml of dichloromethane, cooled (0° C.) and treated with a solution of 4.48 g (39.29 mmol, 0.9 eq) of 2,3,6,7-tetrahydro-(1H)-1,4-diazepin-5(4H)-one and 12.17 ml (87.30 mmol, 2 eq) of triethylamine in 80 ml of dichloromethane. The reaction was warmed up over night to RT, and then partitioned between dichloromethane/MeOH 9:1 (×3)/ aqueous 10% $KHSO_4$, the organic phases were washed with aqueous saturated $NaHCO_3$ and aqueous 10% NaCl, dried over $Na_2SO_4$ and evaporated. The residue was dissolved and evaporated with toluene and crystallized with dichloromethane/$Et_2O$ to give 7.99 g (58%) of the titled compound as white solid. MS: 312.8 ($MH^+$, 2Cl).

B) 3-{4-[(E)-3-(3,4-Dichloro-phenyl)-acryloyl]-7-oxo-[1,4]diazepan-1-yl}-propionic acid ethyl ester A suspension of 4.00 g (12.77 mmol) of 1-[(E)-3-(3,4-dichloro-phenyl)-acryloyl]-[1,4]diazepan-5-one and 1.63 ml (12.77 mmol) of ethyl 3-bromopropionate in 60 ml of DMF was treated at 0° C. with 0.61 g (14.05 mmol) of NaH (55% in oil) in two portions. The suspension was stirred after 30 min at RT to get a solution and further stirred over night at 0° C. The reaction was neutralized with cold aqueous 10% $KHSO_4$ and extracted with EtOAc (3×). The organic phases were washed with aqueous 10% NaCl, dried over $Na_2SO_4$ evaporated and crystallized (dichloromethane/MeOH) to yield 3.71 g (70%) of the titled compound as an off-white solid. MS: 413.1 ($MH^+$, 2Cl).

C) 3-{4-[(E)-3-(3,4-Dichloro-phenyl)-acryloyl]-7-oxo-[1,4]diazepan-1-yl}-propionic acid A solution of 3.50 g (8.47 mmol) of 3-{4-[(E)-3-(3,4-dichloro-phenyl)-acryloyl]-7-oxo-[1,4]diazepan-1-yl}-propionic acid ethyl ester in 80 ml of tetrahydrofuran/ethanol (1:1) was treated at 0° C. with 16.94 ml (16.94 mmol) of 1 M aq. lithium hydroxide solution, and kept 3 h at this temperature. The reaction was neutralized with cold aqueous 10% $KHSO_4$ and extracted with EtOAc (3×). The organic phases were washed with aqueous 10% NaCl, dried over $Na_2SO_4$ and evaporated to yield 3.20 g (98%) of the titled compound as white solid. MS: 385.0 ($MH^+$, 2Cl).

Intermediate 6

(rac)-2-{4-[(E)-3-(3,4-Dichloro-phenyl)-acryloyl]-7-oxo-[1,4]diazepan-1-yl}-4-hydroxy-butyric acid methyl ester

A) (rac)-4-(tert-Butyl-dimethyl-silanyloxy)-2-{4-[(E)-3-(3,4-dichloro-phenyl)-acryloyl]-7-oxo-[1,4]diazepan-1-yl}-butyric acid methyl ester A suspension of 0.313 g (0.100 mmol) of 1-[(E)-3-(3,4-dichloro-phenyl)-acryloyl]-[1,4]diazepan-5-one (intermediate 5A) in 10 ml of THF was treated at 0° C. with 0.135 g (0.120 mmol) of potassium tert-butylate. After 10 min, 0.394 g (0.110 mmol) of (rac)-4-(tert-butyl-dimethyl-silanyloxy)-2-iodo-butyric acid methyl ester (intermediate 1) was added. The reaction was stirred 1 h at 0° C., 15 h at RT and then neutralized with cold 10% aq. potassium hydrogensulfate solution and extracted with diethyl ether (3×). The organic phases were washed with sat. aq. sodium hydrogencarbonate solution, 10% aq. sodium chloride solution, dried over $Na_2SO_4$ evaporated and purified by flash silica gel column (n-heptane/ethyl acetate 1:1 to 2:3) to yield 0.19 g (35%) of the titled compound as light yellow viscous oil. MS: 543.3 ($MH^+$, 2Cl).

B) (rac)-2-{4-[(E)-3-(3,4-Dichloro-phenyl)-acryloyl]-7-oxo-[1,4]diazepan-1-yl}-4-hydroxy-butyric acid methyl ester A solution of 0.175 g (0.320 mmol) of (rac)-4-(tert-butyl-dimethyl-silanyloxy)-2-{4-[(E)-3-(3,4-dichloro-phenyl)-acryloyl]-7-oxo-[1,4]diazepan-1-yl}-butyric acid methyl ester in 4.9 ml of methanol was treated at 0° C. with 0.8 ml (3.22 mmol, 4 M in dioxane) of HCl and kept 1.5 h at RT. Extraction with cold sat. aq. sodium hydrogencarbonate solution and diethyl ether (2×) followed by drying ($Na_2SO_4$) and evaporation gave 0.165 g (quantitative) of the titled compound together with 50% of the lactone (1-[(E)-3-(3,4-dichloro-phenyl)-acryloyl]-4-(2-oxo-tetrahydro-furan-3-yl)-[1,4]diazepan-5-one) as a white gum. MS: 429.3 ($MH^+$, 2Cl).

Intermediate 7 rac-(2-{4-[(E)-3-(3,4-Dichloro-phenyl)-acryloyl]-7-oxo-[1,4]diazepan-1-yl}-succinic acid 1-methyl ester)

A) {4-[(E)-3-(3,4-Dichloro-phenyl)-acryloyl]-7-oxo-[1,4]diazepan-1-yl}-acetic acid methyl ester A suspension of 2.60 g (8.30 mmol) of 1-[(E)-3-(3,4-dichloro-phenyl)-acryloyl]-[1,4]diazepan-5-one (intermediate 5A) in 46 ml of THF was treated slowly at −78° C. with 9.30 ml (9.30 mmol) of lithium hexamethyldisilylazide 1M in THF. After 20 min at −78° C., the mixture was warmed to nearly −10° C. to go entirely in solution and cooled to −78° C. just after. Then, a solution of 1.18 ml (12.45 mmol) of methyl bromoacetate in 15 ml of THF was added dropwise. Over night, the solution was naturally warmed to RT, poured on aqueous 10% $KHSO_4$ solution and extracted with EtOAc (3×). The organic phase was dried ($Na_2SO_4$) and evaporated to give 3.21 g (quant.) of the titled compound as a light brown solid containing max 5% of methyl bromoacetate. MS: 385.3 ($MH^+$, 2Cl).

B) 2-{4-[(E)-3-(3,4-Dichloro-phenyl)-acryloyl]-7-oxo-[1,4]diazepan-1-yl}-succinic acid 4-tert-butyl ester 1-methyl ester A solution of 0.50 g (1.30 mmol) of {4-[(E)-3-(3,4-dichloro-phenyl)-acryloyl]-7-oxo-[1,4]diazepan-1-yl}-acetic acid methyl ester in 25 ml of THF was treated slowly at −78° C. with 1.48 ml (1.48 mmol) of lithium hexamethyldisilylazide 1M in THF. After 30 min at −78° C., a solution of 0.67 ml (4.54 mmol) of tert-butyl bromoacetate in 2.5 ml of THF was added dropwise. The solution was stirred at −78° C. for 5 h, poured on cooled aqueous 10% $KHSO_4$ solution and extracted with $Et_2O$ (3×). The organic phases were washed with aqueous 10% NaCl, dried ($Na_2SO_4$) and evaporated. The residue was purified on a $SiO_2$-column (n-heptane/EtOAc 1:1 to 2:3) to afford the titled compound in 18% yield as light yellow foam. MS: 499.1 ($MH^+$, 2Cl).

C) 2-{4-[(E)-3-(3,4-Dichloro-phenyl)-acryloyl]-7-oxo-[1,4]diazepan-1-yl}-succinic acid 1-methyl ester A solution of 0.30 g (0.60 mmol) of) 2-{4-[(E)-3-(3,4-dichloro-phenyl)-acryloyl]-7-oxo-[1,4]diazepan-1-yl}-succinic acid 4-tert-butyl ester 1-methyl ester in 1.2 ml of dioxane was cooled down to ~6° C. and 1.50 ml (6.01 mmol) of hydrochloric acid 4M in dioxane, then 1 drop of water were added and stirring was continued overnight at RT. The solution was evaporated, dissolved in acetonitrile and evaporated (2×) to give the titled compound in quant. yield as yellow oil. MS: 441.2 ($M-H^-$, 2Cl).

Intermediate 8 rac-(2-{4-[(E)-3-(3-Chloro-phenyl)-acryloyl]-7-oxo-[1,4]diazepan-1-yl}-succinic acid 1-methyl ester)

A) 1-[(E)-3-(3-Chloro-phenyl)-acryloyl]-[1,4]diazepan-5-one

A solution of 20.00 g (109.52 mmol) of (E)-3-chlorocinnamic acid in 500 ml of dichloromethane was treated at RT with 6 drops of DMF. 10.08 ml (115.00 mmol) of oxalyl chloride in 60 ml dichloromethane were added dropwise and stirring was continued for 3 h30. The solution was evaporated, redissolved in 400 ml of dichloromethane, cooled (0° C.) and treated with a solution of 12.50 g (109.52 mmol) of [1,4]diazepan-5-one and 30.49 ml (219.05 mmol) of triethylamine in 190 ml of dichloromethane. The reaction was warmed up over night to RT and then evaporated. The precipitate was suspended in 90 ml of water, stirred 30 min, and filtered, washed with water to give, after drying under reduced pressure overnight, 28.03 g (92%) of the titled compound as a off-white powder. MS: 278.9 ($MH^+$, 1Cl).

B) {4-[(E)-3-(3-Chloro-phenyl)-acryloyl]-7-oxo-[1,4]azepan-1-yl}-acetic acid methyl ester In analogy to the procedure described in intermediate 7A, 1-[(E)-3-(3-chloro-phenyl)-acryloyl]-[1,4]diazepan-5-one gave, after purification on a $SiO_2$-column (n-heptane/EtOAc 4:1-0:1 gradient then EtOAc/MeOH 98:2), the titled compound in 85% yield as white foam. MS: 351.1 ($MH^+$, 1Cl).

C) 2-{4-[(E)-3-(3-Chloro-phenyl)-acryloyl]-7-oxo-[1,4]diazepan-1-yl}-succinic acid 4-tert-butyl ester 1-methyl ester In analogy to the procedure described in intermediate 7B, {4-[(E)-3-(3-chloro-phenyl)-acryloyl]-7-oxo-[1,4]diazepan- 1-yl}-acetic acid methyl ester gave, after purification on a SiO$_2$-column (n-heptane/EtOAc 1:1-0:1 gradient), the titled compound in 20% yield as white foam. MS: 351.1 (MH$^+$, 1Cl).

D) 2-{4-[(E)-3-(3-Chloro-phenyl)-acryloyl]-7-oxo-[1,4]diazepan-1-yl}-succinic acid 1-methyl ester In analogy to the procedure described in intermediate 7C, 2-{4-[(E)-3-(3-chloro-phenyl)-acryloyl]-7-oxo-[1,4]diazepan-1-yl}-succinic acid 4-tert-butyl ester 1-methyl ester gave the titled compound in quant. yield as light yellow foam. MS: 407.2 (M−H$^−$, 1Cl).

Intermediate 9

(cis)-(rac)-3,4-Bis-(tert-butyl-dimethyl-silanyloxy)-piperidine

Prepared via (cis)-(rac)-3,4-dihydroxy-piperidine-1-carboxylic acid benzyl ester (*Tetrahedron* 2006, 62, 3284-3291), followed by silylation (tert-Butyl-chloro-dimethyl-silane/imidazol in DMF) and hydrogenation (10% Pd/C, H$_2$ in ethanol).

Intermediate 10

(rac, cis)-4-Hydroxymethyl-4-methyl-piperidin-3-ol; hydrochloride

A) (rac)-1-Benzyl-4-methyl-3-oxo-piperidine-4-carboxylic acid ethyl ester

A milky solution of 7.75 g (69.02 mmol) of potassium tert-butylate in 125 ml of THF was cooled (0° C.) and treated portion wise with 10.44 g (34.00 mmol) of ethyl-N-benzyl-3-oxo-4-piperidin-carboxylate hydrochloride so the temperature did not rise over 5° C. After 1 h at RT, the reaction was cooled (0° C.) and ad treated slowly with 5.07 ml (35.70 mmol) of iodomethane in 4 ml of THF. After 4.5 h at RT, the reaction was cooled (0° C.) and neutralized with 40 ml of aqueous saturated NH$_4$Cl solution. The aqueous phase was extracted with Et$_2$O (3×). The organic phases were washed with aqueous saturated NaCl, dried over Na$_2$SO$_4$ and evaporated to give 4.97 g (53%) of the titled compound as orange oil. MS: 276.1 (MH$^+$).

B) (rac, cis)-1-Benzyl-4-hydroxymethyl-4-methyl-piperidin-3-ol and (rac, trans)-1-Benzyl-4-hydroxymethyl-4-methyl-piperidin-3-ol 24.33 ml (1.2 M in toluene, 29.20 mmol) of DIBALH was dropped to a dry ice cooled (−30° C.) solution of 2.01 g (7.30 mmol) (rac)-1-benzyl-4-methyl-3-oxo-piperidine-4-carboxylic acid ethyl ester in 37 ml of THF. Over night, the solution was naturally warmed to RT, cooled (0° C.) and treated again with 6.08 ml (1.2 M in toluene, 7.30 mmol) of DIBALH. After 4 h at RT, the reaction was neutralized with ice cooled aqueous 10% KHSO$_4$ solution. The mixture was extracted with ether (3×), the organic phases were washed with aqueous 10% KHSO$_4$ and aqueous 10% NaCl solution, dried (Na$_2$SO$_4$) and evaporated to give after flash silica gel column (dichloromethane/MeOH 99:1 to 95:5) 0.28 g (16%) of (rac, cis)-1-benzyl-4-hydroxymethyl-4-methyl-piperidin-3-ol as a viscous orange oil, MS: 236.1 (MH$^+$), 0.20 g (12%) of a cis/trans mixture of (rac)-1-benzyl-4-hydroxymethyl-4-methyl-piperidin-3-ol and 0.19 g (11%) (rac, trans)-1-benzyl-4-hydroxymethyl-4-methyl-piperidin-3-ol as a viscous orange oil. MS: 236.3 (MH$^+$)

C) (rac, cis)-4-Hydroxymethyl-4-methyl-piperidin-3-ol; hydrochloride

Hydrogenation of (rac, cis)-1-benzyl-4-hydroxymethyl-4-methyl-piperidin-3-ol with 1 equivalent of aqueous 1N HCl and Pd/C (10%) over H$_2$-atmosphere in MeOH gave the titled compound as light yellow solid. MS: 146.1 (MH$^+$).

Intermediate 11

(3SR, 4SR)-4-Fluoro-piperidin-3-ol; hydrochloride

A) (3SR,4SR)-4-Fluoro-piperidin-3-ol-1-carboxylic acid tert-butyl ester (rac)-7-Oxa-3-aza-bicyclo[4.1.0]heptane-3-carboxylic acid tert-butyl ester (*Heterocycles* 1994, 39, 163) (2.0 g, 10 mmol) was dissolved in a mixture of DCE (1.5 ml) and trisHF.Et$_3$N (1.6 g, 10 mmol) and heated to 80° C. for 12 h after which time the reaction was diluted with dichloromethane, washed with sat. NaHCO$_3$, then sat. NH$_4$Cl, dried (Na$_2$SO$_4$) and concentrated. Purification by flash column chromatography (EtOAc:n-heptane 3:7) afforded the titled compound (1.5 g, 66%) as a yellow liquid. MS: 220.1 (MH$^+$). Also obtained was the regioisomer (rac, trans)-3-fluoro-4-hydroxy-piperidine-1-carboxylic acid tert-butyl ester (0.26 g, 12%) as a yellow oil. MS: 220.1 (MH$^+$).

B) (3SR,4SR)-4-Fluoro-piperidin-3-ol; hydrochloride (rac, trans)-4-Fluoro-piperidin-3-ol-1-carboxylic acid tert-butyl ester (0.5 g, 2 mmol) was deprotected with HCl in dioxane affording the titled product (0.34 g, 95%) as a white powder. MS: 120.1 (MH$^+$).

Intermediate 12

3-[(S)-4-(3,4-Dichloro-phenylcarbamoyl)-3-methyl-2-oxo-piperazin-1-yl]-propionic acid A) (S)-2-(2,2-Dimethoxy-ethylamino)-propionic acid methyl ester To a solution of L-alanine methyl ester hydrochloride (5.00 g, 35.8 mmol) in methanol (100 mL) were added at 0° C. dimethoxyaldehyde (45% solution in tert-butyl methyl ether, 12.0 mL, 47 mmol) magnesium sulfate (38.8 g, 322 mmol), and sodium cyanoborohydride (3.08 g, 46.6 mmol). The ice bath was removed, then after 16 h the excess reagent was destroyed by careful addition of sat. aq. sodium hydrogencarbonate solution at 0° C. The reaction mixture was partitioned between sat. aq. sodium hydrogencarbonate solution and ethyl acetate. The organic layer was washed with brine, dried (MgSO$_4$), filtered, and evaporated to afford the titled compound (5.50 g, 80%). Light yellow liquid, MS (ISP)=192.2 (M+H)$^+$.

B) (S)-2-[Benzyloxycarbonyl-(2,2-dimethoxy-ethyl)-amino]-propionic acid methyl ester Benzyl chloroformate (4.46 g, 24.8 mmol) was added at 0° C. to a mixture of (S)-2-(2,2-dimethoxy-ethylamino)-propionic acid methyl ester (4.75 g, 24.8 mmol) and sodium hydrogencarbonate (4.17 g, 49.7 mmol) in acetone (25 mL) and water (25 mL). The ice bath was removed, then after 2 h the reaction mixture was poured onto ice water and extracted with ethyl acetate. The organic layer was dried (MgSO$_4$), filtered, and evaporated. Chromatography (SiO$_2$; heptane-ethyl acetate gradient afforded the titled compound (5.84 g, 72%). Yellow oil, MS (ISP)=348.2 (M+Na)$^+$.

C) (S)-2-[Benzyloxycarbonyl-(2-oxo-ethyl)-amino]-propionic acid methyl ester

A solution of (S)-2-[benzyloxycarbonyl-(2,2-dimethoxy-ethyl)-amino]-propionic acid methyl ester (26.0 g, 80.0 mmol) and pyridinium toluene-4-sulfonate (10.0 g, 40.0 mmol) in 2-butanone (260 mL) and water (8.6 mL, 0.48 mol) was heated under reflux for 16 h, then the solution was partitioned between ethyl acetate and water. The organic layer was washed with brine, dried (MgSO$_4$), filtered, and evaporated to afford the titled compound (24.3 g), which was directly used in the next step. Yellow oil, MS (ISP)=348.3 (M+Na)$^+$.

D) (S)-4-(2-tert-Butoxycarbonyl-ethyl)-2-methyl-3-oxo-piperazine-1-carboxylic acid benzyl ester A solution of (S)-2-[benzyloxycarbonyl-(2-oxo-ethyl)-amino]-propionic acid methyl ester (1.25 g, 4.50 mmol) in dichloromethane (25 mL) was added at room temperature dropewise to a suspension of 3-amino-propionic acid tert-butyl ester hydrochloride (0.86 g, 4.70 mmol), triethylamine (0.66 ml, 4.70 mmol), acetic acid (0.51, 9.00 mmol), and sodium triacetoxyborohydride (1.09 g, 5.10 mmol) in dichloromethane (12.5 mL) and stirred over night. The reaction was extracted with aqueous 10% KHSO$_4$/EtOAc (3x). The organic phases were washed with aqueous saturated NaHCO$_3$, 10% NaCl and dried over Na$_2$SO$_4$ to yield after evaporation of the solvent 1.21 g (58%) of the titled compound as light yellow oil. MS: 377.3 (MH$^+$)

E) 3-((S)-3-Methyl-2-oxo-piperazin-1-yl)-propionic acid tert-butyl ester with 0.1 HCl A solution of 1.19 g (3.20 mmol) (S)-4-(2-tert-butoxycarbonyl-ethyl)-2-methyl-3-oxo-piperazine-1-carboxylic acid benzyl ester in 15 ml of methanol was treated with a solution of 0.32 ml of 1 M aq. hydrochloric acid solution and 0.12 g of Pd/C (10%) and was stirred over H$_2$-atmosphere for 1 h. After filtration, the solution was evaporated, dissolved in dichloromethane, dried (Na$_2$SO$_4$) and evaporated under reduced pressure to yield 0.77 g (90%) of the titled compound as light yellow oil. MS: 243.3 (MH$^+$).

F) 3-[(S)-4-(3,4-Dichloro-phenylcarbamoyl)-3-methyl-2-oxo-piperazin-1-yl]-propionic acid tert-butyl ester A solution of 0.75 g (3.10 mmol) of 3-((S)-3-methyl-2-oxo-piperazin-1-yl)-propionic acid tert-butyl ester with 0.1HCl in 16 ml of dichloromethane was treated at 0° C. with 0.70 g (3.70 mmol) of 3,4-dichlorophenyl isocyanate and 0.52 ml (3.70 mmol) of triethylamine. After 30 min the reaction was warmed to room temperature and extracted with aqueous 10% KHSO$_4$/EtOAc (3x). The organic phases were washed with aqueous saturated NaHCO$_3$, 10% NaCl and dried over Na$_2$SO$_4$ to yield after purification by flash silica gel column (EtOAc/n-heptane 1:2 to 3:1) 0.91 g (68%) of the titled compound as white foam. MS: 374.1 (MH$^+$, 2Cl).

G) 3-[(S)-4-(3,4-Dichloro-phenylcarbamoyl)-3-methyl-2-oxo-piperazin-1-yl]-propionic acid A solution of 0.45 g (1.10 mmol) of 3-[(S)-4-(3,4-dichloro-phenylcarbamoyl)-3-methyl-2-oxo-piperazin-1-yl]-propionic acid tert-butyl ester in 3.0 ml of dichloromethane was treated at 0° C. with 5.40 ml (21.60 mmol, 4 M in dioxane) of HCl and stirred and warmed up to RT over night. The reaction was evaporated, dissolved in toluene and evaporated (3x) to give 0.52 g (quant.) of the titled compound as light yellow foam. MS: 372.1 (M−H$^−$, 2Cl).

Intermediate 13

(S)-1-[4-((S)-4-Hydroxy-6-aza-spiro[2.5]oct-6-yl)-4-oxo-butyl]-3-methyl-piperazin-2-one A) (S)-4-(3-tert-Butoxycarbonyl-propyl)-2-methyl-3-oxo-piperazine-1-carboxylic acid benzyl ester In analogy to intermediate 12D, (S)-2-[benzyloxycarbonyl-(2-oxo-ethyl)-amino]-propionic acid methyl ester (intermediate 12C) and 4-amino-butyric acid tert-butyl ester hydrochloride gave the titled compound in 98% yield as orange oil. MS: 413.2 (M+Na$^+$).

B) (S)-4-(3-Carboxy-propyl)-2-methyl-3-oxo-piperazine-1-carboxylic acid benzyl ester In analogy to intermediate 12G, (S)-4-(3-tert-butoxycarbonyl-propyl)-2-methyl-3-oxo-piperazine-1-carboxylic acid benzyl ester gave the titled compound in quantitative yield as brown oil. MS: 335.2 (MH$^+$).

C) (S)-4-[4-((S)-4-Hydroxy-6-aza-spiro[2.5]oct-6-yl)-4-oxo-butyl]-2-methyl-3-oxo-piperazine-1-carboxylic acid benzyl ester In analogy to the procedure described in Example 15, (S)-4-(3-carboxy-propyl)-2-methyl-3-oxo-piperazine-1-carboxylic acid benzyl ester and 1.1 eq. of (S)-6-aza-spiro[2.5]octan-4-ol; hydrochloride (intermediate 2) gave after flash chromatography (SiO$_2$, EtOAc/2-propanol 100% EtOAc to 1/2) the titled compound in 64% yield as light yellow foam. MS: 444.2 (MH$^+$).

D) (S)-1-[4-((S)-4-Hydroxy-6-aza-spiro[2.5]oct-6-yl)-4-oxo-butyl]-3-methyl-piperazin-2-one In analogy to intermediate 12E, (S)-4-[4-((S)-4-hydroxy-6-aza-spiro[2.5]oct-6-yl)-4-oxo-butyl]-2-methyl-3-oxo-piperazine-1-carboxylic acid benzyl ester was hydrogenated without aqueous HCl to give the titled compound in 98% yield as light yellow oil. MS: 310.2 (MH$^+$).

Intermediate 14

1-Isocyanato-4-trifluoromethoxy-benzene

To a solution of 0.41 ml (3.00 mmol) of 4-(trifluoromethoxy)aniline in 5.4 ml of THF was added 0.22 ml (1.80 mmol) of trichloromethyl chloroformate an heated to reflux for 45 min. The solution was evaporated under reduced pressure, dissolved in toluene and evaporated (2×) to give 0.60 g (99%) of the titled compound as pink solid. MS: 203 M⁺.

Intermediate 15

1-Isocyanato-3-trifluoromethoxy-benzene

In analogy to intermediate 14, 3-(trifluoromethoxy)aniline gave 97% of the titled compound as white solid. MS: 203 M⁺.

Intermediate 16

2-Chloro-4-isocyanato-1-trifluoromethyl-benzene

In analogy to intermediate 14, 3-chloro-4-(trifluoromethyl)aniline gave 73% of the titled compound as light brown oil. MS: 221 (M⁺, 10).

Intermediate 17

2-Chloro-4-isocyanato-1-trifluoromethoxy-benzene

In analogy to intermediate 14, 3-chloro-4-(trifluoromethoxy)aniline gave 86% of the titled compound as light brown oil. MS: 237 (M⁺, 1Cl).

Intermediate 18

1-Chloro-4-isocyanato-2-trifluoromethoxy-benzene

In analogy to intermediate 14, 4-chloro-3-(trifluoromethoxy)aniline gave 87% of the titled compound as light brown oil. MS: 237 (M⁺, 1Cl).

Intermediate 19

4-[(S)-4-(3-Chloro-phenylcarbamoyl)-3-methyl-2-oxo-piperazin-1-yl]-butyric acid

A) 4-[(S)-4-(3-Chloro-phenylcarbamoyl)-3-methyl-2-oxo-piperazin-1-yl]-butyric acid tert-butyl ester In analogy to example 25, 3-((S)-3-methyl-2-oxo-piperazin-1-yl)-propionic acid tert-butyl ester with 0.1HCl (intermediate 12E) and 3-chlorophenyl isocyanate gave 79% of the titled compound as white foam. MS: 354.12 (M-tBu+H⁺, 1Cl).

B) 4-[(S)-4-(3-Chloro-phenylcarbamoyl)-3-methyl-2-oxo-piperazin-1-yl]-butyric acid In analogy to intermediate 12G, 4-[(S)-4-(3-chloro-phenylcarbamoyl)-3-methyl-2-oxo-piperazin-1-yl]-butyric acid tert-butyl ester and HCl in dioxane gave quantitative the titled compound as white foam. MS: 354.12 (MH⁺, 1Cl).

Intermediate 20

2-Oxa-7-aza-spiro[3.5]nonane trifluoro-acetic acid salt

Trifluoroacetic acid (125 mg, 1.1 mmol) was added at 0° C. to a solution of 2-oxa-7-azaspiro[3.5]nonane-7-carboxylic acid tert-butyl ester (U.S. Pat. No. 7,105,507 B2; 50 mg, 0.22 mmol) in dichloromethane, then after 1 h the reaction mixture was concentrated to afford the title compound (83 mg), which contained approximately one additional equivalent of trifluoroacetic acid. Colorless oil, ¹H-NMR (300 MHz, DMSO-d₆): 8.4 (br. s, 2H), 4.32 (s, 4H), 3.05-2.95 (m, 4H), 1.95-1.9 (m, 4H).

Intermediate 21

(S)-1-[5-((S)-4-Hydroxy-6-aza-spiro[2.5]oct-6-yl)-5-oxo-pentyl]-3-methyl-piperazin-2-one A) (S)-4-(4-tert-Butoxycarbonyl-butyl)-2-methyl-3-oxo-piperazine-1-carboxylic acid benzyl ester In analogy to intermediate 12D, (S)-2-[benzyloxycarbonyl-(2-oxo-ethyl)-amino]-propionic acid methyl ester (intermediate 12C) and 4-amino-pentanoic acid tert-butyl ester hydrochloride gave the titled compound in 86% yield as light yellow oil. MS: 349.18 (MH⁺).

B) (S)-4-(4-Carboxy-butyl)-2-methyl-3-oxo-piperazine-1-carboxylic acid benzyl ester In analogy to intermediate 12G, (S)-4-(4-tert-butoxycarbonyl-butyl)-2-methyl-3-oxo-piperazine-1-carboxylic acid benzyl ester and HCl in dioxane gave the titled compound in 99% yield as brown oil. MS: 349.18 (MH⁺).

C) (S)-4-[5-((S)-4-Hydroxy-6-aza-spiro[2.5]oct-6-yl)-5-oxo-pentyl]-2-methyl-3-oxo-piperazine-1-carboxylic acid benzyl ester In analogy to the procedure described in Example 15, (S)-4-(4-carboxy-butyl)-2-methyl-3-oxo-piperazine-1-carboxylic acid benzyl ester and 1.1 eq. of (S)-6-aza-spiro[2.5]octan-4-ol; hydrochloride (intermediate 2) gave after flash chromatography (SiO₂, dichloromethane/MeOH 100% dichloromethane to 85/15) the titled compound in 61% yield as light yellow amorphous solid. MS: 458.26 (MH⁺).

D) (S)-1-[5-((S)-4-Hydroxy-6-aza-spiro[2.5]oct-6-yl)-5-oxo-pentyl]-3-methyl-piperazin-2-one In analogy to intermediate 12E, (S)-4-[5-((S)-4-hydroxy-6-aza-spiro[2.5]oct-6-yl)-5-oxo-pentyl]-2-methyl-3-oxo-piperazine-1-carboxylic acid benzyl ester was hydrogenated without aqueous HCl to give the titled compound in 83% yield as light yellow oil. MS: 324.23 (MH⁺).

Intermediate 22

(rac)-4-Amino-3-hydroxy-butyric acid methyl ester; HCl 1.95 ml (27.40 mmol) of acetylchloride was carefully added at 0° C. to 20 ml of MeOH followed by 1.19 g (10.00 mmol) of DL-4-amino-3-hydroxybutyric acid. Stirring was continued for 2 h at 0° C., the reaction was then evaporated and dried under reduced pressure to yield 1.76 g (quantitative) of the titled compound as colorless viscous oil. MS: 134.08 (MH⁺).

Intermediate 23

(S)-1-[(R,S)-2-Hydroxy-4-((S)-4-hydroxy-6-aza-spiro[2.5]oct-6-yl)-4-oxo-butyl]-3-methyl-piperazin-2-one A) (S)-4-((R,S)-2-Hydroxy-3-methoxycarbonyl-propyl)-2-methyl-3-oxo-piperazine-1-carboxylic acid benzyl ester Note: Both starting materials were evaporated with toluene (2×) before using!

A solution of 0.88 g (5.18 mmol) of (rac)-4-amino-3-hydroxy-butyric acid methyl ester; HCl (intermediate 22) and 1.38 ml (9.89 mmol) of triethylamine in 23.6 ml of dichloromethane at 0° C. was treated dropwise (10 min) with a solution of 1.31 ml (10.36 mmol) chlorotrimethylsilane in 11.8 ml of dichloromethane. The cooling bath was removed and after 1.5 h at RT the solvent was evaporated under reduced pressure.

The crude product was suspended in 23.6 ml of dichloromethane and 0.70 ml (4.94 mmol) of triethylamine, 0.54 ml (9.42 mmol) of AcOH (pH~5) and 1.18 g (5.41 mmol) of sodium triacetoxyborohydride were added. The reaction was cooled (0° C.) and treated dropwise over 20 min with (S)-2-[benzyloxycarbonyl-(2-oxo-ethyl)-amino]-propionic acid methyl ester (intermediate 12C) in 20 ml of dichloromethane. The cooling bath was removed and the reaction was stirred overnight at RT. The reaction was poured on aqueous 10% $KHSO_4/Et_2O$ (3×). The organic phases were washed with aqueous saturated $NaHCO_3$ (2×), 10% NaCl and dried over $Na_2SO_4$ to yield after evaporation 1.83 g of the crude compound as yellow oil. This oil was dissolved in 80 ml of THF, 40 ml of 25% AcOH were added, and after 1.5 h the mixture was extracted with aqueous 10% $KHSO_4/Et_2O$ (3×). The organic phases were washed with aqueous saturated $NaHCO_3$ (2×), 10% NaCl and dried over $Na_2SO_4$ to yield after flash chromatography ($SiO_2$, n-heptane/AcOEt 2:1 to 1:4) 1.15 g (61%) of the titled compound as colorless viscous oil. MS: 365.17 ($MH^+$).

B) (S)-4-((R,S)-3-Carboxy-2-hydroxy-propyl)-2-methyl-3-oxo-piperazine-1-carboxylic acid benzyl ester A solution of 0.91 g (2.50 mmol) of (S)-4-((R,S)-2-hydroxy-3-methoxycarbonyl-propyl)-2-methyl-3-oxo-piperazine-1-carboxylic acid benzyl ester in 12.6 ml of tetrahydrofuran/ethanol (1:1) was treated at 0° C. with 5.0 ml (5.00 mmol) of 1 M aq. lithium hydroxide solution, and stirred 1.5 h at RT. The reaction was neutralized with cold aqueous 10% $KHSO_4$ and extracted with $Et_2O$ (3×). The organic phases were washed with aqueous 10% NaCl, dried over $Na_2SO_4$ and evaporated to yield after precipitation (dichloromethane/n-pentane) 0.66 g (75%) of the titled compound as light yellow viscous oil. MS: 351.15 ($MH^+$).

C) (S)-4-[(R,S)-2-Hydroxy-4-((S)-4-hydroxy-6-aza-spiro[2.5]oct-6-yl)-4-oxo-butyl]-2-methyl-3-oxo-piperazine-1-carboxylic acid benzyl ester In analogy to the procedure described in Example 15, (S)-4-((R,S)-3-carboxy-2-hydroxy-propyl)-2-methyl-3-oxo-piperazine-1-carboxylic acid benzyl ester and 1.1 eq. of (S)-6-aza-spiro[2.5]octan-4-ol; hydrochloride (intermediate 2) gave after precipitation (dichlromethane/n-pentane) the titled compound in quantitative yield as off-white solid. MS: 460.24 ($MH^+$).

D) (S)-1-[(R,S)-2-Hydroxy-4-((S)-4-hydroxy-6-aza-spiro[2.5]oct-6-yl)-4-oxo-butyl]-3-methyl-piperazin-2-one In analogy to intermediate 12E, (S)-4-[(R,S)-2-hydroxy-4-((S)-4-hydroxy-6-aza-spiro[2.5]oct-6-yl)-4-oxo-butyl]-2-methyl-3-oxo-piperazine-1-carboxylic acid benzyl ester was hydrogenated without aqueous HCl to give after precipitation (dichloromethane/$Et_2O$) the titled compound in quantitative yield as white amorphous solid. MS: 326.20 ($MH^+$).

Intermediate 24

(S)-4-Amino-3-hydroxy-butyric acid methyl ester, hydrochloride

In analogy to intermediate 22, (S)-(+)-4-amino-3-hydroxybutyric acid and acetylchloride in MeOH gave quantitative the titled compound as light yellow oil. MS: 134.08 ($MH^+$).

Intermediate 25

(S)-1-[(S)-2-Hydroxy-4-((S)-4-hydroxy-6-aza-spiro[2.5]oct-6-yl)-4-oxo-butyl]-3-methyl-piperazin-2-one A) (S)-4-((S)-2-Hydroxy-3-methoxycarbonyl-propyl)-2-methyl-3-oxo-piperazine-1-carboxylic acid benzyl ester In analogy to the procedure described in Example 12D, (S)-2-[benzyloxycarbonyl-(2-oxo-ethyl)-amino]-propionic acid methyl ester (intermediate 12C) and (S)-4-amino-3-hydroxy-butyric acid methyl ester, hydrochloride (intermediate 24) gave the titled compound in 59% yield as light yellow oil. MS: 365.17 ($MH^+$).

B) (S)-4-((S)-3-Carboxy-2-hydroxy-propyl)-2-methyl-3-oxo-piperazine-1-carboxylic acid benzyl ester In analogy to the procedure described in Example 23B, (S)-4-((S)-2-hydroxy-3-methoxycarbonyl-propyl)-2-methyl-3-oxo-piperazine-1-carboxylic acid benzyl ester and 1 M aq. lithium hydroxide solution gave after extraction with EtOAc and precipitation (dichloromethane/n-pentane) the titled compound in 81% yield as light yellow waxy solid. MS: 351.15 ($MH^+$).

C) (S)-4-[(S)-2-Hydroxy-4-((S)-4-hydroxy-6-aza-spiro[2.5]oct-6-yl)-4-oxo-butyl]-2-methyl-3-oxo-piperazine-1-carboxylic acid benzyl ester In analogy to the procedure described in Example 15, (S)-4-((S)-3-carboxy-2-hydroxy-propyl)-2-methyl-3-oxo-piperazine-1-carboxylic acid benzyl ester and 1.1 eq. of (S)-6-aza-spiro[2.5]octan-4-ol; hydrochloride (intermediate 2) gave after precipitation (dichlromethane/n-pentane) the titled compound in 87% yield as white solid. MS: 460.24 ($MH^+$).

D) (S)-1-[(S)-2-Hydroxy-4-((S)-4-hydroxy-6-aza-spiro[2.5]oct-6-yl)-4-oxo-butyl]-3-methyl-piperazin-2-one In analogy to intermediate 12E, (S)-4-[(S)-2-hydroxy-4-((S)-4-hydroxy-6-aza-spiro[2.5]oct-6-yl)-4-oxo-butyl]-2-methyl-3-oxo-piperazine-1-carboxylic acid benzyl ester was hydrogenated without aqueous HCl to give the titled compound in 64% yield as off-white waxy solid. MS: 326.21 ($MH^+$).

Intermediate 26

4-Isocyanato-1,2-bis-trifluoromethyl-benzene

In analogy to intermediate 14, 3,4-bis(trifluoromethyl)aniline gave 79% of the titled compound as yellow solid. MS: 255 (M$^+$).

Intermediate 27

4-Amino-2,2-dimethyl-butyric acid methyl ester, hydrochloride

In analogy to intermediate 22, 4-amino-2,2-dimethylbutyric acid and acetylchloride in MeOH gave the titled compound in 98% as off-white solid. MS: 146.12 (MH$^+$).

Intermediate 28

(S)-1-[4-((S)-4-Hydroxy-6-aza-spiro[2.5]oct-6-yl)-3,3-dimethyl-4-oxo-butyl]-3-methyl-piperazin-2-one

A) (S)-4-(3-Methoxycarbonyl-3-methyl-butyl)-2-methyl-3-oxo-piperazine-1-carboxylic acid benzyl ester In analogy to the procedure described in Example 12D, (S)-2-[benzyloxycarbonyl-(2-oxo-ethyl)-amino]-propionic acid methyl ester (intermediate 12C) and 4-amino-2,2-dimethyl-butyric acid methyl ester, hydrochloride (intermediate 27) gave the titled compound in 90% yield as light yellow oil. MS: 377.21 (MH$^+$).

B) (S)-4-(3-Carboxy-3-methyl-butyl)-2-methyl-3-oxo-piperazine-1-carboxylic acid benzyl ester In analogy to the procedure described in Example 23B, (S)-4-(3-methoxycarbonyl-3-methyl-butyl)-2-methyl-3-oxo-piperazine-1-carboxylic acid benzyl ester and 1 M aq. lithium hydroxide solution gave the titled compound in 70% yield as light yellow oil. MS: 363.19 (MH$^+$).

C) (S)-4-[4-((S)-4-Hydroxy-6-aza-spiro[2.5]oct-6-yl)-3,3-dimethyl-4-oxo-butyl]-2-methyl-3-oxo-piperazine-1-carboxylic acid benzyl ester In analogy to the procedure described in Example 15, (S)-4-(3-carboxy-3-methyl-butyl)-2-methyl-3-oxo-piperazine-1-carboxylic acid benzyl ester and 1.7 eq. of (S)-6-aza-spiro[2.5]octan-4-ol; hydrochloride (intermediate 2) gave after purification with flash chromatography (SiO$_2$, dichloromethane/methanol 98:2 to 95:5) the titled compound in 67% yield as light yellow foam. MS: 472.28 (MH$^+$).

D) (S)-1-[4-((S)-4-Hydroxy-6-aza-spiro[2.5]oct-6-yl)-3,3-dimethyl-4-oxo-butyl]-3-methyl-piperazin-2-one In analogy to intermediate 12E, (S)-4-[4-((S)-4-hydroxy-6-aza-spiro[2.5]oct-6-yl)-3,3-dimethyl-4-oxo-butyl]-2-methyl-3-oxo-piperazine-1-carboxylic acid benzyl ester was hydrogenated without aqueous HCl to give the titled compound in 99% yield as light yellow oil. MS: 338.24 (MH$^+$).

Intermediate 29

(S)-5-((S)-4-Hydroxy-6-aza-spiro[2.5]oct-6-yl)-2-((S)-3-methyl-2-oxo-piperazin-1-yl)-5-oxo-pentanoic acid methyl ester; hydrochloride

A) (S)-2-(S)-4-Benzyloxycarbonyl-3-methyl-2-oxo-piperazin-1-yl)-pentanedioic acid 5-tert-butyl ester 1-methyl ester In analogy to the procedure described in Example 12D, (S)-2-[benzyloxycarbonyl-(2-oxo-ethyl)-amino]-propionic acid methyl ester (intermediate 12C) and L-glutamic acid gamma-t-butyl ester alpha-methylester; hydrochloride gave the titled compound in 97% yield as light yellow oil. MS: 471.21 (M+Na$^+$).

B) (S)-2-(S)-4-Benzyloxycarbonyl-3-methyl-2-oxo-piperazin-1-yl)-pentanedioic acid 1-methyl ester In analogy to the procedure described in intermediate 12G, (S)-2-(S)-4-benzyloxycarbonyl-3-methyl-2-oxo-piperazin-1-yl)-pentanedioic acid 5-tert-butyl ester 1-methyl ester and HCl in dioxane gave the titled compound in 97% yield as brown oil. MS: 393.17 (MH$^+$)

C) (S)-4-[(S)-4-((S)-4-Hydroxy-6-aza-spiro[2.5]oct-6-yl)-1-methoxycarbonyl-4-oxo-butyl]-2-methyl-3-oxo-piperazine-1-carboxylic acid benzyl ester In analogy to the procedure described in Example 15, (S)-2-(S)-4-benzyloxycarbonyl-3-methyl-2-oxo-piperazin-1-yl)-pentanedioic acid 1-methyl ester and 1.1 eq. of (S)-6-aza-spiro[2.5]octan-4-ol; hydrochloride (intermediate 2) gave after purification with flash chromatography (SiO$_2$, dichloromethane/methanol 98:2 to 9:1) the titled compound in 71% yield as light brown oil. MS: 502.26 (MH$^+$).

D) (S)-5-((S)-4-Hydroxy-6-aza-spiro[2.5]oct-6-yl)-2-(S)-3-methyl-2-oxo-piperazin-1-yl)-5-oxo-pentanoic acid methyl ester; hydrochloride In analogy to intermediate 12E, (S)-4-[(S)-4-((S)-4-hydroxy-6-aza-spiro[2.5]oct-6-yl)-1-methoxycarbonyl-4-oxo-butyl]-2-methyl-3-oxo-piperazine-1-carboxylic acid benzyl ester was hydrogenated with 1 eq. of aqueous HCl to give after precipitation (dichloromethane/Et$_2$O) the titled compound in quantitative yield as off-white solid. MS: 366.20 (M−H).

Intermediate 30

4-(2,2-Dimethoxy-ethylamino)-butyric acid tert-butyl ester

To a cooled solution (0° C.) of 2.94 g (15.00 mmol) of 4-aminobutyric acid ter-butylester; hydrochloride in 75 ml of MeOH were added 2.51 ml (18.00 mmol) of dimethoxyacetaldehyde (45% solution in TBME), 3.86 ml (15.00 mmol) of triethylamine, 16.75 g (135.00 mmol) of magnesium sulfate, 3.43 ml (60.00 mmol) of AcOH and 1.29 g (19.50 mmol) of sodium cyanoborohydride (1.99 g, 31.6 mmol). The reaction was stirred 2 h at RT, another 0.39 ml (1.50 mmol) of dimethoxyacetaldehyde (45% solution in TBME) was added and after 1.5 h, the reaction mixture was partitioned between aqueous saturated NaHCO$_3$ and EtOAc/Et$_2$O (1:1) (3×). The organic phases were washed with aqueous saturated NaHCO$_3$, 10% NaCl and dried over Na$_2$SO$_4$ to yield after evaporation of the solvent 1.87 g (50%) of the titled compound as light yellow oil. MS: 248.18 (MH$^+$).

Intermediate 31

(R)-2-(3,4-Dichloro-phenylamino)-propionic acid (62% ee)

A mixture of 6.00 g (22.00 mmol) 3,4-dichloroiodobenzene, 2.94 g (33.00 mmol) D-alanine, 0.42 g (2.20 mmol) copper(I) iodide, 0.96 g (4.40 mmol) 2-hydroxybenzaldehyde phenylhydrazone, 14.00 g (66.00 mmol) tri-potassium phosphate in 32 ml of N,N-dimethylformamide was stirred at 80° C. for 16 h under argon, then after cooling diluted with water and acidified to pH 3 by addition of 25% aq. HCl solution. The mixture was extracted with EtOAc (3×), the organic phases were washed with brine, dried (Na$_2$SO$_4$), filtered and evaporated. Flash chromatography (SiO$_2$; dichloromethane/MeOH 95:5 to 4:1) afforded 3.11 g (60%) of the title compound (as 81:19 mixture of the (R) and (S) stereoisomers, BGB-175*0.25 column) as light brown solid. MS: 231.9 (M–H$^-$, 2Cl).

Intermediate 32

(S)-2-(3-Chloro-4-trifluoromethyl-phenylamino)-propionic acid (26% ee)

In analogy to intermediate 31, L-alanine and 4-bromo-2-chlorobenzotrifluoride gave 69% of the title compound (as 63:37 mixture of the (S) and (R) stereoisomers, BGB-175*0.25 column) as light brown solid. MS: 266.02 (M–H$^-$, Cl).

Intermediate 33

(S)-2-(4-Chloro-3-trifluoromethoxy-phenylamino)-propionic acid (22% ee)

In analogy to intermediate 31, L-alanine and 5-bromo-2-chloro(trifluoromethoxy)benzene gave 38% of the title compound (as 61:39 mixture of the (S) and (R) stereoisomers, BGB-175*0.25 column) as light brown solid. MS: 282.01 (M–H$^-$, Cl).

Intermediate 34

4-[(R)-4-(3-Chloro-4-trifluoromethyl-phenyl)-3-methyl-7-oxo-2,3,4,7-tetrahydro-[1,4]diazepin-1-yl]-butyric acid (22% ee)

A) (R)-2-(3-Chloro-4-trifluoromethyl-phenylamino)-propionic acid

In analogy to intermediate 31, D-alanine and 4-bromo-2-chlorobenzotrifluoride gave 73% of the title compound (as 61:39 mixture of the (R) and (S) stereoisomers, BGB-175*0.25 column) as yellow solid. MS: 266.02 (M–H$^-$, Cl).

B) (R)-2-(3-Chloro-4-trifluoromethyl-phenylamino)-propan-1-ol (22% ee)

20.55 ml (20.55 mmol, 1 M in THF) of a borane-tetrahydrofuran complex solution was added dropwise at 0° C. to a solution of 2.20 g (8.20 mmol) of (R)-2-(3-chloro-4-trifluoromethyl-phenylamino)-propionic acid (22% ee) in 33 ml THF, then after 10 min the ice bath was removed and the solution stirred for 2.5 h at RT. After cooling, 14 ml of MeOH and 0.7 ml of H$_2$SO$_4$ were added, and after 30 min at RT and 1 h at reflux the reaction mixture was concentrated in vacuo. The residue was partitioned between 1 M aq. sodium hydroxide saturated with NaCl solution and EtOAc (3×). The organic layer was washed with brine, dried (Na$_2$SO$_4$), filtered, and evaporated. Flash silica gel column (CH$_2$Cl$_2$/MeOH 99:1) afforded 1.94 g (93%) of the title compound as a 61:39 mixture of the (R) and (S) stereoisomers as yellow oil. MS: 252.04 (M–H$^-$, Cl)

C) 4-[(R)-2-(3-Chloro-4-trifluoromethyl-phenylamino)-propylamino]-butyric acid tert-butyl ester (22% ee)

To a solution of 0.36 ml (4.10 mmol) of oxalyl chloride in 10 ml CH$_2$Cl$_2$ at –50 to –60° C. was added a solution of 0.60 ml (8.50 mmol) dimethylsulfoxide in 2.4 ml of CH$_2$Cl$_2$ within 10 min. The solution was stirred for 5 min and a solution of 0.90 (3.50 mmol) (R)-2-(3-chloro-4-trifluoromethyl-phenylamino)-propan-1-ol (22% ee) in 10 ml of CH$_2$Cl$_2$ was added within 10 min. The mixture was stirred for 15 min and 2.47 ml (17.70 mmol) of triethylamine were added within 20 min. The suspension was stirred for 75 min and slowly warmed to 0° C. (complete oxidation followed by TLC, SiO$_2$, EtOAc:n-heptane 1:1). 0.73 g (3.70 mmol) of 4-aminobutyric acid tert-butyl ester; hydrochlorid was added and 0.41 ml (7.10 mmol) of acetic acid to adjust the pH to 5 followed by 0.85 g (3.90 mmol) of sodium triacetoxyborohydride. After 5 min at 0° C. and 1.5 h at RT, the reaction was poured on a solution of sat. aq. NaHCO$_3$ solution and extracted with EtOAc (3 times). The organic phases were washed with a solution of 10% aq. NaCl solution. The combined organic phases were dried over Na$_2$SO$_4$ and the solvent was removed under vacuum to give 1.31 g (94%) of the title compound as a 61:39 mixture of the (R) and (S) diastereomers as orange oil. MS: 395.17 (MH$^+$, Cl).

D) 4-[[(R)-2-(3-Chloro-4-trifluoromethyl-phenylamino)-propyl]-(3,3-dimethoxy-propionyl)-amino]-butyric acid tert-butyl ester (22% ee)

A solution of 1.25 g (3.20 mmol) of 4-[(R)-2-(3-chloro-4-trifluoromethyl-phenylamino)-propylamino]-butyric acid tert-butyl ester (22% ee) in 25 ml CH$_2$Cl$_2$ was treated with a solution of 1.00 g (3.80 mmol) of 2-chloro-1-methylpyridinium iodide and 0.51 g (3.80 mmol) of 3,3-dimethoxy-propionic acid (synthesized from methyl 3,3-dimethoxy-propionate by hydrolysis with LiOH) in 5 ml of CH$_2$Cl$_2$. The suspension was cooled and treated at 0° C. with 1.89 ml (7.90 mmol) of tributylamine. The reaction was naturally warmed to RT over night. The reaction was extracted with 10% aq. KHSO$_4$ solution/diethyl ether (3×). The organic phases were washed with 10% aq. KHSO$_4$ solution (2×), sat. aq. NaHCO$_3$ solution, 10% aq. NaCl solution and dried over Na$_2$SO$_4$ to yield 1.68 g (quantitative) of the title compound as a 61:39 mixture of the (R) and (S) diastereomers as light brown oil. MS: 511.22 (MH$^+$, Cl).

E) 4-[(R)-4-(3-Chloro-4-trifluoromethyl-phenyl)-3-methyl-7-oxo-2,3,4,7-tetrahydro-[1,4]diazepin-1-yl]-butyric acid (22% ee)

A cooled solution (0° C.) of 1.00 g (2.00 mmol) of 4-[[(R)-2-(3-chloro-4-trifluoromethyl-phenylamino)-propyl]-(3,3- dimethoxy-propionyl)-amino]-butyric acid tert-butyl ester (22% ee) in 18 ml CH$_2$Cl$_2$ was treated with 2.25 ml (29.40 mmol) of trifluoroacetic acid and after 2 h at RT with 1.55 ml (9.80 mmol) of triethylsilane. The reaction was stirred at RT for 16 h, cooled (0° C.) and neutralized with 4.09 ml (29.40 mmol) of triethylamine. The residue was dissolved in diethyl ether and cold water. The reaction was extracted with 10% aq. KHSO$_4$ solution/EtOAc (3×). The organic phases were washed with 10% aq. KHSO$_4$ solution, dried over Na$_2$SO$_4$ and evaporated. Flash silica gel column (CH$_2$Cl$_2$/MeOH 99:2 to 9:1) afforded 0.57 g (74%) of the title compound as a 61:39 mixture of the (R) and (S) diastereomers as brown oil. MS: 389.09 (M−H⁻, Cl).

Intermediate 35

4-[(R)-4-(4-Chloro-3-trifluoromethyl-phenyl)-3-methyl-7-oxo-2,3,4,7-tetrahydro-[1,4]diazepin-1-yl]-butyric acid (46% ee)

A) (R)-2-(4-Chloro-3-trifluoromethyl-phenylamino)-propionic acid (46% ee)

In analogy to intermediate 31, D-alanine and 1-chloro-4-iodo-2-trifluoromethyl-benzene gave 66% of the title compound (as 73:27 mixture of the (R) and (S) stereoisomers, Reprosil Chiral-NR column) as brown solid. MS: 266.02 (M−H⁻, Cl).

B) (R)-2-(4-Chloro-3-trifluoromethyl-phenylamino)-propan-1-ol (46% ee)

In analogy to intermediate 34B, (R)-2-(4-chloro-3-trifluoromethyl-phenylamino)-propionic acid (46% ee) and borane-tetrahydrofuran complex gave 87% of the title compound as light brown oil. MS: 254.06 (MH⁺, Cl).

C) 4-[(R)-2-(4-Chloro-3-trifluoromethyl-phenylamino)-propylamino]-butyric acid methyl ester (46% ee)

In analogy to intermediate 34C, (R)-2-(3-chloro-4-trifluoromethyl-phenylamino)-propan-1-ol (46% ee) and methyl 4-aminobutyrate hydrochloride gave 94% of the title compound as red oil. MS: 353.12 (MH⁺, Cl).

D) 4-[[(R)-2-(4-Chloro-3-trifluoromethyl-phenylamino)-propyl]-(3,3-dimethoxy-propionyl)-amino]-butyric acid methyl ester (46% ee)

In analogy to intermediate 34D, 4-[(R)-2-(4-chloro-3-trifluoromethyl-phenylamino)-propylamino]-butyric acid methyl ester (46% ee) and 3,3-dimethoxy-propionic acid gave 87% of the title compound as brown oil. MS: 469.17 (MH⁺, Cl).

E) 4-[(R)-4-(4-Chloro-3-trifluoromethyl-phenyl)-3-methyl-7-oxo-2,3,4,7-tetrahydro-[1,4]diazepin-1-yl]-butyric acid methyl ester (46% ee)

In analogy to intermediate 34E, 4-[[(R)-2-(4-chloro-3-trifluoromethyl-phenylamino)-propyl]-(3,3-dimethoxy-propionyl)-amino]-butyric acid methyl ester (46% ee) and TFA/triethylsilane gave 37% of the title compound as brown waxy solid. MS: 405.12 (MH⁺, Cl).

F) 4-[(R)-4-(4-Chloro-3-trifluoromethyl-phenyl)-3-methyl-7-oxo-2,3,4,7-tetrahydro-[1,4]diazepin-1-yl]-butyric acid (46% ee)

In analogy to the procedure described for intermediate 5C, 4-[(R)-4-(4-chloro-3-trifluoromethyl-phenyl)-3-methyl-7-oxo-2,3,4,7-tetrahydro-[1,4]diazepin-1-yl]-butyric acid methyl ester (46% ee) gave with 1 M aq. lithium hydroxide solution in THF/MeOH the title compound in 96% yield as light brown solid. MS: 391.10 (MH⁺, Cl).

Intermediate 36

{4-[(E)-3-(3,4-Dichloro-phenyl)-acryloyl]-7-oxo-[1,4]diazepan-1-yl}-acetic acid

A) {4-[(E)-3-(3,4-Dichloro-phenyl)-acryloyl]-7-oxo-[1,4]diazepan-1-yl}-acetic acid ethyl ester In analogy to the procedure described in intermediate 5B, 1-[(E)-3-(3,4-dichloro-phenyl)-acryloyl]-[1,4]diazepan-5-one (intermediate 5A) and ethyl bromoacetate gave, after purification on a SiO$_2$-column (n-heptane/EtOAc 1:2 to 100% EtOAc), the titled compound in 51% yield as white foam. MS: 399.1 (MH⁺, 2Cl).

B) {4-[(E)-3-(3,4-Dichloro-phenyl)-acryloyl]-7-oxo-[1,4]diazepan-1-yl}-acetic acid In analogy to the procedure described in intermediate 5C, {4-[(E)-3-(3,4-dichloro-phenyl)-acryloyl]-7-oxo-[1,4]diazepan-1-yl}-acetic acid ethyl ester and 1 M aq. lithium hydroxide solution gave after acidification with aqueous 10% KHSO$_4$, filtration and washing with water the title compound in quantitative yield as white solid. MS: 371.0 (MH⁺, 2Cl).

Intermediate 37

(rac)-(2-Methyl-pyrrolidin-2-yl)-methanol 1.6 g (6.4 mmol) of 2-Hydroxymethyl-2-methyl-pyrrolidine-1-carboxylic acid benzyl ester (WO2008/81910 A1) was dissolved in 10 ml MeOH, 0.1 g of 10% palladium on charcoal was added and the mixture stirred under an atmosphere of hydrogen (ballon) for 30 minutes. The reaction is then filtered through Hyflo and concentrated affording the titled compound in quantitative yield as white foam. $^1$H-NMR (300 MHz, DMSO-d$_6$): 3.1 (s, 2H), 2.83-2.74 (m, 2 H), 1.68-1.60 (m, 4H), 0.98 (s, 3H).

Intermediate 38

3-{(R)-4-[(E)-3-(3-Chloro-phenyl)-acryloyl]-3-methyl-7-oxo-[1,4]diazepan-1-yl}-propionic acid A) {(R)-2-[tert-Butoxycarbonyl-(3-hydroxy-propyl)-amino]-1-methyl-ethyl}-carbamic acid benzyl Ester To an ice cold solution of 25 g (0.12 mol) of Z-alaminol in 200 ml of CH$_2$Cl$_2$ and 25 ml (0.18 mol) of triethylamine was added 10 ml (0.13 mol) of methanesulfonyl chloride. The reaction was stirred for 0.5 h after which time it was washed with 10% citric acid solution, dried (Na$_2$SO$_4$) and concentrated, affording 30.5 g of crystalline mesyate. This was then added portionwise to 43 ml (0.84 mol) of 3-amino-propan-1-ol pre-heated to 70° C. After a further 1 h heating at 80° C. the reaction was allowed to cool and poured into water (200 ml)

and extracted with EtOAc. The EtOAc was partially concentrated to approximately 200 ml and 26 g (0.12 mol) of Boc₂O added and the mixture stirred for 3 h after which time it was washed with 10% citric acid, dried (Na₂SO₄) and concentrated. Purification on a SiO₂-column (n-heptane/EtOAc 1:1 to 1:3), afforded the titled compound in 63% yield as a colorless gum. MS: 367.3 (MH⁺).

B) 3-{{(R)-2-[tert-Butoxycarbonyl-(3-hydroxy-propyl)-amino]-1-methyl-ethyl}-[(E)-3-(3-chloro-phenyl)-acryloyl]-amino}-propionic acid methyl ester To 45.6 g (0.12 mol) of {(R)-2-[tert-Butoxycarbonyl-(3-hydroxy-propyl)-amino]-1-methyl-ethyl}-carbamic acid benzyl ester in 300 ml of MeOH was added 5 g of 10% Pd/C and the mixture was stirred under 1 atmosphere (balloon) of hydrogen for 2 h. The mixture was then filtered through Hyflo (washing with MeOH) and reconcentrated to around 150 ml volume. 11.2 ml (0.12 mol) of methyl acrylate was added and the mixture stirred for 16 h after which time the reaction was concentrated to dryness, the residue redissolved in 50 ml CH₂Cl₂, cooled to 0° C. and rapidly added via cannula a to a cooled (−15° C.) solution of 24.3 g (0.12 mol) of 3-chloro-cinnamoyl chloride and 24 ml (0.17 mol) of triethylamine in 200 ml of CH₂Cl₂. On completion of the addition the reaction was stirred for a further 15 minutes after which time the reaction was washed with 10% citric acid solution, sat. aq. NaHCO₃, dried (Na₂SO₄) and concentrated. Purification on a SiO₂-column (n-heptane/EtOAc 7:3 to 9:1), afforded the titled compound in 64% yield as a colorless gum. MS: 483.3 (MH⁺, Cl).

C) (R)-1-[(E)-3-(3-Chloro-phenyl)-acryloyl]-4-(3-hydroxy-propyl)-2-methyl-[1,4]diazepan-5-one 63.1 g (0.13 mol) of 3-{{(R)-2-[tert-butoxycarbonyl-(3-hydroxy-propyl)-amino]-1-methyl-ethyl}-[(E)-3-(3-chloro-phenyl)-acryloyl]-amino}-propionic acid methyl ester was dissolved in 130 ml of 4 N HCl in MeOH. The reaction was stirred for 4 h after which time it was evaporated to dryness and the residue redissolved in CH₂Cl₂, washed with sat. aq. NaHCO₃, dried (Na₂SO₄) and the mixture concentrated to 300 ml. 3.6 g (0.03 mol) of 1,5,7-triazabucyclodec-5-ene was then added and the mixture stirred for 16 h after which time the solvent was evaporated. The residue was redissolved in 100 ml of MeOH and 6N NaOH was added until the pH was basic and the mixture stirred for 1 h. The solvent was evaporated, the residue redissolved in CH₂Cl₂, washed with 10% citric acid solution, washed with sat. aq. NaHCO₃, dried (Na₂SO₄) and concentrated. This afforded the titled compound in 62% yield as a colorless foam. MS: 351.2 (MH⁺, Cl).

D) 3-{(R)-4-[(E)-3-(3-Chloro-phenyl)-acryloyl]-3-methyl-7-oxo-[1,4]diazepan-1-yl}-propionic acid To 0.52 g (1 mmol) of (R)-1-[(E)-3-(3-Chloro-phenyl)-acryloyl]-4-(3-hydroxy-propyl)-2-methyl-[1,4]diazepan-5-one, 0.002 g (0.01 mmol) TEMPO in 5 ml of ice cold CH₂Cl₂ was added 0.018 g (0.2 mmol) of potassium bromide in a solution of 4.6 ml (6 mmol) of 13% sodium hypochlorite saturated with NaHCO₃. The mixture was rapidly stirred for 5 minutes after which time a few drops of MeOH were added and the phases separated. The aqueous was acidified with 1N HCl and repeatedly extracted with CH₂Cl₂, dried (Na₂SO₄) and concentrated. This afforded the titled compound in 92% yield as a colorless foam. MS: 365.2 (MH⁺, Cl).

Intermediate 39

4-[4-((S)-4-Hydroxy-6-aza-spiro[2.5]oct-6-yl)-4-oxo-butyl]-[1,4]diazepan-5-one

A) 4-[4-(tert-Butyl-dimethyl-silanyloxy)-butyl]-5-oxo-[1,4]diazepane-1-carboxylic acid benzyl ester To 1.4 g (5 mmol) of 6-amino-5-oxo-[1,4]diazepane-1-carboxylic acid benzyl ester and 2.1 g (7 mmol) of (4-iodobutoxy)-t-butyldimethsilane in 15 ml of DMF cooled to 0° C. was added 0.4 g (8 mmol) of sodium hydride (50% dispersion). The reaction was allowed to reach room temperature and stirred for 16 h after which time the reaction was diluted with tert-butylmethyl ether and poured onto cold sat. aq. NH₄Cl. The organic phase was washed with brine, dried (Na₂SO₄) and concentrated. Purification on a SiO₂-column (n-heptane/EtOAc 1:1), afforded the titled compound in 97% yield as a colorless oil. MS: 435.3 (MH⁺).

B) 4-(4-Hydroxy-butyl)-5-oxo-[1,4]azepane-1-carboxylic acid benzyl ester

To 1.1 g (3.0 mmol) of 4-[4-(tert-butyl-dimethyl-silanyloxy)-butyl]-5-oxo-[1,4]diazepane-1-carboxylic acid benzyl ester in 5 ml of MeOH at 0° C. was added 0.03 ml (0.3 mmol) of acetyl chloride. The reaction was allowed to warm to room temperature, after 20 minutes stirring the reaction was evaporated to dryness, affording the titled compound in quantitative yield as a colorless gum. MS: 321.2 (MH⁺).

C) 4-[4-((S)-4-Hydroxy-6-aza-spiro[2.5]oct-6-yl)-4-oxo-butyl]-5-oxo-[1,4]diazepane-1-carboxylic acid benzyl ester To an ice cold solution of 0.44 g (1.4 mmol) of 4-(4-hydroxy-butyl)-5-oxo-[1,4]diazepane-1-carboxylic acid benzyl ester in 5 ml of acetonitrile:water (1:1) was added 0.043 g (0.3 mmol) TEMPO and 0.97 g (3.0 mmol) of (diacetoxyiodo)benzene. The mixture was stirred allowed to reach room temperature and was stirred for a further 3 h after which time it was evaporated to dryness. The crude residue was redissolved in 5 ml of DMF, 0.68 g (2 mmol) of HATU and 0.6 ml (4.0 mmol) of triethylamine added followed by addition of 0.25 g (2.0 mmol) of (S)-6-aza-spiro[2.5]octan-4-ol. hydrochloride (intermediate 2). The reaction was stirred for 16 h after which time the mixture was poured onto sat. aq. NaHCO₃, extracted with EtOAc. The combined organic phases were washed with brine, dried (Na₂SO₄) and concentrated. Purification on a SiO₂-column (CH₂Cl₂/MeOH 95:5), afforded the titled compound in 55% yield as a colorless foam. MS: 444.3 (MH⁺).

D) 4-[4-((S)-4-Hydroxy-6-aza-spiro[2.5]oct-6-yl)-4-oxo-butyl]-[1,4]diazepan-5-one To 0.44 g (1 mmol) of 4-[4-((S)-4-hydroxy-6-aza-spiro[2.5]oct-6-yl)-4-oxo-butyl]-5-oxo-[1,4]diazepane-1-carboxylic acid benzyl ester in 10 ml of MeOH was added 0.05 g of 10% palladium on charcoal. The mixture was stirred under 1 atmosphere of hydrogen for 1.5 h after which time the reaction was filtered through Hyflo and concentrated, affording the titled compound in 85% yield as a colorless foam. MS: 310.4 (MH⁺).

Intermediate 40

4-[4-(3-Chloro-4-trifluoromethoxy-phenyl)-7-oxo-[1,4]diazepan-1-yl]-butyric acid

A) 3-(3-Chloro-4-trifluoromethoxy-phenylamino)-propionic acid tert-butyl ester A solution of 9.26 g (42.4 mmol) of 3-chloro-4-trifluoromethoxy-phenylamine and 4.39 ml (42.4 mmol) of 2,6-lutidine in 50 ml of toluene was treated slowly with 7.30 ml (42.4 mmol) of tert-butyl 3-bromopropionate and stirred 2 days at reflux temperature. The reaction was then partitioned between aqueous 10% $KHSO_4$ and EtOAc (3×). The organic phases were washed with 10% NaCl, dried over $Na_2SO_4$ evaporated and purified by flash silica gel column (n-heptane:EtOAc 9:1) to yield 9.59 g (60%) of the title compound as brown liquid. MS: 339 ($M^+$, Cl).

B) 3-[(3-Chloro-4-trifluoromethoxy-phenyl)-methoxycarbonylmethyl-amino]-propionic acid tert-butyl ester A neat solution of 8.50 g (22.5 mmol) of 3-(3-chloro-4-trifluoromethoxy-phenylamino)-propionic acid tert-butyl ester, 10.71 ml (112.6 mmol) of methyl bromoacetate and 13.07 ml (112.6 mmol) of 2,6-lutidine was stirred 14 h at 60° C., diluted with 30 ml of $CH_3CN$ and heated at 115° C. for 20 h. The reaction was then partitioned between aqueous 10% $KHSO_4$ solution and EtOAc (3×). The organic phases were washed with aqueous 10% NaCl, dried over $Na_2SO_4$ evaporated and purified by flash silica gel column (n-heptane:EtOAc 95:5 to 85:1) to yield 5.94 g (64%) of the title compound as light yellow oil. MS: 412.11 ($MH^+$, Cl).

C) 3-[(3-Chloro-4-trifluoromethoxy-phenyl)-(2-hydroxy-ethyl)-amino]-propionic acid tert-butyl ester A solution of 3.00 g (7.3 mmol) of 3-[(3-chloro-4-trifluoromethoxy-phenyl)-methoxycarbonylmethyl-amino]-propionic acid tert-butyl ester in 20 ml of THF was treated with 4.44 ml (8.9 mmol) of $LiBH_4$ (2 M in THF) and 0.59 ml (14.6 mmol) of MeOH (with cooling bath at RT). The reaction was stirred for 2 h at RT, cooled to 0° C. and stopped with 2 ml of acetone. The reaction was diluted with 4.5 ml of cyclohexane, 18 ml of aqueous 2 N NaOH were added and after 30 min extracted with EtOAc (3×). The organic phases were washed with aqueous 10% NaCl, dried ($Na_2SO_4$) and evaporated to give after flash silica gel column (EtOAc:n-heptane 1:4 to 1:1) 2.21 g (78%) of the titled compound as light yellow oil. MS: 384.12 ($MH^+$, Cl).

D) 3-[(3-Chloro-4-trifluoromethoxy-phenyl)-(2-oxo-ethyl)-amino]-propionic acid tert-butyl ester To a solution of 0.55 ml (6.3 mmol) of oxalyl chloride in 21 ml $CH_2Cl_2$ at −50 to −60° C. was added a solution of 0.93 ml (13.1 mmol) dimethylsulfoxide in 7 ml of $CH_2Cl_2$ within 20 min. The solution was stirred for 5 min, then a solution of 2.10 g (5.5 mmol) of 3-[(3-chloro-4-trifluoromethoxy-phenyl)-(2-hydroxy-ethyl)-amino]-propionic acid tert-butyl ester in 14 ml $CH_2Cl_2$ was added within 20 min. The mixture was stirred for 15 min and 3.81 ml (27.4 mmol) of triethylamine were added within 20 min. The suspension was stirred for 3 h and slowly warmed to −5° C. The reaction was neutralized with cold aqueous 10% $KH_2PO_4$ (adjusted with solid $KH_2PO_4$ to pH 4-5) and extracted with EtOAc (3×). The organic phases were washed with aqueous saturated $NaHCO_3$ (freshly prepared), aqueous 10% NaCl, dried over $Na_2SO_4$ evaporated to yield 2.21 g (quantitative) of the title compound as yellow oil. MS: 381 ($M^+$, Cl).

E) 4-{2-[(2-tert-Butoxycarbonyl-ethyl)-(3-chloro-4-trifluoromethoxy-phenyl)-amino]-ethylamino}-butyric acid methyl ester A solution of 0.50 g (1.3 mmol) of 3-[(3-chloro-4-trifluoromethoxy-phenyl)-(2-oxo-ethyl)-amino]-propionic acid tert-butyl ester in 6 ml dichloromethane was added dropwise to a cooled (0° C., pH ca. 5) suspension of 0.22 g (1.4 mmol) methyl 4-aminobutyrate hydrochloride, 0.18 ml (1.3 mmol) triethylamine, 0.15 ml (2.6 mmol) acetic acid and 0.32 g (1.5 mmol) sodium triacetoxyborohydride in 4 ml of dichloromethane and stirred 30 min at 0° C. The reaction was extracted with aqueous saturated $NaHCO_3$/EtOAc (3×). The organic phases were washed with aqueous saturated $NaHCO_3$ and dried over $Na_2SO_4$ to yield after evaporation of the solvent 0.61 g (83%) of the titled compound as yellow oil. MS: 483.19 ($MH^+$, Cl).

F) 4-{2-[(2-Carboxy-ethyl)-(3-chloro-4-trifluoromethoxy-phenyl)-amino]-ethylamino}-butyric acid methyl ester dihydrochloride A solution of 0.30 g (0.6 mmol) of 4-{2-[(2-tert-butoxycarbonyl-ethyl)-(3-chloro-4-trifluoromethoxy-phenyl)-amino]-ethylamino}-butyric acid methyl ester in 2 ml of dichloromethane was cooled (0° C.), treated with 3.10 ml (12.4 mmol) of HCl solution (4 M in dioxane) and stirred at RT for 16 h. The solution was evaporated, suspended in acetonitrile and evaporated (3×) to yield 0.33 g (97%) of the title compound as light yellow oil. MS: 427.12 ($MH^+$, Cl).

G) 4-[4-(3-Chloro-4-trifluoromethoxy-phenyl)-7-oxo-[1,4]diazepan-1-yl]-butyric acid methyl ester A solution of 0.16 g (0.3 mmol) of 4-{2-[(2-carboxy-ethyl)-(3-chloro-4-trifluoromethoxy-phenyl)-amino]-ethylamino}-butyric acid methyl ester dihydrochloride in 2.5 ml $CH_2Cl_2$ was treated with 0.04 ml (0.3 mmol) of triethylamine and at 0° C. with 0.08 g (0.4 mmol) of EDCI. The cooling bath was allowed to come to RT and after 15 h the reaction was extracted with aqueous 10% $KHSO_4/Et_2O$ (3×). The organic phases were washed with 10% $KHSO_4$, 10% NaCl and dried over $Na_2SO_4$ to yield after evaporation of the solvent 0.11 g (76%) of the title compound as a yellow oil. MS: 409.11 ($MH^+$, Cl).

H) 4-[4-(3-Chloro-4-trifluoromethoxy-phenyl)-7-oxo-[1,4]diazepan-1-yl]-butyric acid In analogy to the procedure described for intermediate 5C, 4-[4-(3-chloro-4-trifluoromethoxy-phenyl)-7-oxo-[1,4]diazepan-1-yl]-butyric acid methyl ester gave with 1 M aq. lithium hydroxide solution in THF/MeOH the title compound in 99% yield as light yellow oil. MS: 395.10 ($MH^+$, Cl).

Intermediate 41

(S)-2-Amino-5-((S)-4-hydroxy-6-aza-spiro[2.5]oct-6-yl)-5-oxo-pentanoic acid methyl ester; compound with HCl

A) (S)-2-tert-Butoxycarbonylamino-5-((S)-4-hydroxy-6-aza-spiro[2.5]oct-6-yl)-5-oxo-pentanoic acid methyl ester In analogy to the procedure described for example 15, BOC-L-glutamic acid alpha methylester and 1.05 equivalent of (S)-6-aza-spiro[2.5]octan-4-ol; hydrochloride (intermediate 2) gave the title compound in 59% yield as light yellow oil. MS: 371.22 (MH$^+$).

B) (S)-2-Amino-5-((S)-4-hydroxy-6-aza-spiro[2.5]oct-6-yl)-5-oxo-pentanoic acid methyl ester; compound with HCl In analogy to the procedure described for intermediate 12G, (S)-2-tert-butoxycarbonylamino-5-((S)-4-hydroxy-6-aza-spiro[2.5]oct-6-yl)-5-oxo-pentanoic acid methyl ester and 10 equivalents of HCl in dioxane gave after 30 min at 0° C., 30 min at RT, evaporation with acetonitrile and precipitation with CH$_2$Cl$_2$/Et$_2$O the title compound in quantitative yield as off-white powder. MS: 271.16 (MH$^+$).

Intermediate 42

(S)-2-[(R,S)-4-(3,4-Bis-trifluoromethyl-phenyl)-3-methyl-7-oxo-[1,4]diazepan-1-yl]-pentanedioic acid 1-methyl ester A)
2-(3,4-Bis-trifluoromethyl-phenylamino)-propionic acid ethyl ester In analogy to intermediate 40B, 3,4-bis(trifluoromethyl)aniline and ethyl 2-bromopropionate with 2,6-lutidine were heated for 20 h at 82° C., diluted with acetonitrile and treated with 1 equivalent of ethyl 2-bromopropionate and 2,6-lutidine and refluxed for 2 days, treated again with 1 equivalent of ethyl 2-bromopropionate and 2,6-lutidine and continued to reflux for 2 days. Workup and purification by flash silica gel column (n-heptane/ethyl acetate 9:1 to 2:1) yielded 49% of the titled compound as yellow oil. MS: 328.08 (M−H$^-$).

B)
2-(3,4-Bis-trifluoromethyl-phenylamino)-propionic acid

In analogy to intermediate SC, 2-(3,4-bis-trifluoromethyl-phenylamino)-propionic acid ethyl ester and 1 M aq. lithium hydroxide solution gave 97% of the title compound as off-white solid. MS: 300.05 (M−H$^-$).

C) 2-(3,4-Bis-trifluoromethyl-phenylamino)-propan-1-ol

In analogy to intermediate 34B, 2-(3,4-bis-trifluoromethyl-phenylamino)-propionic acid and borane-tetrahydrofuran complex solution gave 71% of the title compound as light yellow oil. MS: 286.07 (M−H$^-$).

D) (S)-2-[(R,S)-2-(3,4-Bis-trifluoromethyl-phenylamino)-propylamino]-pentanedioic acid 5-tert-butyl ester 1-methyl ester In analogy to intermediate 34C, 2-(3,4-bis-trifluoromethyl-phenylamino)-propan-1-ol and L-glutamic acid gamma-t-butyl ester alpha-methylester hydrochloride gave quantitative of the title compound as yellow oil. MS: 487.20 (MH$^+$).

E) (S)-2-[[(R,S)-2-(3,4-Bis-trifluoromethyl-phenylamino)-propyl]-(3,3-dimethoxy-propionyl)-amino]-pentanedioic acid 5-tert-butyl ester 1-methyl ester In analogy to intermediate 34D, (S)-2-[(R,S)-2-(3,4-bis-trifluoromethyl-phenylamino)-propylamino]-pentanedioic acid 5-tert-butyl ester 1-methyl ester and 3,3-dimethoxy-propionic acid gave quantitative of the title compound as orange gum. MS: 603.25 (MH$^+$).

F) (S)-2-[(R,S)-4-(3,4-Bis-trifluoromethyl-phenyl)-3-methyl-7-oxo-2,3,4,7-tetrahydro-[1,4]diazepin-1-yl]-pentanedioic acid 1-methyl ester In analogy to intermediate 34E, (S)-2-[[(R,S)-2-(3,4-bis-trifluoromethyl-phenylamino)-propyl]-(3,3-dimethoxy-propionyl)-amino]-pentanedioic acid 5-tert-butyl ester 1-methyl ester and TFA/triethylsilane gave 46% of the title compound as light brown oil. MS: 483 (MH$^+$).

G) (S)-2-[(R,S)-4-(3,4-Bis-trifluoromethyl-phenyl)-3-methyl-7-oxo-[1,4]azepan-1-yl]-pentanedioic acid 1-methyl ester In analogy to the procedure described for example 126, (S)-2-[(R,S)-4-(3,4-bis-trifluoromethyl-phenyl)-3-methyl-7-oxo-2,3,4,7-tetrahydro-[1,4]diazepin-1-yl]-pentanedioic acid 1-methyl ester gave with PtO$_2$ and H$_2$-atmosphere in EtOH the title compound in 93% yield as light yellow foam. MS: 485.15 (MH$^+$).

Intermediate 43

4-[(S)-4-(3,4-Bis-trifluoromethyl-phenyl)-3-methyl-2-oxo-piperazin-1-yl]-butyric acid A) 4-((S)-3-Methyl-2-oxo-piperazin-1-yl)-butyric acid tert-butyl ester, 0.1 eq. of HCl In analogy to intermediate 12E, (S)-4-(3-tert-butoxycarbonyl-propyl)-2-methyl-3-oxo-piperazine-1-carboxylic acid benzyl ester (intermediate 13A) was hydrogenated with Pd/C (10%) to yield the titled compound in 95% yield as orange oil. MS: 257.19 (MH$^+$).

B) 4-[(S)-4-(3,4-Bis-trifluoromethyl-phenyl)-3-methyl-2-oxo-piperazin-1-yl]-butyric acid tert-butyl ester A mixture of 0.20 g (0.78 mmol) of 4-((S)-3-Methyl-2-oxo-piperazin-1-yl)-butyric acid tert-butyl ester, 0.1 eq. of HCl, 0.53 g (1.56 mmol) of 4-iodo-1,2-bis-trifluoromethyl-benzene (WO2007034282), 0.04 g (0.078 mmol) bis(tri-tert-butylphosphine)palladium(0) and 0.33 g (1.56 mmol) tripotassium phosphate in 2 ml of 1,2-dimethoxyethane was degased and heated at 120° C. for 2 h under microwave irradiation, diluted with dichloromethane, filtered and evaporated. Purification on a SiO$_2$-column (1-propanol in n-heptane 2 to 5%), gave the titled compound in 35% yield as light brown oil. MS: 413.13 (M[-C$_4$H$_8$]H$^+$).

C) 4-[(S)-4-(3,4-Bis-trifluoromethyl-phenyl)-3-methyl-2-oxo-piperazin-1-yl]-butyric acid In analogy to intermediate 12G, 4-[(S)-4-(3,4-bis-trifluoromethyl-phenyl)-3-methyl-2-oxo-piperazin-1-yl]-butyric acid tert-butyl ester and HCl (4 M in dioxane) gave 84% of the title compound as brown foam. MS: 411.11 (M−H$^-$).

Intermediate 44

(S)-4-[(S)-4-(3-Chloro-4-trifluoromethyl-phenyl)-3-methyl-2-oxo-piperazin-1-yl]-3-hydroxy-butyric acid (61% ds)

A) (S)-4-(2,2-Dimethoxy-ethylamino)-3-hydroxy-butyric acid methyl ester

A solution of 2.50 g (14.7 mmol) of (S)-4-amino-3-hydroxy-butyric acid methyl ester; HCl (intermediate 24) in 18 ml of methanol was treated with 6.19 g (73.7 mmol) of natriumhydrogencarbonat, 2.2 ml (14.7 mmol) of dimethoxyacetaldehyde (in H$_2$O 60%), 0.250 g of Pd/C (10%) and was stirred over H$_2$-atmosphere for 4 h. After filtration, the solution was evaporated, dissolved in toluene, evaporated under reduced pressure (2×) to yield 3.781 g (70%) of the titled compound as yellow oil. MS: 222.13 (MH$^+$).

B) (S)-4-[[(S)-2-(3-Chloro-4-trifluoromethyl-phenylamino)-propionyl]-(2,2-dimethoxy-ethyl)-amino]-3-hydroxy-butyric acid methyl ester (61% ds)

To a solution of 0.915 g (3.4 mmol) of (S)-2-(3-chloro-4-trifluoromethyl-phenylamino)-propionic acid (26% ee) (intermediate 32) and 0.394 ml (3.6 mmol) of 4-methylmorpholine in 10.0 ml of DMF, was added at 0° C. 1.86 g (4.9 mmol) of HATU, followed after 30 min by 1.20 g (3.3 mmol) of (S)-4-(2,2-dimethoxy-ethylamino)-3-hydroxy-butyric acid methyl ester in 6.5 ml of DMF. The solution was stirred and warmed up over night. The reaction was poured on aqueous 10% KHSO$_4$/EtOAc (3×). The organic phases were washed with aqueous 10% KHSO$_4$, saturated NaHCO$_3$, 10% NaCl and dried over Na$_2$SO$_4$ to yield 1.91 g (62%) of the titled compound as light brown oil. MS: 469.14 (MH$^+$).

C) (S)-4-[(S)-4-(3-Chloro-4-trifluoromethyl-phenyl)-3-methyl-2-oxo-piperazin-1-yl]-3-hydroxy-butyric acid methyl ester (61% ds)

1.82 g (3.9 mmol) of (S)-4-[[(S)-2-(3-chloro-4-trifluoromethyl-phenylamino)-propionyl]-(2,2-dimethoxy-ethyl)-amino]-3-hydroxy-butyric acid methyl ester were dissolved at RT in 39.0 ml of dichloromethane, cooled (0° C.) and treated with 4.4 ml of trifluoroacetic acid. After 30 min at 0° C. and 2.5 h at RT 3.2 ml (19.3 mmol) of triethylsilane were added and stirred over night at RT. The reaction was neutralized with 8.1 ml (58 mmol) of triethylamine at 0° C. and after 10 min poured on aqueous 10% KHSO$_4$/EtOAc (3×). The organic phases were washed with aqueous 10% KHSO$_4$, saturated NaHCO$_3$, 10% NaCl and dried over Na$_2$SO$_4$ to yield after flash chromatography (SiO$_2$, EtOAc/Heptan from 1:1 to 4:1) 0.114 g (7%) of the titled compound as yellow oil. MS: 409.2 (MH$^+$).

D) (S)-4-[(S)-4-(3-Chloro-4-trifluoromethyl-phenyl)-3-methyl-2-oxo-piperazin-1-yl]-3-hydroxy-butyric acid (61% ds)

In analogy to intermediate 3B, (S)-4-[(S)-4-(3-chloro-4-trifluoromethyl-phenyl)-3-methyl-2-oxo-piperazin-1-yl]-3-hydroxy-butyric acid methyl ester was hydrolyzed with 1 M aqueous lithium hydroxide (1 h) to give after extraction (EtOAc) and precipitation (dichloromethane/n-pentane) the titled compound in 82% yield as light yellow foam. MS: 393.08 (MH$^+$)

Intermediate 45

(S)-4-[(S)-4-(3-Chloro-4-trifluoromethyl-phenyl)-3-methyl-2-oxo-piperazin-1-yl]-5-methoxy-pentanoic acid (61% ds)

A)
(S)-4-Benzyloxycarbonylamino-5-hydroxy-pentanoic acid tert-butyl ester

In analogy to G. Kokotos (Synthesis 1990, 299), a solution of 5.00 g (14.8 mmol) of Z-Glu(OtBu)-OH in 74.0 ml of THF was treated at −10° C. with 1.63 ml (14.8 mmol) of 4-methylmorpholine, 1.41 ml (14.8 mmol) of ethyl chloroformate. After 10 min 1.682 g (44.5 mmol) of natriumborohydrid was added in one portion. Methanol (148 ml) was then added dropwise over a period of 25 min at 0° C. The solution was stirred 20 min, and then neutralized with a 10% KHSO$_4$ solution. The organic solvents are evaporated under reduced pressure and the obtained residue is poured on a 10% KHSO$_4$ extracted with EtOAc (3×). The organic phases were washed with aqueous 10% KHSO$_4$, 10% NaCl, dried over Na$_2$SO$_4$ and evaporated to yield 5.16 g (quantitative) of the titled compound as yellow oil. MS: 324.18 (MH$^+$).

B)
(S)-4-Benzyloxycarbonylamino-5-methoxy-pentanoic acid tert-butyl ester

A solution of 4.82 ml (77.3 mmol) of iodomethane and 2.50 g (7.7 mmol) (S)-4-Benzyloxycarbonylamino-5-hydroxy-pentanoic acid tert-butyl ester in 25 ml of acetonitrile was cooled (0° C.) and treated with 2.72 g (11.8 mmol) of silver(I) oxide. The reaction mixture was stirred at RT for 3 days. The reaction was filtered and evaporated to yield after flash chromatography (SiO$_2$, dichloromethane/ether 2.5%) 1.70 g (65%) of the titled compound as light yellow oil. MS: 360.18 (M+Na).

C) (S)-4-Amino-5-methoxy-pentanoic acid tert-butyl ester; HCl

In analogy to example 14H, (S)-4-benzyloxycarbonylamino-5-methoxy-pentanoic acid tert-butyl ester was hydrogenated with Pd/C (10%) in methanol with 1 eq. of aqueous HCl for 2 h to give after precipitation (dichloromethane/n-pentane) the titled compound in 90% yield as off-white waxy solid. MS: 204.16 (MH$^+$).

D) (S)-4-(2,2-Dimethoxy-ethylamino)-5-methoxy-pentanoic acid tert-butyl ester

In analogy to intermediate 44A, (S)-4-amino-5-methoxy-pentanoic acid tert-butyl ester; HCl and 1 eq. of dimethoxyacetaldehyde (in H2O 60%) gave the titled compound in 69% yield as yellow oil MS: 292.21 (MH$^+$).

E) (S)-4-[[(S)-2-(3-Chloro-4-trifluoromethyl-phenylamino)-propionyl]-(2,2-dimethoxy-ethyl)-amino]-5-methoxy-pentanoic acid tert-butyl ester (61% ds)

In analogy to intermediate 44B, (S)-4-(2,2-dimethoxy-ethylamino)-5-methoxy-pentanoic acid tert-butyl ester and (S)-2-(3-chloro-4-trifluoromethyl-phenylamino)-propionic acid (26% ee) (intermediate 32) gave the titled compound in 79% yield as orange oil. MS: 539.21 (MH$^+$, 1Cl).

F) (S)-4-[(S)-4-(3-Chloro-4-trifluoromethyl-phenyl)-3-methyl-2-oxo-piperazin-1-yl]-5-methoxy-pentanoic acid (61% ds)

In analogy to intermediate 44C, (S)-4-[[(S)-2-(3-chloro-4-trifluoromethyl-phenylamino)-propionyl]-(2,2-dimethoxy-ethyl)-amino]-5-methoxy-pentanoic acid tert-butyl ester was cyclized with trifluoroacetic acid/triethylsilane to give the titled compound in 36% yield as brown oil. MS: 421.2 (MH$^+$, 1Cl).

Intermediate 46

(S)-1-[(R,S)-3-Hydroxy-4-((S)-4-hydroxy-6-aza-spiro[2.5]oct-6-yl)-4-oxo-butyl]-3-methyl-piperazin-2-one

A) (rac)-4-Amino-2-hydroxy-butyric acid methyl ester; HCl 7.79 ml (109.6 mmol) of acetylchloride was carefully added at 0° C. to 70 ml of MeOH followed by 8.60 g (40.0 mmol) of (rac)-4-amino-2-hydroxybutyric acid. Stirring was continued for 2 h at 0° C., the reaction was then evaporated and dried under reduced pressure to yield 6.98 g (quantitative) of the titled compound as white solid. MS: 134.08 (MH$^+$).

B) (S)-4-((R,S)-3-Hydroxy-3-methoxycarbonyl-propyl)-2-methyl-3-oxo-piperazine-1-carboxylic acid benzyl ester A solution of 0.840 g (5.0 mmol) of (rac)-4-amino-2-hydroxy-butyric acid methyl ester; HCl, 0.690 ml (5.0 mmol) of triethylamine, 0.514 ml (9.0 mmol) of acetic acid, 1.13 g (5.2 mmol) of sodium triacetoxyborohydride (pH~5) in 17.5 ml of dichloromethane at RT was treated dropwise (10 min) with a solution of 1.26 g (4.5 mmol) of (S)-2-[benzyloxycarbonyl-(2-oxo-ethyl)-amino]-propionic acid methyl ester (interemdiate 12C) in 35.0 ml of dichloromethane. The reaction was stirred overnight at RT. The reaction was poured on aqueous 10% KHSO$_4$/EtOAc (3×). The organic phases were washed with aqueous 10% KHSO$_4$, saturated NaHCO$_3$, 10% NaCl and dried over Na$_2$SO$_4$ to yield after flash chromatography (SiO$_2$, n-heptane/AcOEt 1:1 to 0:10) 0.428 g (26%) of the titled compound as light yellow viscous oil. MS: 365.17 (MH$^+$).

C) (S)-4-((R,S)-3-Carboxy-3-hydroxy-propyl)-2-methyl-3-oxo-piperazine-1-carboxylic acid benzyl ester A solution of 0.556 g (1.5 mmol) of (S)-4-((R,S)-3-hydroxy-3-methoxycarbonyl-propyl)-2-methyl-3-oxo-piperazine-1-carboxylic acid benzyl ester in 8.0 ml of tetrahydrofuran/ethanol (1:1) was treated at 0° C. with 3.5 ml (3.1 mmol) of 1 M aqueous lithium hydroxide solution, and stirred 5 h at RT. The reaction was neutralized with aqueous 10% KHSO$_4$ and extracted with EtOAc (3×). The organic phases were washed with aqueous 10% KHSO$_4$, 10% NaCl, dried over Na$_2$SO$_4$ and evaporated to yield 0.585 g (quantitative) of the titled compound as light grey oil. MS: 351.15 (MH$^+$).

D) (S)-4-[(R,S)-3-Hydroxy-4-((S)-4-hydroxy-6-aza-spiro[2.5]oct-6-yl)-4-oxo-butyl]-2-methyl-3-oxo-piperazine-1-carboxylic acid benzyl ester 0.557 g (1.6 mmol) of (S)-4-((R,S)-3-carboxy-3-hydroxy-propyl)-2-methyl-3-oxo-piperazine-1-carboxylic acid benzyl ester were dissolved at RT in 16 ml DMF followed by addition of 0.222 g (1.7 mmol) of (S)-6-aza-spiro[2.5]octan-4-ol, hydrochloride (intermediate 2), 0.443 ml (3.2 mmol) of thiethylamine and after 10 min at 0° C. with 0.665 g (1.7 mmol) of HATU. The solution was stirred over night and warmed up to RT. The reaction was neutralized with aqueous 10% KHSO$_4$ and extracted with EtOAc (3×). The organic phases were washed with aqueous 10% KHSO$_4$, 10% NaCl, dried over Na$_2$SO$_4$ and evaporated to yield after precipitation (dichloromethane/n-pentane) 0.564 g (77%) of the titled compound as off-white solid. MS: 460.24 (MH$^+$).

E) (S)-1-[(R,S)-3-Hydroxy-4-((S)-4-hydroxy-6-aza-spiro[2.5]oct-6-yl)-4-oxo-butyl]-3-methyl-piperazin-2-one A solution of 0.546 g (1.2 mmol) of (S)-4-[(R,S)-2-hydroxy-4-((S)-4-hydroxy-6-aza-spiro[2.5]oct-6-yl)-4-oxo-butyl]-2-methyl-3-oxo-piperazine-1-carboxylic acid benzyl ester in 18 ml of methanol was treated with 0.055 g of Pd/C (10%) and was stirred over H$_2$-atmosphere for 1 night. After filtration, the solution was evaporated, dissolved in dichloromethane, evaporated under reduced pressure (3×) and precipitated with ether to yield 0.363 g (94%) of the titled compound as off-white powder. MS: 326.21 (MH$^+$).

Intermediate 47

(S)-1-[(S)-3-Hydroxy-4-((S)-4-hydroxy-6-aza-spiro[2.5]oct-6-yl)-4-oxo-butyl]-3-methyl-piperazin-2-one; HCl

A) (S)-4-Amino-2-hydroxy-butyric acid methyl ester; HCl

In analogy to intermediate 46A, (S)-(+)-4-amino-2-hydroxybutyric acid and acetylchloride in MeOH gave quantitatively the titled compound as white waxy solid. MS: 134.1 (MH$^+$)

B) (S)-4-((S)-2-Hydroxy-3-methoxycarbonyl-propyl)-2-methyl-3-oxo-piperazine-1-carboxylic acid benzyl ester In analogy to intermediate 46B, (S)-4-amino-2-hydroxybutyric acid methyl ester, hydrochloride and (S)-2-[benzyloxycarbonyl-(2-oxo-ethyl)-amino]-propionic acid methyl ester (interemdiate 12C) gave the titled compound in 15% yield as light yellow oil. MS: 365.17 (MH$^+$).

C) (S)-4-(S)-3-Carboxy-3-hydroxy-propyl)-2-methyl-3-oxo-piperazine-1-carboxylic acid benzyl ester In analogy to intermediate 46C, (S)-4-(S)-3-hydroxy-3-methoxycarbonyl-propyl)-2-methyl-3-oxo-piperazine-1-carboxylic acid benzyl ester and 1 M aqueous lithium hydroxide solution gave after extraction with EtOAc the titled compound in 98% yield as light yellow viscous oil. MS: 351.15 (MH$^+$).

D) (S)-4-[(S)-3-Hydroxy-4-((S)-4-hydroxy-6-aza-spiro[2.5]oct-6-yl)-4-oxo-butyl]-2-methyl-3-oxo-piperazine-1-carboxylic acid benzyl ester In analogy to intermediate 46D, (S)-4-(S)-3-carboxy-3-hydroxy-propyl)-2-methyl-3-oxo-piperazine-1-carboxylic acid benzyl ester and 1.1 eq. of (S)-6-aza-spiro[2.5]octan-4-ol; hydrochloride (intermediate 2) gave after precipitation (dichloromethane/n-pentane) the titled compound in 75% yield as white solid. MS: 460.24 (MH$^+$).

E) (S)-1-[(S)-3-Hydroxy-4-((S)-4-hydroxy-6-aza-spiro[2.5]oct-6-yl)-4-oxo-butyl]-3-methyl-piperazin-2-one; HCl In analogy to intermediate 46E, (S)-4-[(S)-3-hydroxy-4-((S)-4-hydroxy-6-aza-spiro[2.5]oct-6-yl)-4-oxo-butyl]-2-methyl-3-oxo-piperazine-1-carboxylic acid benzyl ester was hydrogenated with Pd/C (10%) in methanol with 1 eq. of

Intermediate 48

(S)-1-[(R,S)-3-Fluoro-4-((S)-4-hydroxy-6-aza-spiro[2.5]oct-6-yl)-4-oxo-butyl]-3-methyl-piperazin-2-one; HCl

A) rac-4-Amino-2-fluoro-butyric acid methyl ester; HCl

In analogy to intermediate 46A, rac-4-amino-2-fluoro-butyric acid and acetylchloride in MeOH gave (after 22 h) 90% yield of the titled compound as off-white waxy solid. MS: 136.08 (MH$^+$)

B) (S)-4-((R,S)-3-Fluoro-3-methoxycarbonyl-propyl)-2-methyl-3-oxo-piperazine-1-carboxylic acid benzyl ester In analogy to intermediate 46B, rac-4-amino-2-fluoro-butyric acid methyl ester; HCl and (S)-2-[benzyloxycarbonyl-(2-oxo-ethyl)-amino]-propionic acid methyl ester (interemdiate 12C) gave the titled compound in 25% yield as colorless oil. MS: 367.17 (MH$^+$).

C) (S)-4-((R,S)-3-Carboxy-3-fluoro-propyl)-2-methyl-3-oxo-piperazine-1-carboxylic acid benzyl ester In analogy to intermediate 46C, (S)-4-((R,S)-3-fluoro-3-methoxycarbonyl-propyl)-2-methyl-3-oxo-piperazine-1-carboxylic acid benzyl ester and 1 M aqueous lithium hydroxide solution gave after 30 min and extraction with EtOAc the titled compound in quantitative yield as white foam. MS: 353.15 (MH$^+$).

D) (S)-4-[(R,S)-3-Fluoro-4-((S)-4-hydroxy-6-aza-spiro[2.5]oct-6-yl)-4-oxo-butyl]-2-methyl-3-oxo-piperazine-1-carboxylic acid benzyl ester In analogy to intermediate 46D, (S)-4-((R,S)-3-carboxy-3-fluoro-propyl)-2-methyl-3-oxo-piperazine-1-carboxylic acid benzyl ester and 1.1 eq. of (S)-6-aza-spiro[2.5]octan-4-ol; hydrochloride (intermediate 2) gave after precipitation (dichloromethane/n-pentane and dichloromethane/ether) the titled compound in 84% yield as white powder. MS: 462.24 (MH$^+$).

E) (S)-1-[(R,S)-3-Fluoro-4-((S)-4-hydroxy-6-aza-spiro[2.5]oct-6-yl)-4-oxo-butyl]-3-methyl-piperazin-2-one; HCl In analogy to intermediate 46E, (S)-4-[(R,S)-3-fluoro-4-((S)-4-hydroxy-6-aza-spiro[2.5]oct-6-yl)-4-oxo-butyl]-2-methyl-3-oxo-piperazine-1-carboxylic acid benzyl ester was hydrogenated with Pd/C (10%) in methanol with 1 eq. of aqueous HCl for 1 h to give after evaporation with acetonitrile (3×) the titled compound in quantitative yield as white powder. MS: 328.20 (MH$^+$).

Intermediate 49

(S)-1-[(S)-4-((S)-4-Hydroxy-6-aza-spiro[2.5]oct-6-yl)-1-methoxymethyl-4-oxo-butyl]-3-methyl-piperazin-2-one; HCl

A) (S)-4-(S)-3-tert-Butoxycarbonyl-1-methoxymethyl-propyl)-2-methyl-3-oxo-piperazine-1-carboxylic acid benzyl ester In analogy to intermediate 46B, (S)-2-[benzyloxycarbonyl-(2-oxo-ethyl)-amino]-propionic acid methyl ester (interemdiate 12C) and (S)-4-amino-5-methoxy-pentanoic acid tert-butyl ester; HCl (intermediate 45C) gave the titled compound in 39% yield as light yellow oil. MS: 435.25 (MH$^+$).

B) (S)-4-((S)-3-Carboxy-1-methoxymethyl-propyl)-2-methyl-3-oxo-piperazine-1-carboxylic acid benzyl ester A solution of 0.620 g (1.4 mmol) of (S)-4-(S)-3-tert-butoxycarbonyl-1-methoxymethyl-propyl)-2-methyl-3-oxo-piperazine-1-carboxylic acid benzyl ester in 4.2 ml of dichloromethane was treated at 0° C. with 7.13 ml (28.5 mmol, 20 eq.) of 4 N aqueous HCl in dioxane. The solution was stirred over night and warmed up to RT. The solution was evaporated, suspended in toluene, evaporated (3×), suspended in acetonitrile and evaporated (3×) to give 0.551 g (quantitative) of the titled compound as light yellow oil. MS: 379.19 (MH$^+$).

C) (S)-4-[(S)-4-((S)-4-Hydroxy-6-aza-spiro[2.5]oct-6-yl)-1-methoxymethyl-4-oxo-butyl]-2-methyl-3-oxo-piperazine-1-carboxylic acid benzyl ester In analogy to intermediate 46D, (S)-4-(S)-3-carboxy-1-methoxymethyl-propyl)-2-methyl-3-oxo-piperazine-1-carboxylic acid benzyl ester and 1.1 eq. of (S)-6-aza-spiro[2.5]octan-4-ol; hydrochloride (intermediate 2) gave after precipitation (dichloromethane/n-pentane) the titled compound in quantitative yield as off-white solid. MS: 488.28 (MH$^+$).

D) (S)-1-[(S)-4-((S)-4-Hydroxy-6-aza-spiro[2.5]oct-6-yl)-1-methoxymethyl-4-oxo-butyl]-3-methyl-piperazin-2-one; HCl In analogy to intermediate 46E, (S)-4-[(S)-4-((S)-4-hydroxy-6-aza-spiro[2.5]oct-6-yl)-1-methoxymethyl-4-oxo-butyl]-2-methyl-3-oxo-piperazine-1-carboxylic acid benzyl ester was hydrogenated with Pd/C (10%) in methanol with 1 eq. of aqueous HCl for 1 h to give after precipitation (dichloromethane/ether) the titled compound in 93% yield as white solid. MS: 354.24 (MH$^+$).

Intermediate 50

(R)-5-((S)-4-Hydroxy-6-aza-spiro[2.5]oct-6-yl)-2-(S)-3-methyl-2-oxo-piperazin-1-yl)-5-oxo-pentanoic acid methyl ester; HCl

A) (R)-2-(S)-4-Benzyloxycarbonyl-3-methyl-2-oxo-piperazin-1-yl)-pentanedioic acid 5-tert-butyl ester 1-methyl ester In analogy to the procedure described in intermediate 12D, (S)-2-[benzyloxycarbonyl-(2-oxo-ethyl)-amino]-propionic acid methyl ester (intermediate 12C) and D-glutamic acid gamma-t-butyl ester alpha-methylester; hydrochloride gave the titled compound in 97% yield as yellow oil. MS: 449.22 (MH⁺).

B) (R)-2-(S)-4-Benzyloxycarbonyl-3-methyl-2-oxo-piperazin-1-yl)-pentanedioic acid 1-methyl ester In analogy to the procedure described in intermediate 12G, (R)-2-(S)-4-benzyloxycarbonyl-3-methyl-2-oxo-piperazin-1-yl)-pentanedioic acid 5-tert-butyl ester 1-methyl ester and HCl in dioxane gave the titled compound in 96% yield as viscous brown oil. MS: 393.16 (MH⁺).

C) (S)-4-[(R)-4-((S)-4-Hydroxy-6-aza-spiro[2.5]oct-6-yl)-1-methoxycarbonyl-4-oxo-butyl]-2-methyl-3-oxo-piperazine-1-carboxylic acid benzyl ester In analogy to the procedure described in example 15, (R)-2-(S)-4-benzyloxycarbonyl-3-methyl-2-oxo-piperazin-1-yl)-pentanedioic acid 1-methyl ester and 1.1 eq. of (S)-6-aza-spiro[2.5]octan-4-ol; hydrochloride (intermediate 2) gave after purification with flash chromatography (SiO$_2$, EtOAc) and precipitation from dichloromethane/n-pentane the titled compound in 61% yield as amorphous off-white solid. MS: 502.25 (MH⁺).

D) (R)-5-((S)-4-Hydroxy-6-aza-spiro[2.5]oct-6-yl)-2-(S)-3-methyl-2-oxo-piperazin-1-yl)-5-oxo-pentanoic acid methyl ester; HCl In analogy to intermediate 12E, (S)-4-[(R)-4-((S)-4-hydroxy-6-aza-spiro[2.5]oct-6-yl)-1-methoxycarbonyl-4-oxo-butyl]-2-methyl-3-oxo-piperazine-1-carboxylic acid benzyl ester was hydrogenated with 1 eq. of aqueous HCl to give after precipitation (dichloromethane/Et$_2$O) the titled compound in quantitative yield as off-white amorphous solid. MS: 368.21 (MH⁺).

Example 1

1-[(E)-3-(3,4-Dichloro-phenyl)-acryloyl]-4-[3-(4-hydroxy-piperidin-1-yl)-3-oxo-propyl]-[1,4]diazepan-5-one

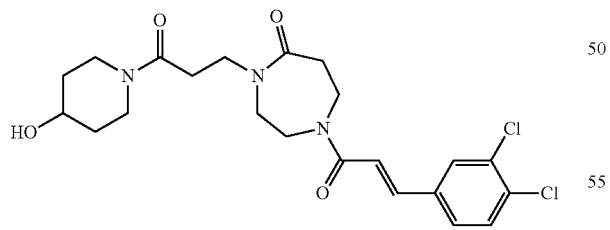

A solution of 0.100 g (0.26 mmol) of 3-{4-[(E)-3-(3,4-dichloro-phenyl)-acryloyl]-7-oxo-[1,4]diazepan-1-yl}-propionic acid (intermediate 5) and 0.032 g (0.31 mmol) of 4-hydroxypiperidine in 5 ml of dichloromethane was treated at 0° C. with 0.060 g (0.31 mmol) of EDCI. The cooling bath was allowed to come to RT and after 4 h the reaction was extracted with aqueous 10% KHSO$_4$/EtOAc (3×). The organic phases were washed with aqueous saturated NaHCO$_3$, 10% NaCl and dried over Na$_2$SO$_4$ to yield after evaporation of the solvent 0.108 g (89%) of the titled compound as white solid. MS: 468.3 (MH⁺, 1Cl).

Example 2

1-[(E)-3-(3,4-Dichloro-phenyl)-acryloyl]-4-[3-((3RS,4SR)-3,4-dihydroxy-piperidin-1-yl)-3-oxo-propyl]-[1,4]diazepan-5-one

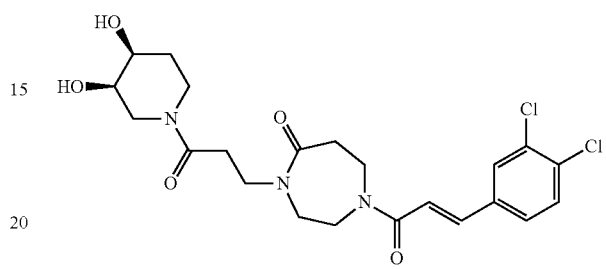

A) (rac)-cis-3,4-Bis-(tert-butyl-dimethyl-silanyloxy)-piperidin-1-yl]-3-oxo-propyl}-1-[(E)-3-(3,4-dichloro-phenyl)-acryloyl]-[1,4]diazepan-5-one In analogy to the procedure described in Example 1,3-{4-[(E)-3-(3,4-dichloro-phenyl)-acryloyl]-7-oxo-[1,4]diazepan-1-yl}-propionic acid (intermediate 5) and (cis)-(rac)-3,4-bis-(tert-butyl-dimethyl-silanyloxy)-piperidine (intermediate 9) gave the titled compound in 95% yield as a white solid. MS: 712.5 (MH⁺, 2Cl).

B) (rac)-cis-1-[(E)-3-(3,4-Dichloro-phenyl)-acryloyl]-4-[3-((3R,4S)-3,4-dihydroxy-piperidin-1-yl)-3-oxo-propyl]-[1,4]diazepan-5-one In analogy to the procedure described in intermediate 6B, treatment of (rac)-cis-3,4-bis-(tert-butyl-dimethyl-silanyloxy)-piperidin-1-yl]-3-oxo-propyl}-1-[(E)-3-(3,4-dichloro-phenyl)-acryloyl]-[1,4]diazepan-5-one with HCl in dioxane gave the titled compound in 82% yield as an off-white foam. MS: 484.2 (MH⁺, 2Cl).

Example 3

(rac)-2-{4-[(E)-3-(3,4-Dichloro-phenyl)-acryloyl]-7-oxo-[1,4]diazepan-1-yl}-4-hydroxy-N,N-dimethyl-butyramide

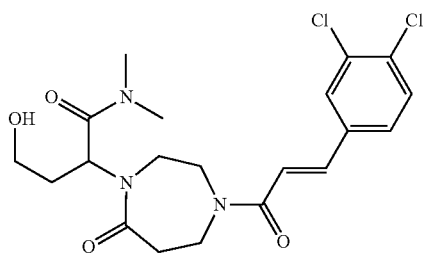 [SMILES: CN(C)C(=O)C(CCO)N1CCN(C(=O)/C=C/c2ccc(Cl)c(Cl)c2)CCC1=O]

A solution of 0.081 g (0.19 mmol) of (rac)-2-{4-[(E)-3-(3,4-dichloro-phenyl)-acryloyl]-7-oxo-[1,4]diazepan-1-yl}-4-hydroxy-butyric acid methyl ester (with 50% of the lactone, 1-[(E)-3-(3,4-dichloro-phenyl)-acryloyl]-4-(2-oxo-tetrahydro-furan-3-yl)-[1,4]diazepan-5-one) (intermediate 6) was suspended in 1 ml of THF, treated with 0.34 ml (1.89 mmol, 33% in EtOH) of dimethylamine and heated at 50° C. for 16 h. Evaporation of the solvent and drying gave 0.08 g (96%) of the titled compound as light yellow foam. MS: 442.3 (MH+, 2Cl).

Example 4

(rac)-2-{4-[(E)-3-(3,4-Dichloro-phenyl)-acryloyl]-7-oxo-[1,4]diazepan-1-yl}-4-hydroxy-N,N-dimethyl-butyramide

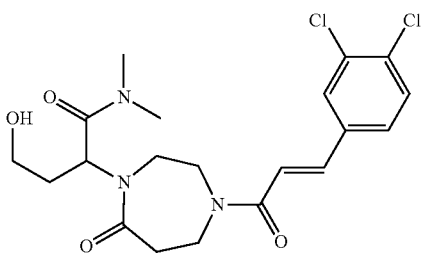

In analogy to the procedure described in example 3, treatment of (rac)-2-{4-[(E)-3-(3,4-dichloro-phenyl)-acryloyl]-7-oxo-[1,4]diazepan-1-yl}-4-hydroxy-butyric acid methyl ester (with 50% of the lactone, 1-[(E)-3-(3,4-dichloro-phenyl)-acryloyl]-4-(2-oxo-tetrahydro-furan-3-yl)-[1,4]diazepan-5-one) (intermediate 6) in EtOH with piperidine for 1.5 days at 60° C. and 2 days at RT gave 43% of the titled compound as light yellow foam. MS: 482.2 (MH+, 2Cl).

Example 5 rac-(1-[(E)-3-(3,4-Dichloro-phenyl)-acryloyl]-4-[3-hydroxy-1-(pyrrolidine-1-carbonyl)-propyl]-[1,4]diazepan-5-one)

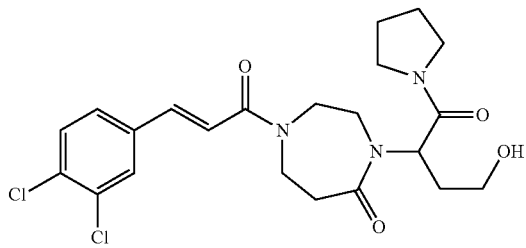 [SMILES: O=C(/C=C/c1ccc(Cl)c(Cl)c1)N1CCC(=O)N(C(CCO)C(=O)N2CCCC2)CC1]

In analogy to the procedure described in example 3, treatment of (rac)-2-{4-[(E)-3-(3,4-dichloro-phenyl)-acryloyl]-7-oxo-[1,4]diazepan-1-yl}-4-hydroxy-butyric acid methyl ester (with 50% of the lactone, 1-[(E)-3-(3,4-dichloro-phenyl)-acryloyl]-4-(2-oxo-tetrahydro-furan-3-yl)-[1,4]diazepan-5-one) (intermediate 6) in EtOH with pyrrolidine over night at RT gave 88% of the titled compound as white foam. MS: 468.1 (MH+, 2Cl).

Example 6 rac-(1-[(E)-3-(3,4-Dichloro-phenyl)-acryloyl]-4-(1-hydroxymethyl-3-oxo-3-piperidin-1-yl-propyl)-[1,4]diazepan-5-one)

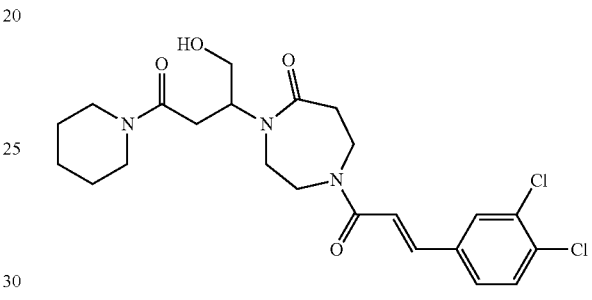

A) rac-2-{4-[(E)-3-(3,4-Dichloro-phenyl)-acryloyl]-7-oxo-[1,4]diazepan-1-yl}-4-oxo-4-piperidin-1-yl-butyric acid methyl ester A solution of 0.286 g (0.65 mmol) of 2-{4-[(E)-3-(3,4-dichloro-phenyl)-acryloyl]-7-oxo-[1,4]diazepan-1-yl}-succinic acid 1-methyl ester (intermediate 7) in 15 ml of dichloromethane was treated with 0.070 ml (0.71 mmol) of piperidine and at 0° C. with 0.148 g (0.77 mmol) of EDCI and 0.009 g (0.06 mmol) of HOBT. Over night, the suspension was naturally warmed to RT, poured on aqueous 10% KHSO$_4$ solution and extracted with EtOAc (3x). The organic phases were washed with aqueous saturated NaHCO$_3$ and aqueous 10% NaCl, dried (Na$_2$SO$_4$) and evaporated to give 0.332 g (quant.) of the titled compound as white foam. MS: 510.1 (MH+, 2Cl).

B) rac-(1-[(E)-3-(3,4-Dichloro-phenyl)-acryloyl]-4-(1-hydroxymethyl-3-oxo-3-piperidin-1-yl-propyl)-[1,4]diazepan-5-one)

A cooled (0° C.) solution of 0.150 g (0.29 mmol) of 2-{4-[(E)-3-(3,4-dichloro-phenyl)-acryloyl]-7-oxo-[1,4]diazepan-1-yl}-4-oxo-4-piperidin-1-yl-butyric acid methyl ester in 3.7 ml of EtOH was treated with 0.013 g (0.59 mmol) of LiBH$_4$ (in 3 portions during 48 h until to the end of the reaction). The mixture was stirred at RT for 48 h, cooled to 0° C. and aqueous 10% KHSO$_4$ solution was slowly added. The mixture was partitioned between aqueous saturated NaHCO$_3$/EtOAc (3x). The organic phases were dried (Na$_2$SO$_4$) and evaporated to give 0.136 g (96%) of the titled compound as white foam. MS: 482.2 (MH+, 2Cl).

Example 7

(R,S)-2-{4-[(E)-3-(3,4-Dichloro-phenyl)-acryloyl]-7-oxo-[1,4]diazepan-1-yl}-4-((S)-4-hydroxy-6-aza-spiro[2.5]oct-6-yl)-4-oxo-butyric acid methyl ester

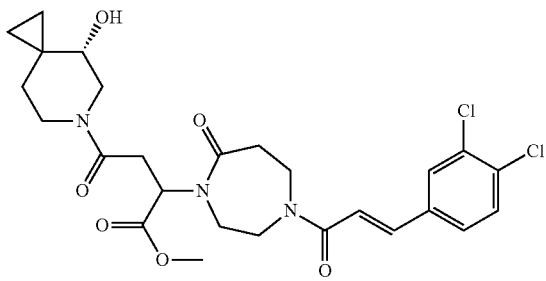 [SMILES: COC(=O)C(CC(=O)N1CCC2(CC2)[C@H](O)C1)N1CCN(C(=O)/C=C/c2ccc(Cl)c(Cl)c2)CCC1=O]

In analogy to the procedure described in example 6A, 2-{4-[(E)-3-(3,4-dichloro-phenyl)-acryloyl]-7-oxo-[1,4]diazepan-1-yl}-succinic acid 1-methyl ester (intermediate 7) with 1.5 eq. of Et$_3$N (added before cooling) and 1.05 eq. of (S)-6-aza-spiro[2.5]octan-4-ol; hydrochloride (intermediate 2) gave, after purification on a SiO$_2$-column (dichloromethane/Isopropanol 97.5:2.5-9:1 gradient), the titled compound in 33% yield as white foam. MS: 552.0 (MH$^+$, 2Cl).

Example 8 rac-(2-{4-[(E)-3-(3,4-Dichloro-phenyl)-acryloyl]-7-oxo-[1,4]diazepan-1-yl}-N,N-dimethyl-succinamic acid methyl ester)

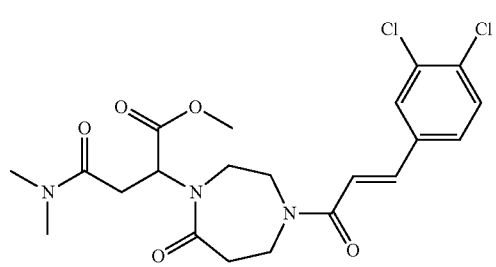 [SMILES: COC(=O)C(CC(=O)N(C)C)N1CCN(C(=O)/C=C/c2ccc(Cl)c(Cl)c2)CCC1=O]

In analogy to the procedure described in example 6A, 2-{4-[(E)-3-(3,4-dichloro-phenyl)-acryloyl]-7-oxo-[1,4]diazepan-1-yl}-succinic acid 1-methyl ester (intermediate 7) with 4 eq. of Et$_3$N (added before cooling) and dimethylamine hydrochloride gave, after purification on a SiO$_2$-column (dichloromethane/MeOH 98:2), the titled compound in 57% yield as white foam. MS: 470.0 (MH$^+$, 2Cl).

Example 9

(R,S)-2-{4-[(E)-3-(3,4-Dichloro-phenyl)-acryloyl]-7-oxo-[1,4]diazepan-1-yl}-4-((3S,5S)-3-hydroxy-5-methyl-piperidin-1-yl)-4-oxo-butyric acid methyl ester

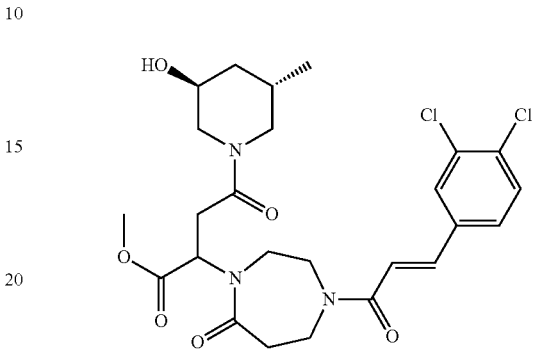

In analogy to the procedure described in example 6A, 2-{4-[(E)-3-(3,4-dichloro-phenyl)-acryloyl]-7-oxo-[1,4]diazepan-1-yl}-succinic acid 1-methyl ester (intermediate 7), 1.5 eq. of Et$_3$N (added before cooling) and 1 eq. of (3S,5S)-5-methyl-piperidin-3-ol; hydrochloride (intermediate 4) gave, after purification on a SiO$_2$-column (dichloromethane/Isopropanol 97:3-9:1 gradient), the titled compound in 54% yield as white foam. MS: 540.0 (MH$^+$, 2Cl).

Example 10

R,S)-2-{4-[(E)-3-(3-Chloro-phenyl)-acryloyl]-7-oxo-[1,4]diazepan-1-yl}-4-((S)-4-hydroxy-6-aza-spiro[2.5]oct-6-yl)-4-oxo-butyric acid methyl ester

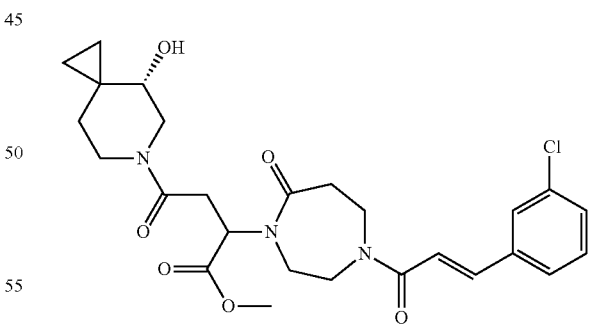

In analogy to the procedure described in example 6A, 2-{4-[(E)-3-(3-chloro-phenyl)-acryloyl]-7-oxo-[1,4]diazepan-1-yl}-succinic acid 1-methyl ester (intermediate 8) with 1.1 eq. of Et$_3$N (added before cooling) and 1.05 eq. of (S)-6-aza-spiro[2.5]octan-4-ol; hydrochloride (intermediate 2) gave, after purification on a SiO$_2$-column (dichloromethane/MeOH 98:2-95:5), the titled compound in 76% yield as white foam. MS: 518.3 (MH$^+$, 1Cl).

Example 11

1-[(E)-3-(3-Chloro-phenyl)-acryloyl]-4-[(R,S)-3-((S)-4-hydroxy-6-aza-spiro[2.5]oct-6-yl)-1-hydroxymethyl-3-oxo-propyl]-[1,4]diazepan-5-one

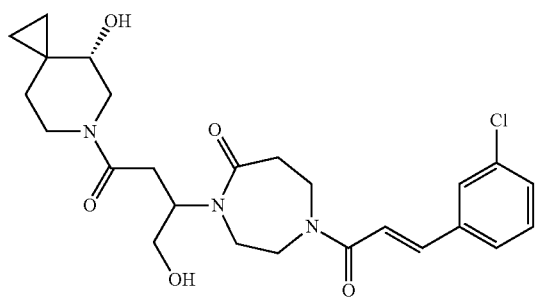 [SMILES: O=C(/C=C/c1cccc(Cl)c1)N1CCC(=O)N(C(CO)CC(=O)N2CCC3(CC3)[C@H](O)C2)CC1]

In analogy to the procedure described in example 6B, (R,S)-2-{4-[(E)-3-(3-chloro-phenyl)-acryloyl]-7-oxo-[1,4]diazepan-1-yl}-4-((S)-4-hydroxy-6-aza-spiro[2.5]oct-6-yl)-4-oxo-butyric acid methyl ester (example 10) and 2 eq. of LiBH$_4$ gave, after only 1 night of stirring and purification on a SiO$_2$-column (dichloromethane/MeOH 98:2-95:5), the titled compound in 88% yield as white foam. MS: 490.1 (MH$^+$, 1Cl).

Example 12 rac-(2-{4-[(E)-3-(3-Chloro-phenyl)-acryloyl]-7-oxo-[1,4]diazepan-1-yl}-N,N-dimethyl-succinamic acid methyl ester)

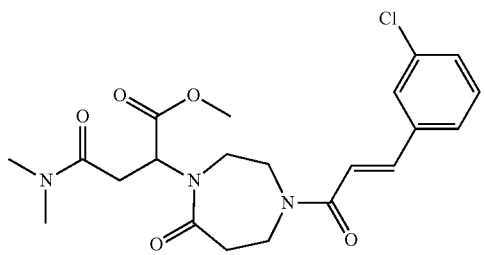 [SMILES: COC(=O)C(CC(=O)N(C)C)N1CCN(C(=O)/C=C/c2cccc(Cl)c2)CCC1=O]

In analogy to the procedure described in example 6A, 2-{4-[(E)-3-(3-chloro-phenyl)-acryloyl]-7-oxo-[1,4]diazepan-1-yl}-succinic acid 1-methyl ester (intermediate 8), 1.2 eq. of Et$_3$N (added before cooling) and dimethylamine hydrochloride gave, after purification on a SiO$_2$-column (dichloromethane/MeOH 99:1-95:5), the titled compound in 73% yield as white foam. MS: 436.3 (MH$^+$, 1Cl).

Example 13

1-[(E)-3-(3-Chloro-phenyl)-acryloyl]-4-[(R,S)-3-((S)-4-hydroxy-6-aza-spiro[2.5]oct-6-yl)-1-methoxymethyl-3-oxo-propyl]-[1,4]diazepan-5-one

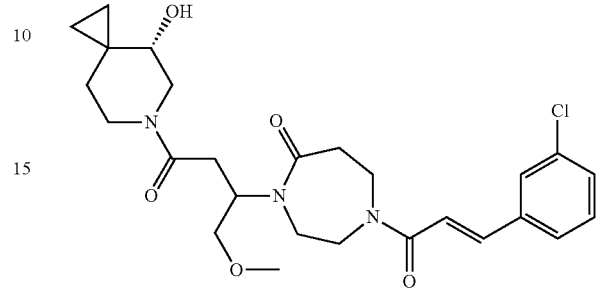

A) 3-{4-[(E)-3-(3-Chloro-phenyl)-acryloyl]-7-oxo-[1,4]diazepan-1-yl}-4-hydroxy-butyric acid tert-butyl ester In analogy to the procedure described in example 6B, 2-{4-[(E)-3-(3-chloro-phenyl)-acryloyl]-7-oxo-[1,4]diazepan-1-yl}-succinic acid 4-tert-butyl ester 1-methyl ester (intermediate 8C) and 2 eq. of LiBH$_4$ gave, after only 1 night of stirring and purification on a SiO$_2$-column (dichloromethane/MeOH 98:2-95:5), the titled compound in 84% yield as white foam. MS: 436.9 (MH$^+$, 1Cl).

B) 3-{4-[(E)-3-(3-Chloro-phenyl)-acryloyl]-7-oxo-[1,4]diazepan-1-yl}-4-methoxy-butyric acid tert-butyl ester To a solution of 0.200 g (0.46 mmol) of 3-{4-[(E)-3-(3-chloro-phenyl)-acryloyl]-7-oxo-[1,4]diazepan-1-yl}-4-hydroxy-butyric acid tert-butyl ester in 0.73 ml of DMF was added dropwise 0.142 ml (2.29 mmol) of iodomethane. The solution was treated at 0° C. with 0.024 g (0.55 mmol) of NaH (55% in oil). The reaction was stirred for 3 h at 0° C., neutralized with cold aqueous 10% KHSO$_4$ and extracted with EtOAc (3×). The organic phases were washed with aqueous saturated NaHCO$_3$ and aqueous 10% NaCl, dried (Na$_2$SO$_4$), evaporated and purified on a SiO$_2$-column (dichloromethane/Isopropanol 99:1-98:2) to give the titled compound in 61% yield as colorless gum. MS: 451.2 (MH$^+$, 1Cl).

C) 3-{4-[(E)-3-(3-Chloro-phenyl)-acryloyl]-7-oxo-[1,4]diazepan-1-yl}-4-methoxy-butyric acid In analogy to the procedure described in intermediate 7C, 3-{4-[(E)-3-(3-chloro-phenyl)-acryloyl]-7-oxo-[1,4]diazepan-1-yl}-4-methoxy-butyric acid tert-butyl ester gave the titled compound in quant. yield as light yellow gum. MS: 393.0 (M−H, 1Cl).

D) 1-[(E)-3-(3-Chloro-phenyl)-acryloyl]-4-[(R,S)-3-((S)-4-hydroxy-6-aza-spiro[2.5]oct-6-yl)-1-methoxymethyl-3-oxo-propyl]-[1,4]diazepan-5-one In analogy to the procedure described in example 6A, 3-{4-[(E)-3-(3-chloro-phenyl)-acryloyl]-7-oxo-[1,4]diazepan-1-yl}-4-methoxy-butyric with 1.1 eq. of Et₃N (added before cooling) and 1.05 eq. of (S)-6-aza-spiro[2.5]octan-4-ol; hydrochloride (intermediate 2) gave, after purification on a SiO₂-column (dichloromethane/Isopropanol 98:2-9:1), the titled compound in 66% yield as white foam. MS: 504.2 (MH⁺, 1Cl).

Example 14

(R)-2-{4-[(E)-3-(3-Chloro-phenyl)-acryloyl]-7-oxo-[1,4]diazepan-1-yl}-4-hydroxy-N,N-dimethyl-butyramide

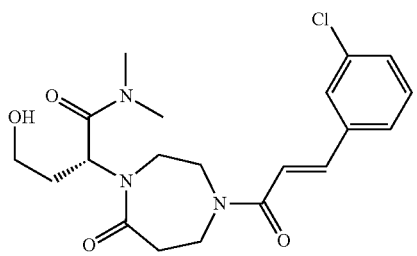 [SMILES: CN(C)C(=O)[C@@H](CCO)N1CCN(C(=O)/C=C/c2cccc(Cl)c2)CCC1=O]

A) 3-[Benzyloxycarbonyl-(2-hydroxy-ethyl)-amino]-propionic acid tert-butyl ester 6.11 g (100 mmol) of ethanolamine were cooled (0° C.), treated with 14.52 ml (100 mmol) of ter-butyl-acrylate and stirred 15 min at this temperature. During warming up to room temperature the reaction started and was kept with cooling at 25-30° C. and then stirred 18 h at room temperature. The oil was dissolved in 500 ml of tetrahydrofuran and 500 ml of water, 27.42 (110 mmol) of N-(benzyloxycarbonyloxy)succinimide were added at 0° C. followed by 27.88 ml (200 mmol) of triethlamine. The reaction was stirred at room temperature over 3 h, then partitioned between 10% aq. potassium hydrogensulfate solution and diethyl ether (3x). The organic phases were washed with 10% aq. potassium hydrogensulfate solution, sat. aq. sodium hydrogencarbonate solution, 10% aq. sodium chloride solution, dried over Na₂SO₄ evaporated and purified by flash silica gel column (n-heptane/ethyl acetate 4:1 to 1:1) to yield 27.53 g (85%) of the titled compound as light yellow oil. MS: 324.2 (MH⁺).

B) 3-[Benzyloxycarbonyl-(2-oxo-ethyl)-amino]-propionic acid tert-butyl ester

To a solution of 4.53 ml (35.65 mmol) of oxalyl chloride in 76 ml dichloromethane at −50 to −60° C. was added a solution of 5.81 ml (74.40 mmol) dimethylsulfoxide in 16 ml of dichloromethane within 20 min. The solution was stirred for 5 min and a solution of 10.03 g (31.0 mmol) 3-[benzyloxycarbonyl-(2-hydroxy-ethyl)-amino]-propionic acid tert-butyl ester in 67 ml dichloromethane was added within 20 min. The mixture was stirred for 15 min and 21.6 ml (155 mmol) of triethylamine were added within 25 min. The suspension was stirred for 2 h and slowly warmed to 0° C. The reaction was neutralized with cold 10% aq. potassium dihydrogenphosphate solution (adjusted with solid potassium dihydrogenphosphate to pH 4-5) and extracted with diethyl ether (3x). The organic phases were washed with 10% aq. potassium dihydrogenphosphate solution, sat. aq. sodium hydrogencarbonate solution, 10% aq. sodium chloride solution, dried over Na₂SO₄ evaporated to yield 9.94 g (99.8%) of the titled compound as yellow oil. MS: 322.1 (MH⁺).

C) (S)-4-Benzyloxy-2-{2-[benzyloxycarbonyl-(2-tert-butoxycarbonyl-ethyl)-amino]-ethylamino}-butyric acid methyl ester 3.71 g (11.55 mmol) of 3-[benzyloxycarbonyl-(2-oxo-ethyl)-amino]-propionic acid tert-butyl ester and 3.00 g (11.55 mmol) of (S)-2-amino-4-benzyloxy-butyric acid methyl ester; hydrochloride (intermediate 7) were dissolved in 1,2-dichloroethane/ethanol 1:1 80 ml) and treated with 1.93 ml (13.86 mmol) of triethylamine, 3.03 ml of acetic acid and 3.03 ml (24.25 mmol, 8 M in pyridine) of pyridine-borane complex (cooling with a water bath to room temperature). The reaction was stirred at room temperature over 1¼ h, then partitioned between aq. sodium hydrogencarbonate solution and diethyl ether (3x). The organic phases were washed with sat. aq. sodium hydrogencarbonate solution, 10% aq. sodium chloride solution, dried over Na₂SO₄ evaporated and purified by flash silica gel column (dichloromethane/n-heptane 1:1 to dichloromethane, then dichloromethane/ethyl acetate 4:1 to ethyl acetate) to yield 4.81 g (79%) of the titled compound as colorless oil. MS: 529.2 (MH⁺).

D) (S)-4-Benzyloxy-2-{2-[benzyloxycarbonyl-(2-carboxy-ethyl)-amino]-ethylamino}-butyric acid methyl ester; hydrochloride A solution of 4.58 g (8.66 mmol) of (S)-4-benzyloxy-2-{2-[benzyloxycarbonyl-(2-tert-butoxycarbonyl-ethyl)-amino]-ethylamino}-butyric acid methyl ester in 17 ml of dioxane was cooled (10° C.), treated with 21.7 ml (86.7 mmol) of 4 M hydrogen chloride solution in dioxane, 10 drops of water and stirred at room temperature for 12 h. The solution was evaporated, suspended in acetonitrile and evaporated (2x), dissolved in dichloromethane, treated with Na₂SO₄, filtered and evaporated to yield 4.42 g (quantitative) of the titled compound as light yellow foam. MS: 471.2 (M−H⁻).

E) 4-((S)-3-Benzyloxy-1-methoxycarbonyl-propyl)-5-oxo-[1,4]diazepane-1-carboxylic acid benzyl ester A solution of 4.40 g (8.64 mmol) of (S)-4-benzyloxy-2-{2-[benzyloxycarbonyl-(2-carboxy-ethyl)-amino]-ethylamino}-butyric acid methyl ester; hydrochloride in 85 ml dichloromethane was treated with 1.20 (8.64 mmol) of triethylamine and at 0° C. with 1.99 g (10.37 mmol) of N-(3-dimethylaminopropyl)-N'-ethylcarbodiimide hydrochloride. The cooling bath was allowed to come to room temperature and after 15 h the reaction was extracted with 10% aq. potassium hydrogensulfate solution/diethyl ether (3x). The organic phases were washed with 10% aq. potassium hydrogensulfate solution, 10% sodium chloride solution and dried over Na₂SO₄ to yield after evaporation of the solvent 3.74 g (95%) of the titled compound as light yellow oil. MS: 455.2 (MH⁺).

F) Lithium (R)-4-benzyloxy-2-(4-benzyloxycarbonyl-7-oxo-[1,4]diazepan-1-yl)-butyrate A solution of 2.01 g (4.40 mmol) of 4-((S)-3-benzyloxy-1-methoxycarbonyl-propyl)-5-oxo-[1,4]diazepane-1-carboxylic acid benzyl ester in 12 ml of tetrahydrofuran/methanol (1:1) was treated at 0° C. with 4.43 ml (4.40 mmol) of 1 M aq. lithium hydroxide solution, and kept 3 h at this temperature. The reaction was evaporated, dissolved in acetonitrile and evaporated again (3x) to give 1.94 g (98%) of the titled compound as light yellow foam. MS: 439.2 (M–H⁻).

G) 4-((R)-3-Benzyloxy-1-dimethylcarbamoyl-propyl)-5-oxo-[1,4]diazepane-1-carboxylic acid benzyl ester 1.90 g (4.30 mmol) of lithium; (R)-4-benzyloxy-2-(4-benzyloxycarbonyl-7-oxo-[1,4]diazepan-1-yl)-butyrate was suspended at room temperature in 25 ml of N,N-dimethylformamide followed by addition of 0.38 g (4.70 mmol) dimethylamine hydrochloride, 2.37 ml (17.00 mmol) of triethylamine and at 0° C. with 1.84 g (4.70 mmol) of O-(7-azabenzotriazol-1-yl)-1,1,3,3-tetramethyluronium hexafluorophosphate. The solution was stirred overnight and warmed up to room temperature. The reaction was poured on a 10% aq. potassium hydrogensulfate solution, followed by extraction with Et₂O (3 times). The organic phases were washed with a solution of sat. aq. sodium hydrogencarbonate and with a solution of 10% aq. sodium chloride. The combined organic phases were dried over Na₂SO₄ and the solvent was removed under vacuum to give 2.00 g (quant.) of the titled compound as orange oil. MS: 468.3 (MH⁺)

H) (R)-4-Hydroxy-N,N-dimethyl-2-(7-oxo-[1,4]diazepan-1-yl)-butyramide hydrochloride A solution of 1.85 g (4.00 mmol) 4-((R)-3-benzyloxy-1-dimethylcarbamoyl-propyl)-5-oxo-[1,4]diazepane-1-carboxylic acid benzyl ester in 57 ml of methanol was treated with a solution of 3.96 ml of 1 M aq. hydrochloric acid solution and 0.20 g of Pd/C (10%) and was stirred over H₂-atmosphere for 16 h. After filtration, the solution was evaporated, dissolved in methanol and evaporated (3x), followed with dichloromethane and evaporated (3x) under reduced pressure to yield 1.10 g (99%) of the titled compound as a white foam. MS: 244.1 (MH⁺).

I) (R)-2-{4-[(E)-3-(3-Chloro-phenyl)-acryloyl]-7-oxo-[1,4]diazepan-1-yl}-4-hydroxy-N,N-dimethyl-butyramide In analogy to the procedure described in example 1, (R)-4-hydroxy-N,N-dimethyl-2-(7-oxo-[1,4]diazepan-1-yl)-butyramide hydrochloride and (E)-3-chlorocinnamic acid with 1.1 eq. of triethylamine gave the titled compound in 72% yield as white foam. MS: 408.1 (MH⁺, 1Cl).

Example 15

(S)-4-[3-((S)-4-Hydroxy-6-aza-spiro[2.5]oct-6-yl)-3-oxo-propyl]-2-methyl-3-oxo-piperazine-1-carboxylic acid (3,4-dichloro-phenyl)-amide

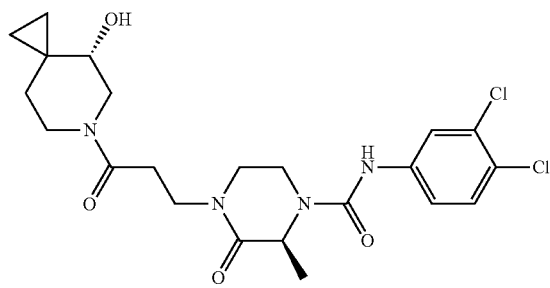 [SMILES: C[C@H]1C(=O)N(CCC(=O)N2CCC3(CC3)[C@H](O)C2)CCN1C(=O)Nc1ccc(Cl)c(Cl)c1]

A solution of 0.070 g (0.20 mmol) of 3-[(S)-4-(3,4-dichloro-phenylcarbamoyl)-3-methyl-2-oxo-piperazin-1-yl]-propionic acid (intermediate 12) in 1.5 ml of DMF was treated with 0.045 ml (0.28 mmol) of (S)-6-aza-spiro[2.5]octan-4-ol; hydrochloride (intermediate 2), 0.054 ml (0.40 mmol) of triethylamine and at 0° C. with 0.081 g (0.22 mmol) of HATU. Over night, the suspension was naturally warmed to RT, poured on aqueous 10% KHSO₄ solution and extracted with EtOAc (3x). The organic phases were washed with aqueous saturated NaHCO₃ and aqueous 10% NaCl, dried (Na₂SO₄) and evaporated to give after purification with flash chromatography (SiO₂, dichloromethane/methanol 99:1 to 96:4) 0.069 g (70%) of the titled compound as white foam. MS: 483.2 (MH⁺, 2Cl).

Example 16

(S)-2-Methyl-3-oxo-4-(3-oxo-3-piperidin-1-yl-propyl)-piperazine-1-carboxylic acid (3,4-dichloro-phenyl)-amide

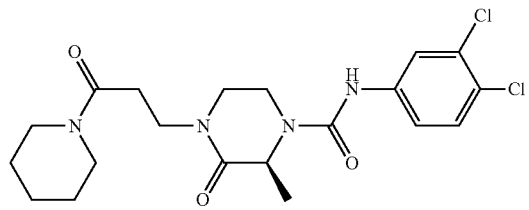 [SMILES: C[C@H]1C(=O)N(CCC(=O)N2CCCCC2)CCN1C(=O)Nc1ccc(Cl)c(Cl)c1]

In analogy to the procedure described in Example 15, 3-[(S)-4-(3,4-dichloro-phenylcarbamoyl)-3-methyl-2-oxo-piperazin-1-yl]-propionic acid (intermediate 12) and piperidine gave the titled compound in 73% yield as white solid. MS: 441.1 (MH⁺, 2Cl).

Example 17

(S)-4-[3-((R,S)-3-Hydroxy-piperidin-1-yl)-3-oxo-propyl]-2-methyl-3-oxo-piperazine-1-carboxylic acid (3,4-dichloro-phenyl)-amide

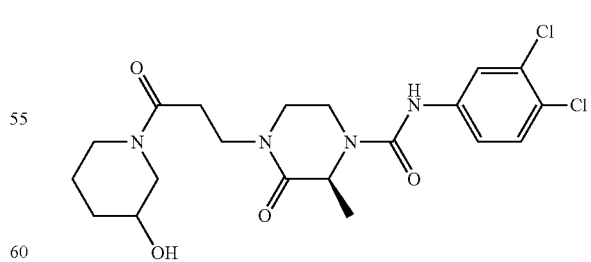

In analogy to the procedure described in Example 15, 3-[(S)-4-(3,4-dichloro-phenylcarbamoyl)-3-methyl-2-oxo-piperazin-1-yl]-propionic acid (intermediate 12) and rac-3-hydroxypiperidine gave the titled compound in 56% yield as off-white solid. MS: 457.1 (MH⁺, 2Cl).

Example 18

(S)-4-[3-(4-Hydroxy-4-methyl-piperidin-1-yl)-3-oxo-propyl]-2-methyl-3-oxo-piperazine-1-carboxylic acid (3,4-dichloro-phenyl)-amide

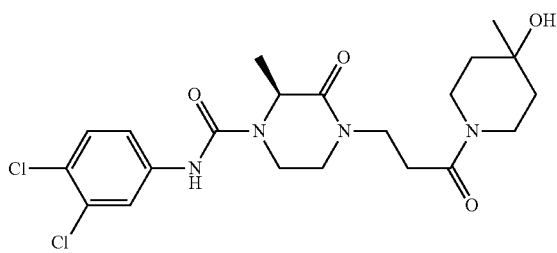 [SMILES: C[C@H]1C(=O)N(CCC(=O)N2CCC(C)(O)CC2)CCN1C(=O)Nc1ccc(Cl)c(Cl)c1]

In analogy to the procedure described in Example 15, 3-[(S)-4-(3,4-dichloro-phenylcarbamoyl)-3-methyl-2-oxo-piperazin-1-yl]-propionic acid (intermediate 12) and 4-methyl-piperidin-4-ol gave the titled compound in 51% yield as off-white solid. MS: 471.2 (MH+, 2Cl).

Example 19

(S)-4-[3-((3S,5S)-3-Hydroxy-5-methyl-piperidin-1-yl)-3-oxo-propyl]-2-methyl-3-oxo-piperazine-1-carboxylic acid (3,4-dichloro-phenyl)-amide

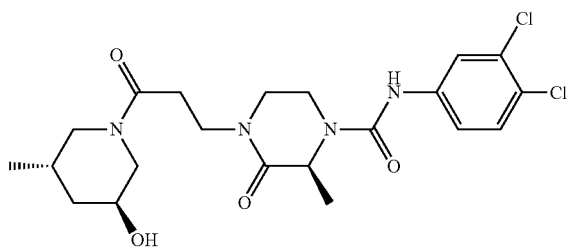 [SMILES: C[C@H]1C[C@H](O)CN(C(=O)CCN2CCN(C(=O)Nc3ccc(Cl)c(Cl)c3)[C@@H](C)C2=O)C1]

In analogy to the procedure described in Example 15, 3-[(S)-4-(3,4-dichloro-phenylcarbamoyl)-3-methyl-2-oxo-piperazin-1-yl]-propionic acid (intermediate 12) and 1.1 eq. (3S,5S)-5-methyl-piperidin-3-ol; hydrochloride (intermediate 4) gave the titled compound in 84% yield as off-white solid. MS: 471.3 (MH+, 2Cl).

Example 20

(S)-4-[3-((3S,4S)-3-Hydroxy-4-methyl-piperidin-1-yl)-3-oxo-propyl]-2-methyl-3-oxo-piperazine-1-carboxylic acid (3,4-dichloro-phenyl)-amide

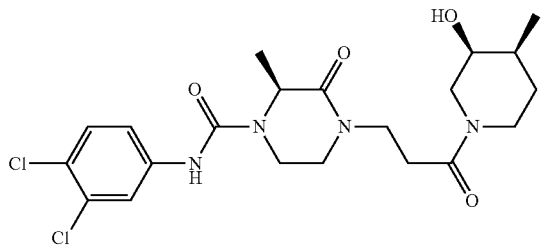 [SMILES: C[C@H]1CCN(C(=O)CCN2CCN(C(=O)Nc3ccc(Cl)c(Cl)c3)[C@@H](C)C2=O)C[C@H]1O]

In analogy to the procedure described in Example 15, 3-[(S)-4-(3,4-dichloro-phenylcarbamoyl)-3-methyl-2-oxo-piperazin-1-yl]-propionic acid (intermediate 12) and 1.1 eq. (3S,4S)-4-methyl-piperidin-3-ol; hydrochloride (intermediate 3) gave the titled compound in 84% yield as off-white solid. MS: 471.3 (MH+, 2Cl).

Example 21

(S)-4-[3-((3SR,4RS)-3-Hydroxy-4-hydroxymethyl-4-methyl-piperidin-1-yl)-3-oxo-propyl]-2-methyl-3-oxo-piperazine-1-carboxylic acid (3,4-dichloro-phenyl)-amide

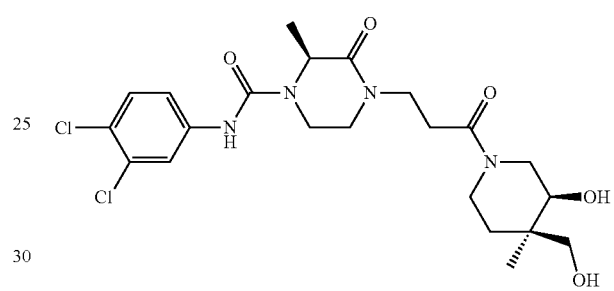

In analogy to the procedure described in Example 15, 3-[(S)-4-(3,4-dichloro-phenylcarbamoyl)-3-methyl-2-oxo-piperazin-1-yl]-propionic acid (intermediate 12) and 1.1 eq. (rac, cis)-4-hydroxymethyl-4-methyl-piperidin-3-ol; hydrochloride (intermediate 10) gave the titled compound in 81% yield as white foam. MS: 499.2 (M–H−, 2Cl).

Example 22

(S)-2-Methyl-4-(3-morpholin-4-yl-3-oxo-propyl)-3-oxo-piperazine-1-carboxylic acid (3,4-dichloro-phenyl)-amide

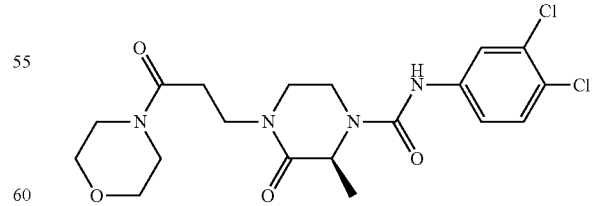

In analogy to the procedure described in Example 15, 3-[(S)-4-(3,4-dichloro-phenylcarbamoyl)-3-methyl-2-oxo-piperazin-1-yl]-propionic acid (intermediate 12) and morpholine gave the titled compound in 45% yield as white foam. MS: 441.1 (M–H−, 2Cl).

Example 23

(S)-4-[3-((3SR,4SR)-4-Fluoro-3-hydroxy-piperidin-1-yl)-3-oxo-propyl]-2-methyl-3-oxo-piperazine-1-carboxylic acid (3,4-dichloro-phenyl)-amide

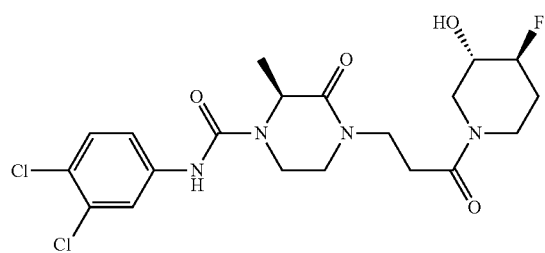 [SMILES: C[C@H]1C(=O)N(CCC(=O)N2CC[C@H](F)[C@@H](O)C2)CCN1C(=O)Nc1ccc(Cl)c(Cl)c1]

In analogy to the procedure described in Example 15, 3-[(S)-4-(3,4-dichloro-phenylcarbamoyl)-3-methyl-2-oxo-piperazin-1-yl]-propionic acid (intermediate 12) and 1.1 eq. (rac, trans)-4-fluoro-piperidin-3-ol; hydrochloride (intermediate 11) gave the titled compound in 59% yield as white foam. MS: 475.13 (MH$^+$, 2Cl).

Example 24

(S)-2-Methyl-3-oxo-4-[3-oxo-3-(4-trifluoromethyl-piperidin-1-yl)-propyl]-piperazine-1-carboxylic acid (3,4-dichloro-phenyl)-amide

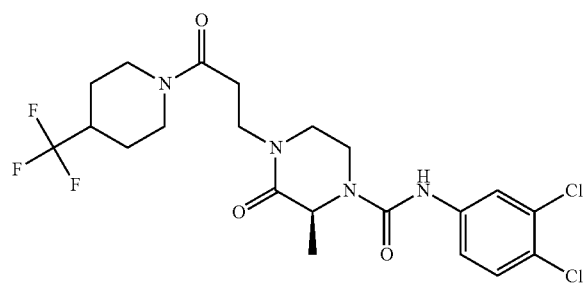 [SMILES: C[C@H]1C(=O)N(CCC(=O)N2CCC(C(F)(F)F)CC2)CCN1C(=O)Nc1ccc(Cl)c(Cl)c1]

In analogy to the procedure described in Example 15, 3-[(S)-4-(3,4-dichloro-phenylcarbamoyl)-3-methyl-2-oxo-piperazin-1-yl]-propionic acid (intermediate 12) and 4-trifluoromethyl-piperidine hydrochloride gave the titled compound in 31% yield as white foam. MS: 509.13 (MH$^+$, 2Cl).

Example 25

(S)-4-[4-((S)-4-Hydroxy-6-aza-spiro[2.5]oct-6-yl)-4-oxo-butyl]-2-methyl-3-oxo-piperazine-1-carboxylic acid (3,4-dichloro-phenyl)-amide

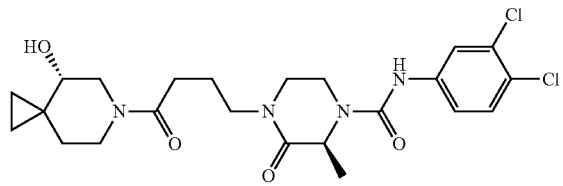 [SMILES: C[C@H]1C(=O)N(CCCC(=O)N2CCC3(CC3)[C@H](O)C2)CCN1C(=O)Nc1ccc(Cl)c(Cl)c1]

A solution of 0.050 g (0.20 mmol) of (S)-1-[4-((S)-4-hydroxy-6-aza-spiro[2.5]oct-6-yl)-4-oxo-butyl]-3-methyl-piperazin-2-one (intermediate 13) in 1 ml of dichloromethane was treated with 0.030 g (0.20 mmol) of 3,4-dichlorophenyl isocyanate. After 1 h the reaction was evaporated and purified by flash silica gel column (dichloromethane/methanol 98/2 to 9:1) to yield 0.039 g (48%) of the titled compound as white foam. MS: 495.2 (M−H$^-$, 2Cl).

Example 26

(S)-4-[4-((S)-4-Hydroxy-6-aza-spiro[2.5]oct-6-yl)-4-oxo-butyl]-2-methyl-3-oxo-piperazine-1-carboxylic acid (3-chloro-phenyl)-amide

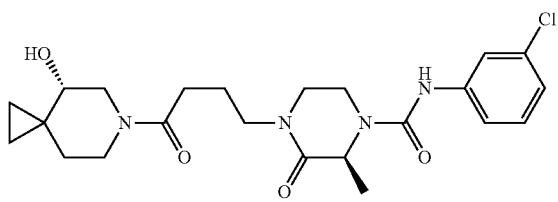 [SMILES: C[C@H]1C(=O)N(CCCC(=O)N2CCC3(CC3)[C@H](O)C2)CCN1C(=O)Nc1cccc(Cl)c1]

In analogy to the procedure described in Example 25, (S)-1-[4-((S)-4-hydroxy-6-aza-spiro[2.5]oct-6-yl)-4-oxo-butyl]-3-methyl-piperazin-2-one (intermediate 13) and 3-chlorophenyl isocyanate gave the titled compound in 17% yield as white foam. MS: 463.2 (MH$^+$, Cl).

Example 27

(S)-4-[4-((S)-4-Hydroxy-6-aza-spiro[2.5]oct-6-yl)-4-oxo-butyl]-2-methyl-3-oxo-piperazine-1-carboxylic acid (4-chloro-phenyl)-amide

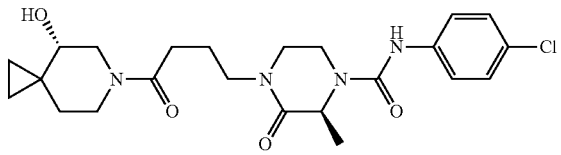 [SMILES: C[C@H]1C(=O)N(CCCC(=O)N2CCC3(CC3)[C@H](O)C2)CCN1C(=O)Nc1ccc(Cl)cc1]

In analogy to the procedure described in Example 25, (S)-1-[4-((S)-4-hydroxy-6-aza-spiro[2.5]oct-6-yl)-4-oxo-butyl]-3-methyl-piperazin-2-one (intermediate 13) and 4-chlorophenyl isocyanate gave the titled compound in 72% yield as white foam. MS: 463.2 (MH$^+$, Cl).

Example 28

(S)-4-[4-((S)-4-Hydroxy-6-aza-spiro[2.5]oct-6-yl)-4-oxo-butyl]-2-methyl-3-oxo-piperazine-1-carboxylic acid (3-trifluoromethyl-phenyl)-amide

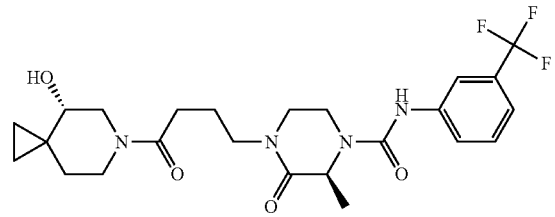 [SMILES: C[C@H]1C(=O)N(CCCC(=O)N2CCC3(CC3)[C@H](O)C2)CCN1C(=O)Nc1cccc(C(F)(F)F)c1]

In analogy to the procedure described in Example 25, (S)-1-[4-((S)-4-hydroxy-6-aza-spiro[2.5]oct-6-yl)-4-oxo-butyl]-3-methyl-piperazin-2-one (intermediate 13) and 3-(trifluoromethyl)phenyl isocyanate gave the titled compound in 24% yield as white foam. MS: 497.2 (MH+).

Example 29

(S)-4-[4-((S)-4-Hydroxy-6-aza-spiro[2.5]oct-6-yl)-4-oxo-butyl]-2-methyl-3-oxo-piperazine-1-carboxylic acid (4-trifluoromethyl-phenyl)-amide

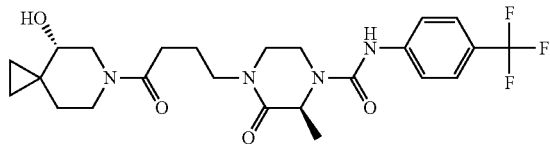 [SMILES: C[C@H]1C(=O)N(CCCC(=O)N2CCC3(CC3)[C@H](O)C2)CCN1C(=O)Nc1ccc(C(F)(F)F)cc1]

In analogy to the procedure described in Example 25, (S)-1-[4-((S)-4-hydroxy-6-aza-spiro[2.5]oct-6-yl)-4-oxo-butyl]-3-methyl-piperazin-2-one (intermediate 13) and 4-(trifluoromethyl)phenyl isocyanate gave the titled compound in 32% yield as white foam. MS: 497.2 (MH+).

Example 30

(S)-4-[4-((S)-4-Hydroxy-6-aza-spiro[2.5]oct-6-yl)-4-oxo-butyl]-2-methyl-3-oxo-piperazine-1-carboxylic acid (4-trifluoromethoxy-phenyl)-amide

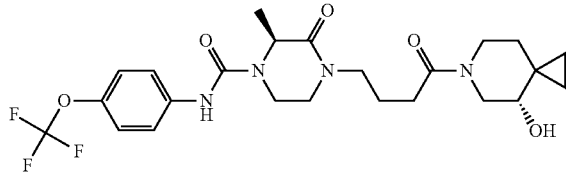 [SMILES: C[C@H]1C(=O)N(CCCC(=O)N2CCC3(CC3)[C@H](O)C2)CCN1C(=O)Nc1ccc(OC(F)(F)F)cc1]

A solution of 0.050 g (0.16 mmol) of (S)-1-[4-((S)-4-hydroxy-6-aza-spiro[2.5]oct-6-yl)-4-oxo-butyl]-3-methyl-piperazin-2-one (intermediate 13) and 0.053 ml (0.48 mmol) of 4-methylmorpholine in 1 ml of dichloromethane was treated at RT with 0.033 g (0.16 mmol) of 1-isocyanato-4-trifluoromethoxy-benzene (intermediate 14) in 1 ml of dichloromethane. After 1 h again 0.005 g of 0.033 g (0.16 mmol) of 1-isocyanato-4-trifluoromethoxy-benzene (intermediate 14) were added and after 30 min the reaction was extracted with aqueous 10% KHSO4/EtOAc (3×). The organic phases were washed with aqueous saturated NaHCO3, 10% NaCl and dried over Na2SO4 to yield, after precipitation with dichloromethane/pentane, 0.077 g (93%) of the titled compound as white amorphous solid. MS: 513.23 (MH+).

Example 31

(S)-4-[4-((S)-4-Hydroxy-6-aza-spiro[2.5]oct-6-yl)-4-oxo-butyl]-2-methyl-3-oxo-piperazine-1-carboxylic acid (3-trifluoromethoxy-phenyl)-amide

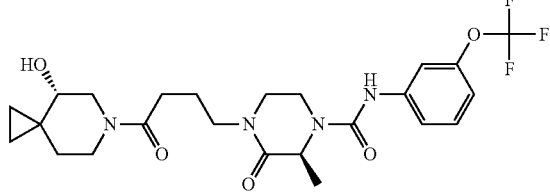

In analogy to the procedure described in Example 30, (S)-1-[4-((S)-4-hydroxy-6-aza-spiro[2.5]oct-6-yl)-4-oxo-butyl]-3-methyl-piperazin-2-one (intermediate 13) and 1-isocyanato-3-trifluoromethoxy-benzene (intermediate 15) gave the titled compound in 70% yield as white amorphous solid. MS: 513.23 (MH+).

Example 32

(S)-4-[4-((S)-4-Hydroxy-6-aza-spiro[2.5]oct-6-yl)-4-oxo-butyl]-2-methyl-3-oxo-piperazine-1-carboxylic acid (4-chloro-3-trifluoromethyl-phenyl)-amide

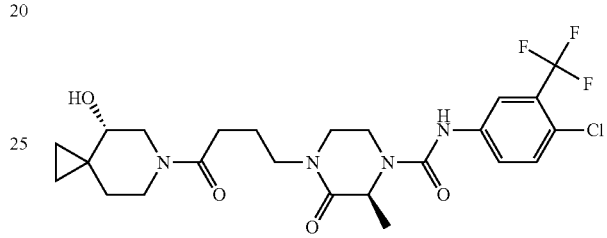

In analogy to the procedure described in Example 25, (S)-1-[4-((S)-4-hydroxy-6-aza-spiro[2.5]oct-6-yl)-4-oxo-butyl]-3-methyl-piperazin-2-one (intermediate 13) and 1-chloro-4-isocyanato-2-trifluoromethyl-benzene gave the titled compound in quantitative yield as white foam. MS: 531.20 (MH+, 1Cl).

Example 33

(S)-4-[4-((S)-4-Hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

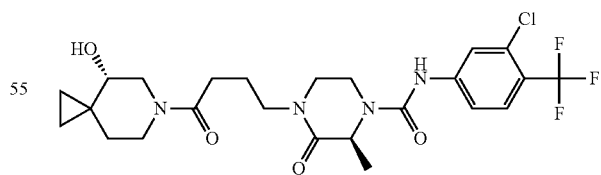

In analogy to the procedure described in Example 30, (S)-1-[4-((S)-4-hydroxy-6-aza-spiro[2.5]oct-6-yl)-4-oxo-butyl]-3-methyl-piperazin-2-one (intermediate 13) and 2-chloro-4-isocyanato-1-trifluoromethyl-benzene (intermediate 16) gave the titled compound in 83% yield as white foam. MS: 531.20 (MH+, 1Cl).

Example 34

(S)-4-[4-((S)-4-Hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide

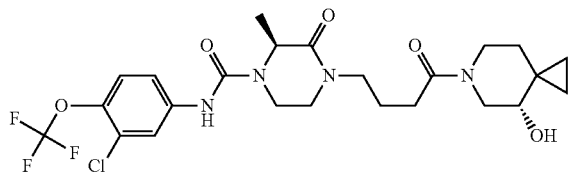 [SMILES: C[C@H]1C(=O)N(CCCC(=O)N2CCC3(CC3)[C@H](O)C2)CCN1C(=O)Nc1ccc(OC(F)(F)F)c(Cl)c1]

In analogy to the procedure described in Example 30, (S)-1-[4-((S)-4-hydroxy-6-aza-spiro[2.5]oct-6-yl)-4-oxo-butyl]-3-methyl-piperazin-2-one (intermediate 13) and 2-chloro-4-isocyanato-1-trifluoromethoxy-benzene (intermediate 17) gave the titled compound in 68% yield as light brown foam. MS: 547.19 (MH+, 1Cl).

Example 35

(S)-4-[4-((S)-4-Hydroxy-6-aza-spiro[2.5]oct-6-yl)-4-oxo-butyl]-2-methyl-3-oxo-piperazine-1-carboxylic acid (4-chloro-3-trifluoromethoxy-phenyl)-amide

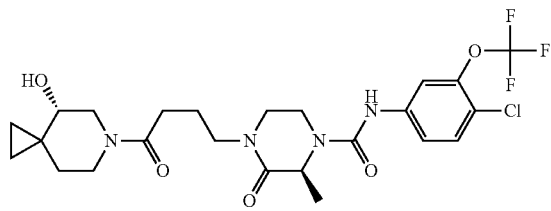 [SMILES: C[C@H]1C(=O)N(CCCC(=O)N2CCC3(CC3)[C@H](O)C2)CCN1C(=O)Nc1ccc(Cl)c(OC(F)(F)F)c1]

In analogy to the procedure described in Example 30, (S)-1-[4-((S)-4-hydroxy-6-aza-spiro[2.5]oct-6-yl)-4-oxo-butyl]-3-methyl-piperazin-2-one (intermediate 13) and 1-chloro-4-isocyanato-2-trifluoromethoxy-benzene (intermediate 18) gave the titled compound in 67% yield as light brown foam. MS: 547.19 (MH+, 1Cl).

Example 36

(S)-2-Methyl-4-[4-(2-oxa-7-aza-spiro[3.5]non-7-yl)-4-oxo-butyl]-3-oxo-piperazine-1-carboxylic acid (3-chloro-phenyl)-amide

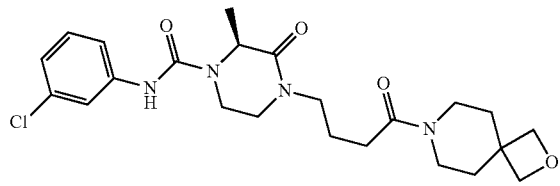 [SMILES: C[C@H]1C(=O)N(CCCC(=O)N2CCC3(CC2)COC3)CCN1C(=O)Nc1cccc(Cl)c1]

A suspension of 0.035 g (0.10 mmol) of 4-[(S)-4-(3-chloro-phenylcarbamoyl)-3-methyl-2-oxo-piperazin-1-yl]-butyric acid (intermediate 19) and 0.012 g (0.11 mmol) N-hydroxy-2-pyridon in 1.5 ml of DMF was treated at 0° C. with 0.021 g (0.11 mmol) of EDCI and was naturally warmed to RT over night. A solution of 0.035 g (0.10 mmol) of 2-oxa-7-aza-spiro[3.5]nonane trifluoro-acetic acid salt (1:2) (intermediate 20) and 0.030 ml (0.30 mmol) of triethylamine in 1.5 ml of DMF was then added and the reaction was stirred for 1 h at RT. The solution was poured on aqueous 10% KHSO₄ solution and extracted with Et₂O (3×). The organic phases were washed with aqueous saturated NaHCO₃ and aqueous 10% NaCl, dried (Na₂SO₄) and evaporated to give 0.013 g of the titled compound with maximal 60% purity. The aqueous phases were reextracted with EtOAc (3×), the organic phases were dried (NaSO₄), evaporated and dried under reduced pressure to give 0.029 g (62%) of the titled compound as light yellow foam. MS: 463.21 (MH+, Cl).

Example 37 and 38

Acetic acid (S)-1-{4-[(S)-4-(3,4-dichloro-phenylcarbamoyl)-3-methyl-2-oxo-piperazin-1-yl]-butyryl}-4,4-dimethyl-piperidin-3-yl ester and (S)-4-[4-((8)-3-Hydroxy-4,4-dimethyl-piperidin-1-yl)-4-oxo-butyl]-2-methyl-3-oxo-piperazine-1-carboxylic acid (3,4-dichloro-phenyl)-amide Example 37

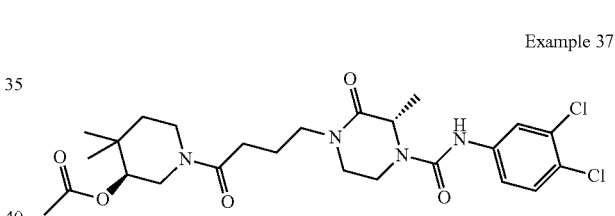

Example 38

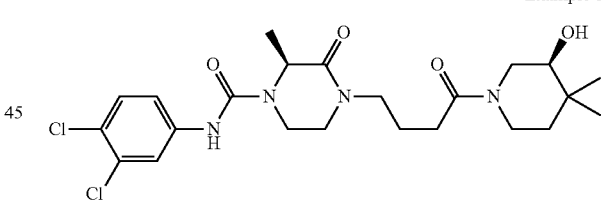

A) (S)-1-[4-((S)-3-Hydroxy-4,4-dimethyl-piperidin-1-yl)-4-oxo-butyl]-3-methyl-piperazin-2-one; Acetate A solution of 0.050 g (0.1 mmol) of (S)-4-[4-((S)-4-hydroxy-6-aza-spiro[2.5]oct-6-yl)-4-oxo-butyl]-2-methyl-3-oxo-piperazine-1-carboxylic acid benzyl ester (intermediate 13C) in 3 ml acetic acid was treated with 0.026 g of PtO₂ and was stirred over H₂-atmosphere for 2 days. After filtration and evaporation, the crude compound was again hydrogenated with 0.026 g of PtO₂/H₂ for 3 days in 3 ml of acetic acid. After filtration and evaporation, the residue was reevaporated (3 times) with toluene and the solvent was removed under vacuum to give 0.057 g (99%) of the titled compound as light yellow oil. MS: 312.23 (MH+).

B) Acetic acid (S)-1-{4-[(S)-4-(3,4-dichloro-phenyl-carbamoyl)-3-methyl-2-oxo-piperazin-1-yl]-butyryl}-4,4-dimethyl-piperidin-3-yl ester and (S)-4-[4-((S)-3-Hydroxy-4,4-dimethyl-piperidin-1-yl)-4-oxo-butyl]-2-methyl-3-oxo-piperazine-1-carboxylic acid (3,4-dichloro-phenyl)-amide In analogy to the procedure described in Example 30, (S)-1-[4-((S)-3-hydroxy-4,4-dimethyl-piperidin-1-yl)-4-oxo-butyl]-3-methyl-piperazin-2-one; Acetate and 3,4-dichlorophenyl isocyanate with 5 eq. of 4-methylmorpholine gave after flash silica gel column (dichloromethane/methanol 100% dichloromethane to 85:15): 17% of acetic acid (S)-1-{4-[(S)-4-(3,4-dichloro-phenylcarbamoyl)-3-methyl-2-oxo-piperazin-1-yl]-butyryl}-4,4-dimethyl-piperidin-3-yl ester (example 37) as white foam, MS: 563.18 (M+Na$^+$, 2Cl), Rf 0.55 (dichloromethane/methanol 9:1) and 38% of (S)-4-[4-((S)-3-hydroxy-4,4-dimethyl-piperidin-1-yl)-4-oxo-butyl]-2-methyl-3-oxo-piperazine-1-carboxylic acid (3,4-dichloro-phenyl)-amide (example 38) as white foam, MS: 499.19 (MH$^+$, 2Cl), Rf 0.50 (dichloromethane/methanol 9:1).

Example 39

(S)-4-[4-((S)-4-Hydroxy-6-aza-spiro[2.5]oct-6-yl)-4-oxo-butyl]-2-methyl-3-oxo-piperazine-1-carboxylic acid (3-chloro-phenyl)-amide

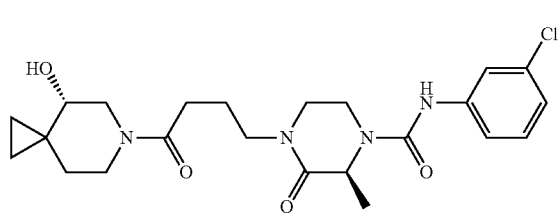 [SMILES: C[C@H]1C(=O)N(CCCC(=O)N2CCC3(CC3)[C@H](O)C2)CCN1C(=O)Nc1cccc(Cl)c1]

In analogy to the procedure described in Example 25, (S)-1-[5-((S)-4-hydroxy-6-aza-spiro[2.5]oct-6-yl)-5-oxo-pentyl]-3-methyl-piperazin-2-one (intermediate 21) and 3,4-dichlorophenyl isocyanate gave the titled compound in 74% yield as white foam. MS: 511.19 (MH$^+$, 2Cl).

Example 40

(S)-4-[(R,S)-2-Hydroxy-4-((S)-4-hydroxy-6-aza-spiro[2.5]oct-6-yl)-4-oxo-butyl]-2-methyl-3-oxo-piperazine-1-carboxylic acid (3,4-dichloro-phenyl)-amide

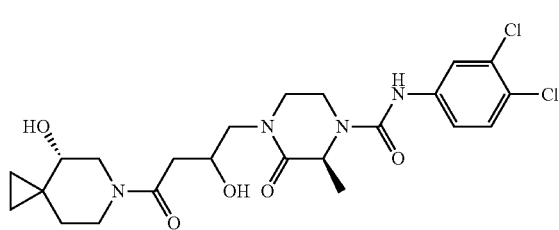 [SMILES: C[C@H]1C(=O)N(CC(O)CC(=O)N2CCC3(CC3)[C@H](O)C2)CCN1C(=O)Nc1ccc(Cl)c(Cl)c1]

In analogy to the procedure described in Example 25, (S)-1-[(R,S)-2-hydroxy-4-((S)-4-hydroxy-6-aza-spiro[2.5]oct-6-yl)-4-oxo-butyl]-3-methyl-piperazin-2-one (intermediate 23) and 3,4-dichlorophenyl isocyanate in dichloromethane/DMF gave the titled compound in 57% yield as white powder. MS: 513.16 (MH$^+$, 2Cl).

Example 41

(S)-4-[(R,S)-2-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

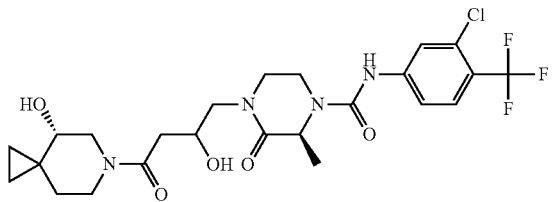

In analogy to the procedure described in Example 30, (S)-1-[(R,S)-2-hydroxy-4-((S)-4-hydroxy-6-aza-spiro[2.5]oct-6-yl)-4-oxo-butyl]-3-methyl-piperazin-2-one (intermediate 23) and 1.2 eq. of 2-chloro-4-isocyanato-1-trifluoromethyl-benzene (intermediate 16) gave the titled compound in 57% yield as white powder. MS: 547.19 (MH$^+$, Cl).

Example 42

(S)-4-[(S)-2-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

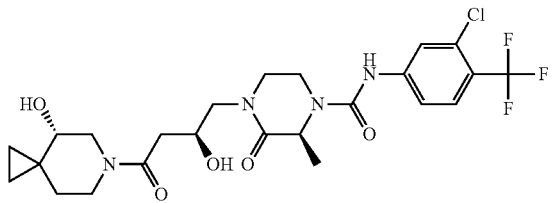 [SMILES: C[C@H]1C(=O)N(C[C@@H](O)CC(=O)N2CCC3(CC3)[C@H](O)C2)CCN1C(=O)Nc1ccc(C(F)(F)F)c(Cl)c1]

In analogy to the procedure described in Example 30, (S)—(S)-1-[2-hydroxy-4-((S)-4-hydroxy-6-aza-spiro[2.5]oct-6-yl)-4-oxo-butyl]-3-methyl-piperazin-2-one (intermediate 25) and 1.2 eq. of 2-chloro-4-isocyanato-1-trifluoromethyl-benzene (intermediate 16) gave the titled compound in 36% yield as white powder. MS: 547.19 (MH$^+$, Cl).

Example 43

(S)-4-[(R)-2-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

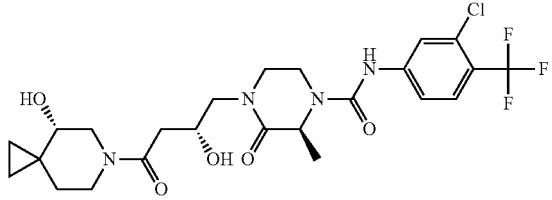 [SMILES: C[C@H]1C(=O)N(C[C@H](O)CC(=O)N2CCC3(CC3)[C@H](O)C2)CCN1C(=O)Nc1ccc(C(F)(F)F)c(Cl)c1]

The title compounds were prepared by chiral separation of (S)-4-[(R,S)-2-hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (example 41) on a Reprosil Chiral NR, (40% 2-propanol in n-heptane) to give 36% of (S)-4-[(S)-2-hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (example 42) as off-white amorphous solid, MS: 547.19 (MH+, Cl) and 30% of (S)-4-[(R)-2-hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (example 43) as an off-white amorphous solid. MS: 547.19 (MH+, Cl).

Example 44

(S)-4-[(R,S)-2-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide

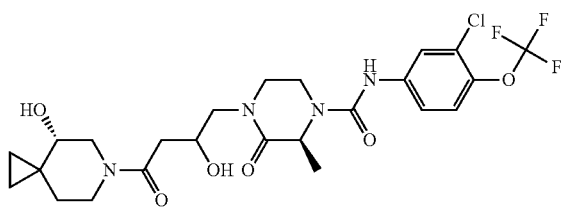 [SMILES: C[C@H]1C(=O)N(CC(O)CC(=O)N2CCC3(CC3)[C@H](O)C2)CCN1C(=O)Nc1ccc(OC(F)(F)F)c(Cl)c1]

In analogy to the procedure described in Example 30, (S)-1-[(R,S)-2-hydroxy-4-((S)-4-hydroxy-6-aza-spiro[2.5]oct-6-yl)-4-oxo-butyl]-3-methyl-piperazin-2-one (intermediate 23) and 1.3 eq. of 2-chloro-4-isocyanato-1-trifluoromethoxy-benzene (intermediate 17) in dichloromethane/DMF gave the titled compound in 52% yield as white solid. MS: 563.19 (MH+, Cl).

Example 45 and Example 46

(S)-4-[(S)-2-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide and (S)-4-[(R)-2-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide Example 45

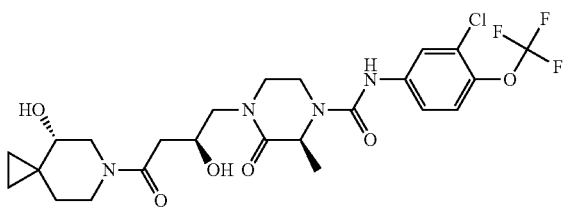

Example 46

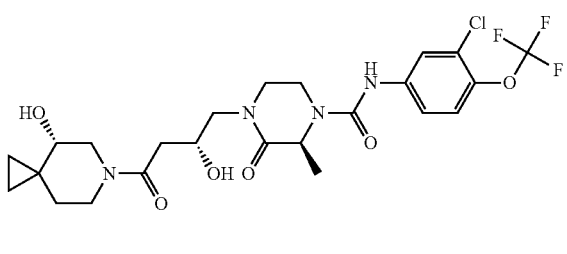

The title compounds were prepared by chiral separation of (S)-4-[(R,S)-2-hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide (example 44) on a Reprosil Chiral NR, (40% 2-propanol in n-heptane) to give 39% of (S)-4-[(S)-2-hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide (example 45) as white solid, MS: 563.19 (MH+, Cl) and 38% of (S)-4-[(R)-2-hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethoxy-phenyl)-amide (example 46) as an white solid. MS: 563.19 (MH+, Cl).

Example 47

(S)-4-[(R,S)-2-Hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide

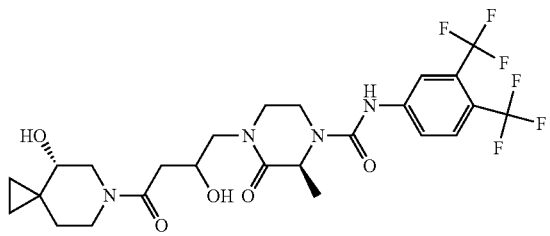 [SMILES: C[C@H]1C(=O)N(CC(O)CC(=O)N2CCC3(CC3)[C@H](O)C2)CCN1C(=O)Nc1ccc(C(F)(F)F)c(C(F)(F)F)c1]

In analogy to the procedure described in Example 30, (S)-1-[(R,S)-2-hydroxy-4-((S)-4-hydroxy-6-aza-spiro[2.5]oct-6-yl)-4-oxo-butyl]-3-methyl-piperazin-2-one (intermediate 23) and 1.2 eq. of 4-isocyanato-1,2-bis-trifluoromethyl-benzene (intermediate 26) gave the titled compound in 51% yield as white powder. MS: 581.21 (MH+).

Example 48 and Example 49

(S)-4-[(S)-2-Hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide and (S)-4-[(R)-2-Hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide Example 48

Example 49

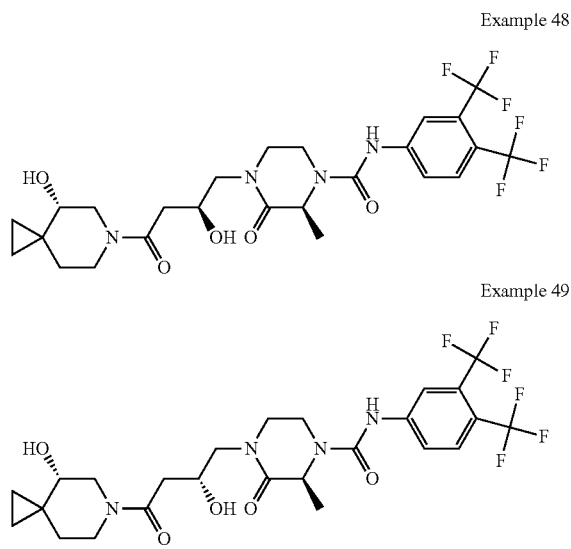

The title compounds were prepared by chiral separation of (S)-4-[(R,S)-2-hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide (example 47) on a Reprosil Chiral NR, (40% 2-propanol in n-heptane) to give 41% of (S)-4-[(S)-2-Hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide (example 48) as white powder, MS: 581.22 (MH+) and 24% of (S)-4-[(R)-2-Hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide (example 49) as white powder. MS: 581.22 (MH+).

Example 50

(S)-4-[4-((S)-4-Hydroxy-6-aza-spiro[2.5]oct-6-yl)-3,3-dimethyl-4-oxo-butyl]-2-methyl-3-oxo-piperazine-1-carboxylic acid (3-chloro-4-trifluoromethyl-phenyl)-amide

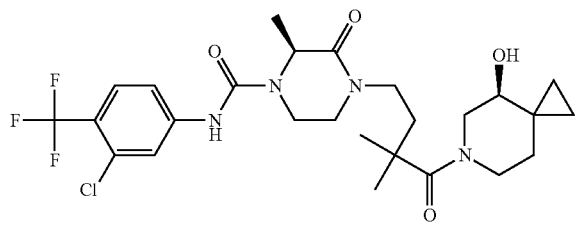 [SMILES: C[C@H]1C(=O)N(CCC(C)(C)C(=O)N2CCC3(CC3)[C@H](O)C2)CCN1C(=O)Nc1ccc(C(F)(F)F)c(Cl)c1]

In analogy to the procedure described in Example 30, (S)-1-[4-((S)-4-hydroxy-6-aza-spiro[2.5]oct-6-yl)-3,3-dimethyl-4-oxo-butyl]-3-methyl-piperazin-2-one (intermediate 28) and 1.2 eq. of 2-chloro-4-isocyanato-1-trifluoromethyl-benzene (intermediate 16) gave the titled compound in 53% yield as off-white foam. MS: 559.23 (MH+, Cl).

Example 51

(S)-4-[4-((S)-4-Hydroxy-6-aza-spiro[2.5]oct-6-yl)-3,3-dimethyl-4-oxo-butyl]-2-methyl-3-oxo-piperazine-1-carboxylic acid (3-chloro-4-trifluoromethoxy-phenyl)-amide

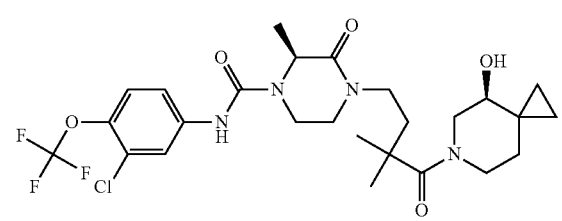 [SMILES: C[C@H]1C(=O)N(CCC(C)(C)C(=O)N2CCC3(CC3)[C@H](O)C2)CCN1C(=O)Nc1ccc(OC(F)(F)F)c(Cl)c1]

In analogy to the procedure described in Example 30, (S)-1-[4-((S)-4-hydroxy-6-aza-spiro[2.5]oct-6-yl)-3,3-dimethyl-4-oxo-butyl]-3-methyl-piperazin-2-one (intermediate 28) and 1.2 eq. of 2-chloro-4-isocyanato-1-trifluoromethoxy-benzene (intermediate 17) gave the titled compound in 53% yield as light yellow foam. MS: 575.22 (MH+, Cl).

Example 52

(S)-2-[(S)-4-(3-Chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester

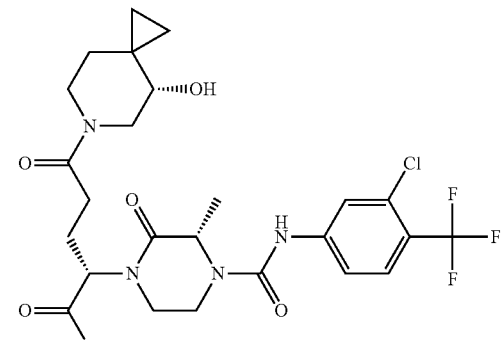

In analogy to the procedure described in Example 30, (S)-5-((S)-4-hydroxy-6-aza-spiro[2.5]oct-6-yl)-2-((S)-3-methyl-2-oxo-piperazin-1-yl)-5-oxo-pentanoic acid methyl ester; hydrochloride (intermediate 29) with 1.4 eq. of 4-methylmorpholine and 1.4 eq. of 2-chloro-4-isocyanato-1-trifluoromethyl-benzene (intermediate 16) gave the titled compound in 75% yield as off-white foam. MS: 589.20 (MH+, Cl).

Example 53

(S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethyl-phenyl)-amide

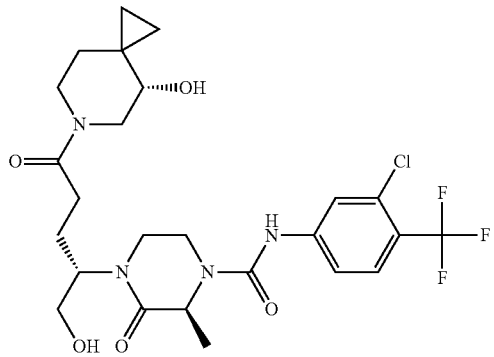 [SMILES: C[C@H]1C(=O)N([C@H](CO)CCC(=O)N2CCC3(CC3)[C@H](O)C2)CCN1C(=O)Nc1ccc(C(F)(F)F)c(Cl)c1]

A cooled (−20° C.) solution of 0.29 g (0.50 mmol) of (S)-2-[(S)-4-(3-Chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester in 1.5 ml of THF was treated with 0.25 ml (0.50 mmol) of LiBH$_4$ (2 M in THF) and 0.04 ml (1.00 mmol) of MeOH in 0.3 ml of THF. The reaction was warmed to +15° C. (during 3 h) and stirred for 1.5 h at RT, cooled to 0° C. and stopped with 0.17 ml (2.28 mmol) of acetone. The reaction was partitioned between aqueous 10% KHSO$_4$/EtOAc (3×). The organic phases were washed with aqueous saturated NaHCO$_3$, aqueous 10% NaCl, dried (Na$_2$SO$_4$) and evaporated to give after flash silica gel column (dichloromethane/MeOH 96:4 to 95:5) and precipitation (dichloromethane/ether) 0.19 g (68%) of the title compound as white amorphous powder. MS: 561.21 (MH+, Cl).

Example 54

(S)-2-[(S)-4-(3-Chloro-4-trifluoromethoxy-phenyl-carbamoyl)-3-methyl-2-oxo-piperazin-1-yl]-5-((S)-4-hydroxy-6-aza-spiro[2.5]oct-6-yl)-5-oxo-pentanoic acid methyl ester

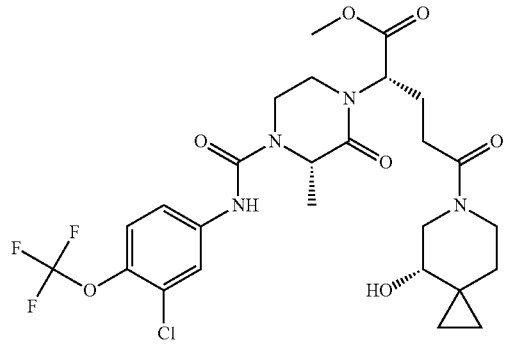 [SMILES: COC(=O)[C@H](CCC(=O)N1CCC2(CC2)[C@H](O)C1)N1CCN(C(=O)Nc2ccc(OC(F)(F)F)c(Cl)c2)[C@@H](C)C1=O]

In analogy to the procedure described in Example 30, (S)-5-((S)-4-hydroxy-6-aza-spiro[2.5]oct-6-yl)-2-((S)-3-methyl-2-oxo-piperazin-1-yl)-5-oxo-pentanoic acid methyl ester (intermediate 29) with 3 eq. of 4-methylmorpholine and 1.2 eq. of 2-chloro-4-isocyanato-1-trifluoromethoxy-benzene (intermediate 17) gave the titled compound in 67% yield as white foam. MS: 605.20 (MH+, Cl).

Example 55

(S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethoxy-phenyl)-amide

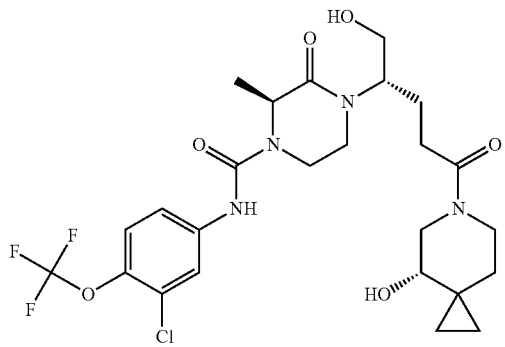 [SMILES: C[C@H]1C(=O)N([C@H](CO)CCC(=O)N2CCC3(CC3)[C@H](O)C2)CCN1C(=O)Nc1ccc(OC(F)(F)F)c(Cl)c1]

A solution of 0.200 g (0.34 mmol) of (S)-2-[(S)-4-(3-chloro-4-trifluoromethoxy-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester (example 54) in 1.0 ml of THF was treated with 0.17 ml (0.34 mmol) of LiBH$_4$ (2 M in THF) and 0.027 ml (0.68 mmol) of MeOH (with cooling bath at RT). The reaction was stirred for 2 h at RT, cooled to 0° C. and stopped with 0.1 ml of acetone. The reaction was diluted with 0.3 ml of cyclohexane, 0.9 ml of aqueous 2 N NaOH were added and after 30 min extracted with EtOAc (3×). The organic phases were washed with aqueous 10% NaCl, dried (Na$_2$SO$_4$) and evaporated to give after flash silica gel column (dichloromethane/MeOH 98:2 to 9:1) 0.172 g (88%) of the titled compound as white foam. MS: 577.20 (MH+, Cl).

Example 56

Lithium; (S)-2-[(S)-4-(3-chloro-4-trifluoromethoxy-phenylcarbamoyl)-3-methyl-2-oxo-piperazin-1-yl]-5-((S)-4-hydroxy-6-aza-spiro[2.5]oct-6-yl)-5-oxo-pentanoate

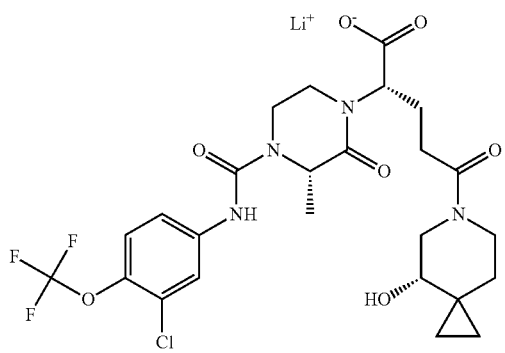 [SMILES: C[C@H]1C(=O)N([C@@H](CCC(=O)N2CCC3(CC3)[C@H](O)C2)C(=O)[O-])CCN1C(=O)Nc1ccc(OC(F)(F)F)c(Cl)c1 ; [Li+]]

A solution of 0.050 g (0.10 mmol) of (S)-2-[(S)-4-(3-chloro-4-trifluoromethoxy-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester (example 54) in 0.2 ml of tetrahydrofuran/MeOH (1:1) was treated at 0° C. with 0.083 ml (0.10 mmol) of 1 M aq. lithium hydroxide solution and kept 2 h at this temperature warmed up to RT (their was still a trace of starting material) and cooled to again to add 0.008 ml (0.01 mmol) of 1 M aq. lithium hydroxide solution. After 2 h at RT, the reaction was evaporated, dissolved in acetonitrile and evaporated (3×) and precipitated (dichloromethane/n-pentane) to give 0.027 g (54%) of the titled compound as a white foam. MS: 589.17 (M–H⁻, Cl).

Example 57

(S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethoxy-phenyl)-methyl-amide

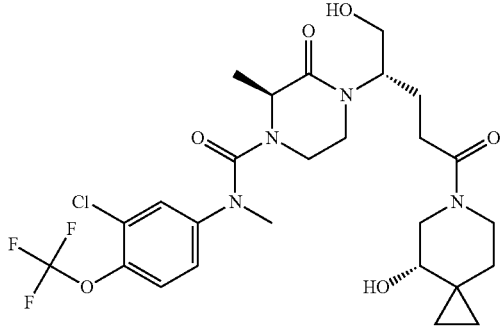 [SMILES: C[C@H]1C(=O)N([C@H](CO)CCC(=O)N2CCC3(CC3)[C@H](O)C2)CCN1C(=O)N(C)c1ccc(OC(F)(F)F)c(Cl)c1]

A solution of 0.02 ml (0.345 mmol) of iodomethane and 0.040 g (0.069 mmol) (S)-4-[(S)-4-(S)-4-hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethoxy-phenyl)-amide (example 55) in 1.5 ml of acetonitrile was cooled (0° C.) and treated with 0.023 g (0.100 mmol) of silver(I) oxide. The reaction mixture was stirred at RT for 1 day, treated again with 0.02 ml (0.345 mmol) of iodomethane and stirred for 3 days. The reaction was partitioned between aqueous 10% KHSO₄/EtOAc (3×). The organic phases were washed with aqueous saturated NaHCO₃, aqueous 10% NaCl, dried (Na₂SO₄) and evaporated to give 0.040 g (88%) of the titled compound as off-white foam. MS: 591.22 (MH⁺, Cl).

Example 58 and Example 59

(R)-4-(3,4-Dichloro-phenyl)-1-[4-((S)-4-hydroxy-6-aza-spiro[2.5]oct-6-yl)-4-oxo-butyl]-3-methyl-piperazin-2-one and (S)-4-(3,4-Dichloro-phenyl)-1-[4-((S)-4-hydroxy-6-aza-spiro[2.5]oct-6-yl)-4-oxo-butyl]-3-methyl-piperazin-2-one Example 58

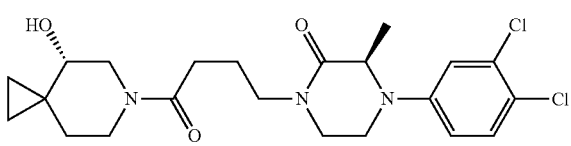

Example 59

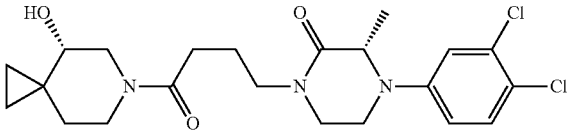

A) 4-[[(R)-2-(3,4-Dichloro-phenylamino)-propionyl]-(2,2-dimethoxy-ethyl)-amino]-butyric acid tert-butyl ester (62% ee)

A solution of 0.99 g (4.00 mmol) of 4-(2,2-dimethoxy-ethylamino)-butyric acid tert-butyl ester (intermediate 30) in 24 ml of DMF was treated with 1.03 ml (4.40 mmol) of (R)-2-(3,4-dichloro-phenylamino)-propionic acid (62% ee) (intermediate 31), 0.48 ml (4.40 mmol) of triethylamine and at 0° C. with 2.28 g (6.00 mmol) of HATU. Over night, the suspension was naturally warmed to RT, poured on aqueous 10% KHSO₄ solution and extracted with Et₂O (3×). The organic phases were washed with aqueous saturated NaHCO₃ and aqueous 10% NaCl, dried (Na₂SO₄) and evaporated to give after purification with flash chromatography (SiO₂, dichloromethane/Et₂O 97.5:2.5 to 4:1) 1.37 g (74%) of the titled compound as light yellow viscous oil. MS: 463.17 (MH⁺, 2Cl).

B) 4-[(R)-4-(3,4-Dichloro-phenyl)-3-methyl-2-oxo-piperazin-1-yl]-butyric acid (62% ee)

0.69 ml (9.00 mmol) of trifluoroacetic acid was added to a cooled solution (0° C.) of 0.28 g (0.60 mmol) 4-[[(R)-2-(3,4-dichloro-phenylamino)-propionyl]-(2,2-dimethoxy-ethyl)-amino]-butyric acid tert-butyl ester (62% ee) in 6 ml of dichloromethane. After 30 min the ice bath was removed, then after 1 h, 0.49 ml (3.00 mmol) of triethylsilane was added. After 16 h the reaction mixture was cooled to 0° C. and treated with 1.25 ml (9.00 mmol) of triethylamine, then after 15 min partitioned between Et₂O (3×)/aqueous 10% KHSO₄, the organic phases were washed with aqueous 10% KHSO₄ and aqueous 10% NaCl, dried over Na₂SO₄ and evaporated. The residue was precipitated (dichloromethane/n-pentane) to give 0.198 g (96%) of the titled compound as brown viscous oil. MS: 345.07 (MH⁺, 2Cl).

C) (R)-4-(3,4-Dichloro-phenyl)-1-[4-((S)-4-hydroxy-6-aza-spiro[2.5]oct-6-yl)-4-oxo-butyl]-3-methyl-piperazin-2-one (81% ds)

In analogy to the procedure described in Example 15, 4-[(R)-4-(3,4-dichloro-phenyl)-3-methyl-2-oxo-piperazin-1-yl]-butyric acid (62% ee) and 1.1 eq. of (S)-6-aza-spiro[2.5]octan-4-ol; hydrochloride (intermediate 2) gave after precipitation (Et₂O/n-pentane) the titled compound in 77% yield as light yellow foam. MS: 454.16 (MH⁺, 2Cl).

D) (R)-4-(3,4-Dichloro-phenyl)-1-[4-((S)-4-hydroxy-6-aza-spiro[2.5]oct-6-yl)-4-oxo-butyl]-3-methyl-piperazin-2-one and (S)-4-(3,4-Dichloro-phenyl)-1-[4-((S)-4-hydroxy-6-aza-spiro[2.5]oct-6-yl)-4-oxo-butyl]-3-methyl-piperazin-2-one The title compounds were prepared by chiral separation of (R)-4-(3,4-dichloro-phenyl)-1-[4-((S)-4-hydroxy-6-aza-spiro[2.5]oct-6-yl)-4-oxo-butyl]-3-methyl-piperazin-2-one (81% ds) on a Reprosil Chiral NR, (40% EtOH in n-heptane) to give 64% of (R)-4-(3,4-dichloro-phenyl)-1-[4-((S)-4-hydroxy-6-aza-spiro[2.5]oct-6-yl)-4-oxo-butyl]-3-methyl-piperazin-2-one (example 58) as light yellow foam, MS: 454.16 (MH$^+$, 2Cl) and 14% of (S)-4-(3,4-dichloro-phenyl)-1-[4-((S)-4-hydroxy-6-aza-spiro[2.5]oct-6-yl)-4-oxo-butyl]-3-methyl-piperazin-2-one (example 59) as an white solid. MS: 454.16 (MH$^+$, 2Cl).

Example 60 and Example 61

(S)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one and (R)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one

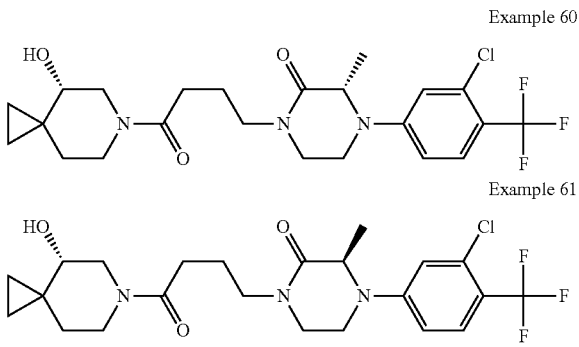

Example 60

Example 61

A) 4-[[(S)-2-(3-Chloro-4-trifluoromethyl-phenylamino)-propionyl]-(2,2-dimethoxy-ethyl)-amino]-butyric acid tert-butyl ester (26% ee)

In analogy to example 58 and example 59A, 4-(2,2-dimethoxy-ethylamino)-butyric acid tert-butyl ester (intermediate 30) and (S)-2-(3-chloro-4-trifluoromethyl-phenylamino)-propionic acid (26% ee) (intermediate 32) gave 73% of the titled compound as light yellow viscous oil. MS: 519.18 (M+Na$^+$, Cl).

B) 4-[(S)-4-(3-Chloro-4-trifluoromethyl-phenyl)-3-methyl-2-oxo-piperazin-1-yl]-butyric acid (26% ee)

In analogy to example 58 and example 59B, 4-[[(S)-2-(3-chloro-4-trifluoromethyl-phenylamino)-propionyl]-(2,2-dimethoxy-ethyl)-amino]-butyric acid tert-butyl ester (26% ee) gave 94% of the titled compound as light green foam. MS: 379.10 (MH$^+$, Cl).

C) (S)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one (63% ds)

In analogy to the procedure described in Example 15, 4-[(S)-4-(3-chloro-4-trifluoromethyl-phenyl)-3-methyl-2-oxo-piperazin-1-yl]-butyric acid (26% ee) and 1.1 eq. of (S)-6-aza-spiro[2.5]octan-4-ol; hydrochloride (intermediate 2) gave after precipitation (Et$_2$O/n-pentane) the titled compound in 95% yield as light yellow foam. MS: 488.19 (MH$^+$, Cl).

D) (S)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one and (R)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one The title compounds were prepared by chiral separation of (S)-4-(3-chloro-4-trifluoromethyl-phenyl)-1-[4-((S)-4-hydroxy-6-aza-spiro[2.5]oct-6-yl)-4-oxo-butyl]-3-methyl-piperazin-2-one (63% ds) on a Reprosil Chiral NR, (40% EtOH in n-heptane) to give 27% of (R)-4-(3-chloro-4-trifluoromethyl-phenyl)-1-[4-((S)-4-hydroxy-6-aza-spiro[2.5]oct-6-yl)-4-oxo-butyl]-3-methyl-piperazin-2-one (example 61) as off-white foam, MS: 488.19 (MH$^+$, Cl) and 42% of (S)-4-(3-chloro-4-trifluoromethyl-phenyl)-1-[4-((S)-4-hydroxy-6-aza-spiro[2.5]oct-6-yl)-4-oxo-butyl]-3-methyl-piperazin-2-one (example 60) as off-white foam, MS: 488.19 (MH$^+$, Cl).

Example 62 and Example 63

(S)-4-(4-Chloro-3-trifluoromethoxy-phenyl)-1-[4-((S)-4-hydroxy-6-aza-spiro[2.5]oct-6-yl)-4-oxo-butyl]-3-methyl-piperazin-2-one and (R)-4-(4-Chloro-3-trifluoromethoxy-phenyl)-1-[4-((S)-4-hydroxy-6-aza-spiro[2.5]oct-6-yl)-4-oxo-butyl]-3-methyl-piperazin-2-one

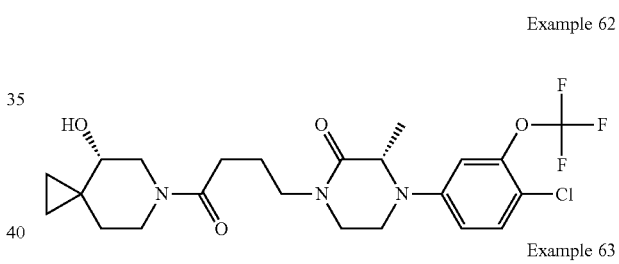

Example 62

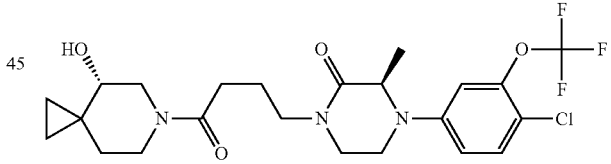

Example 63

A) 4-[[(S)-2-(4-Chloro-3-trifluoromethoxy-phenylamino)-propionyl]-(2,2-dimethoxy-ethyl)-amino]-butyric acid tert-butyl ester (22% ee)

In analogy to example 58 and example 59A, 4-(2,2-dimethoxy-ethylamino)-butyric acid tert-butyl ester (intermediate 30) and (S)-2-(4-chloro-3-trifluoromethoxy-phenylamino)-propionic acid (22% ee) (intermediate 33) gave 46% of the titled compound as light yellow oil. MS: 513.19 (MH$^+$, Cl).

B) 4-[(S)-4-(4-Chloro-3-trifluoromethoxy-phenyl)-3-methyl-2-oxo-piperazin-1-yl]-butyric acid (22% ee)

In analogy to example 58 and example 59B, 4-[[(S)-2-(4-chloro-3-trifluoromethoxy-phenylamino)-propionyl]-(2,2- dimethoxy-ethyl)-amino]-butyric acid tert-butyl ester (22% ee) gave 98% of the titled compound as green viscous. MS: 395.09 (MH+, Cl).

C) (S)-4-(4-Chloro-3-trifluoromethoxy-phenyl)-1-[4-((S)-4-hydroxy-6-aza-spiro[2.5]oct-6-yl)-4-oxo-butyl]-3-methyl-piperazin-2-one (61% ds)

In analogy to the procedure described in Example 15, 4-[(S)-4-(4-Chloro-3-trifluoromethoxy-phenyl)-3-methyl-2-oxo-piperazin-1-yl]-butyric acid (22% ee) and 1.1 eq. of (S)-6-aza-spiro[2.5]octan-4-ol; hydrochloride (intermediate 2) gave after precipitation (Et$_2$O/n-pentane) the titled compound in 63% yield as light yellow foam. MS: 504.19 (MH+, Cl).

D) (S)-4-(4-Chloro-3-trifluoromethoxy-phenyl)-1-[4-((S)-4-hydroxy-6-aza-spiro[2.5]oct-6-yl)-4-oxo-butyl]-3-methyl-piperazin-2-one and (R)-4-(4-Chloro-3-trifluoromethoxy-phenyl)-1-[4-((S)-4-hydroxy-6-aza-spiro[2.5]oct-6-yl)-4-oxo-butyl]-3-methyl-piperazin-2-one The title compounds were prepared by chiral separation of (S)-4-(4-chloro-3-trifluoromethoxy-phenyl)-1-[4-((S)-4-hydroxy-6-aza-spiro[2.5]oct-6-yl)-4-oxo-butyl]-3-methyl-piperazin-2-one (61% ds) on a Reprosil Chiral NR, (40% EtOH in n-heptane) to give 25% of (R)-4-(4-chloro-3-trifluoromethoxy-phenyl)-1-[4-((S)-4-hydroxy-6-aza-spiro[2.5] oct-6-yl)-4-oxo-butyl]-3-methyl-piperazin-2-one (example 63) as white foam, MS: 504.19 (MH+, Cl) and 33% of (S)-4-(4-chloro-3-trifluoromethoxy-phenyl)-1-[4-((S)-4-hydroxy-6-aza-spiro[2.5]oct-6-yl)-4-oxo-butyl]-3-methyl-piperazin-2-one (example 62) as white foam, MS: 504.19 (MH+, Cl).

Example 64

(S)-4-[(E)-3-(3-Chloro-4-fluoro-phenyl)-acryloyl]-1-[3-((S)-4-hydroxy-6-aza-spiro[2.5]oct-6-yl)-3-oxo-propyl]-3-methyl-piperazin-2-one

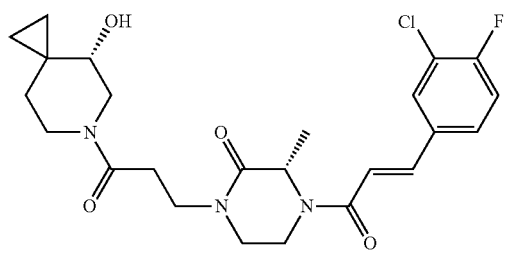 [SMILES: C[C@H]1C(=O)N(CCC(=O)N2CCC3(CC3)[C@H](O)C2)CCN1C(=O)/C=C/c1ccc(F)c(Cl)c1]

A) 3-{(S)-4-[(E)-3-(3-Chloro-4-fluoro-phenyl)-acryloyl]-3-methyl-2-oxo-piperazin-1-yl}-propionic acid Saturated aqueous sodium hydrogencarbonate solution (15 ml) was added to a solution of (S)-4-[(E)-3-(3-chloro-4-fluoro-phenyl)-acryloyl]-1-(3-hydroxy-propyl)-3-methyl-piperazin-2-one (PCT Int. Appl. WO 2009010429 A2; 5.70 g, 16.1 mmol), potassium bromide (191 mg, 1.61 mmol), and 2,2,6,6-tetramethylpiperidin-1-oxyl (25 mg, 0.16 mmol) in dichloromethane (300 mL). Sodium hypochlorite solution (10% in water, 9.6 ml, 16 mmol) was added portionwise at 0° C., and the course of the oxidation was monitored by thin layer chromatography. After all starting material had reacted, the reaction mixture was washed with sodium hydrogencarbonate, and the aqueous layer was extracted twice with dichloromethane. The organic phases were pooled, dried over magnesium sulfate, filtered, and evaporated, thus affording 3-{(S)-4-[(E)-3-(3-chloro-4-fluoro-phenyl)-acryloyl]-3-methyl-2-oxo-piperazin-1-yl}-propionaldehyde (5.15 g, 91%). The aqueous layer was acidified to pH 3 with 1 M aq. hydrochloric acid solution and extracted with dichloromethane. The organic layer was dried over magnesium sulfate, filtered, and evaporated to afford the title compound (254 mg, 4%). Colorless gum, MS: 367.3 (M−H, Cl)−.

B) (S)-4-[(E)-3-(3-Chloro-4-fluoro-phenyl)-acryloyl]-1-[3-((S)-4-hydroxy-6-aza-spiro[2.5]oct-6-yl)-3-oxo-propyl]-3-methyl-piperazin-2-one To a solution of 3-{(S)-4-[(E)-3-(3-chloro-4-fluoro-phenyl)-acryloyl]-3-methyl-2-oxo-piperazin-1-yl}-propionic acid (50 mg, 0.14 mmol), (S)-6-aza-spiro[2.5]octan-4-ol hydrochloride (intermediate 2; 24 mg, 0.15 mmol) and 4-methylmorpholine (41 mg, 0.41 mmol) in N,N-dimethylformamide (1 mL) was added O-(7-azabenzotriazol-1-yl)-N,N,N', N'-tetramethyluronium hexafluoro-phosphate (77 mg, 0.20 mmol) at room temperature, then after 16 h the reaction mixture was partitioned between water and ethyl acetate. The organic layer was washed with brine, dried over magnesium sulfate, filtered, and evaporated. Chromatography (SiO$_2$; dichloromethane→dichloromethane/methanol/25% aq. ammonia solution 90:10:0.25) produced the title compound (37 mg, 54%). White solid, MS: 478.2 (M+H, Cl)+.

Example 65

(R)-1-(3-Chloro-4-trifluoromethyl-phenyl)-4-[4-((S)-4-hydroxy-6-aza-spiro[2.5]oct-6-yl)-4-oxo-butyl]-2-methyl-1,2,3,4-tetrahydro-[1,4]diazepin-5-one (61% ds)

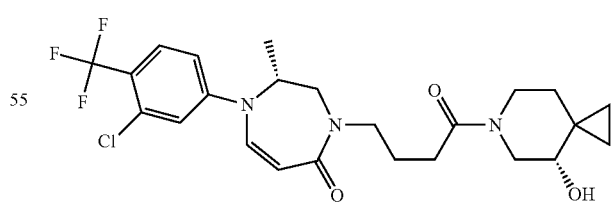

In analogy to the procedure described in Example 15, 4-[(R)-4-(3-chloro-4-trifluoromethyl-phenyl)-3-methyl-7-oxo-2,3,4,7-tetrahydro-[1,4]diazepin-1-yl]-butyric acid (22% ee) (intermediate 34) and 1.1 eq. of (S)-6-aza-spiro[2.5] octan-4-ol; hydrochloride (intermediate 2) gave after purification by flash chromatography (50 g amine-silica, ethyl acetate/n-heptane 1:1, 4:1, 9:1, 100%, ethyl acetate/ethanol 99:1 to 95:5) 69% of the title compound as off-white foam. MS: 500.19 (MH+, Cl).

Example 66

(R)-1-(3-Chloro-4-trifluoromethyl-phenyl)-4-[4-((S)-4-hydroxy-6-aza-spiro[2.5]oct-6-yl)-4-oxo-butyl]-2-methyl-[1,4]diazepan-5-one (61% ds)

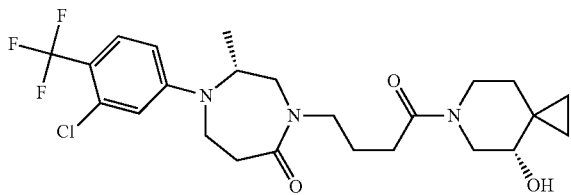 [SMILES: C[C@@H]1CN(CCCC(=O)N2CCC3(CC3)[C@H](O)C2)C(=O)CCN1c1ccc(C(F)(F)F)c(Cl)c1]

A solution of 0.066 g (0.1 mmol) of (R)-1-(3-chloro-4-trifluoromethyl-phenyl)-4-[4-((S)-4-hydroxy-6-aza-spiro[2.5]oct-6-yl)-4-oxo-butyl]-2-methyl-1,2,3,4-tetrahydro-[1,4]diazepin-5-one (61% ds) (example 65) in 2 ml MeOH was treated with 0.007 g of PtO$_2$ and was stirred over H$_2$-atmosphere for 2 days. After filtration and evaporation, the crude compound was again hydrogenated in 2 ml of MeOH and 0.007 ml (0.1 mmol) of acetic acid with 0.007 g of PtO$_2$/H$_2$ over night. After filtration and evaporation, the residue was reevaporated (3 times) with toluene and the solvent was removed under vacuum to give 0.057 g (86%) of the titled compound as white foam. MS: 502.21 (MH+, Cl).

Examples 67-94

General Procedure for Examples 67-94

To a solution of 0.04 g (0.1 mmol) of 3-{4-[(E)-3-(3,4-dichloro-phenyl)-acryloyl]-7-oxo-[1,4]diazepan-1-yl}-propionic acid (intermediate 5) and 0.04 ml of triethylamine (0.3 mmol) in 0.8 ml DMF was added 0.05 g (0.12 mmol) of HATU. The mixture was shaken for 10 minutes before being added to the appropriate amine (0.12 mmol) and the mixture shaken overnight. The mixture was then directly purified by preparative HPLC.

TABLE 1

| Example No. | Compound Name | Amine | MS: (MH+) |
|---|---|---|---|
| 67 | (rac)-1-[(E)-3-(3,4-Dichloro-phenyl)-acryloyl]-4-[3-(2-hydroxymethyl-piperidin-1-yl)-3-oxo-propyl]-[1,4]diazepan-5-one | (rac)-Piperidin-2-yl-methanol | 482.3 |
| 68 | (rac)-1-[(E)-3-(3,4-Dichloro-phenyl)-acryloyl]-4-[3-(3-hydroxymethyl-piperidin-1-yl)-3-oxo-propyl]-[1,4]diazepan-5-one | (rac)-Piperidin-3-yl-methanol | 482.3 |
| 69 | 1-[(E)-3-(3,4-Dichloro-phenyl)-acryloyl]-4-[3-(4-hydroxymethyl-piperidin-1-yl)-3-oxo-propyl]-[1,4]diazepan-5-one | Piperidin-4-yl-methanol | 482.3 |

TABLE 1-continued

| Example No. | Compound Name | Amine | MS: (MH+) |
|---|---|---|---|
| 70 | (rac)-1-[(E)-3-(3,4-Dichloro-phenyl)-acryloyl]-4-[3-(3-hydroxy-piperidin-1-yl)-3-oxo-propyl]-[1,4]diazepan-5-one | (rac)-Piperidin-3-ol | 468.3 |
| 71 | (rac)-1-[(E)-3-(3,4-Dichloro-phenyl)-acryloyl]-4-[3-(3-hydroxy-4-methyl-piperidin-1-yl)-3-oxo-propyl]-[1,4]diazepan-5-one | (rac)-4-Methyl-piperidin-3-ol hydrochloride (WO2007122103A1) | 482.3 |
| 72 | 1-[(E)-3-(3,4-Dichloro-phenyl)-acryloyl]-4-[3-(4-hydroxy-4-phenyl-piperidin-1-yl)-3-oxo-propyl)-[1,4]diazepan-5-one | 4-Phenyl-piperidin-4-ol | 544.3 |
| 73 | 1-[(E)-3-(3,4-Dichloro-phenyl)-acryloyl]-4-[3-(4-hydroxy-4-methyl-piperidin-1-yl)-3-oxo-propyl]-[1,4]diazepan-5-one | 4-Methyl-piperidin-4-ol | 482.3 |

TABLE 1-continued

| Example No. | Compound Name | Amine | MS: (MH+) |
|---|---|---|---|
| 74 | (rac)-1-[(E)-3-(3,4-Dichloro-phenyl)-acryloyl]-4-[3-(3-hydroxy-3-methyl-piperidin-1-yl)-3-oxo-propyl]-[1,4]diazepan-5-one | (rac)-3-Methyl-piperidin-3-ol | 482.3 |
| 75 | (rac)-1-[(E)-3-(3,4-Dichloro-phenyl)-acryloyl]-4-[3-(2-hydroxymethyl-2-methyl-piperidin-1-yl)-3-oxo-propyl]-[1,4]diazepan-5-one | (rac)-2-Methyl-piperidin-2-yl)-methanol hydrochloride (WO2007122103A1) | 496.3 |
| 76 | 1-[(E)-3-(3,4-Dichloro-phenyl)-acryloyl]-4-[3-(4'-hydroxy-3',4',5',6'-tetrahydro-2'H-[2,4']bipyridinyl-1'-yl)-3-oxo-propyl]-[1,4]diazepan-5-one | 2',3',5',6'-Tetrahydro-1'H-[2,4']bipyridinyl-4'-ol | 545.3 |
| 77 | 1-[(E)-3-(3,4-Dichloro-phenyl)-acryloyl]-4-[3-(4'-hydroxy-3',4',5',6'-tetrohydro-2'H-[3,4']bipyridinyl-1'-yl)-3-oxo-propyl]-[1,4]diazepan-5-one | 2',3',5',6'-Tetrahydro-1'H-[3,4']bipyridinyl-4'-ol | 545.3 |

TABLE 1-continued

| Example No. | Compound Name | Amine | MS: (MH+) |
|---|---|---|---|
| 78 | 1-[(E)-3-(3,4-Dichloro-phenyl)-acryloyl]-4-[3-(4-hydroxy-3,4,5,6-tetrahydro-2H-[4,4']bipyridinyl-1-yl)-3-oxo-propyl)-[1,4]diazepan-5-one | 2,3,5,6-Tetrahydro-1H-[4,4']bipyridinyl-4-ol | 545.3 |
| 79 | 1-[(E)-3-(3,4-Dichloro-phenyl)-acryloyl]-4-[3-oxo-3-(3-oxo-piperidin-1-yl)-propyl]-[1,4]diazepan-5-one | Piperidin-3-one | 466.4 |
| 80 | 1-[(E)-3-(3,4-Dichloro-phenyl)-acryloyl]-4-[3-(4-methyl-3-oxo-piperazin-1-yl)-3-oxo-propyl]-[1,4]diazepan-5-one | Methyl-piperazin-2-one | 481.3 |
| 81 | (rac)-1-[(E)-3-(3,4-Dichloro-phenyl)-acryloyl]-4-[3-(2-hydroxymethyl-2-methyl-pyrrolidin-1-yl)-3-oxo-propyl]-[1,4]diazepan-5-one | (rac)-(2-Methyl-pyrrolidin-2-yl)-methanol (intermediate 37) | 482.3 |

TABLE 1-continued

| Example No. | Compound Name | Amine | MS: (MH+) |
|---|---|---|---|
| 82 | 1-[(E)-3-(3,4-Dichloro-phenyl)-acryloyl]-4-(3-oxo-3-piperidin-1-yl-propyl)-[1,4]diazepan-5-one | Piperidine | 452.3 |
| 83 | 4-[3-(8-Aza-spiro[4.5]dec-8-yl)-3-oxo-propyl]-1-[(E)-3-(3,4-dichloro-phenyl)-acryloyl]-[1,4]diazepan-5-one | 8-Aza-spiro[4.5]decane | 506.3 |
| 84 | 4-[3-(4-tert-Butyl-4-hydroxy-piperidin-1-yl)-3-oxo-propyl]-1-[(E)-3-(3,4-dichloro-phenyl)-acryloyl]-[1,4]diazepan-5-one | 4-tert-Butyl-piperidin-4-ol (Chem. Pharm. Bull. 1993, 41(11), 1971) | 524.3 |
| 85 | 1-[(E)-3-(3,4-Dichloro-phenyl)-acryloyl]-4-[3-(4-methyl-piperidin-1-yl)-3-oxo-propyl]-[1,4]diazepan-5-one | 4-Methyl-piperidine | 466.3 |

TABLE 1-continued

| Example No. | Compound Name | Amine | MS: (MH+) |
|---|---|---|---|
| 86 | 1-[(E)-3-(3,4-Dichloro-phenyl)-acryloyl]-4-[3-(1-oxa-8-aza-spiro[4.5]dec-8-yl)-3-oxo-propyl]-[1,4]diazepan-5-one | 1-Oxa-8-aza-spiro[4.5]decane | 508.3 |
| 87 | 1-[(E)-3-(3,4-Dichloro-phenyl)-acryloyl]-4-[3-(4-hydroxymethyl-4-methyl-piperidin-1-yl)-3-oxo-propyl]-[1,4]diazepan-5-one | (4-Methyl-piperidin-4-yl)-methanol | 496.3 |
| 88 | [1-(3-{4-[(E)-3-(3,4-Dichloro-phenyl)-acryloyl]-7-oxo-[1,4]diazepan-1-yl}-propionyl)-piperidin-4-yl]-carbamic acid methyl ester | Piperidin-4-yl-carbamic acid methyl ester (WO2007122103A1) | 525.3 |
| 89 | 8-(3-{4-[(E)-3-(3,4-Dichloro-phenyl)-acryloyl]-7-oxo-[1,4]diazepan-1-yl}-propionyl)-1,3,8-triaza-spiro[4.5]decane-2,4-dione | 1,3,8-Triaza-spiro[4.5]decane-2,4-dione (J. Org. Chem. 1996, 61, 22, 7650-7651) | 536.2 |

TABLE 1-continued

| Example No. | Compound Name | Amine | MS: (MH+) |
|---|---|---|---|
| 90 | 8-(3-{4-[(E)-3-(3,4-Dichloro-phenyl)-acryloyl]-7-oxo-[1,4]diazepan-1-yl}-propionyl)-1-oxa-3,8-diaza-spiro[4.5]decan-2-one | 1-Oxa-3,8-diaza-spiro[4.5]decan-2-one (J. Med. Chem. 1995, 38, 3772) | 523.3 |
| 91 | 1-[(E)-3-(3,4-Dichloro-phenyl)-acryloyl]-4-{3-oxo-3-[4-(1H-pyrazol-3-yl)-piperidin-1-yl]-propyl}-[1,4]diazepan-5-one | 4-(1H-Pyrazol-3-yl)-piperidine (WO2004/094371A2) | 518.3 |
| 92 | 1-[(E)-3-(3,4-Dichloro-phenyl)-acryloyl]-4-{3-oxo-3-[4-(2-oxo-imidazolidin-1-yl)-piperidin-1-yl]-propyl}-[1,4]diazepan-5-one | 1-Piperidin-4-yl-imidazolidin-2-one (WO2005/101989 A2) | 536.3 |

TABLE 1-continued

| Example No. | Compound Name | Amine | MS: (MH+) |
|---|---|---|---|
| 93 | 8-(3-{4-[(E)-3-(3,4-Dichloro-phenyl)-acryloyl]-7-oxo-[1,4]diazepan-1-yl}-propionyl)-2,8-diaza-spiro[4.5]decane-1,3-dione | 2,8-Diaza-spiro[4.5]decane-1,3-dione (WO2004169256A1) | 535.3H |
| 94 | 1-(3-{4-[(E)-3-(3,4-Dichloro-phenyl)-acryloyl]-7-oxo-[1,4]diazepan-1-yl}-propionyl)-piperidine-4-carboxylic acid amide | Piperidine-4-carboxylic acid | 495.3 |

Examples 95-100

General Procedure for Examples 95-100

To a solution of 0.04 g (0.1 mmol) of {4-[(E)-3-(3,4-dichloro-phenyl)-acryloyl]-7-oxo-[1,4]diazepan-1-yl}-acetic acid (intermediate 36) and 0.04 ml of triethylamine (0.3 mmol) in 0.8 ml DMF was added 0.05 g (0.12 mmol) of HATU. The mixture was shaken for 10 minutes before being added to the appropriate amine (0.12 mmol) and the mixture shaken overnight. The mixture was then directly purified by preparative HPLC.

TABLE 2

| Example No. | Compound Name | Amine | MS: (MH+) |
|---|---|---|---|
| 95 | 1-[(E)-3-(3,4-Dichloro-phenyl)-acryloyl]-4-(2-oxo-2-piperidin-1-yl-ethyl)-[1,4]diazepan-5-one | piperdine | 438.2 |

TABLE 2-continued

| Example No. | Compound Name | Amine | MS: (MH+) |
|---|---|---|---|
| 96 | 4-[2-(8-Aza-spiro[4.5]dec-8-yl)-2-oxo-ethyl]-1-[(E)-3-(3,4-dichloro-phenyl)-acryloyl]-[1,4]diazepan-5-one | 8-Aza-spiro[4.5]decane | 492.3 |
| 98 | 1-[(E)-3-(3,4-Dichloro-phenyl)-acryloyl]-4-[2-(1-oxa-8-aza-spiro[4.5]dec-8-yl)-2-oxo-ethyl]-[1,4]diazepan-5-one | 1-Oxa-8-aza-spiro[4.5]decane | 494.3 |
| 99 | 1-[(E)-3-(3,4-Dichloro-phenyl)-acryloyl]-4-[2-(4-hydroxymethyl-4-methyl-piperidin-1-yl)-2-oxo-ethyl]-[1,4]diazepan-5-one | (4-Methyl-piperidin-4-yl)-methanol | 482.3 |
| 100 | (rac)-1-[(E)-3-(3,4-Dichloro-phenyl)-acryloyl]-4-[2-(3-hydroxy-3-methyl-piperidin-1-yl)-2-oxo-ethyl]-[1,4]diazepan-5-one | (rac)-3-Methyl-piperidin-3-ol | 468.3 |

Examples 101-104

General Procedure for Examples 101-104

To a solution of 0.04 g (0.1 mmol) of 3-{(R)-4-[(E)-3-(3-chloro-phenyl)-acryloyl]-3-methyl-7-oxo-[1,4]diazepan-1-yl}-propionic acid (intermediate 38) and 0.04 ml of triethylamine (0.3 mmol) in 0.8 ml DMF was added 0.05 g (0.12 mmol) of HATU. The mixture was shaken for 10 minutes before being added to the appropriate amine (0.12 mmol) and the mixture shaken overnight. The mixture was then directly purified by preparative HPLC.

TABLE 3

| Example No. | Compound Name | Amine | MS: (MH+) |
|---|---|---|---|
| 101 | (R)-1-[(E)-3-(3-Chloro-phenyl)-acryloyl]-2-methyl-4-(3-oxo-3-piperidin-1-yl-propyl)-[1,4]diazepan-5-one | piperidine | 432.3 |
| 102 | (R)-1-[(E)-3-(3-Chloro-phenyl)-acryloyl]-4-[3-(4-hydroxy-4-methyl-piperidin-1-yl)-3-oxo-propyl]-2-methyl-[1,4]diazepan-5-one | 4-Methyl-piperidin-4-ol | 462.2 |
| 103 | (R)-1-[(E)-3-(3-Chloro-phenyl)-acryloyl]-4-[3-((3S,5S)-3-hydroxy-5-methyl-piperidin-1-yl)-3-oxo-propyl]-2-methyl-[1,4]diazepan-5-one | (3S,5S)-5-Methyl-piperidin-3-ol (intermediate 4) | 462.2 |
| 104 | (R)-1-[(E)-3-(3-Chloro-phenyl)-acryloyl]-4-[3-((S)-4-hydroxy-6-aza-spiro[2.5]oct-6-yl)-3-oxo-propyl]-2-methyl-[1,4]diazepan-5-one | (S)-6-Aza-spiro[2.5]octan-4-ol (intermediate 2) | 474.3 |

Examples 105-115

General Procedure for Examples 105-115

To a solution of 0.04 g (0.1 mmol) of 4-[(S)-4-(3-chloro-phenylcarbamoyl)-3-methyl-2-oxo-piperazin-1-yl]-butyric acid (intermediate 19) and 0.04 ml of triethylamine (0.3 mmol) in 0.8 ml DMF was added 0.05 g (0.12 mmol) of HATU. The mixture was shaken for 10 minutes before being added to the appropriate amine (0.12 mmol) and the mixture shaken overnight. The mixture was then directly purified by preparative HPLC.

| Example No. | Compound Name | Amine | MS: (MH+) |
|---|---|---|---|
| 105 | (S)-4-[4-(4-Hydroxy-4-methyl-piperidin-1-yl)-4-oxo-butyl]-2-methyl-3-oxo-piperazine-1-carboxylic acid (3-chloro-phenyl)-amide | 4-Methyl-piperidin-4-ol | 451.11 |
| 106 | (S)-2-Methyl-3-oxo-4-[4-oxo-4-(4-trifluoromethyl-piperidin-1-yl)-butyl]-piperazine-1-carboxylic acid (3-chloro-phenyl)-amide | 4-Trifluoromethyl-piperidine | 489.1 |
| 107 | (S)-2-Methyl-3-oxo-4-[4-oxo-4-(2-oxo-1-oxa-3,8-diaza-spiro[4.5]dec-8-yl)-butyl]-piperazine-1-carboxylic acid (3-chloro-phenyl)-amide | 1-Oxa-3,8-diaza-spiro[4.5]decan-2-one (J. Med. Chem. 1995, 38, 3772) | 492.1 |
| 108 | (S)-2-Methyl-4-[4-(1-oxa-8-aza-spiro[4.5]dec-8-yl)-4-oxo-butyl]-3-oxo-piperazine-1-carboxylic acid (3-chloro-phenyl)-amide | 1-Oxa-8-aza-spiro[4.5]decane | 477.1 |
| 109 | (S)-4-[4-(4-Hydroxymethyl-piperidin-1-yl)-4-oxo-butyl]-2-methyl-3-oxo-piperazine-1-carboxylic acid (3-chloro-phenyl)-amide | Piperidin-4-yl-methanol | 451.1 |

TABLE 4-continued

| Example No. | Compound Name | Amine | MS: (MH+) |
|---|---|---|---|
| 110 | (S)-4-[4-(1,1-Dioxo-1 lambda*6*-thiomorpholin-4-yl)-4-oxo-butyl]-2-methyl-3-oxo-piperazine-1-carboxylic acid (3-chloro-phenyl)-amide | Thiomorpholine 1,1-dioxide | 471.1 |
| 111 | (S)-4-[4-((3S,4S)-3-Hydroxy-4-methyl-piperidin-1-yl)-4-oxo-butyl]-2-methyl-3-oxo-piperazine-1-carboxylic acid (3-chloro-phenyl)-amide | (3S,4S)-4-Methyl-piperidin-3-ol hydrochloride (intermediate 3) | 451.1 |
| 112 | (S)-4-[4-((RS)-3-Hydroxy-piperidin-1-yl)-4-oxo-butyl]-2-methyl-3-oxo-piperazine-1-carboxylic acid (3-chloro-phenyl)-amide | (rac)-Piperidin-3-ol | 437.1 |
| 113 | (S)-4-[4-((3S,5S)-3-Hydroxy-5-methyl-piperidin-1-yl)-4-oxo-butyl]-2-methyl-3-oxo-piperazine-1-carboxylic acid (3-chloro-phenyl)-amide | (3S,5S)-5-Methyl-piperidin-3-ol Hydrochloride (intermediate 4) | 451.1 |
| 114 | (S)-4-[4-((3SR,4RS)-3-Hydroxy-4-hydroxymethyl-4-methyl-piperidin-1-yl)-4-oxo-butyl]-2-methyl-3-oxo-piperazine-1-carboxylic acid (3-chloro-phenyl)-amide | (3SR,4RS)-4-Hydroxymethyl-4-methyl-piperidin-3-ol hydrochloride (WO2007122103 A1) | 481.1 |

TABLE 4-continued

| Example No. | Compound Name | Amine | MS: (MH+) |
|---|---|---|---|
| 115 | (S)-4-[4-((3SR,4SR)-4-Fluoro-3-hydroxy-piperidin-1-yl)-4-oxo-butyl]-2-methyl-3-oxo-piperazine-1-carboxylic acid (3-chloro-phenyl)-amide | (3SR,4SR)-4-Fluoro-piperidin-3-ol hydrochloride (intermediate 11) | 455.2 |

Examples 116-119

General Procedure for examples 116-119

A solution of 0.03 g (0.1 mmol) of 4-[4-((S)-4-Hydroxy-6-aza-spiro[2.5]oct-6-yl)-4-oxo-butyl]-[1,4]diazepan-5-one (intermediate 39) in 0.8 ml DMF was added to the appropriate isocyanate (0.1 mmol) and the mixture shaken for 1 h. The mixture was then directly purified by preparative HPLC.

TABLE 5

| Example No. | Compound Name | Isocyanate | MS: (MH+) |
|---|---|---|---|
| 116 | 4-[4-((S)-4-Hydroxy-6-aza-spiro[2.5]oct-6-yl)-4-oxo-butyl]-5-oxo-[1,4]diazepane-1-carboxylic acid (3-chloro-phenyl)-amide | 3-chlorophenylisocyanate | 463.1 |
| 117 | 4-[4-((S)-4-Hydroxy-6-aza-spiro[2.5]oct-6-yl)-4-oxo-butyl]-5-oxo-[1,4]diazepane-1-carboxylic acid (3,4-dichloro-phenyl)-amide | 3,4-dichlorophenylisocyanate | 496.9 |
| 118 | 4-[4-((S)-4-Hydroxy-6-aza-spiro[2.5]oct-6-yl)-4-oxo-butyl]-5-oxo-[1,4]diazepane-1-carboxylic acid (4-chloro-3-trifluoromethyl-phenyl)-amide | 1-Chloro-4-isocyanato-2-trifluoromethyl-benzene | 531.0 |

| Example No. | Compound Name | Isocyanate | MS: (MH+) |
|---|---|---|---|
| 119 | 4-[4-((S)-4-Hydroxy-6-aza-spiro[2.5]oct-6-yl)-4-oxo-butyl]-5-oxo-[1,4]diazepane-1-carboxylic acid (3-chloro-4-trifluoromethyl-phenyl)-amide | 2-Chloro-4-isocyanato-1-trifluoromethyl-benzene (intermediate 16) | 531.0 |

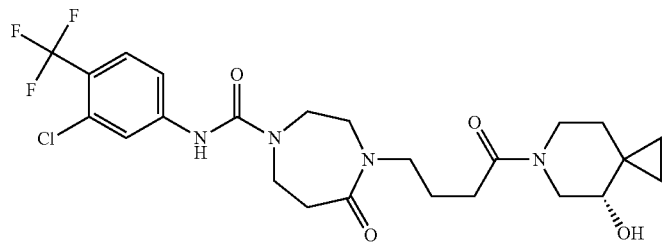 [SMILES: O=C1CCN(C(=O)Nc2ccc(C(F)(F)F)c(Cl)c2)CCN1CCCC(=O)N1CCC2(CC2)[C@H](O)C1]

Example 120

(2RS,5S)-4-(3,4-Dichloro-phenylcarbamoyl)-1-[4-((S)-4-hydroxy-6-aza-spiro[2.5]oct-6-yl)-4-oxo-butyl]-5-methyl-6-oxo-piperazine-2-carboxylic acid (60% ds)

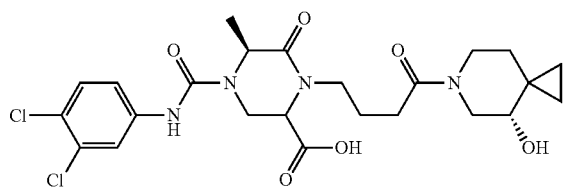 [SMILES: C[C@H]1C(=O)N(CCCC(=O)N2CCC3(CC3)[C@H](O)C2)C(C(=O)O)CN1C(=O)Nc1ccc(Cl)c(Cl)c1]

A) 4-[({[Benzloxcarbonyl-((S)-1-methoxcarbonyl-ethyl)-amino]-methyl}-cyano-methyl)-amino]-butyric acid tert-butyl ester To 2.0 g (7 mmol) of (S)-2-[benzyloxycarbonyl-(2-oxo-ethyl)-amino]-propionic acid methyl ester (intermediate 12C) in 15 ml of CH$_2$Cl$_2$ was added 1.4 g (7 mmol) of 4-aminobutyric acid tert-butyl ester hydrochloride, 0.7 g (2 mmol) of ZnI$_2$ and finally 1 ml (8 mmol) of trimethylsilyl-cyanide. The reaction was stirred for 3 h after which time it was washed with aqueous saturated NaHCO$_3$, dried (Na$_2$SO$_4$) and evaporated to give after flash silica gel column (n-heptane/EtOAc 4:6 to 1:1) the title compound in 31% yield as a colorless gum. MS: 448.3 (MH$^+$).

B) (S)-4-(3-tert-Butoxycarbonyl-propyl)-5-cyano-2-methyl-3-oxo-piperazine-1-carboxylic acid benzyl ester To 1.0 g (2 mmol) of 4-[({[benzyloxycarbonyl-((S)-1-methoxycarbonyl-ethyl)-amino]-methyl}-cyano-methyl)-amino]-butyric acid tert-butyl ester in 2 ml of THF was added 0.1 g (2 mmol) of lithium hydroxide monohydrate in 0.5 ml of water. The reaction was stirred for 16 h after which time it was evaporated to dryness. The residue was redissolved in 2 ml of DMF and 0.5 g (2 mmol) of EDCI and 0.3 g (2 mmol) of HOBT was added and the mixture stirred for 2 h. The reaction was then evaporated, the residue redissolved in EtOAc, washed with water, brine, dried (Na$_2$SO$_4$) and concentrated to give after flash silica gel column (n-heptane/EtOAc 4:6 to 1:1) the title compound in 78% yield as a colorless gum. MS: 416.3 (MH$^+$).

C) (S)-4-(3-tert-Butoxycarbonyl-propyl)-6-methyl-5-oxo-piperazine-1,3-dicarboxylic acid 1-benzyl ester 3-methyl ester To 0.63 g (2 mmol) of (S)-4-(3-tert-butoxycarbonyl-propyl)-5-cyano-2-methyl-3-oxo-piperazine-1-carboxylic acid benzyl ester in 10 ml of DMSO was added 0.21 g (2 mmol) of potassium carbonate, followed by 0.6 ml (6 mmol) of 35% aqueous hydrogen peroxidide. The mixture was heated until the reaction began to bubble and then heating was stopped. The reaction was filtered, diluted with water and extracted repeatedly with tert-butyl methyl ether. The combined organic washings were dried (Na$_2$SO$_4$) and concentrated to give crude carboxamide. This was then dissolved in 15 ml of acetic anhydride/acetic acid (3:2), cooled to 0° C. and 0.76 g (11 mmol) of sodium nitrite added and the reaction stirred for 16 h. The reaction was then concentrated to dryness, partioned between CH$_2$Cl$_2$ and aqueous saturated NaHCO$_3$, the organic phase was collected, dried (Na$_2$SO$_4$) and evaporated. The residue was dissolved in 10 ml THF and 0.1 g 82 mmol) of lithium hydroxide monohydrate added in 0.5 ml water and the reaction stirred for 16 h after which time Amberlite IR120 resin was added until the pH was 5, the reaction filtered and concentrated. The residue was dissolved in 5 ml of MeOH/CH$_2$Cl$_2$ (1:1) and 0.83 ml (2 mmol) of 2 M trimethylsilyldiazomethane in diethylether was added (vigorous bubbling) and the reaction stirred for 15 minutes. Concentration and purification by flash silica gel column (n-heptane/EtOAc 4:6 to 1:1) the title compound in 30% yield as a light yellow gum. MS: 449.3 (MH$^+$)

D) (S)-4-[4-((S)-4-Hydroxy-6-aza-spiro[2.5]oct-6-yl)-4-oxo-butyl]-6-methyl-5-oxo-piperazine-1,3-dicarboxylic acid 1-benzyl ester 3-methyl ester To 0.15 g (0.3 mmol) of (S)-4-(3-tert-butoxycarbonyl-propyl)-6-methyl-5-oxo-piperazine-1,3-dicarboxylic acid 1-benzyl ester 3-methyl ester in 5 ml of THF was added 1.5 ml of 37% hydrochloric acid. The reaction was stirred for 2 h after which time it was evaporated to dryness. The residue was redissolved in 2 m of DMF, 0.14 g (0.4 mmol) of HATU and 0.06 g (0.4 mmol) of (S)-6-aza-spiro[2.5]octan-4-ol hydrochloride (intermediate 2) were added followed by 0.2 ml (1.2 mmol) of triethylamine. The reaction was stirred for 1 h after which time the solvent was evaporated, the residue redissolved in EtOAc, washed with water, brine, dried (Na$_2$SO$_4$) and concentrated to give after flash silica gel column (CH$_2$Cl$_2$/MeOH 95:5) the title compound in quantitative yield as a colorless foam. MS: 502.4 (MH$^+$).

E) (S)-4-(3,4-Dichloro-phenylcarbamoyl)-1-[4-((S)-4-hydroxy-6-aza-spiro[2.5]oct-6-yl)-4-oxo-butyl]-5-methyl-6-oxo-piperazine-2-carboxylic acid methyl ester To 0.17 g (0.33 mmol) of (S)-4-[4-((S)-4-hydroxy-6-aza-spiro[2.5]oct-6-yl)-4-oxo-butyl]-6-methyl-5-oxo-piperazine-1,3-dicarboxylic acid 1-benzyl ester 3-methyl ester in 5 ml of MeOH was added 0.05 g of 10% palladium on charcoal and the reaction was stirred under 1 atmosphere of hydrogen (balloon) for 1 h. The mixture was then filtered through Hyflo and concentrated. The residue was redissolved in 2 ml of CH$_2$Cl$_2$ and 0.06 g (0.34 mmol) of 3,4-dichlorophenylsocyanate was added. The reaction was stirred for 0.5 h after which time it was concentrated to give after flash silica gel column (EtOAc/MeOH 1:0-9:1) the title compound in 77% yield as a colorless gum. MS: 555.1 (MH$^+$, 2Cl).

F) (2RS,5S)-4-(3,4-Dichloro-phenylcarbamoyl)-1-[4-((S)-4-hydroxy-6-aza-spiro[2.5]oct-6-yl)-4-oxo-butyl]-5-methyl-6-oxo-piperazine-2-carboxylic acid (60% ds)

To 0.15 g (0.26 mmol) of (S)-4-(3,4-dichloro-phenylcarbamoyl)-1-[4-((S)-4-hydroxy-6-aza-spiro[2.5]oct-6-yl)-4-oxo-butyl]-5-methyl-6-oxo-piperazine-2-carboxylic acid methyl ester in 2 ml of MeOH was added 0.01 g (0.26 mmol) of lithium hydroxide monohydrate. The reaction was stirred for 16 h after which time Amberlite IR120 resin was added until the pH was 5 and the reaction filtered and concentrated to afford the titled compound in 73% yield, a 6:4 mixture of diasteriomers as a colorless gum. MS: 541.3 (MH$^+$, 2Cl).

Example 121

(3RS,6S)-4-[4-((S)-4-Hydroxy-6-aza-spiro[2.5]oct-6-yl)-4-oxo-butyl]-6-methyl-5-oxo-piperazine-1,3-dicarboxylic acid 3-amide 1-[(3,4-dichloro-phenyl)-amide] (50% ds)

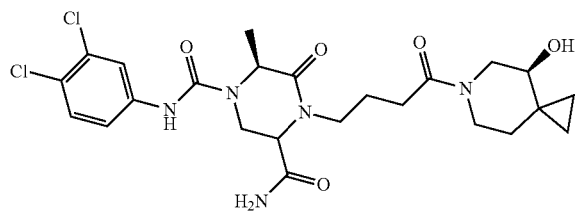 [SMILES: C[C@H]1C(=O)N(CCCC(=O)N2CCC3(CC3)[C@H](O)C2)C(C(N)=O)CN1C(=O)Nc1ccc(Cl)c(Cl)c1]

To 0.05 g (0.1 mmol) of (S)-4-(3,4-dichloro-phenylcarbamoyl)-1-[4-((S)-4-hydroxy-6-aza-spiro[2.5]oct-6-yl)-4-oxo-butyl]-5-methyl-6-oxo-piperazine-2-carboxylic acid in 1 ml of DMF was added 0.04 g (0.1 mmol) of HATU and 0.05 ml of triethylamine followed by 0.02 g (0.03 mmol) of ammonium carbonate. The mixture was stirred for 1 h after which time the reaction was concentrated, the reside redissolved in CH$_2$Cl$_2$, washed with washed with aqueous saturated NaHCO$_3$, dried (Na$_2$SO$_4$) and concentrated to give after flash silica gel column (CH$_2$Cl$_2$/MeOH 95:5) the title compound in 89% yield as a colorless solid. MS: 540.3 (MH$^+$, 2Cl).

Example 122

1-(3-Chloro-4-trifluoromethoxy-phenyl)-4-[4-((S)-4-hydroxy-6-aza-spiro[2.5]oct-6-yl)-4-oxo-butyl]-[1,4]diazepan-5-one

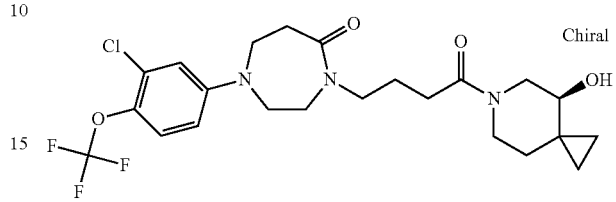

In analogy to the procedure described for example 15, 4-[4-(3-chloro-4-trifluoromethoxy-phenyl)-7-oxo-[1,4]diazepan-1-yl]-butyric acid (intermediate 40) and (S)-6-aza-spiro[2.5]octan-4-ol; hydrochloride (intermediate 2) gave the title compound in 54% yield as light yellow oil. MS: 504.19 (MH$^+$, Cl).

Example 123

(S)-2-[4-(3-Chloro-4-trifluoromethyl-phenyl)-7-oxo-[1,4]diazepan-1-yl]-5-((S)-4-hydroxy-6-aza-spiro[2.5]oct-6-yl)-5-oxo-pentanoic acid methyl ester

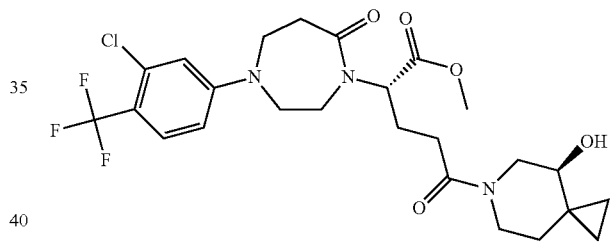

A) 3-(3-Chloro-4-trifluoromethyl-phenylamino)-propionic acid tert-butyl ester

In analogy to the procedure described for intermediate 31, 4-bromo-2-chloro-1-trifluoromethyl-benzene and tert-butyl 3-bromopropionate gave the title compound in 53% yield as yellow oil. MS: 323 (M$^+$, Cl).

B) 3-[(3-Chloro-4-trifluoromethyl-phenyl)-methoxycarbonylmethyl-amino]-propionic acid tert-butyl ester In analogy to the procedure described for intermediate 40B, 3-(3-chloro-4-trifluoromethyl-phenylamino)-propionic acid tert-butyl ester and methyl bromoacetate gave the title compound in 34% yield as yellow oil. MS: 396.12 (MH$^+$, Cl).

C) 3-[(3-Chloro-4-trifluoromethyl-phenyl)-(2-hydroxy-ethyl)-amino]-propionic acid tert-butyl ester In analogy to the procedure described for intermediate 40C, 3-[(3-chloro-4-trifluoromethyl-phenyl)-methoxycarbonylmethyl-amino]-propionic acid tert-butyl ester and LiBH$_4$ (2 M in THF)/MeOH gave the title compound in 84% yield as yellow oil. MS: 368.12 (MH$^+$, Cl).

D) 3-[(3-Chloro-4-trifluoromethyl-phenyl)-(2-oxo-ethyl)-amino]-propionic acid tert-butyl ester In analogy to the procedure described for intermediate 40D, 3-[(3-chloro-4-trifluoromethyl-phenyl)-(2-hydroxy-ethyl)-amino]-propionic acid tert-butyl ester was oxidized to the title compound in quantitative yield as yellow oil. MS: 365 (M+, Cl).

E) (S)-2-{2-[(2-tert-Butoxycarbonyl-ethyl)-(3-chloro-4-trifluoromethyl-phenyl)-amino]-ethylamino}-5-((S)-4-hydroxy-6-aza-spiro[2.5]oct-6-yl)-5-oxo-pentanoic acid methyl ester In analogy to the procedure described for example 14C, 3-[(3-chloro-4-trifluoromethyl-phenyl)-(2-oxo-ethyl)-amino]-propionic acid tert-butyl ester and (S)-2-amino-5-((S)-4-hydroxy-6-aza-spiro[2.5]oct-6-yl)-5-oxo-pentanoic acid methyl ester; compound with HCl (intermediate 41) gave the title compound in 52% yield as light yellow foam. MS: 620.27 (MH+, Cl).

F) (S)-2-{2-[(2-Carboxy-ethyl)-(3-chloro-4-trifluoromethyl-phenyl)-amino]-ethylamino}-5-((S)-4-hydroxy-6-aza-spiro[2.5]oct-6-yl)-5-oxo-pentanoic acid methyl ester dihydrochloride A solution of 0.47 g (0.8 mmol) of (S)-2-{2-[(2-tert-butoxycarbonyl-ethyl)-(3-chloro-4-trifluoromethyl-phenyl)-amino]-ethylamino}-5-((S)-4-hydroxy-6-aza-spiro[2.5]oct-6-yl)-5-oxo-pentanoic acid methyl ester in 2.2 ml of dioxan was cooled (10° C.), treated with 1.9 ml (7.6 mmol) of HCl solution (4 M in dioxane), 2 drops of water and stirred at RT for 22 h. The solution was evaporated, suspended in acetonitrile and evaporated (3×) to yield 0.47 g (92%) of the title compound as light yellow foam. MS (LC/MS): 564 (MH+, Cl).

G) (S)-2-[4-(3-Chloro-4-trifluoromethyl-phenyl)-7-oxo-[1,4]diazepan-1-yl]-5-((S)-4-hydroxy-6-aza-spiro[2.5]oct-6-yl)-5-oxo-pentanoic acid methyl ester In analogy to the procedure described for intermediate 40G, (S)-2-{2-[(2-carboxy-ethyl)-(3-chloro-4-trifluoromethyl-phenyl)-amino]-ethylamino}-5-((S)-4-hydroxy-6-aza-spiro[2.5]oct-6-yl)-5-oxo-pentanoic acid methyl ester dihydrochloride was cyclized to the title compound in 27% yield as off-white solid. MS: 546.20 (MH+, Cl).

Example 124

1-(3-Chloro-4-trifluoromethyl-phenyl)-4-[(S)-4-((S)-4-hydroxy-6-aza-spiro[2.5]oct-6-yl)-1-hydroxymethyl-4-oxo-butyl]-[1,4]diazepan-5-one

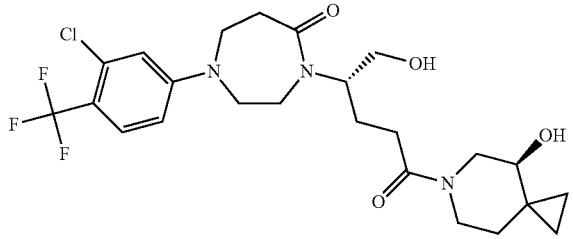 [SMILES: O=C(CC[C@@H](CO)N1CCN(c2ccc(C(F)(F)F)c(Cl)c2)CCC1=O)N1CCC2(CC2)[C@H](O)C1]

In analogy to the procedure described for intermediate 40C, (S)-2-[4-(3-Chloro-4-trifluoromethyl-phenyl)-7-oxo-[1,4]diazepan-1-yl]-5-((S)-4-hydroxy-6-aza-spiro[2.5]oct-6-yl)-5-oxo-pentanoic acid methyl ester (example 123) and LiBH4 (2 M in THF)/MeOH gave the title compound in 62% yield as yellow oil. MS: 518.20 (MH+, Cl).

Example 125

(R)-1-(4-Chloro-3-trifluoromethyl-phenyl)-4-[4-((S)-4-hydroxy-6-aza-spiro[2.5]oct-6-yl)-4-oxo-butyl]-2-methyl-1,2,3,4-tetrahydro-[1,4]diazepin-5-one (73% ds)

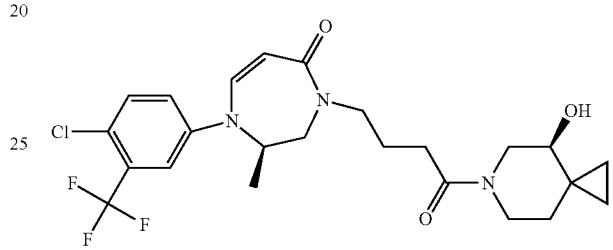

In analogy to the procedure described for example 15, 4-[(R)-4-(4-chloro-3-trifluoromethyl-phenyl)-3-methyl-7-oxo-2,3,4,7-tetrahydro-[1,4]diazepin-1-yl]-butyric acid (46% ee) (intermediate 35) and (S)-6-aza-spiro[2.5]octan-4-ol; hydrochloride (intermediate 2) gave the title compound in 69% yield as light yellow oil. MS: 544.19 (M+HCOO−, Cl).

Example 126

(R)-1-(4-Chloro-3-trifluoromethyl-phenyl)-4-[4-((S)-4-hydroxy-6-aza-spiro[2.5]oct-6-yl)-4-oxo-butyl]-2-methyl-[1,4]diazepan-5-one (73% ds)

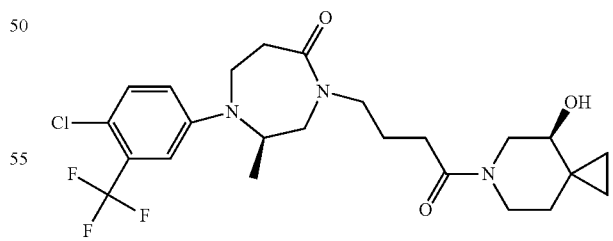

A solution of 0.049 g (0.1 mmol) of (R)-1-(4-chloro-3-trifluoromethyl-phenyl)-4-[4-((S)-4-hydroxy-6-aza-spiro[2.5]oct-6-yl)-4-oxo-butyl]-2-methyl-1,2,3,4-tetrahydro-[1,4]diazepin-5-one (73% ds) and 0.006 ml (0.1 mmol) of acetic acid in 2 ml MeOH was treated with 0.005 g of PtO2 and was stirred over H2-atmosphere for 1 days. After filtration and evaporation, the residue was reevaporated (3 times) with toluene and the solvent was removed under vacuum to give 0.048 g (98%) of the titled compound as white foam. MS: 502.21 (MH⁺, Cl).

Example 127

(S)-2-[(R,S)-4-(3,4-Bis-trifluoromethyl-phenyl)-3-methyl-7-oxo-[1,4]diazepan-1-yl]-5-((S)-4-hydroxy-6-aza-spiro[2.5]oct-6-yl)-5-oxo-pentanoic acid methyl ester

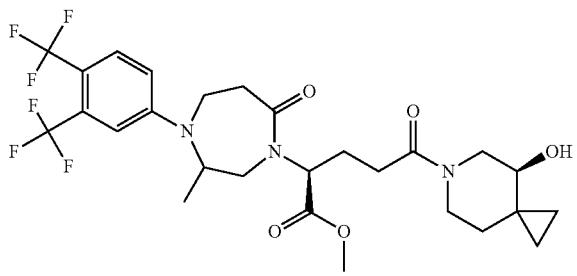 [SMILES: COC(=O)[C@H](CCC(=O)N1CCC2(CC2)[C@H](O)C1)N1CC(C)N(c2ccc(C(F)(F)F)c(C(F)(F)F)c2)CCC1=O]

In analogy to the procedure described for example 15, (S)-2-[(R,S)-4-(3,4-bis-trifluoromethyl-phenyl)-3-methyl-7-oxo-[1,4]diazepan-1-yl]-pentanedioic acid 1-methyl ester (intermediate 42) and (S)-6-aza-spiro[2.5]octan-4-ol; hydrochloride (intermediate 2) gave the title compound in 73% yield as off-white foam. MS: 594.24 (MH⁺).

Example 128 and 129

(R)-1-(3,4-Bis-trifluoromethyl-phenyl)-4-[(S)-4-((S)-4-hydroxy-6-aza-spiro[2.5]oct-6-yl)-1-hydroxymethyl-4-oxo-butyl]-2-methyl-[1,4]diazepan-5-one and (S)-4-[4-((S)-3-Hydroxy-4,4-dimethyl-piperidin-1-yl)-4-oxo-butyl]-2-methyl-3-oxo-piperazine-1-carboxylic acid (3,4-dichloro-phenyl)-amide Example 128

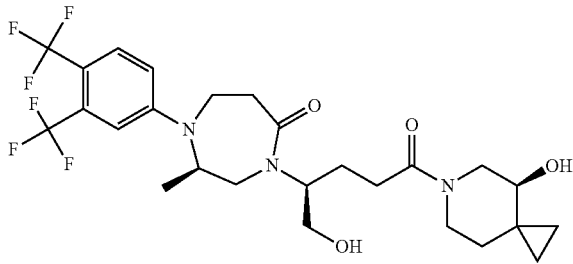

Example 129

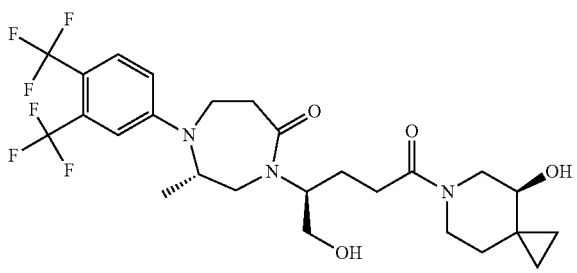

In analogy to the procedure described in example 53, (S)-2-[(R,S)-4-(3,4-bis-trifluoromethyl-phenyl)-3-methyl-7-oxo-[1,4]diazepan-1-yl]-5-((S)-4-hydroxy-6-aza-spiro[2.5]oct-6-yl)-5-oxo-pentanoic acid methyl ester and LiBH₄ (2 M in THF)/MeOH gave after flash silica gel column (dichloromethane/methanol 95:5): 47% of (R)-1-(3,4-bis-trifluoromethyl-phenyl)-4-[(S)-4-((S)-4-hydroxy-6-aza-spiro[2.5]oct-6-yl)-1-hydroxymethyl-4-oxo-butyl]-2-methyl-[1,4]diazepan-5-one (example 128) as white foam, MS: 566.25 (MH⁺), Rf 0.18 (dichloromethane/methanol 9:1) and 29% of (S)-1-(3,4-bis-trifluoromethyl-phenyl)-4-[(S)-4-((S)-4-hydroxy-6-aza-spiro[2.5]oct-6-yl)-1-hydroxymethyl-4-oxo-butyl]-2-methyl-[1,4]diazepan-5-one (example 129) as white solid, MS: 566.25 (MH⁺), Rf 0.08 (dichloromethane/methanol 9:1).

Example 130

(S)-4-(3,4-Bis-trifluoromethyl-phenyl)-1-[4-((S)-4-hydroxy-6-aza-spiro[2.5]oct-6-yl)-4-oxo-butyl]-3-methyl-piperazin-2-one

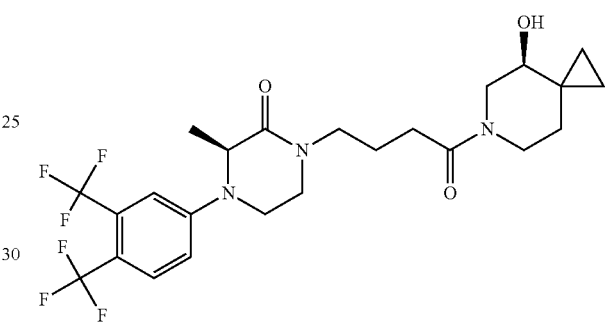

In analogy to the procedure described for example 15, 4-[(S)-4-(3,4-bis-trifluoromethyl-phenyl)-3-methyl-2-oxo-piperazin-1-yl]-butyric acid (intermediate 43) and (S)-6-aza-spiro[2.5]octan-4-ol; hydrochloride (intermediate 2) gave the title compound in 39% yield as off-white foam (in 80% diastereoselectivity, coming probably from the harsh microwave conditions during the synthesis of intermediate 43). MS: 522.22 (MH⁺).

Example 131

(S)-4-(3-Chloro-4-trifluoromethyl-phenyl)-1-[(S)-2-hydroxy-4-((S)-4-hydroxy-6-aza-spiro[2.5]oct-6-yl)-4-oxo-butyl]-3-methyl-piperazin-2-one (80% ds)

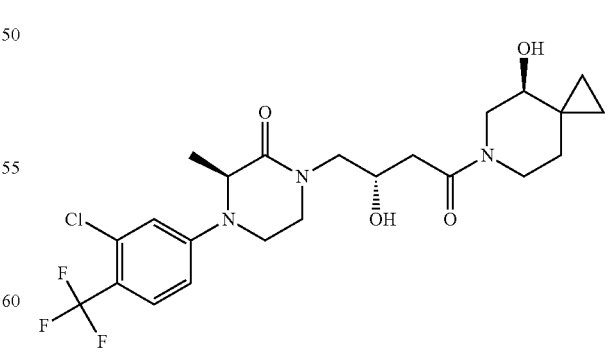

In analogy to example 15, (S)-4-[(S)-4-(3-chloro-4-trifluoromethyl-phenyl)-3-methyl-2-oxo-piperazin-1-yl]-3-hydroxy-butyric acid (61% ds) (intermediate 44) and 1.1 eq. of (S)-6-aza-spiro[2.5]octan-4-ol; hydrochloride (intermediate

Example 132

(S)-4-(3-Chloro-4-trifluoromethyl-phenyl)-1-[(S)-4-((S)-4-hydroxy-6-aza-spiro[2.5]oct-6-yl)-1-methoxymethyl-4-oxo-butyl]-3-methyl-piperazin-2-one (90% ds)

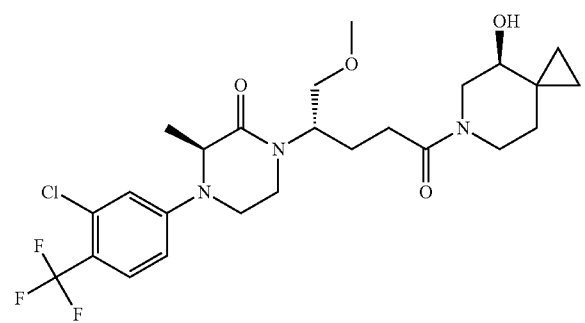 [SMILES: COC[C@H](CCC(=O)N1CCC2(CC2)[C@H](O)C1)N1CCN(c2ccc(C(F)(F)F)c(Cl)c2)[C@@H](C)C1=O]

In analogy to intermediate 15, (S)-4-[(S)-4-(3-chloro-4-trifluoromethyl-phenyl)-3-methyl-2-oxo-piperazin-1-yl]-5-methoxy-pentanoic acid (61% ds) (intermediate 45) and 1.1 eq. of (S)-6-aza-spiro[2.5]octan-4-ol; hydrochloride (intermediate 2) gave after flash chromatography (SiO$_2$, n-heptane/isopropanol 1:1) the titled compound in 30% yield (90% ds) as off-white waxy solid. MS: 532.22 (MH$^+$, 1Cl).

Example 133

(S)-4-[(R,S)-3-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

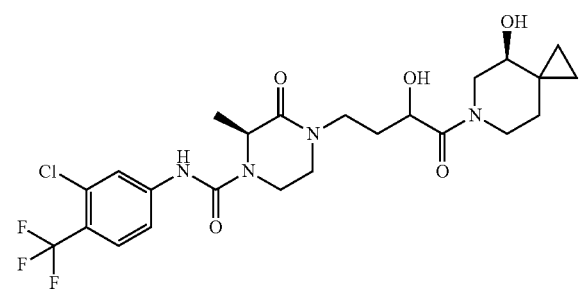 [SMILES: C[C@H]1C(=O)N(CCC(O)C(=O)N2CCC3(CC3)[C@H](O)C2)CCN1C(=O)Nc1ccc(C(F)(F)F)c(Cl)c1]

A solution of 0.079 g (0.2 mmol) of (S)-1-[(R,S)-3-hydroxy-4-((S)-4-hydroxy-6-aza-spiro[2.5]oct-6-yl)-4-oxo-butyl]-3-methyl-piperazin-2-one (intermediate 46) and 0.080 ml (0.7 mmol) of 4-methylmorpholine in 1.25 ml of dichloromethane was treated at RT with 0.065 g (0.3 mmol) of 2-chloro-4-isocyanato-1-trifluoromethyl-benzene (intermediate 16) in 1.25 ml of dichloromethane. After 1 h the reaction was extracted with aqueous 10% KHSO$_4$/EtOAc (3×). The organic phases were washed with aqueous saturated NaHCO$_3$, 10% NaCl and dried over Na$_2$SO$_4$ to yield, after flash chromatography (SiO$_2$, dichloromethane/methanol 4%), 0.087 g (66%) of the titled compound as off-white foam. MS: 547.19 (MH$^+$, 1Cl).

Example 134

(S)-4-[(S)-3-Hydroxy-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

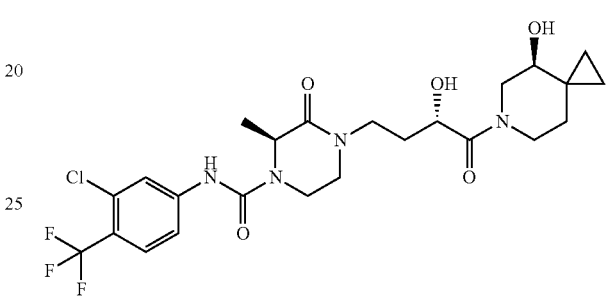

In analogy to the procedure described in example 133, (S)-1-[(S)-3-hydroxy-4-((S)-4-hydroxy-6-aza-spiro[2.5]oct-6-yl)-4-oxo-butyl]-3-methyl-piperazin-2-one; HCl (intermediate 47) and 1.2 eq. of 2-chloro-4-isocyanato-1-trifluoromethyl-benzene (intermediate 16) gave the titled compound in 74% yield as white powder. MS: 547.2 (MH$^+$, 1Cl).

Example 135

(S)-4-[(R,S)-3-Hydroxy-4-((S)-4-hydroxy-6-aza-spiro[2.5]oct-6-yl)-4-oxo-butyl]-2-methyl-3-oxo-piperazine-1-carboxylic acid (3,4-bis-trifluoromethyl-phenyl)-amide

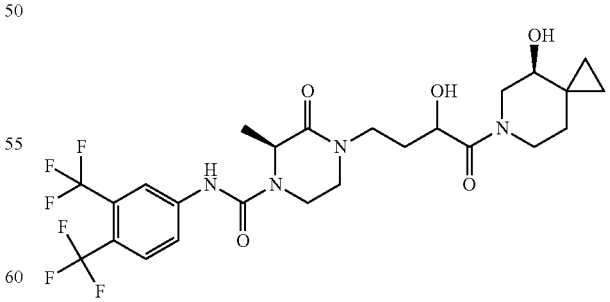

In analogy to the procedure described in example 133, (S)-1-[(R,S)-3-hydroxy-4-((S)-4-hydroxy-6-aza-spiro[2.5]oct-6-yl)-4-oxo-butyl]-3-methyl-piperazin-2-one (intermediate 46) and 1.2 eq. of 4-isocyanato-1,2-bis-trifluoromethylbenzene (intermediate 26) gave the titled compound in 90% yield as off-white powder. MS: 581.22 (MH+).

Example 136

(S)-4-[(R,S)-3-Fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

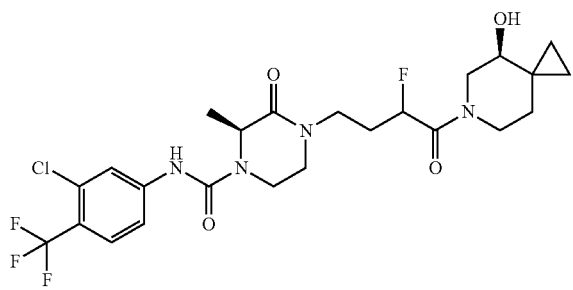 [SMILES: C[C@H]1C(=O)N(CCC(F)C(=O)N2CCC3(CC3)[C@H](O)C2)CCN1C(=O)Nc1ccc(C(F)(F)F)c(Cl)c1]

In analogy to the procedure described in example 133, (S)-1-[(R,S)-3-fluoro-4-((S)-4-hydroxy-6-aza-spiro[2.5]oct-6-yl)-4-oxo-butyl]-3-methyl-piperazin-2-one; HCl (intermediate 48) and 1.2 eq. of 2-chloro-4-isocyanato-1-trifluoromethyl-benzene (intermediate 16) gave the titled compound in 57% yield as white powder. MS: 549.19 (MH+, 1Cl).

Example 137 and 138

(S)-4-[(R or S)-3-Fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide and (S)-4-[(S or R)-3-Fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide

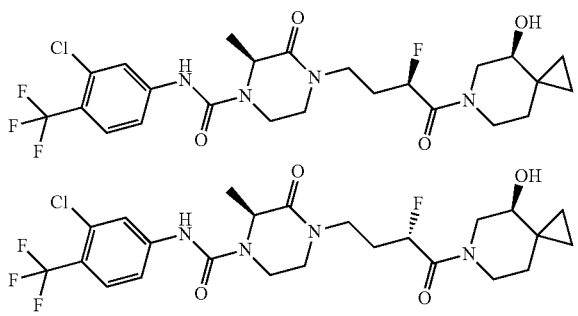

The title compounds were prepared by chiral separation of ((S)-4-[(R,S)-3-fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (example 136) on a Reprosil Chiral NR, (40% isopropanol in n-heptane) to give the two diastereoisomers: 33% (7.9% calculated for the synthesis and separation) of (S)-4-[(R or S)-3-fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (Example 137) as white powder, MS: 549.19 (MH+, 1Cl) and 37% (8.4% calculated for the synthesis and separation) of (S)-4-[(S or R)-3-fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (Example 138) as white powder, MS: 549.19 (MH+, 1Cl).

Example 139

(S)-4-[(S)-4-((S)-4-Hydroxy-6-aza-spiro[2.5]oct-6-yl)-1-methoxymethyl-4-oxo-butyl]-2-methyl-3-oxo-piperazine-1-carboxylic acid (3-chloro-4-trifluoromethyl-phenyl)-amide

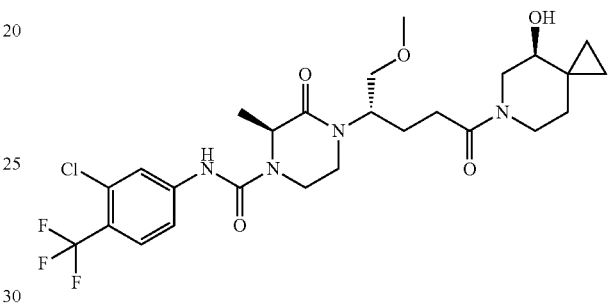

In analogy to the procedure described in example 133, (S)-1-[(S)-4-((S)-4-hydroxy-6-aza-spiro[2.5]oct-6-yl)-1-methoxymethyl-4-oxo-butyl]-3-methyl-piperazin-2-one; HCl (intermediate 49) and 1.2 eq. of 2-chloro-4-isocyanato-1-trifluoromethyl-benzene (intermediate 16) gave the titled compound in 74% yield as white powder. MS: 575.23 (MH+, 1Cl).

Example 140

(S)-2-[(S)-4-(3-Chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid

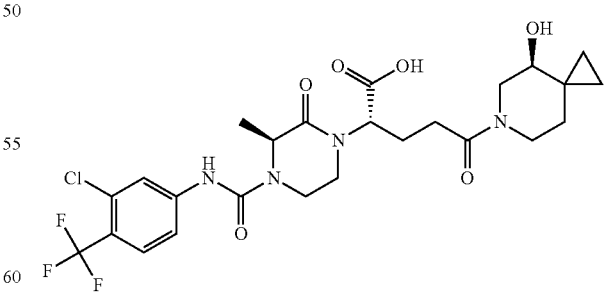

In analogy to intermediate 5C, (S)-2-[(S)-4-(3-chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester (example 52) gave with 1.1 equivalent of 1 M aq. lithium hydroxide solution in THF/

MeOH after warming up to RT over night, quantitative the titled compound as white solid. MS: 575.2 (MH+, 1Cl).

Example 141

(S)-4-[(S)-1-Carbamoyl-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide (80% ds, probably (S)-1-Carbamoyl and (R)-1-Carbamoyl)

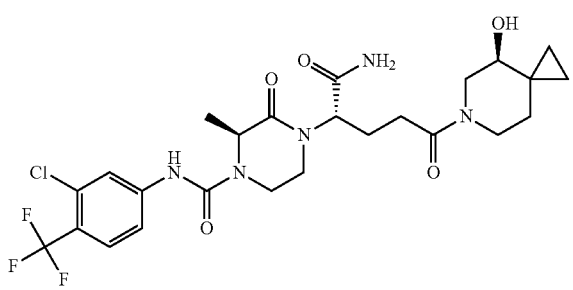 [SMILES: C[C@H]1C(=O)N([C@@H](CCC(=O)N2CCC3(CC3)[C@H](O)C2)C(N)=O)CCN1C(=O)Nc1ccc(C(F)(F)F)c(Cl)c1]

A solution of 0.068 g (0.10 mmol) of (S)-2-[(S)-4-(3-chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid (example 140) in 1 ml of DMF was treated at 0° C. with 0.033 ml (0.20 mmol) of triethylamine and 0.049 g (0.11 mmol) of HATU. After 1 h, 0.009 g (0.10 mmol) of ammonium bicarbonate were added, then the suspension was naturally warmed to RT over night, poured on aqueous 10% KHSO₄ solution and extracted with EtOAc (3×). The organic phases were washed with aqueous saturated NaHCO₃ and aqueous 10% NaCl, dried (Na₂SO₄) and evaporated to give after purification with flash chromatography (SiO₂, dichloromethane/MeOH 95:5) and precipitation (dichloromethane/n-pentane) 0.031 g (46%) of the titled compound as weight solid (80% ds, ¹H-NMR in d₆-DMSO at 120° C.). MS: 574.20 (MH+, Cl).

Example 142

(S)-4-[(S)-4-((S)-4-Hydroxy-6-aza-spiro[2.5]oct-6-yl)-1-methylcarbamoyl-4-oxo-butyl]-2-methyl-3-oxo-piperazine-1-carboxylic acid (3-chloro-4-trifluoromethyl-phenyl)-amide (95.5% ds)

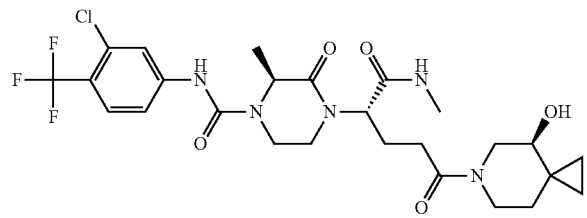 [SMILES: CNC(=O)[C@H](CCC(=O)N1CCC2(CC2)[C@H](O)C1)N1CCN(C(=O)Nc2ccc(C(F)(F)F)c(Cl)c2)[C@@H](C)C1=O]

In analogy to example 141, (S)-2-[(S)-4-(3-chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid (example 140) after 5 min of preactivation with HATU and 1.5 equivalent of methalymine (8M in ethanol) gave the titled compound in 53% yield as off-white solid (95.5% ds, reprosil chiral-NR, n-heptane:ethanol 3:2). MS: 588.22 (MH+, 1Cl).

Example 143

(S)-2-[(S)-4-(3,4-Bis-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester

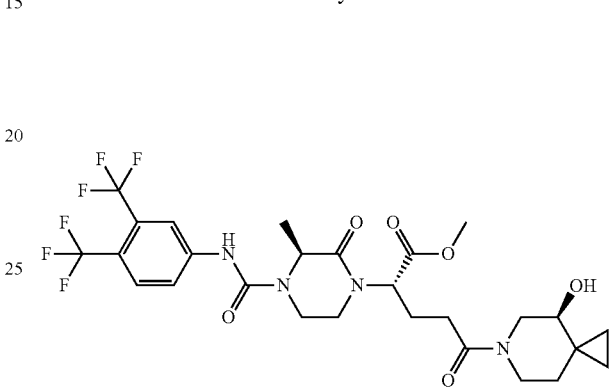

In analogy to the procedure described in example 133, (S)-5-(S)-4-hydroxy-6-aza-spiro[2.5]oct-6-yl)-2-((S)-3-methyl-2-oxo-piperazin-1-yl)-5-oxo-pentanoic acid methyl ester; hydrochloride (intermediate 29) and 1.3 eq. of 4-isocyanato-1,2-bis-trifluoromethyl-benzene (intermediate 26) gave the titled compound in 89% yield as amorphous white solid. MS: 623.22 (MH+)

Example 144

(S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3,4-bis-trifluoromethyl-phenyl)-amide

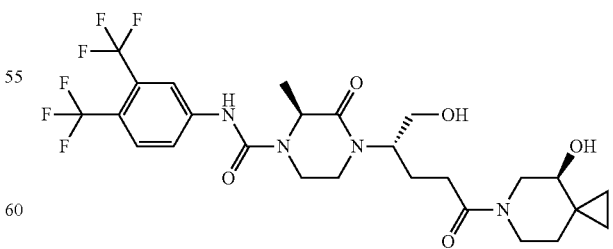

In analogy to the procedure described in Example 53, (S)-2-[(S)-4-(3,4-bis-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester (example 143) and LiBH₄ (2 M in THF)/MeOH gave the titled compound in 79% yield as amorphous white solid. MS: 595.23 (MH⁺).

Example 145

(R)-2-[(S)-4-(3-Chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester

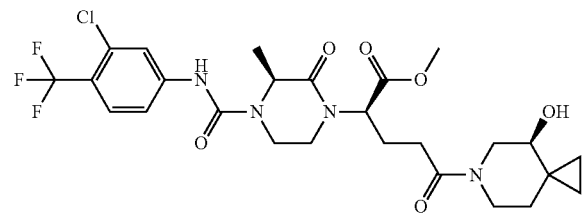 [SMILES: COC(=O)[C@@H](CCC(=O)N1CCC2(CC2)[C@H](O)C1)N1CCN(C(=O)Nc2ccc(C(F)(F)F)c(Cl)c2)[C@@H](C)C1=O]

In analogy to the procedure described in example 133, (R)-5-((S)-4-hydroxy-6-aza-spiro[2.5]oct-6-yl)-2-((S)-3-methyl-2-oxo-piperazin-1-yl)-5-oxo-pentanoic acid methyl ester; hydrochloride (intermediate 50) and 1.2 eq. of 2-chloro-4-isocyanato-1-trifluoromethyl-benzene (intermediate 16) gave the titled compound in 85% yield as white amorphous solid. MS: 589.20 (MH⁺, Cl).

Example 146

(S)-4-[(R)-4-((S)-4-Hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethyl-phenyl)-amide

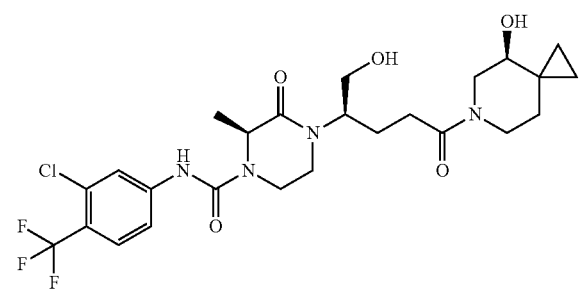 [SMILES: C[C@H]1C(=O)N([C@@H](CO)CCC(=O)N2CCC3(CC3)[C@H](O)C2)CCN1C(=O)Nc1ccc(C(F)(F)F)c(Cl)c1]

In analogy to the procedure described in example 53, (R)-2-[(S)-4-(3-chloro-4-trifluoromethyl-phenylcarbamoyl)-3-methyl-2-oxo-piperazin-1-yl]-5-((S)-4-hydroxy-6-aza-spiro[2.5]oct-6-yl)-5-oxo-pentanoic acid methyl ester (example 145) and LiBH₄ (2 M in THF)/MeOH gave the titled compound in 66% yield as amorphous white solid. MS: 561.20 (MH⁺, 1Cl).

Example 147

(3S,6S)—N1-(3-chloro-4-(trifluoromethyl)phenyl)-4-(4-((S)-4-hydroxy-6-azaspiro[2.5]octan-6-yl)-4-oxobutyl)-6-methyl-5-oxopiperazine-1,3-dicarboxamide

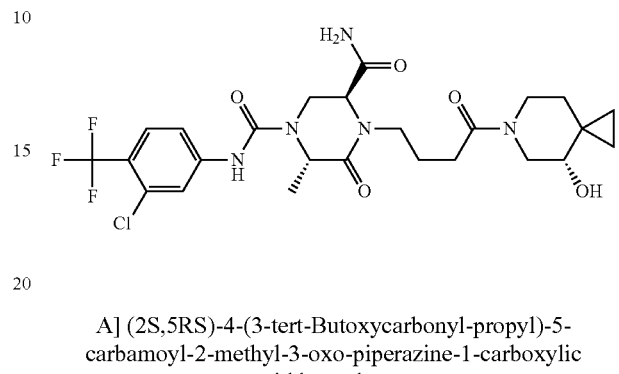

A] (2S,5RS)-4-(3-tert-Butoxycarbonyl-propyl)-5-carbamoyl-2-methyl-3-oxo-piperazine-1-carboxylic acid benzyl ester The title compound was prepared as described in the first step of the preparation of example 120 (step C) affording a colorless gum. MS: 434.30 (MH⁺)

B] (2S,5R)-5-Carbamoyl-4-[4-((S)-4-hydroxy-6-aza-spiro[2.5]oct-6-yl)-4-oxo-butyl]-2-methyl-3-oxo-piperazine-1-carboxylic acid benzyl ester and (2S,5S)-5-Carbamoyl-4-[4-((S)-4-hydroxy-6-aza-spiro[2.5]oct-6-yl)-4-oxo-butyl]-2-methyl-3-oxo-piperazine-1-carboxylic acid benzyl ester In analogy to the procedure described in example 120 step D, (2S,5RS)-4-(3-tert-butoxycarbonyl-propyl)-5-carbamoyl-2-methyl-3-oxo-piperazine-1-carboxylic acid benzyl ester was first hydrolysed with HCl and then coupled with (S)-6-aza-spiro[2.5]octan-4-ol hydrochloride (intermediate 2). The two diasterioisomers could be separated by flash column chromatography (SiO₂, EtOAc/MeOH 1:0-9:1) affording first (2S,5R)-5-carbamoyl-4-[4-((S)-4-hydroxy-6-aza-spiro[2.5]oct-6-yl)-4-oxo-butyl]-2-methyl-3-oxo-piperazine-1-carboxylic acid benzyl ester in 22% yield as an amorphous white solid, MS: 487.30 (MH⁺) and then (2S,5S)-5-carbamoyl-4-[4-((S)-4-hydroxy-6-aza-spiro[2.5]oct-6-yl)-4-oxo-butyl]-2-methyl-3-oxo-piperazine-1-carboxylic acid benzyl ester in 20% yield as a colorless foam MS: 487.30 (MH⁺).

C] (2S,5S)-1-[4-((S)-4-Hydroxy-6-aza-spiro[2.5]oct-6-yl)-4-oxo-butyl]-5-methyl-6-oxo-piperazine-2-carboxylic acid amide In analogy to the procedure described in the first part of example 120 step E, (2S,5S)-5-carbamoyl-4-[4-((S)-4-hydroxy-6-aza-spiro[2.5]oct-6-yl)-4-oxo-butyl]-2-methyl-3-oxo-piperazine-1-carboxylic acid benzyl ester was treated with 10% palladium on charcoal and the reaction was stirred under 1 atmosphere of hydrogen affording the titled compound in quantitative yield as a colorless foam. MS: 353.4 (MH⁺).

D] (3S,6S)—N1-(3-chloro-4-(trifluoromethyl)phenyl)-4-(4-((S)-4-hydroxy-6-azaspiro[2.5]octan-6-yl)-4-oxobutyl)-6-methyl-5-oxopiperazine-1,3-dicarboxamide In analogy to the procedure described in the second part of example 120 step E, (2S,5S)-1-[4-((S)-4-hydroxy-6-aza-spiro[2.5]oct-6-yl)-4-oxo-butyl]-5-methyl-6-oxo-piperazine-2-carboxylic acid amide was reacted with 2-chloro-4-isocyanato-1-trifluoromethyl-benzene (intermediate 16) to give the titled compound in 88% yield as a colorless solid. MS: 574.3 (MH+, 1Cl).

Example 148

(3R,6S)—N1-(3-chloro-4-(trifluoromethyl)phenyl)-4-(4-((S)-4-hydroxy-6-azaspiro[2.5]octan-6-yl)-4-oxobutyl)-6-methyl-5-oxopiperazine-1,3-dicarboxamide

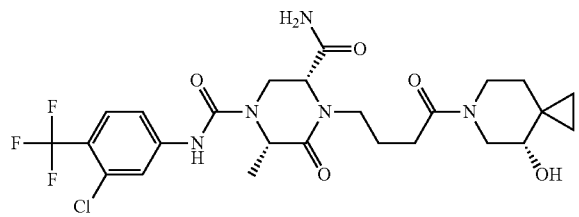 [SMILES: C[C@H]1C(=O)N(CCCC(=O)N2CCC3(CC3)[C@H](O)C2)[C@H](C(N)=O)CN1C(=O)Nc1ccc(C(F)(F)F)c(Cl)c1]

In analogy to the procedure described in the example 120 step E, (2S,5R)-5-carbamoyl-4-[4-((S)-4-hydroxy-6-aza-spiro[2.5]oct-6-yl)-4-oxo-butyl]-2-methyl-3-oxo-piperazine-1-carboxylic acid benzyl ester (example 147 step B) was first deprotected using 10% palladium on charcoal and then subsequently reacted with 2-chloro-4-isocyanato-1-trifluoromethyl-benzene (intermediate 16) to give the titled compound in 73% yield as a colorless solid. MS: 574.3 (MH+, 1Cl).

Example 149

(3S,6S)-4-[4-((S)-4-Hydroxy-6-aza-spiro[2.5]oct-6-yl)-4-oxo-butyl]-6-methyl-5-oxo-piperazine-1,3-dicarboxylic acid 3-amide 1-[(3,4-bis-trifluoromethyl-phenyl)-amide]

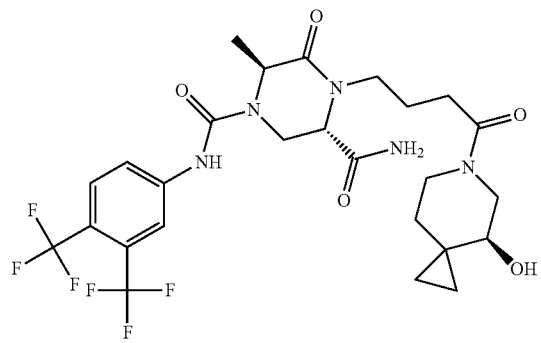 [SMILES: C[C@H]1C(=O)N(CCCC(=O)N2CCC3(CC3)[C@H](O)C2)[C@H](C(N)=O)CN1C(=O)Nc1ccc(C(F)(F)F)c(C(F)(F)F)c1]

In analogy to the procedure described in the example 147 step D, (2S,5S)-1-[4-((S)-4-hydroxy-6-aza-spiro[2.5]oct-6-yl)-4-oxo-butyl]-5-methyl-6-oxo-piperazine-2-carboxylic acid amide was reacted with 4-isocyanato-1,2-bis-trifluoromethyl-benzene (intermediate 26) to give the titled compound in 70% yield as a colorless solid. MS: 608.1 (MH+).

Example 150

(3R,6R)-4-[4-((S)-4-Hydroxy-6-aza-spiro[2.5]oct-6-yl)-4-oxo-butyl]-6-methyl-5-oxo-piperazine-1,3-dicarboxylic acid 3-amide 1-[(3-chloro-4-trifluoromethyl-phenyl)-amide]

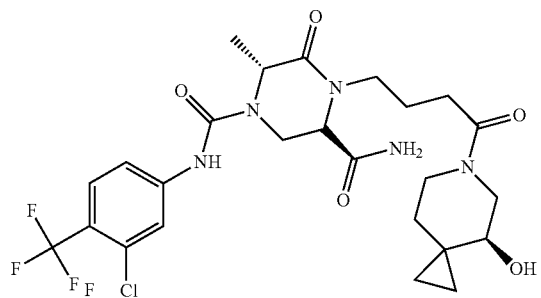

The title compound was prepared in analogy to example 147, except that instead of starting with (S)-2-[benzyloxycarbonyl-(2-oxo-ethyl)-amino]-propionic acid methyl ester (intermediate 12C), (R)-2-[benzyloxycarbonyl-(2-oxo-ethyl)-amino]-propionic acid methyl ester was used (having been prepared analogously from D-alanine methyl ester) to give a white solid. MS: 574.2 (MH+, 1Cl).

Example 151

(3R,6R)-4-[4-((S)-4-Hydroxy-6-aza-spiro[2.5]oct-6-yl)-4-oxo-butyl]-6-methyl-5-oxo-piperazine-1,3-dicarboxylic acid 3-amide 1-[(3,4-dichloro-phenyl)-amide]

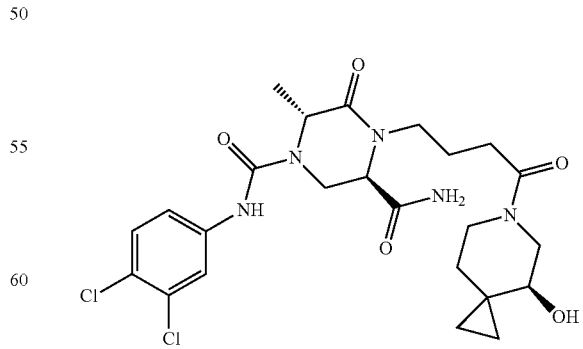

The title compound was prepared in analogy of example 150, with 3,4-dichorophenylisocyanate being used in the last step to give a white solid. MS: 540.3 (MH+, 2Cl).

Example 152

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example 153

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 154

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | Ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example 155

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 156

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavouring additives and filled into sachets.

Example 157

The following describes the procedure for receptor binding assays.

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer)

plates, equilibrated with 0.3% polyethylenimine, 0.2% BSA, air dried and binding was determined by counting in a top-counter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Example 158

Calcium Mobilization Assay

CHOK1-CCR2B-A5 cells (from Euroscreen) stably over-expressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of the present invention exhibit $IC_{50}$ values in the Ca mobilisation assay of 1 nM to 10 µM, preferably 1 nM to 1.5 µM for CCR2. The following table shows measured values for some selected compounds of the present invention.

| Example | IC50 (µM) |
|---|---|
| 1 | 2.6628 |
| 2 | 1.9714 |
| 3 | 0.5630 |
| 4 | 0.3701 |
| 5 | 0.5830 |
| 6 | 2.0229 |
| 7 | 0.4535 |
| 8 | 0.8630 |
| 9 | 2.3540 |
| 10 | 0.7077 |
| 11 | 0.4645 |
| 12 | 1.9352 |
| 13 | 0.7707 |
| 14 | 0.9073 |
| 15 | 0.2372 |
| 16 | 4.1057 |
| 17 | 3.1674 |
| 18 | 1.0430 |
| 19 | 3.8311 |
| 20 | 1.0767 |
| 21 | 0.8443 |
| 22 | 3.0737 |
| 23 | 3.8571 |
| 24 | 3.1704 |
| 25 | 0.0036 |
| 26 | 0.0181 |
| 27 | 0.0850 |
| 28 | 0.0549 |
| 29 | 0.0206 |
| 30 | 0.0204 |
| 31 | 0.0510 |
| 32 | 0.0059 |
| 33 | 0.0044 |
| 34 | 0.0017 |
| 35 | 0.0049 |
| 36 | 2.3419 |
| 38 | 0.0219 |
| 39 | 0.9650 |
| 40 | 0.0076 |
| 41 | 0.0056 |
| 42 | 0.0082 |
| 43 | 0.0040 |
| 44 | 0.0027 |
| 45 | 0.0020 |
| 46 | 0.0042 |
| 47 | 0.0054 |
| 48 | 0.0024 |
| 49 | 0.0058 |
| 50 | 1.1393 |
| 51 | 0.7498 |
| 52 | 0.7377 |
| 53 | 0.0043 |
| 54 | 0.2157 |
| 55 | 0.0018 |
| 56 | 0.3873 |
| 57 | 2.5674 |
| 59 | 0.0232 |
| 60 | 0.0050 |
| 62 | 0.0417 |
| 64 | 1.2352 |
| 65 | 0.6104 |
| 66 | 0.1094 |
| 67 | 1.6038 |
| 68 | 0.7577 |
| 69 | 0.4807 |
| 70 | 1.3020 |
| 71 | 0.6814 |
| 72 | 0.1625 |
| 73 | 0.0659 |
| 74 | 1.5436 |
| 75 | 0.9688 |
| 76 | 0.9713 |
| 77 | 0.1294 |
| 78 | 0.0512 |
| 79 | 1.8247 |
| 80 | 3.2549 |
| 81 | 1.6828 |
| 82 | 1.8261 |
| 83 | 0.3066 |
| 84 | 0.0479 |
| 85 | 1.5181 |
| 86 | 0.3259 |
| 87 | 0.3372 |
| 88 | 1.7498 |
| 89 | 3.9984 |
| 90 | 0.1836 |
| 91 | 0.1459 |
| 92 | 0.9523 |
| 93 | 1.1565 |
| 94 | 1.7964 |
| 95 | 0.1504 |
| 96 | 3.2062 |
| 97 | 3.8502 |
| 98 | 1.7028 |
| 99 | 4.9611 |
| 100 | 0.4107 |
| 101 | 2.4772 |
| 102 | 0.1517 |
| 103 | 1.2877 |
| 104 | 0.1004 |
| 105 | 3.4149 |
| 106 | 3.1250 |

-continued

| Example | IC50 (μM) |
| --- | --- |
| 107 | 4.8685 |
| 108 | 4.0711 |
| 109 | 4.6488 |
| 110 | 1.3365 |
| 111 | 0.8927 |
| 112 | 3.2015 |
| 113 | 1.4161 |
| 114 | 0.0315 |
| 115 | 1.3606 |
| 116 | 1.2934 |
| 117 | 0.0202 |
| 118 | 0.0517 |
| 119 | 0.0176 |
| 120 | 0.3860 |
| 121 | 0.0110 |
| 122 | 0.1667 |
| 123 | 0.0631 |
| 124 | 0.0080 |
| 125 | 2.7468 |
| 126 | 2.6747 |
| 127 | 0.1911 |
| 128 | 0.0046 |
| 130 | 0.0368 |
| 131 | 0.0131 |
| 132 | 0.3096 |
| 133 | 0.1337 |
| 134 | 0.1878 |
| 135 | 0.0622 |
| 136 | 0.0047 |
| 137 | 0.0105 |
| 138 | 0.0014 |
| 139 | 0.1518 |
| 140 | 0.7509 |
| 141 | 0.5000 |
| 142 | 1.3171 |
| 143 | 0.3373 |
| 144 | 0.0045 |
| 145 | 6.3123 |
| 146 | 0.1571 |
| 147 | 0.0035 |
| 148 | 0.0305 |
| 149 | 0.0022 |
| 150 | 0.0180 |
| 151 | 0.0621 |

The invention claimed is:

1. A compound of formula (I'),

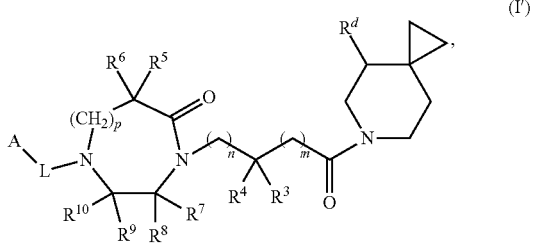

wherein

A is phenyl substituted by one or two substituents selected from the group consisting of halogen atoms, trifluoromethyl and trifluoromethoxy;

L is selected from the group consisting of: a bond, N(R')—C(=O), NH—C(=S), and CH=CH—C(=O), wherein R' is hydrogen or $C_{1-4}$ alkyl;

$R^3$ and $R^4$ are, independently of each other, selected from the group consisting of:
hydrogen,
hydroxy,
$C_{1-6}$ alkyl,
$C_{1-6}$ alkoxy,
$C_{3-7}$ cycloalkyl,
$C_{3-7}$ cycloalkyl $C_{1-6}$ alkyl,
$C_{1-6}$ alkoxycarbonyl,
carboxyl,
carbamoyl,
mono or di-$C_{1-6}$ alkyl substituted carbamoyl,
$C_{1-6}$ alkoxycarbonyloxy,
mono or di-$C_{1-6}$ alkyl substituted aminocarbonyloxy,
$C_{1-20}$ alkylcarbonyloxy-$C_{1-6}$ alkyl,
$C_{1-20}$ alkoxycarbonyloxy-$C_{1-6}$ alkyl,
arylcarbonyloxy-$C_{1-6}$ alkyl, in which said aryl is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;
mono or di-$C_{1-6}$ alkyl substituted aminocarbonyloxy-$C_{1-6}$ alkyl,
aryl substituted aminocarbonyloxy-$C_{1-6}$ alkyl, in which said aryl is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;
hydroxy-$C_{1-6}$ alkyl,
$C_{1-6}$ alkoxy-$C_{1-6}$ alkyl,
halogen and
halo $C_{1-6}$ alkyl;
p is 0 or 1;
one of $R^5$ and $R^6$ is hydrogen or $C_{1-4}$ alkyl and the other is hydrogen;
$R^7$, $R^8$, $R^9$ and $R^{10}$ are each independently selected from the group consisting of: hydrogen, $C_{1-6}$ alkyl and carbamoyl;
n is 0, 1, or 2;
m is 0, 1, or 2; and
m+n is 0, 1, 2, or 3;
or a pharmaceutically acceptable salt thereof.

2. A compound according to claim 1, wherein A is phenyl substituted by one or two substituents selected from the group consisting of chloro, fluoro, trifluoromethyl and trifluoromethoxy.

3. A compound according to claim 1 wherein A is selected from the group consisting of: 3-chloro-4-trifluoromethyl-phenyl, 4 trifluoromethyl-phenyl, 3,4 bis trifluoromethyl-phenyl and 3,4-dichlorophenyl.

4. A compound according to claim 1, wherein p is 0.

5. A compound according to claim 1, wherein n is 0 or 1, m is 1 or 2 and n+m is 1 or 2.

6. A compound according to claim 1, wherein one of $R^3$ and $R^4$ is hydrogen and the other is selected from the group consisting of: hydrogen, halogen, hydroxy, $C_{1-4}$ alkyl, hydroxy-$C_{1-4}$ alkyl, $C_{1-4}$alkoxy-$C_{1-4}$alkyl, carboxyl carbamoyl, mono-$C_{1-4}$ alkyl substituted carbamoyl, and $C_{1-4}$ alkoxy-carbonyl.

7. A compound according to claim 1, wherein one of $R^3$ and $R^4$ is hydrogen or hydroxy-$C_{1-4}$ alkyl and the other is hydrogen.

8. A compound according to claim 1, wherein one of $R^9$ and $R^{10}$ is hydrogen or $C_{1-4}$alkyl and the other is hydrogen, and one of $R^7$ and $R^8$ is hydrogen and the other is selected from the group consisting of: carbamoyl, carboxyl and hydrogen.

9. A compound according to claim 1, wherein one of $R^9$ or $R^{10}$ is methyl and the other is hydrogen, and $R^7$ and $R^8$ are both hydrogen.

10. A compound according to claim 1, wherein L is selected from the group consisting of: a bond, NH—C(=O) and CH=CH—C(=O).

11. A compound according to claim 1, wherein L is NH—C(=O) or a bond.

12. A compound according to claim 1, wherein one of $R^5$ and $R^6$ is hydrogen or methyl and the other is hydrogen, $R^7$, $R^8$, $R^9$ and $R^{10}$ are each hydrogen, L is NHC(=O), and $R^1$ and $R^2$ together with the nitrogen atom to which they are attached form (S)-4-hydroxy-6-aza-spiro[2,5]oct-6-yl.

13. A compound according to claim 1, having the formula of formula (I'')

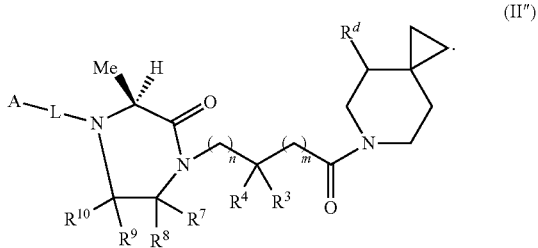

(II'')

14. A compound of claim 1, selected from the group consisting of:
- (S)-4-[4-((S)-4-Hydroxy-6-aza-spiro[2.5]oct-6-yl)-4-oxo-butyl]-2-methyl-3-oxo-piperazine-1-carboxylic acid (4-trifluoromethyl-phenyl)-amide;
- (S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3-chloro-4-trifluoromethyl-phenyl)-amide;
- (S)-4-(3-Chloro-4-trifluoromethyl-phenyl)-1-[4-((S)-4-hydroxy-6-aza-spiro[2.5]oct-6-yl)-4-oxo-butyl]-3-methyl-piperazin-2-one;
- 4-[4-((S)-4-Hydroxy-6-aza-spiro[2.5]oct-6-yl)-4-oxo-butyl]-5-oxo-[1,4]diazepane-1-carboxylic acid (3-chloro-4-trifluoromethyl-phenyl)-amide;
- 1-(3-Chloro-4-trifluoromethyl-phenyl)-4-[(S)-4-((S)-4-hydroxy-6-aza-spiro[2.5]oct-6-yl)-1-hydroxymethyl-4-oxo-butyl]-[1,4]diazepan-5-one;
- (R)-1-(3,4-Bis-trifluoromethyl-phenyl)-4-[(S)-4-((S)-4-hydroxy-6-aza-spiro[2.5]oct-6-yl)-1-hydroxymethyl-4-oxo-butyl]-2-methyl-[1,4]diazepan-5-one;
- (S)-4-[(S or R)-3-Fluoro-4-((S)-4-hydroxy-6-aza-spiro[2.5]oct-6-yl)-4-oxo-butyl]-2-methyl-3-oxo-piperazine-1-carboxylic acid (3-chloro-4-trifluoromethyl-phenyl)-amide;
- (S)-4-[(S)-4-((S)-4-Hydroxy-6-aza-spiro[2.5]oct-6-yl)-1-hydroxymethyl-4-oxo-butyl]-2-methyl-3-oxo-piperazine-1-carboxylic acid (3,4-bis-trifluoromethyl-phenyl)-amide;
- (3S,6S)—N1-(3-chloro-4-(trifluoromethyl)phenyl)-4-(4-((S)-4-hydroxy-6-azaspiro[2.5]octan-6-yl)-4-oxobutyl)-6-methyl-5-oxopiperazine-1,3-dicarboxamide; and
- (3S,6S)-4-[4-((S)-4-Hydroxy-6-aza-spiro[2.5]oct-6-yl)-4-oxo-butyl]-6-methyl-5-oxo-piperazine-1,3-dicarboxylic acid 3-amide 1-[(3,4-bis-trifluoromethyl-phenyl)-amide].

* * * * *